(12) United States Patent
Zhou

(10) Patent No.: US 11,076,938 B2
(45) Date of Patent: Aug. 3, 2021

(54) MULTIFUNCTIONAL VISUAL ORAL CLEANING INSTRUMENT

(71) Applicant: Xing Zhou, Guangzhou (CN)

(72) Inventor: Xing Zhou, Guangzhou (CN)

(*) Notice: Subject to any disclaimer, the term of this patent is extended or adjusted under 35 U.S.C. 154(b) by 130 days.

(21) Appl. No.: 16/211,141

(22) Filed: Dec. 5, 2018

(65) Prior Publication Data
US 2019/0105139 A1 Apr. 11, 2019

Related U.S. Application Data

(63) Continuation of application No. PCT/CN2017/086824, filed on Jun. 1, 2017.

(30) Foreign Application Priority Data

Jun. 5, 2016 (CN) .......................... 201610395433.0
Aug. 10, 2016 (CN) .......................... 201610652404.8
(Continued)

(51) Int. Cl.
A61C 15/04 (2006.01)
A61B 1/06 (2006.01)
(Continued)

(52) U.S. Cl.
CPC ............ *A61C 15/048* (2013.01); *A46B 15/00* (2013.01); *A61B 1/00016* (2013.01);
(Continued)

(58) Field of Classification Search
CPC ....... A61C 15/048; A61C 15/00; A61C 17/22; A61C 17/221; A61C 17/224; A61C 17/06;
(Continued)

(56) References Cited

U.S. PATENT DOCUMENTS 1,796,367 A * 3/1931 Grove ................ A46B 15/0071
132/309
2,140,307 A * 12/1938 Belaschk ............... A61C 17/26
15/28
(Continued)

FOREIGN PATENT DOCUMENTS

CN 201170834 Y 12/2008
CN 102342864 A 2/2012
(Continued)

OTHER PUBLICATIONS

Zhou International Search Report and Written Opinion, PCT/CN2017/086824, dated Aug. 17, 2017, 20 pgs.
(Continued)

*Primary Examiner* — Nicholas D Lucchesi
(74) *Attorney, Agent, or Firm* — Morgan, Lewis & Bockius LLP

(57) ABSTRACT

The present disclosure relates to a multifunctional visual oral cleaning instrument which includes multiple functions of a visual dental floss, and/or visual oral forceps, and/or a visual oral irrigator, and/or a visual toothbrush, and/or a detachable visual interdental brush, and the like. The dental floss, and/or oral forceps, and/or oral irrigator, and/or toothbrush, and/or interdental brush are/is connected with an oral viewer through a connecting mechanism. By using a smartphone or tablet computer, the dental floss, oral forceps, oral irrigator, toothbrush or interdental brush and the gap between teeth can be clearly seen, so that the tooth gaps can be conveniently cleaned and treated under direct vision during use, and the cleaning effect of the tooth gaps can be viewed and recorded in real time.

12 Claims, 83 Drawing Sheets

(30) Foreign Application Priority Data

| Sep. 28, 2016 | (CN) | 201610864603.5 |
|---|---|---|
| Dec. 31, 2016 | (CN) | 201611267716.3 |
| Jan. 16, 2017 | (CN) | 201710029557.1 |

(51) Int. Cl.
*A61C 17/22* (2006.01)
*A61B 1/00* (2006.01)
*A46B 15/00* (2006.01)
*A61B 1/247* (2006.01)
*A61B 1/24* (2006.01)
*A61B 1/05* (2006.01)

(52) U.S. Cl.
CPC ...... *A61B 1/00018* (2013.01); *A61B 1/00034* (2013.01); *A61B 1/00087* (2013.01); *A61B 1/00177* (2013.01); *A61B 1/05* (2013.01); *A61B 1/0607* (2013.01); *A61B 1/0623* (2013.01); *A61B 1/0676* (2013.01); *A61B 1/0684* (2013.01); *A61B 1/24* (2013.01); *A61B 1/247* (2013.01); *A61C 17/22* (2013.01); *A61C 17/221* (2013.01); *A61C 17/224* (2013.01); *A61B 1/00045* (2013.01)

(58) Field of Classification Search
CPC ..... A61C 17/227; A61C 15/047; A61C 17/32; A61C 17/34; A61C 17/3481; A61B 15/00; A61B 1/00016; A61B 1/00018; A61B 1/00034; A61B 1/00087; A61B 1/00177; A61B 1/05; A61B 1/0607; A61B 1/0623; A61B 1/0676; A61B 1/0684; A61B 1/24; A61B 1/247

See application file for complete search history.

(56) References Cited

U.S. PATENT DOCUMENTS

| 2,765,799 | A | * | 10/1956 | Ritter | A46B 15/0055 132/309 |
|---|---|---|---|---|---|
| 3,242,516 | A | * | 3/1966 | Cantor | A61C 17/26 15/28 |
| 4,520,833 | A | * | 6/1985 | Hadary | A61C 15/02 132/328 |
| 4,706,322 | A | * | 11/1987 | Nicolas | A46B 9/04 15/106 |
| 5,623,746 | A | * | 4/1997 | Ichiro | A61C 15/047 15/22.2 |
| 6,247,477 | B1 | * | 6/2001 | Wagner | A45D 44/18 132/309 |
| 6,331,111 | B1 | * | 12/2001 | Cao | A61C 19/004 362/119 |
| 6,468,076 | B2 | * | 10/2002 | Kawamura | A61B 1/24 433/29 |
| 7,156,107 | B2 | * | 1/2007 | Hsu | A46B 3/18 132/309 |
| 8,011,057 | B2 | * | 9/2011 | Nejat | A46B 5/02 15/167.1 |
| 10,667,892 | B2 | * | 6/2020 | Bartschi | A46B 9/06 |
| 2001/0054211 | A1 | * | 12/2001 | Cabedo-Deslierres | A46B 7/023 15/106 |
| 2003/0215765 | A1 | * | 11/2003 | Liu | A46B 15/0055 433/29 |
| 2004/0019990 | A1 | * | 2/2004 | Farrell | A46B 15/0081 15/105 |
| 2008/0041412 | A1 | * | 2/2008 | Jansheski | A61C 15/046 132/322 |
| 2008/0115799 | A1 | * | 5/2008 | Weiss | A61C 15/043 132/328 |
| 2009/0017416 | A1 | | 1/2009 | Nguyen et al. | |
| 2009/0056043 | A1 | * | 3/2009 | Sugimoto | A61C 15/047 15/22.1 |
| 2009/0056044 | A1 | * | 3/2009 | Rizoiu | A46B 15/0034 15/22.1 |
| 2009/0148808 | A1 | * | 6/2009 | Alexander | A61C 19/06 433/29 |
| 2010/0037912 | A1 | * | 2/2010 | Baughman | A61C 15/047 132/323 |
| 2010/0281636 | A1 | * | 11/2010 | Ortins | A46B 15/001 15/4 |
| 2010/0309302 | A1 | * | 12/2010 | Yang | A61C 17/22 348/77 |
| 2011/0041271 | A1 | * | 2/2011 | Huang | A46B 5/02 15/167.1 |
| 2012/0036658 | A1 | * | 2/2012 | Schaefer | A61C 17/222 15/28 |
| 2012/0192367 | A1 | * | 8/2012 | Lin | A61C 17/224 15/22.1 |
| 2012/0266904 | A1 | * | 10/2012 | Aronson | A61C 15/047 132/200 |
| 2013/0061412 | A1 | * | 3/2013 | Vashi | A61B 5/0088 15/106 |
| 2015/0107034 | A1 | * | 4/2015 | Shani | A46B 15/0006 15/22.1 |
| 2015/0257636 | A1 | * | 9/2015 | Kohler | A61C 17/20 433/29 |
| 2016/0022024 | A1 | * | 1/2016 | Vetter | G01D 5/14 324/707 |
| 2016/0022398 | A1 | * | 1/2016 | Vetter | A61C 17/22 433/27 |
| 2018/0168332 | A1 | * | 6/2018 | Wagner | F21V 33/0064 |
| 2019/0090999 | A1 | * | 3/2019 | Vetter | A46B 15/0002 |
| 2019/0117356 | A1 | * | 4/2019 | Bartschi | A61C 17/16 |
| 2020/0054426 | A1 | * | 2/2020 | Prendergast | A46B 15/00 |

FOREIGN PATENT DOCUMENTS

| CN | 103070662 A | 5/2013 |
|---|---|---|
| CN | 203885648 U | 10/2014 |
| CN | 104905547 A | 9/2015 |
| CN | 104921826 A | 9/2015 |
| CN | 204744470 U | 11/2015 |
| CN | 205018520 U | 2/2016 |

OTHER PUBLICATIONS

Zhou, International Preliminary Report on Patentability, PCT/CN2017/086824, dated Dec. 11, 2018, 6 pgs.

Zhou, Communication Pursuant to Rules 161(2) and 162, EP17809657.4, dated Jan. 18, 2019, 3 pgs.

Zhou, Partial Supplementary European Search Report, EP17809657.4, dated Dec. 13, 2019, 12 pgs.

Zhou, Extended European Search Report, EP17809657.4, dated Mar. 30, 2020, 11 pgs.

* cited by examiner

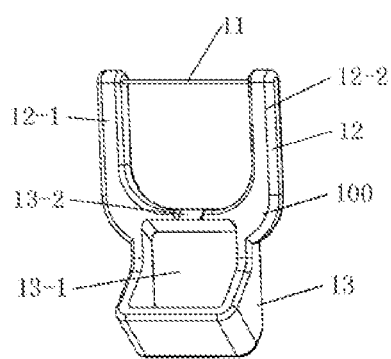
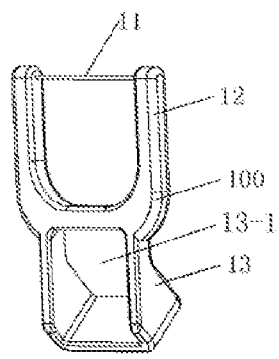
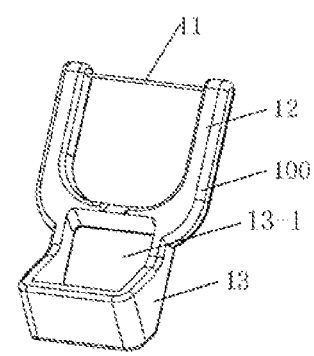
FIG. 3  FIG. 3-1  FIG. 3-2
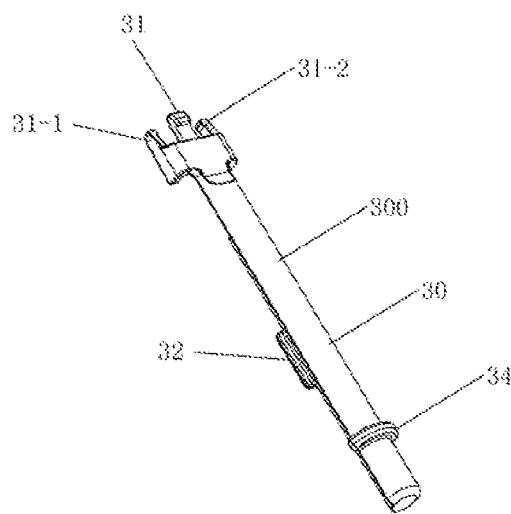
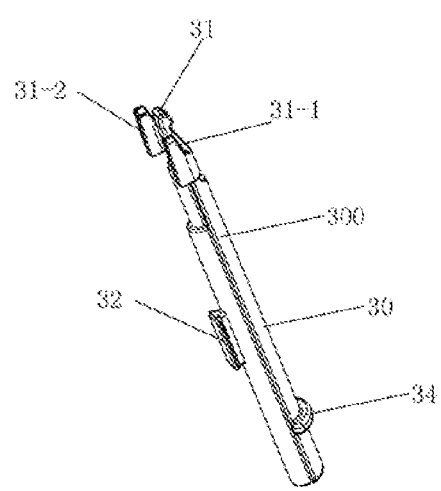
FIG. 4  FIG. 4-1

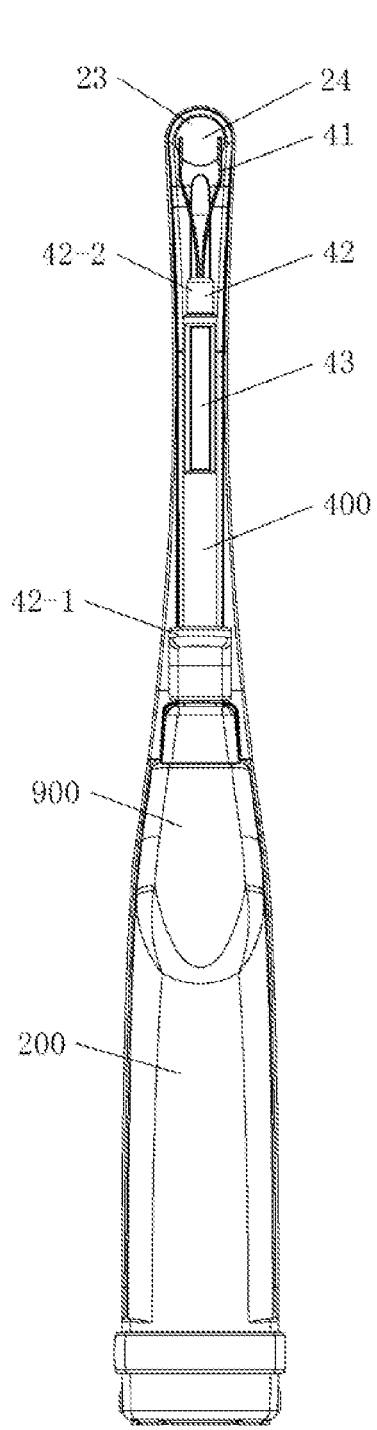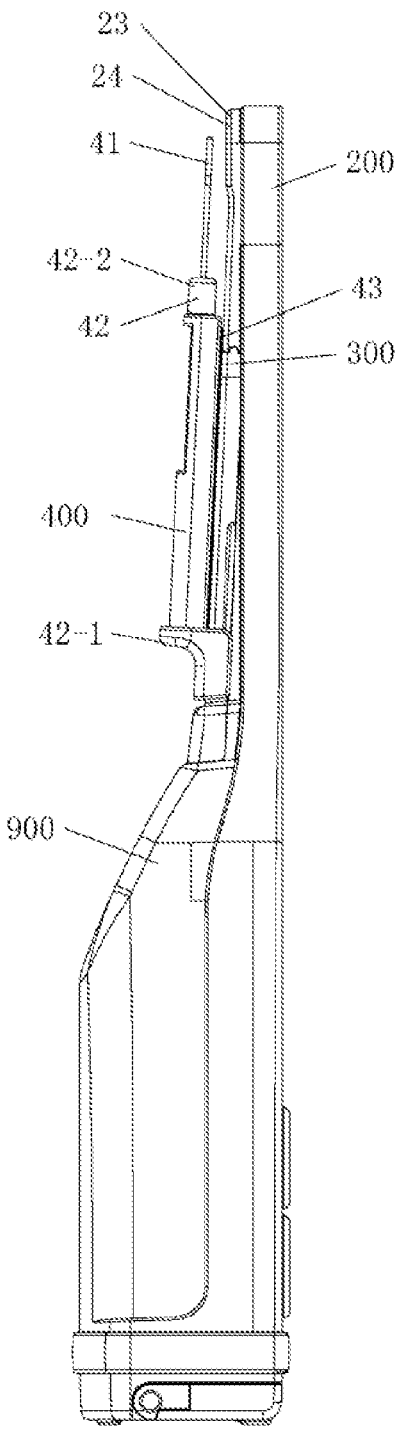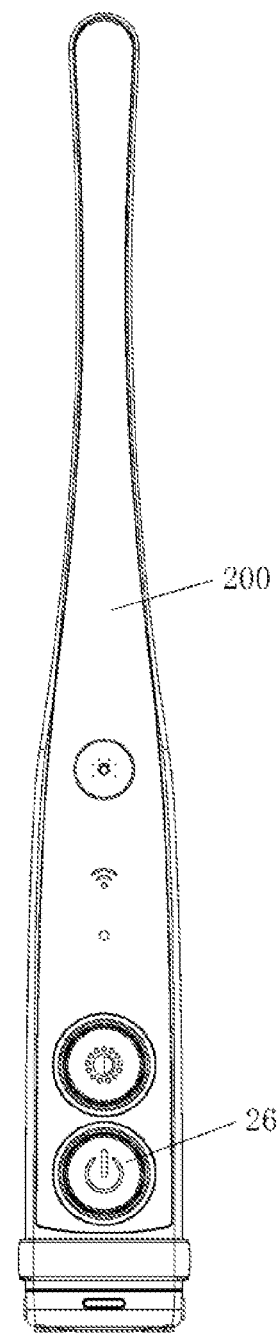
FIG. 11-1          FIG. 11-2          FIG. 11-3

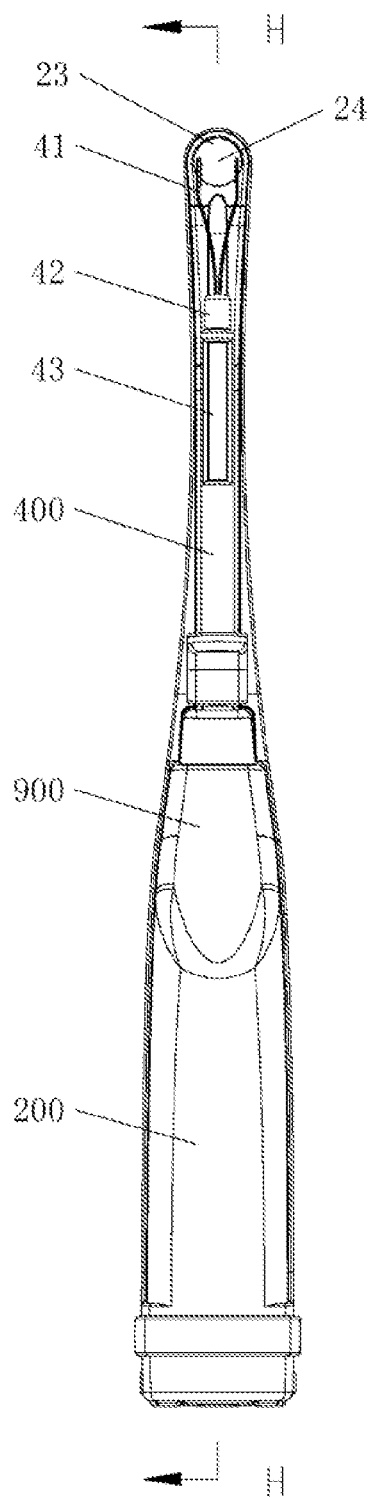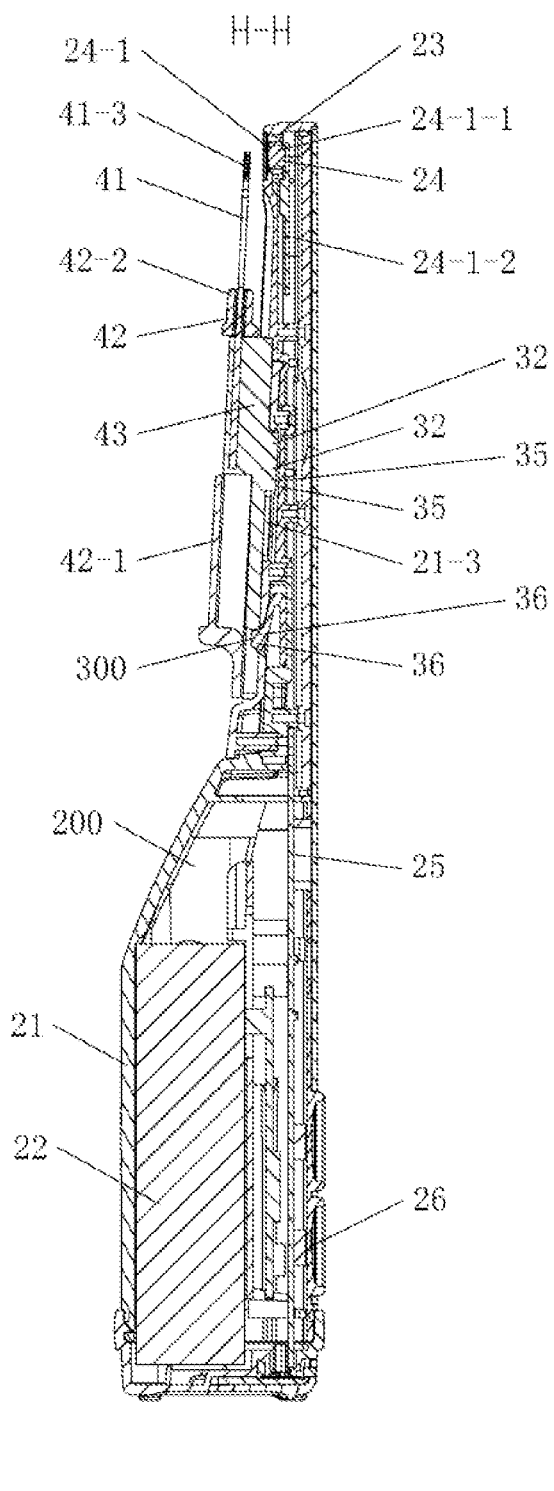
FIG. 11-4  FIG. 11-5

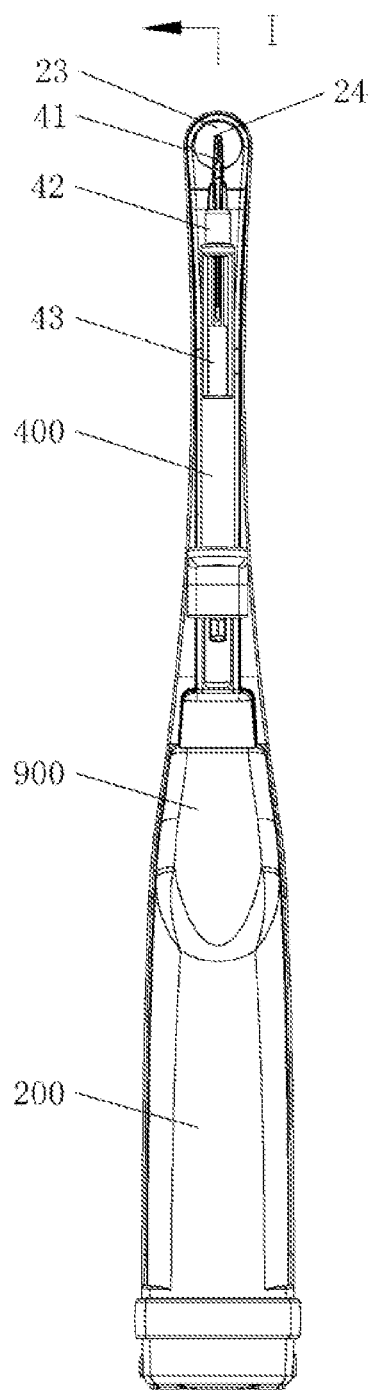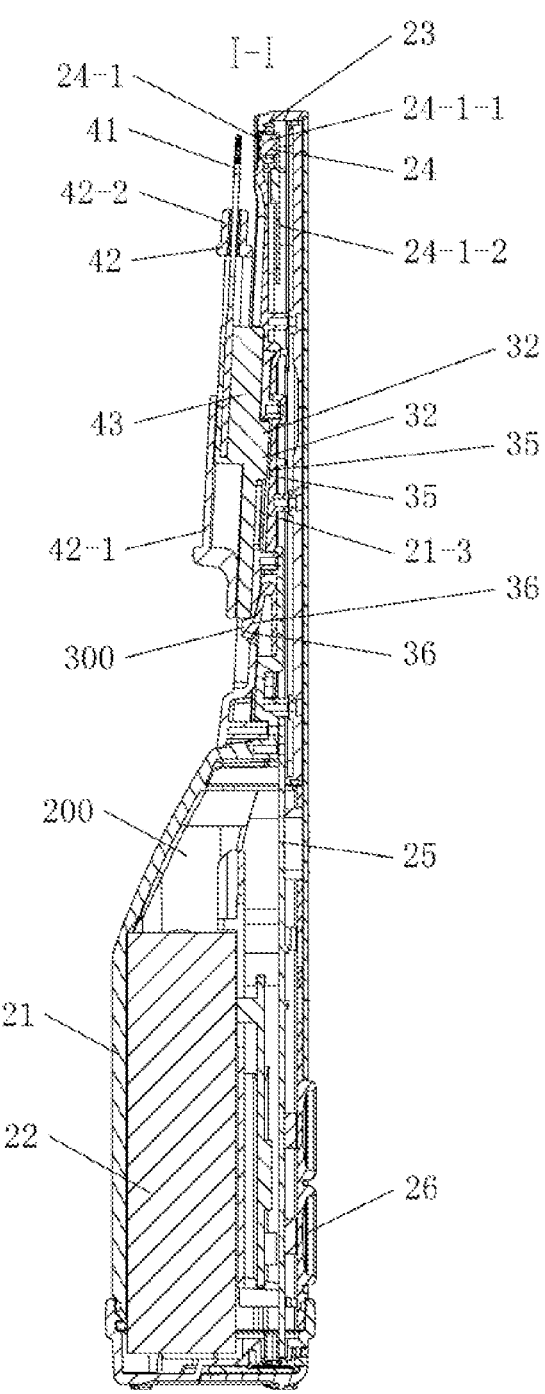
FIG. 11-6  FIG. 11-7

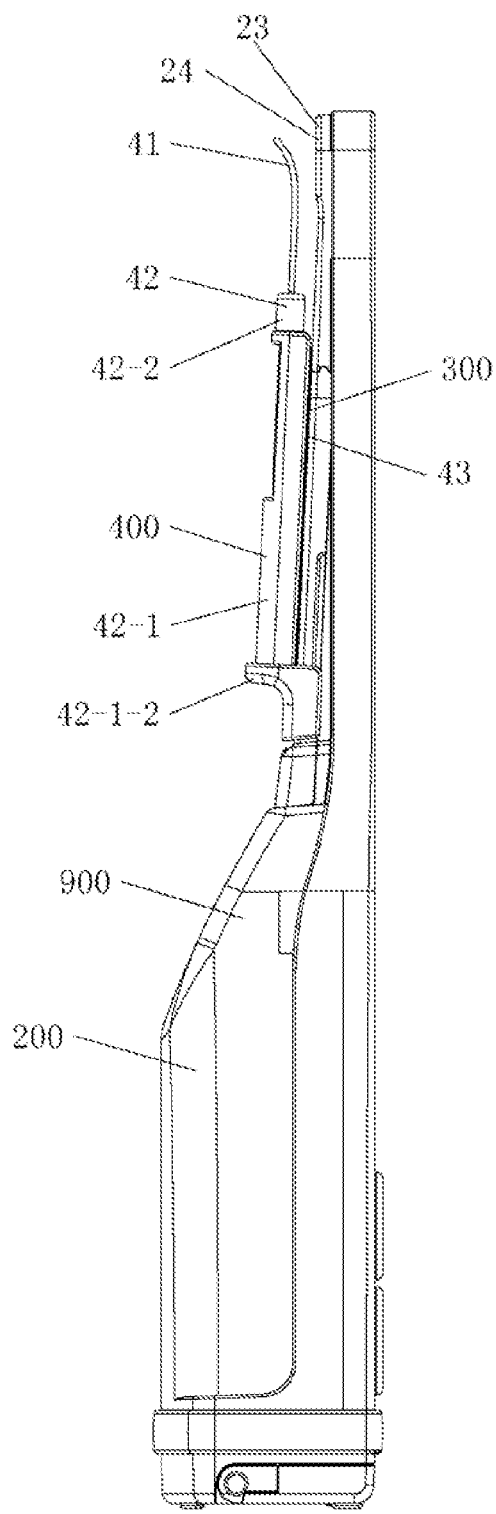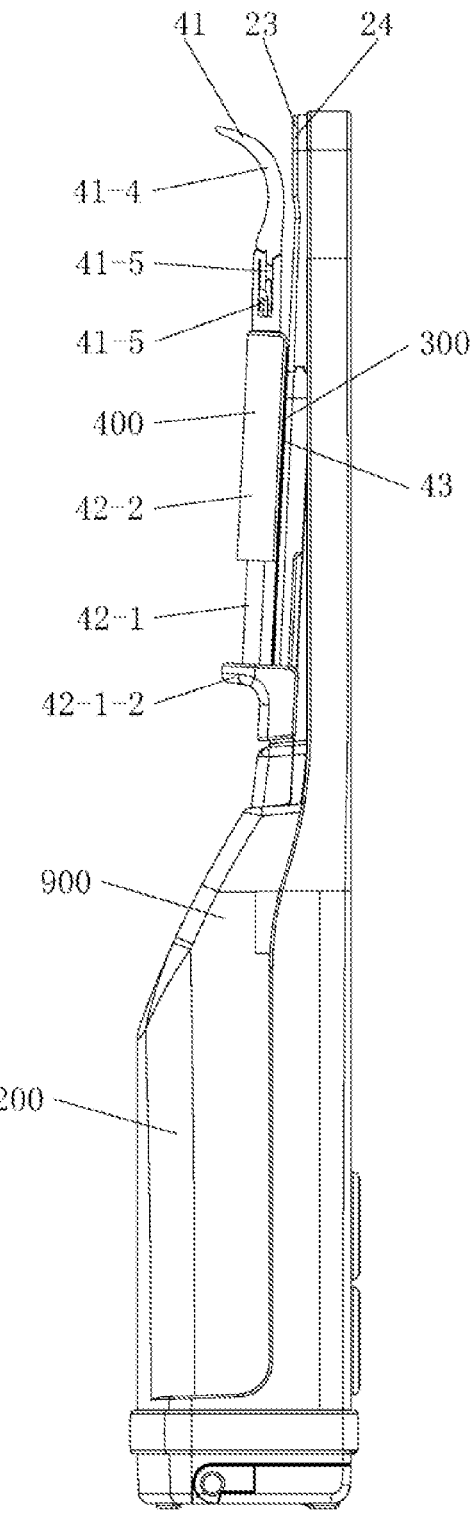
FIG. 14
FIG. 15

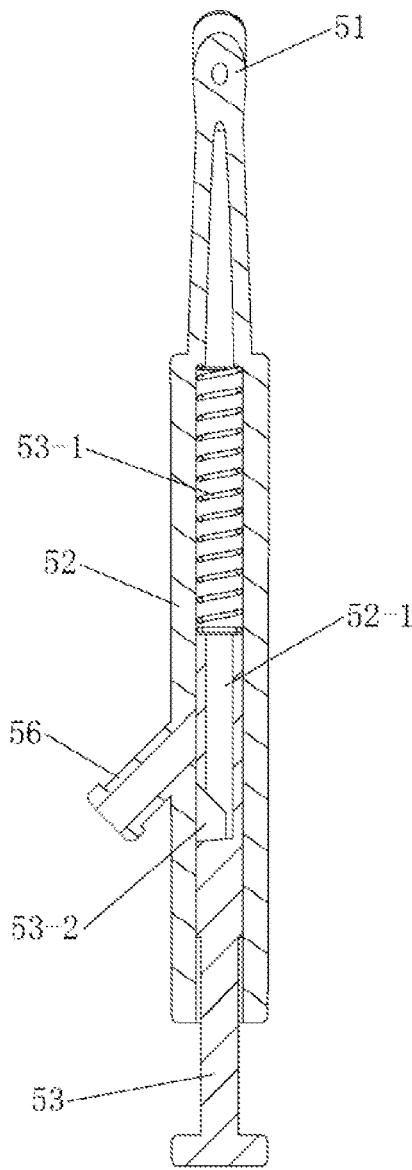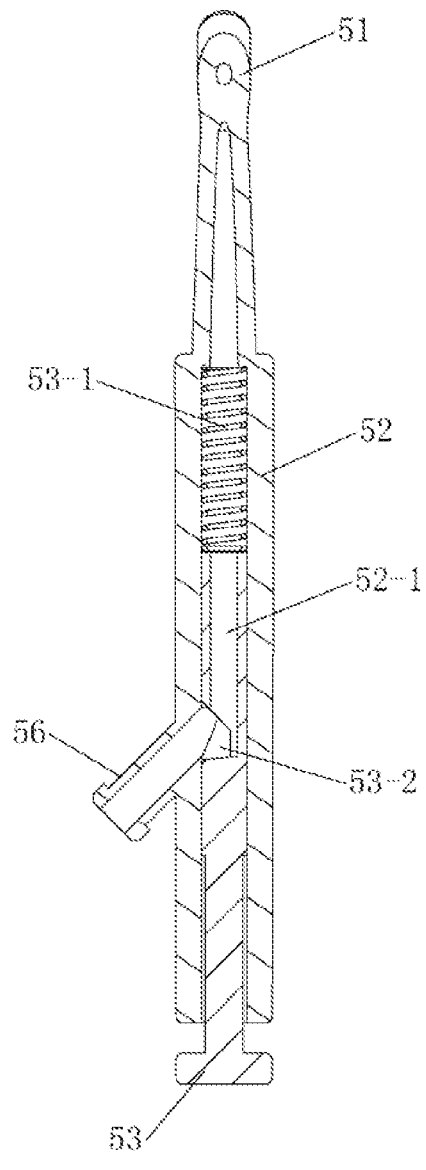
FIG. 21-3    FIG. 21-4

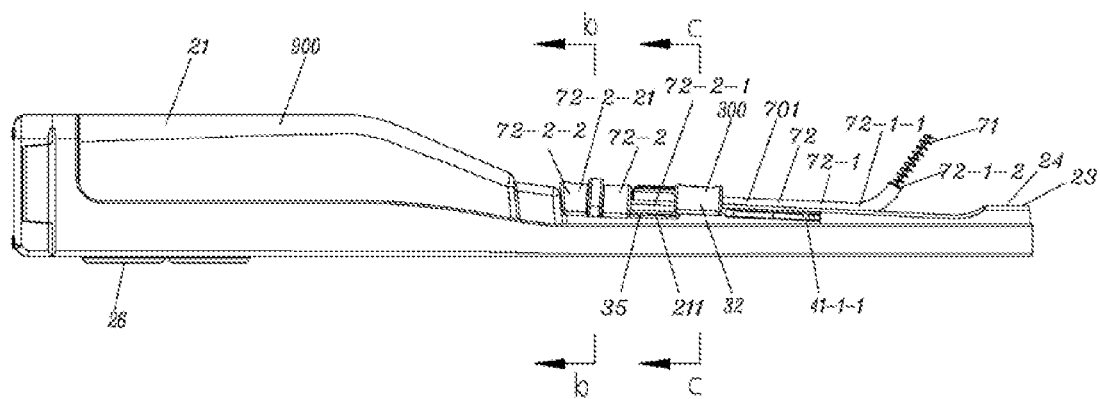
FIG. 51
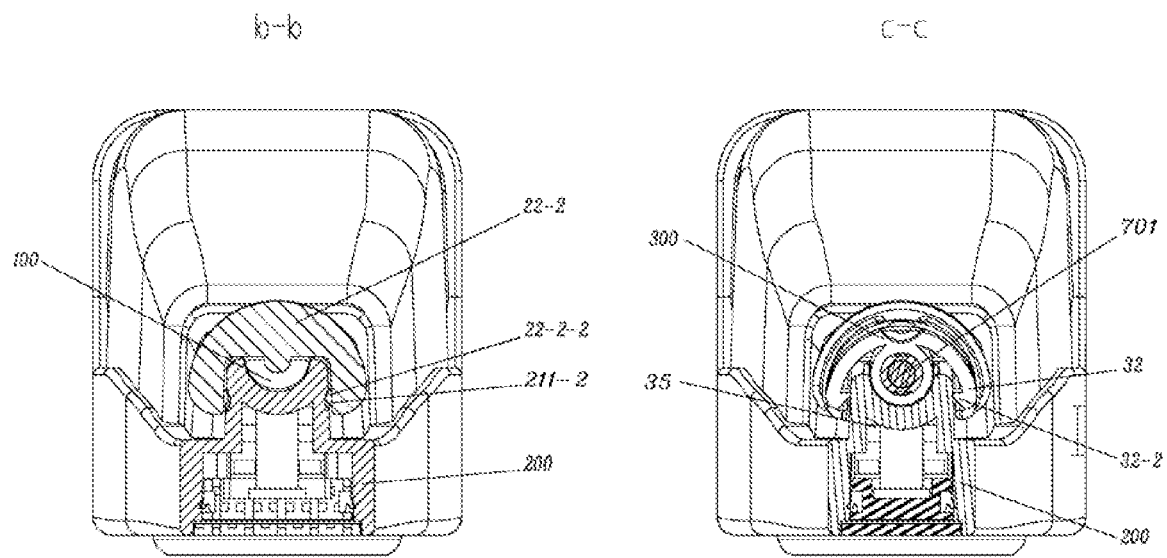
FIG. 51-1
FIG. 51-2

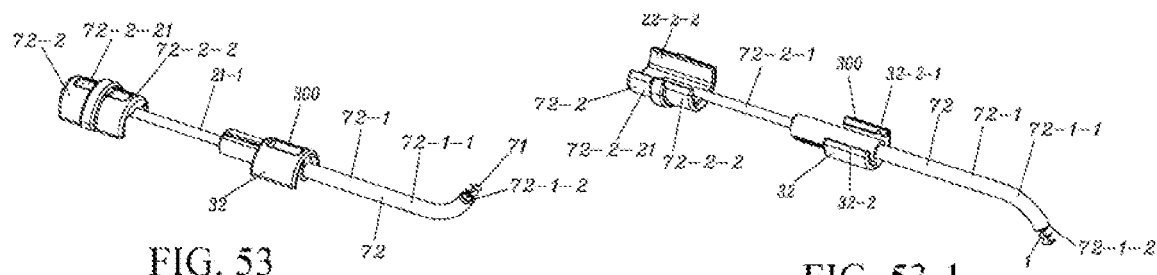
FIG. 53
FIG. 53-1
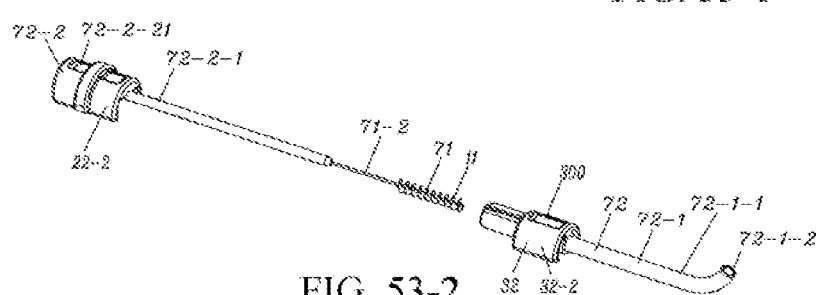
FIG. 53-2
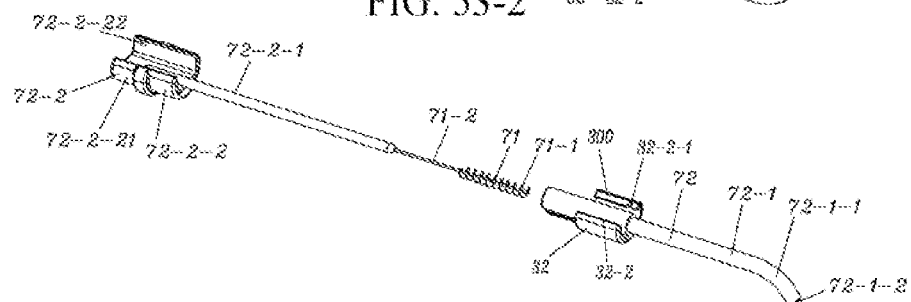
FIG. 53-3
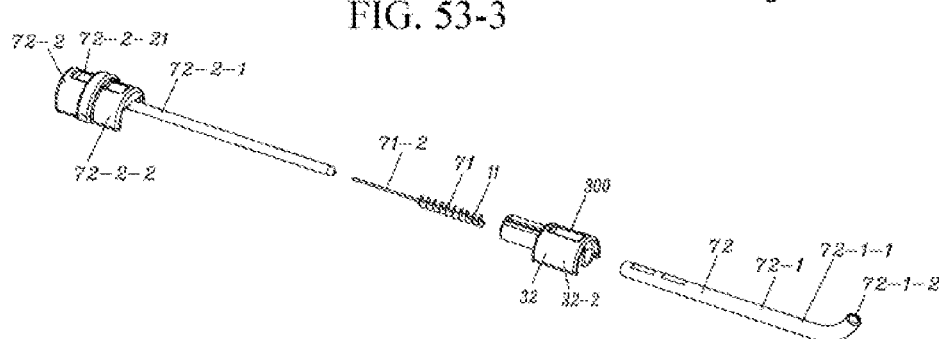
FIG. 53-4
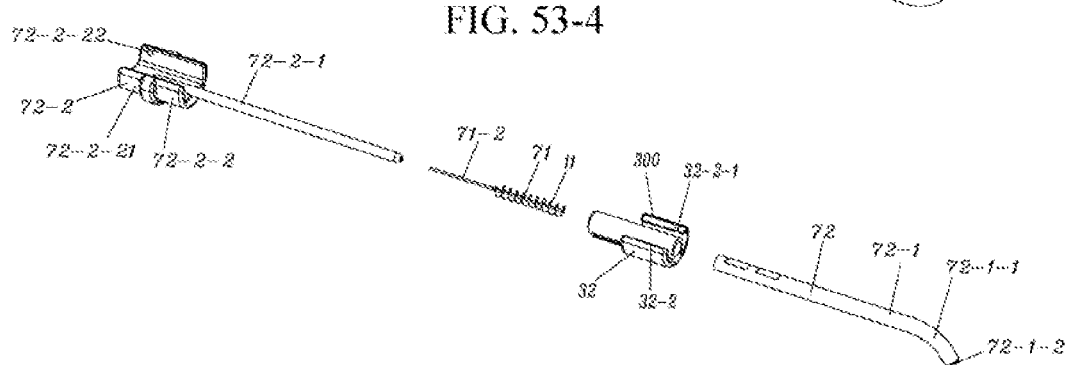
FIG. 53-5

MULTIFUNCTIONAL VISUAL ORAL CLEANING INSTRUMENT

CROSS-REFERENCE TO RELATED APPLICATIONS

The application is a continuation application of PCT/CN2017/086824, entitled "MULTIFUNCTIONAL VISUAL ORAL CLEANING INSTRUMENT" filed on Jun. 1, 2017, which claims priority to (i) Chinese Patent Application No. 201610395433.0, filed with the State Intellectual Property Office of the People's Republic of China on Jun. 5, 2016, and entitled "DETACHABLE VISUAL INTERDENTAL BRUSH", (ii) Chinese Patent Application No. 201610652404.8, filed with the State Intellectual Property Office of the People's Republic of China on Aug. 10, 2016, and entitled "VISUAL DENTAL FLOSS", (iii) Chinese Patent Application No. 201610864603.5, filed with the State Intellectual Property Office of the People's Republic of China on Sep. 28, 2016, and entitled "VISUAL ORAL FORCEPS", (iv) Chinese Patent Application No. 201710029557.1, filed with the State Intellectual Property Office of the People's Republic of China on Jan. 16, 2017, and entitled "VISUAL ORAL CLEANING TOOL", and (v) Chinese Patent Application No. 201611267716.3, filed with the State Intellectual Property Office of the People's Republic of China on Dec. 31, 2016, and entitled "VISUAL TOOTHBRUSH", the entirety of which is incorporated herein by reference.

TECHNICAL FIELD

The present disclosure relates to an oral cleaning tool, and more particularly to a multifunctional visual oral cleaning instrument for cleaning tooth gaps.

BACKGROUND

Due to age, pathology and other reasons, it is easy to cause gingival recession and enlargement of tooth gaps, which can easily cause food residues. If the food residues cannot be cleaned in time, bad breath will be generated on the one hand, and on the other hand, it is easy to cause various dental diseases and oral diseases, especially periodontitis. In addition, when people eat fish, the fish bones will sometimes stick into the gingivae and need to be removed in time.

In response to this situation, various toothbrushes, dental flosses, interdental brushes and other products have been developed on the market for users to choose at present. Although various structures of products with different sizes, such as toothbrushes, dental flosses, interdental brushes and the like exist on the market today, the existing products are generally disadvantageous in that they are not easily viewed. Especially when the position to be cleaned is deep in the oral cavity, such as the gap between the third molar and the second molar, or the gap between the second molar and the first molar, or the gap between the first molar and the second premolar, if the light of the cleaned part is very dim, the position to be cleaned cannot be seen clearly in general cases, so that the user can only operate by feeling inconveniently, and cannot know whether the position to be cleaned to is cleaned completely, which can easily cause gingival bleeding or other accidental injuries.

In order to overcome the disadvantages of the prior art, it is necessary to develop a visual oral cleaning tool through which the inside of the oral cavity, especially deep in the oral cavity, can be viewed clearly and oral cleaning can be performed under direct vision.

SUMMARY

The present disclosure relates to a multifunctional visual oral cleaning instrument which includes a visual dental floss, and/or visual oral forceps, and/or a visual oral irrigator, and/or a visual toothbrush, and/or a detachable visual interdental brush. The dental floss, and/or oral forceps, and/or oral irrigator, and/or toothbrush, and/or interdental brush are/is connected with an oral viewer through a connecting mechanism. By using a smartphone or tablet computer, the dental floss, oral forceps, oral irrigator, toothbrush or interdental brush and the gap between teeth can be clearly seen, so that tooth gaps can be conveniently cleaned and treated under direct vision during use, and the cleaning effect of the tooth gaps can be viewed and recorded in real time.

The visual dental floss of the present disclosure, characterized in that

The visual dental floss 901 includes a dental floss 100, an oral viewer 200 and a connecting mechanism 300;

A. the dental floss 100 includes a floss 11, a bracket 12 and a mounting base 13; both ends of the floss 11 of the dental floss 100 are respectively fixed on a left arm 12-1 and a right arm 12-2 of the bracket 12, and the bracket 12 is arranged on the mounting base 13;

B. the oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; the lighting system 23, the viewing system 24, the power supply system 22 and the switch 26 are connected together through the circuit system 25; and C. the dental floss 100 is mounted on the oral viewer 200 through the connecting mechanism 300.

In particular, the dental floss 100 may be detachably mounted on the oral viewer 200 through the connecting mechanism 300.

The floss 11 of the dental floss 100 is within the visual field of the viewing system 24 of the oral viewer 200. Thus, the dental floss and the gap between teeth can be clearly seen, so that tooth gaps can be conveniently cleaned and treated under direct vision during use, and the cleaning effect of the tooth gaps can be viewed and recorded in real time.

An included angle δ between the floss 11 of the dental floss 100 and the center line of a head 21-1 of the housing of the oral viewer 200 is adjustable. Thus, the included angle β can be adjusted according to the angles of the tooth gaps of different parts, so that the dental floss can conveniently enter the tooth gaps and clean the tooth gaps. The adjustment of the included angle β can be implemented by adopting a passive mechanical structure, such as a thread structure, or a concave-convex snap fit structure, or a moderate interference fit structure or the like, or by an active electric control manner, such as transmission of a motor or the like.

The connecting mechanism 300 is a detachable mechanical connecting mechanism; the connecting mechanism 300 may be a separate component, and may be arranged on the dental floss 100 or arranged on the oral viewer 200; alternatively, the connecting mechanism 300 may also be a combined mechanical connecting mechanism formed by arranging a part of the detachable mechanical connecting mechanism on the dental floss 100 and the other part on the oral viewer 200. The connecting mechanism 300 may be a separate component, and is respectively connected with the dental floss 100 and the oral viewer 200 to connect the dental floss 100 and the oral viewer 200 into an integral body. The connecting mechanism 300 may also be manufactured as a whole with the dental floss 100 or the oral viewer 200, and then connected with the oral view 200 or the dental floss 100 to form an integral body. Regardless of the type of connection, the ultimate goal is to implement a detachable connection between the dental floss 100 and the oral viewer 200. Therefore, the detachable connection between the dental floss 100 and the oral viewer 200 can be implemented as long as the connecting mechanism 300 implements a detachable mechanical connection with one of the dental floss 100 or the oral viewer 200.

The mechanical connecting mechanism may be a concave-convex snap fit connection, or a sliding slot connection, or a pin connection, or a key connection, or a threaded connection, or a screw connection, or a buckle connection, or a hook connection, or an interference fit connection, or the like. Of course, those skilled in the art can select other mechanical connection manners without departing from the protection scope of the present application.

The mounting base 13 of the dental floss 100 is provided with a through hole 13-1, the head 21-1 of the housing of the oral viewer 200 may be embedded in the through hole 13-1, and a detachable connection is formed between the dental floss 100 and the oral viewer 200. When connecting, the head 21-1 of the housing of the oral viewer 200 can be embedded in the through hole 13-1 to form a connection; and when detaching, the dental floss 100 can be removed from the oral viewer 200 by pulling the oral viewer 200 and the dental floss 100 outward with a little force, so the use process is very convenient.

The mounting base 13 of the dental floss 100 is provided with a locating groove 13-2; the connecting mechanism 300 is provided with a locating hook 31 and a locating block 32; the connecting mechanism 300 is mounted on the oral viewer 200 through the locating block 32; and the locating hook 31 on the connecting mechanism 300 is embedded in the locating groove 13-2 of the dental floss 100 to form a concave-convex snap fit connection, and a detachable connection is formed between the dental floss 100 and the oral viewer 200. When detaching, the dental floss 100 can be removed from the oral viewer 200 by pressing down the locating hook 31. The concave-convex snap fit connection manner formed by the locating hook 31 and the locating groove 13-2 is more secure and reliable than the common through hole connection manner due to the effective locating of the locating hook 31.

The mounting base 13 of the dental floss 100 is provided with a thread 13-3; the connecting mechanism 300 is a threaded connecting mechanism 33, and the threaded connecting mechanism 33 is matched with the thread 13-3 and arranged on the head 21-1 of the housing of the oral viewer 200; by rotating the dental floss 100, the thread 13-3 of the dental floss 100 can be mounted on the threaded connecting mechanism 33; and by rotating the dental floss 100 in the opposite direction, the thread 13-3 of the dental floss 100 can be removed from the threaded connecting mechanism 33. At this time, the thread 13-3 on the mounting base 13 may be set as a screw or bolt type, and the threaded connecting mechanism 33 of the connecting mechanism 300 is a corresponding nut; and contrarily, the thread 13-3 on the mounting base 13 may be set as a nut type, and the threaded connecting mechanism 33 of the connecting mechanism 300 is a corresponding screw or bolt.

By rotating the floss 13-3 of the dental floss 100, the included angle δ between the floss 11 of the dental floss 100 and the center line of the head 21-1 of the housing of the oral viewer 200 can be adjusted. Thus, the included angle β can be adjusted in time according to the angles of the tooth gaps of different parts, so that the dental floss can conveniently enter the tooth gaps and clean the tooth gaps.

The connecting mechanism 300 includes a sliding bar 30, a locating hook 31, a left locating hook 31-1, a right locating hook 31-2, a locating block 32 and an antiskid convex line 34; the locating hook 31, the left locating hook 31-1 and the right locating hook 31-2 are arranged at the front end of sliding bar 30, the locating hook 31 is centered, and the left locating hook 31-1 and the right locating hook 31-2 are arranged on both sides respectively; the locating block 32 is positioned in the middle of the sliding bar 30; the antiskid convex line 34 is arranged at the tail of the sliding bar 30; the locating block 32 is mounted in a locating slot 35 of the housing 21 of the oral viewer 200, and a clamping block 36 of the housing 21 of the oral viewer 200 abuts against the tail of the sliding bar 30, so that the connecting mechanism 300 is detachably mounted and fixed to the housing 21 of the oral viewer 200; and the head 21-1 of the housing 21 of the oral viewer 200 is embedded in the through hole 13-1 of the mounting base of the dental floss 100, the locating hook 31 of the connecting mechanism 300 is embedded in the locating groove 13-2 of the mounting base, and the left locating hook 31-1 and the right locating hook 31-2 surround the head 21-1 of the housing 21 of the oral viewer 200 from the left and right sides.

During mounting, the locating block 32 of the connecting mechanism 300 is firstly embedded in the locating slot 35 of the housing 21 of the oral viewer 200, and the sliding bar 30 of the connecting mechanism 300 is slid forward until the clamping block 36 of the housing 21 of the oral viewer 200 is lifted up against the tail of the sliding bar 30; and at this time, the left locating hook 31-1 and the right locating hook 31-2 surround the head 21-1 of the housing 21 of the oral viewer 200 from the left and right sides so as to mount and connect the connecting mechanism 300 onto the oral viewer 200. The design of the antiskid convex line 34 can effectively prevent the sliding bar 30 from slipping when sliding back and forth. The surrounding action of the left locating hook 31-1 and the right locating hook 31-2, and the concave-convex snap fit of the locating block 32 and the locating slot 35 can effectively connect the connecting mechanism 300 firmly to the oral viewer 200.

Then, the head 21-1 of the housing 21 of the oral viewer 200 is embedded in the through hole 13-1 of the mounting base of the dental floss 100, and by pushing the dental floss 100 toward the connecting mechanism 300, the locating hook 31 of the connecting mechanism 300 can be embedded in the locating groove 13-2 of the mounting base 13.

When detaching, the top of the locating hook 31 of the connecting mechanism 300 is pressed down to withdraw the dental floss 100, so that the concave-convex snap fit between the connecting mechanism 300 and the dental floss 100 can be released. When it is necessary to further remove the connecting mechanism 300 from the oral viewer 200, the sliding bar 30 is forced backwards, the clamping block 36 of the oral viewer 200 is pressed down, and the locating block 32 of the connecting mechanism 300 is withdrawn from the locating slot 35 of the oral viewer 200 until the connection of the connecting mechanism 300 and the oral viewer 200 is completely released.

Since the locating block 32 of the connecting mechanism 300 adopts an inverted T-shaped structure, when the T-shaped locating block 32 is embedded in the locating slot 35, the bottom of the inverted T-shaped structure and the locating slot 35 can form a concave-convex snap fit structure, thereby effectively limiting the movement of the connecting mechanism 300 in the vertical direction, and further preventing the connecting mechanism 300 and the oral viewer 200 from departing along the vertical direction during use. Meanwhile, the clamping block 36 of the oral viewer 200 is arranged at the rear end of the connecting mechanism 300; when the clamping block 36 of the oral viewer 200 is lifted up, since the top of the clamping block 36 is higher than the tail of the connecting mechanism 300, the connecting mechanism 300 can be effectively prevented from moving backward; and only when the connecting mechanism 300 is moved backward consciously and forcefully, the connecting mechanism 300 can be released from the oral viewer 200 after withdrawing along the guide surface of the clamping block 36, thereby effectively preventing the dental floss 100 from being accidentally released from the oral viewer 200 due to the fact that the connecting mechanism 300 can easily move backward.

The viewing system 24 is a camera system 24-1, and the camera system 24-1 includes a camera 24-1-1, a data processing and output system 24-1-2, a circuit system 25 and a power supply system 22.

Video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device/television 24-1-33, or a tablet computer 24-1-34.

The lighting system 6 is arranged around the camera 24-1-1.

The oral viewer 200 adopts a waterproof design and includes a sealing device 21-4 for a sealed charging interface 25-3; the sealing device 21-4 includes a seal ring 21-4-1, a pressure plate 21-4-2 and a sliding plate 21-4-3; the seal ring 21-4-1 is mounted in a seal groove 21-4-0 at the tail of the housing 21, the pressure plate 21-4-2 presses on the seal ring 21-4-1, and the sliding plate 21-4-3 detachably presses on the pressure plate 21-4-2; when the sliding plate 21-4-3 slides into a sliding plate locating slot 35-4-4 at the tail of the housing 21, the sliding plate 21-4-3 presses on the pressure plate 21-4-2, and the pressure plate 21-4-2 presses on the seal ring 21-4-1 to form a seal; and when the sliding plate 21-4-3 is pushed outward, the sliding plate 21-4-3 is released from the sliding plate locating slot 35-4-4 at the tail of the housing 21, the sliding plate 21-4-3 is lifted, the pressure of the pressure plate 21-4-2 is released, the pressure plate 21-4-2 may be lifted up to expose the sealed charging interface 25-3, the seal is released, and the oral viewer 200 is charged.

Since the oral viewer 200 adopts a waterproof design, when the oral viewer 200 does not need charging, the sliding plate 21-4-3 slides into the sliding plate locating slot 35-4-4, the seal ring 21-4-1 forms a seal, and at this time, the oral viewer 200 has favorable waterproofness and can be washed and cleaned conveniently.

The visual dental floss 901 of the present disclosure includes a dental floss 100, an oral viewer 200 and a connecting mechanism 300. The dental floss 100 and the oral viewer 200 are detachably connected together through the connecting mechanism 300. The connecting mechanism 300 may be fixed and connected with the dental floss 100 and the oral viewer 200 into an integral body, and may also be a detachable mechanical connecting mechanism. When the connecting mechanism 300 is a detachable mechanical connecting mechanism, it may be a separate component, or arranged on the dental floss 100 or the oral viewer 200. The floss 11 of the dental floss 100 is within the visual field of the viewing system 24 of the oral viewer 200. The dental floss and the gap between teeth can be clearly seen, so that tooth gaps can be conveniently cleaned and treated under direct vision during use, and the cleaning effect of the tooth gaps can be viewed in real time.

The visual oral forceps of the present disclosure, characterized in that

The visual oral forceps characterized in that the visual oral forceps 902 include oral forceps 400, an oral viewer 200 and a connecting mechanism 300;

A. the oral forceps 400 include jaws 41, an opening/closing mechanism 42 and a mounting base 43; the jaws 41 of the oral forceps 400 include a left arm 41-1 and a right arm 41-2, and a fit clamping structure is formed between the left arm 41-1 and the right arm 41-2; the opening/closing mechanism 42 capable of controlling a closing or opening movement of the jaws 41 is arranged on the mounting base 43;

B. the oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; the lighting system 23, the viewing system 24, the power supply system 22 and the switch 26 are connected together through the circuit system 25; and C. the oral forceps 400 are mounted on the oral viewer 200 through the connecting mechanism 300.

Further, the jaws 41 are within the visual field of the viewing system 24 of the oral viewer 200, thereby facilitating viewing.

The jaws 41 of the oral forceps 400 are provided with bite teeth 41-3 which fit each other, thereby increasing the bite force.

The jaws 41 of the oral forceps 400 have a curvature 41-4 that meets the requirements of the human oral cavity, thereby facilitating the capture of foreign objects.

The opening/closing mechanism 42 of the oral forceps 400 includes a sleeve sliding bar opening/closing mechanism, or a hinge opening/closing mechanism, or a lever regulation opening/closing mechanism, or a button regulation opening/closing mechanism, or a spring regulation opening/closing mechanism, or a push-and-pull regulation opening/closing mechanism, or a rotation regulation opening/closing mechanism, or the like. Those skilled in the art can perform various specific product designs according to the technical solutions disclosed in the present disclosure without departing from the protection scope of the present patent.

The mounting base 43 of the oral forceps 400 is provided with a locating block 32 used to be connected with the oral viewer 200.

The connecting mechanism 300 is a detachable mechanical connecting mechanism; the connecting mechanism 300 may be a separate component, and may be arranged on the oral forceps 400 or arranged on the oral viewer 200; alternatively, the connecting mechanism 300 may also be a combined mechanical connecting mechanism formed by arranging a part of the detachable mechanical connecting mechanism on the oral forceps 400 and the other part on the oral viewer 200.

The mechanical connecting mechanism includes: a concave-convex snap fit connection, or a sliding slot connection, or a pin connection, or a key connection, or a threaded connection, or a screw connection, or a buckle connection, or a hook connection, or an interference fit connection, or any other connecting mechanism. Those skilled in the art can perform various specific product designs according to the technical solutions disclosed in the present disclosure without departing from the protection scope of the present patent.

The housing 21 of the oral viewer 200 is provided with a locating slot 35 and a clamping block 36; the locating block 32 of the oral forceps 400 can be embedded in the locating slot 35, and the clamping block 36 can prevent the mounting base 43 of the oral forceps 400 from sliding backward; and the coordination of the locating block 32, the locating slot 35 and the clamping block 36 constitutes the connecting mechanism 300.

The viewing system 24 is a camera system 24-1, and the camera system 24-1 includes a camera 24-1-1, a data processing and output system 24-1-2, a circuit system 25 and a power supply system 22.

Video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device 24-1-33, or a television 24-1-34, or any other display device.

The lighting system 23 is arranged around the camera 24-1-1. In order to increase lighting, more LED lights may also be arranged on the housing 21 of the oral viewer 200 for adjusting the lighting brightness.

The oral viewer 200 adopts a waterproof design, thereby facilitating cleaning and operation.

Further, the jaws 41 of the oral forceps 400 are made of an elastic material, and the jaws 41 remains in an open state when no external force is applied; the rear end of the jaws 41 is fixed on the mounting base 43 and is detachably connected with the oral viewer 200 together through the connecting mechanism 300; the front end of the jaws 41 passes through a hole 42-2-1 of the sleeve 42-2 of the opening/closing mechanism 42; by pushing the push rod 42-1 of the opening/closing mechanism 42 forward, the sleeve 42-2 moves toward the front end of the jaws 41 to close the jaws 41 until the left arm 41-1 and the right arm 41-2 of the jaws 41 fit together; and by pushing the push rod 42-1 of the opening/closing mechanism 42 backward, the sleeve 42-2 moves toward the rear end of the jaws 41, and the left arm 41-1 and the right arm 41-2 of the jaws 41 are opened under the action of the elastic force of the jaws 41. The elastic material is made of a medical elastic material, including but not limited to: an elastic polymer material, an elastic metal material, a metal-plastic composite elastic material and the like, such as a polyurethane material (PU), a polypropylene material (PP), elastic stainless steel, shape memory metal and the like.

The jaws 41 of the oral forceps 400 adopt a hinged structure, and are provided with a pin 41-5; the left arm 41-1 and the right arm 41-2 of the jaws 41 are movably mounted on the sleeve 42-2 through the pin 41-5; the sleeve 42-2 is arranged on the mounting base 43 and is detachably connected with the oral viewer 200 together through the connecting mechanism 300; the rear end of the jaws 41 is connected with the push rod 42-1 of the opening/closing mechanism 42, and when the push rod 42-1 is pulled backward, the left arm 41-1 and the right arm 41-2 of the jaws 41 rotate around the pin 41-5, and the left arm 41-1 and the right arm 41-2 of the jaws 41 are closed until they fit together; and when the push rod 42-1 is pushed forward, the left arm 41-1 and the right arm 41-2 of the jaws 41 rotate around the pin 41-5, and the left arm 41-1 and the right arm 41-2 of the jaws 41 are opened.

In addition, those skilled in the art can perform various specific product designs according to the technical solutions disclosed in the present disclosure, and especially, can perform many specific designs on the shape and structure of the oral forceps 400 without departing from the protection scope of the present patent.

The visual oral forceps 902 of the present disclosure include oral forceps 400, an oral viewer 200 and a connecting mechanism 300. The oral forceps 400 include jaws 41, an opening/closing mechanism 42 and a mounting base 43; the jaws 41 of the oral forceps 400 include a left arm 41-1 and a right arm 41-2, and a fit clamping structure is formed between the left arm 41-1 and the right arm 41-2; the opening/closing mechanism 42 capable of controlling a closing or opening movement of the jaws 41 is arranged on the mounting base 43. The oral forceps 400 and the oral viewer 200 are detachably connected together through the connecting mechanism 300. Since the oral viewer 200 includes the lighting system 23 and the viewing system 24 and transmits the viewed video to a smartphone or any other display device in a wired or wireless manner, by using the visual oral forceps 902 of the present disclosure, the food residues, or fish bones or other foreign objects can be taken out of the oral cavity safely and conveniently under direct vision, and the user can view the taking out process and the effect after taking out, and perform picture or video recording.

The visual oral irrigator of the present disclosure, characterized in that the visual oral irrigator 903 includes an oral irrigator 500, an oral viewer 200 and a connecting mechanism 300;

A. the oral irrigator 500 includes a spray head 51, a spray gun 52, a control switch 53, a pressure vessel 54, a connecting tube 55 and a union joint 56; the spray head 51 is arranged at the front end of the spray gun 52; the control switch 53 can control the spray of a fluid in the spray gun 52; a fluid in the pressure vessel 54 is connected with the spray gun 52 through the connecting tube 55 and the union joint 56;

B. the oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; the lighting system 23, the viewing system 24, the power supply system 22 and the switch 26 are connected together through the circuit system 25; and C. the oral irrigator 500 is mounted on the oral viewer 200 through the connecting mechanism 300.

The control switch 53 may be arranged on the spray gun 52 or on the oral viewer 200. As long as the control switch 53 can control the spray of the fluid in the spray gun 52, it does not depart from the protection scope of the present patent application.

The fluid sprayed by the spray head 51 is within the visual field of the viewing system 24 of the oral viewer 200. Therefore, during use, the cleaning effect of the position to be cleaned can be viewed in real time, and the use process is more convenient.

The spray head 51 of the oral irrigator 500 is provided with a regulating valve 51-1 capable of regulating the shape and speed of the sprayed fluid.

The spray head 51 of the oral irrigator 500 has a curvature 51-2 that meets the requirements of the human oral cavity. Especially when it is necessary to clean the molars on the rear side along the outer side of the teeth, the curvature 51-2 can allow the spray head 51 to smoothly reach the molar position, so the use process is more comfortable.

The control switch 53 of the oral irrigator 500 includes: a sleeve sliding bar opening/closing mechanism, or a button regulation opening/closing mechanism, or a rotation regulation opening/closing mechanism, or a solenoid-operated switch. Of course, those skilled in the art may also perform other designs according to the technical solutions disclosed in the present disclosure without departing from the protection scope of the present patent.

The spray gun 52 of the oral irrigator 500 includes a flow channel 52-1 for allowing a fluid to pass therethrough, a housing 52-2 and a mounting base 52-3; the flow channel 52-1 is arranged in the housing 52-2; and the mounting base 52-3 is arranged on the housing 52-2, and the mounting base 52-3 includes a locating block 32 capable of being connected with the oral viewer 200.

The connecting mechanism 300 is a detachable mechanical connecting mechanism; the connecting mechanism 300 may be a separate component, and may be arranged on the oral irrigator 500 or arranged on the oral viewer 200; alternatively, the connecting mechanism 300 may also be a combined mechanical connecting mechanism formed by arranging a part of the detachable mechanical connecting mechanism on the oral irrigator 500 and the other part on the oral viewer 200.

The mechanical connecting mechanism includes: a concave-convex snap fit connection, or a sliding slot connection, or a pin connection, or a key connection, or a threaded connection, or a screw connection, or a buckle connection, or a hook connection, or an interference fit connection. Those skilled in the art can perform various specific product designs according to the technical solutions disclosed in the present disclosure without departing from the protection scope of the present patent.

The housing 21 of the oral viewer 200 is provided with a locating slot 35 and a clamping block 36 which can be connected with the spray gun 52; the locating block 32 on the spray gun 52 can be embedded in the locating slot 35, and the clamping block 36 can prevent the mounting base 52-3 of the spray gun 52 from sliding backward; and the coordination of the locating block 32, the locating slot 35 and the clamping block 36 constitutes the connecting mechanism 300.

The viewing system 24 is a camera system 24-1, and the camera system 24-1 includes a camera 24-1-1, a data processing and output system 24-1-2, a circuit system 25 and a power supply system 22.

Video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device 24-1-33, or a television 24-1-34.

The lighting system 23 is arranged around the camera 24-1-1. In order to increase lighting, more LED lights may also be arranged on the housing 21 of the oral viewer 200 for adjusting the lighting brightness.

The oral viewer 200 adopts a waterproof design, thereby facilitating cleaning and operation.

The pressure vessel 54 of the oral irrigator 500 includes a pressurizer 54-1, a housing 54-2 and a fluid containing space 54-3; and the pressurizer 54-1 capable of increasing fluid pressure is mounted on the housing 54-2.

In addition, the pressure vessel 54 of the oral irrigator 500 may also be provided with a water filling port 54-4; and the water filling port 54-4 is arranged on the housing 54-2 of the pressure vessel 54, and includes an interface 54-41 and a seal cap 54-42, the far end of the interface 54-41 communicates with the fluid containing space 54-3 of the pressure vessel 54, and the seal cap 54-42 is detachably mounted on the interface 54-41. By adding the water filling port 54-4, after water in the pressure vessel 54 is used up, water can be conveniently refilled into the pressure vessel 54 to perform tooth rinsing.

The pressure vessel 54 of the oral irrigator 500 can be mounted at the near end of the oral viewer 200. The pressure vessel 54 is detachably mounted at the near end of the oral viewer 200, thereby facilitating mounting. After use, the pressure vessel 54 can be removed from the near end of the oral viewer 200, thereby facilitating storage and carrying.

The pressurizer 54-1 is a mechanical pressurizer, or an electric pressurizer.

Further, the pressurizer 54-1 is a manual pressurizer 541; the manual pressurizer 541 includes a front check valve 541-1, a rear check valve 541-2, a valve barrel 541-3, a piston 541-4, a push rod 541-5 and a core rod 541-6; the front check valve 541-1, the rear check valve 541-2, the piston 541-4 and the core rod 541-6 are mounted in the valve barrel 514-3; the front end of the push rod 541-5 is provided with the piston 541-4, the front check valve 541-1 is arranged at the far end of the core rod 541-6, and the rear check valve 541-2 is arranged at the near end of the core rod 541-6; the push rod 541-5 can push the piston 541-4 to reciprocate in the valve barrel 541-3; when the push rod 541-5 is pulled outward, the front check valve 541-1 is in a closed state, the fluid in the fluid containing space 54-3 of the pressure container 54 cannot enter the valve barrel 541-3, the rear check valve 541-2 is in an open state, and an external fluid can enter the valve barrel 541-3; when the push rod 541-5 is pushed inward, the rear check valve 541-2 is in a closed state, the fluid in the valve barrel 541-3 is compressed, the pressure in the valve barrel 541-3 increases, under the action of pressure, the front check valve 541-1 is in an open state, and the fluid compressed in the valve barrel 541-3 enters the fluid containing space 54-3 through the front check valve 541-1; and by repeating in this way, the pressure in the fluid containing space 54-3 of the pressure vessel 54 can be continuously increased.

The front check valve 541-1 includes a front return spring 541-1-1, a front check block 541-1-2 and a front seal ring 541-1-3, the front return spring 541-1-1 abuts against the far end of the front check block 541-1-2, and the front seal ring 541-1-3 is arranged at the near end of the front check block 541-1-2; the rear check valve 541-2 includes a rear return spring 541-2-1, a rear check block 541-2-2 and a rear seal ring 541-2-3, the rear return spring 541-2-1 abuts against the far end of the rear check block 541-2-2, and the rear seal ring 541-2-3 is arranged at the near end of the rear check block 541-2-2; and the rear check block 541-2-2 is provided with a through hole 541-2-21 capable of allowing a fluid to pass therethrough.

In addition, those skilled in the art can perform various specific product designs according to the technical solutions disclosed in the present disclosure, and especially, can perform many specific designs on the shape and structure of the oral irrigator 500 without departing from the protection scope of the present patent.

The pressurizer 54-1 is an electric pressurizer 542. The electric pressurizer 542 can implement automatic pressure increase and keep the pressure stable by just turning on the power supply, so the use process is more convenient. When the pressurizer 54-1 is an electric pressurizer 542, the power supply system 22 may be provided with a boosting device 22-1 to increase the voltage of the power supply system 22 to better drive the electric pressurizer 542 to operate.

The electric pressurizer 542 is an electric air pressurizer 542-1 or electric water pressurizer 542-2.

The electric air pressurizer 542-1 is an electric air compressor 542-51.

The electric air compressor 542-51 includes an air inlet 542-51-1, an inflation tube 542-51-2 and a compressor 542-51-3.

An inflation port 542-51-21 of the inflation tube 542-51-2 of the electric air compressor 542-51 is arranged above the water surface to be pressurized, the switch 26 is turned on, and the electric air compressor 542-51 operates to inflate the pressure vessel 54, thereby increasing the water pressure in the fluid containing space 54-3. When the control switch 53 is turned on, the pressurized water enters the spray gun 52 through the connecting tube 55 and is sprayed out from the spray head 51 to clean the teeth.

The electric water pressurizer 542-2 is a submersible pump 542-21 or water pump 542-22.

The electric water pressurizer 542-2 is a submersible pump 542-21, and the submersible pump 542-21 includes a water inlet system 542-21-1, a pressurizing system 542-21-2 and a water discharge system 542-21-3; the submersible pump 542-21 is mounted on the lower part of the housing 52, and the water discharge system 542-21-3 is connected with the connecting tube 55; and after the power supply system 22 supplies power to the submersible pump 542-21, the pressurizing system 542-21-2 operates to pressurize a fluid entering the submersible pump 542-21 via the water inlet system 542-21-1, and the pressurized fluid is discharged by the drainage system 542-21-3 through the connecting tube 55 to rinse the teeth.

The submersible pump 542-21 is arranged on the lower part of the pressure vessel 54, and a water outlet 542-21-31 of the water discharge system 542-21-3 is connected with the connecting tube 55. During operation, the water surface exceeds the water inlet 542-21-51 of the water inlet system 542-21-1, the power supply system 22 drives the pressurizing system 542-21-2 to operate, and water enters the pressurizing system 542-21-2 from the water inlet 542-21-51 of the water inlet system 542-21-1; after the pressurizing system 542-21-2 pressurizes the water, the water enters the connecting tube 55 after being discharged from a water outlet 542-21-31 of the water discharge system 542-21-3; and when the control switch 53 is turned on, the pressurized water in the connecting tube 55 enters the spray gun 52 and is sprayed out from the spray head 51 to rinse the teeth.

The electric water pressurizer 542-2 is a water pump 542-22, and the water pump 542-22 includes a pumping system 542-21-1, a vacuum suction system 542-22-2 and a water discharge system 542-22-3; the water discharge system 542-22-3 is connected with the connecting tube 55; and after the power supply system 22 supplies power to the water pump 542-22, the vacuum suction system 542-22-2 operates to suck the fluid in the fluid containing space 54-3 into the water pump 542-22 via the pumping system 542-22-1, and the pressurized fluid is discharged by the water discharge system 542-22-3 through the connecting tube 55 to clean the teeth.

A pumping port 542-22-51 of the pumping system 542-22-1 of the water pump 542-22 is arranged on the bottom of the fluid containing space 53; when the power supply system 22 drives the water pump 542-22 to operate, water enters the vacuum suction system 5432-22-2 from the pumping port 542-22-51, and is discharged into the connecting tube 55 from the water outlet 542-22-31 of the water discharge system 542-22-3; and when the control switch 53 is turned on, the pressurized water enters the spray gun 52 through the connecting tube 55 and is sprayed out from the spray head 51 to clean the teeth.

When assembling, the spray gun 52 is firstly mounted to the front of the oral viewer 200; then, water is added into the pressure vessel 54, and the pressure vessel 54 is mounted at the near end of the oral viewer 200; and the pressure vessel 54 and the spray gun 52 are connected together by the connecting tube 55 through the union joint 56, thereby completing the work of mounting the oral irrigator 500 on the oral viewer 200.

Before use, the water pressure is increased by the pressurizer 54-1. With the viewing system 24 of the oral viewer 200, the teeth or tooth gaps can be clearly seen on a display device such as a mobile phone, and the food residues can be aligned. The control switch 53 is turned on, and water is sprayed out from the spray head 51 of the spray gun 52 to clean the teeth and oral cavity under direct vision.

The spray head 51 and the spray gun 52 are built in the housing 21 of the oral viewer 200. The spray head 51 and the spray gun 52 are built in the housing 21 of the oral viewer 200, so more space can be saved, and another cleaning device can be simultaneously combined and mounted at the front end of the oral viewer 200 conveniently; and meanwhile, multiple cleaning functions are provided, and the user can select different function combinations according to needs, so the use process is more convenient.

The spray head 51 is positioned near the viewing system 24, and the fluid sprayed by the spray head 51 is within the visual field of the viewing system 24.

The front end of the oral viewer 200 may also be equipped with another oral cleaning device through the connecting mechanism 300, and the oral cleaning device may be an interdental brush 700, or a dental floss 100, or a toothbrush 600, or oral forceps 400, or the like.

A front end 903-1 of the visual oral irrigator 903 is connected with a main body 903-2 of the visual oral irrigator 903 through a detachable connecting mechanism 903-3, or a front end 903-1 of the visual oral irrigator 903 is connected with a main body 903-2 of the visual oral irrigator 903 through a foldable connecting mechanism 903-4.

When carrying out, how to reduce the space occupied by items and facilitate the storage is an aspect that people are very concerned about. The visual oral irrigator of the present disclosure is designed to have a detachable structure and a foldable structure for easy carrying and storage. In order to implement the detachability or foldability of the visual oral irrigator 903, the oral viewer 200 therein may be separately designed as a detachable structure or a foldable structure, and the oral irrigator 500 therein may also be separately designed as an inquiry structure or foldable structure, or both the oral viewer 200 and the oral irrigator 500 may be designed as a detachable or foldable structure. For the detachable structure or foldable mechanism of the oral viewer 200 and the oral irrigator 500, those skilled in the art may design different combinations according to requirements without departing from the protection scope of the present patent application.

A front end 200-1 of the oral viewer 200 of the visual oral irrigator 903 is connected with a main body 200-2 of the oral viewer 200 through a detachable connecting mechanism 903-3, or a front end 200-1 of the oral viewer 200 is connected with a main body 200-2 of the oral viewer 200 through a foldable connecting mechanism 903-4.

A front end 500-1 of the oral irrigator 500 of the visual oral irrigator 903 is connected with a main body 500-2 of the oral irrigator 500 through a detachable connecting mechanism 903-3, or a front end 500-1 of the oral irrigator 500 is connected with a main body 500-2 of the oral irrigator 500 through a foldable connecting mechanism 903-4.

The detachable connecting mechanism 903-3 includes a connecting and fixing mechanism 903-3-1. The connecting and fixing mechanism 903-3-1 may connect the front end 200-1 of the oral viewer 200 with the main body 200-2 of the oral viewer 200, and may also connect the front end 500-1 of the oral irrigator 500 with the main body 500-2 of the oral irrigator 500.

The connecting and fixing mechanism 903-3-1 is a concave-convex snap fit connecting and fixing mechanism, a rotary connecting and fixing mechanism, or a magnetic connecting and fixing mechanism. Herein, the applicant only enumerates the above three types of connecting and fixing mechanisms, and those skilled in the art may also design other different connecting and fixing mechanisms in conjunction with the related well-known knowledge without departing from the protection scope of the present application.

The foldable connecting mechanism 903-4 is a rotating shaft movement mechanism or a concave-convex snap fit mechanism. Herein, the applicant only enumerates the above two types of foldable connecting and fixing mechanisms, and those skilled in the art may also design other different foldable connecting and fixing mechanisms in conjunction with the related well-known knowledge without departing from the protection scope of the present application.

Further, the foldable connecting mechanism 903-4 is a rotating shaft connecting mechanism, the foldable connecting mechanism 903-4 includes a rotating shaft 903-4-1 and a rotating shaft hole 903-4-2, and the rotating shaft 903-4-1 can move in the rotating shaft hole 903-4-2.

Further, the front end 200-1 of the oral viewer 200 is connected with the main body 200-2 of the oral viewer 200 through the detachable connecting mechanism 903-3; the detachable connecting mechanism 903-3 further includes an electrical joint 903-3-2; the connecting and fixing mechanism 903-3-1 can connect and fix the front end 200-1 of the oral viewer 200 to the main body 200-2; and the electrical joint 903-3-2 can connect a circuit 25-1 at the front end 200-1 of the oral viewer 200 with a circuit 25-2 of the main body 200-2.

If the connection strength of the electrical joint 903-3-2 is sufficient, the connecting and fixing mechanism 903-3-1 and the electrical joint 903-3-2 may be manufactured into an integral body, and in order to enhance the connection strength of the oral viewer 200, the connecting and fixing mechanism 903-3-1 and the electrical joint 903-3-2 may also be separately manufactured.

During storage, the connecting and fixing mechanism 903-3-1 and the electrical joint 903-3-2 are separated, and the front end 200-1 of the oral viewer 200 is removed from the main body 200-2 of the oral viewer 200, so that the front end 200-1 and the main body 200-2 can be stored separately, thereby saving the storage space and being convenient to carry out. During use, it is only necessary to re-plug the fixing mechanism 903-3-1 and the electrical joint 903-3-2 to connect the oral viewer 200.

The front end 200-1 of the oral viewer 200 is connected with the main body 200-2 of the oral viewer 200 through the foldable connecting mechanism 904-4; when the front end 200-1 of the oral viewer 200 rotates around the rotating shaft 903-4-1 of the foldable connecting mechanism 903-4, the front end 200-1 of the oral viewer 200 can be unfolded or folded relative to the main body 200-2 of the oral viewer 200; the circuit 25-1 at the front end 200-1 of the oral viewer 200 is connected with the circuit 25-2 of the main body 200-2 of the oral viewer 200 through a bendable flexible circuit;

Since the circuit 25-1 at the front end 200-1 of the oral viewer 200 and the circuit 25-2 of the main body 200-2 of the oral viewer 200 are connected through a bendable flexible circuit, after use, the front end 200-1 of the oral viewer 200 may be folded relative to the main body 200-2 of the oral viewer 200 by rotating the front end 200-1 of the oral viewer 200 around the rotating shaft 903-4-1, thereby facilitating storage and carrying. During use, it is only necessary to rotate the front end 200-1 of the oral viewer 200 around the rotating shaft 903-4-1 in an opposite direction to unfold the oral viewer 200.

The front end 200-1 of the oral viewer 200 is connected with the main body 200-2 of the oral viewer 200 through the foldable connecting mechanism 904-4; the circuit 25-1 at the front end 200-1 of the oral viewer 200 is connected with the circuit of the main body 200-2 of the oral viewer 200 through a bendable flexible circuit; and the front end 200-1 of the oral viewer 200 can be unfolded or folded through the concave-convex snap fit mechanism relative to the main body 200-2 of the oral viewer 200.

The front end 500-1 of the oral irrigator 500 is connected with the main body 500-2 of the oral irrigator 500 through the detachable connecting mechanism 903-3; the detachable connecting mechanism 903-3 further includes a water joint 903-3-3; the connecting and fixing mechanism 903-3-1 can connect and fix the front end 500-1 of the oral irrigator 500 to the main body 500-2; and the water joint 903-3-3 can connect the waterway at the front end 500-1 of the oral irrigator 500 with the waterway of the main body 500-2.

The oral irrigator 500 may also be designed such that the front end 500-1 of the oral irrigator 500 is detachably connected with the rear end 500-2 of the oral irrigator 500. If the connection strength of the water joint 903-3-3 is sufficient, the connecting and fixing mechanism 903-3-1 and the water joint 903-3-3 may be manufactured into an integral body, and in order to further enhance the connection strength of the oral irrigator 500, the connecting and fixing mechanism 903-3-1 and the water joint 903-3-3 may also be separately manufactured.

During storage, the connecting and fixing mechanism 903-3-1 and the water joint 903-3-3 are separated, and the front end 500-1 of the oral irrigator 500 is removed from the main body 500-2 of the oral irrigator 500, so that the front end 500-1 and the main body 500-2 can be stored separately, thereby saving the storage space and being convenient to carry out. During use, it is only necessary to re-plug the fixing mechanism 903-3-1 and the water joint 903-3-3 to connect the oral irrigator 500 and then rinse the teeth.

The front end 500-1 of the oral irrigator 500 is connected with the main body 500-2 of the oral irrigator 500 through the foldable connecting mechanism 904-4; when the front end 500-1 of the oral irrigator 500 rotates around the rotating shaft 903-4-1 of the foldable connecting mechanism 903-4, the front end 500-1 of the oral irrigator 500 can be unfolded or folded relative to the main body 500-2 of the oral irrigator 500; and the waterway at the front end 500-1 of the oral irrigator 500 is connected with the waterway of the main body 500-2 of the oral irrigator 500 through the bendable flexible waterway.

The front end 500-1 and the main body 500-2 of the oral irrigator 500 are connected by a bendable flexible waterway. Therefore, during storage, it is only necessary to rotate the oral irrigator 500 around the rotating shaft 903-4-1, and the oral irrigator 500 can be folded, thereby facilitating storage and carrying. When in use, it is only necessary to rotate the oral irrigator 500 around the rotating shaft 903-4-1 in a reverse direction, and the oral irrigator 500 can be unfolded. At this time, the oral irrigator 500 can be used to rinse the teeth.

The front end 500-1 of the oral irrigator 500 is connected with the main body 500-2 of the oral irrigator 500 through the foldable connecting mechanism 903-4, or the waterway at the front end 500-1 of the oral irrigator 500 is connected with the waterway of the main body 500-2 of the oral irrigator 500 through the bendable flexible waterway; and the front end 500-1 of the oral irrigator 500 can be unfolded or folded through the concave-convex snap fit mechanism relative to the main body 500-2 of the oral irrigator 500.

Further, the front end 500-1 of the oral irrigator 500 and the main body 500-2 of the oral irrigator 500, and the front end 200-1 of the oral viewer 200 and the main body 200-2 of the oral viewer 200 are simultaneously connected together through the detachable connecting mechanism 903-3 or through the foldable connecting mechanism 903-4.

The foregoing is the situation that the oral viewer 200 and the oral irrigator 500 listed by the applicant are detachably or foldably connected respectively, and for further facilitating storage and use, the oral viewer 200 and the oral irrigator 500 may be connected together by the detachable connecting mechanism 903-3 or the foldable connecting mechanism 903-4 at the same time.

The detachable connecting mechanism 903-3 includes a connecting and fixing mechanism 903-3-1, an electrical joint 903-3-2 and a water joint 903-3-3; the connecting and fixing mechanism 903-3-1 can simultaneously and respectively connect and fix the front end 500-1 of the oral irrigator 500 and the front end 200-1 of the oral viewer 200 to the main body 500-2 of the oral irrigator 500 and the main body 200-2 of the oral viewer 200; the electrical joint 903-3-2 can connect a circuit 25-1 at the front end 200-1 of the oral viewer 200 with a circuit 25-2 of the main body 200-2; and the water joint 903-3-3 can connect the waterway at the front end 500-1 of the oral irrigator 500 with the waterway of the main body 500-2.

When the oral viewer 200 and the oral irrigator 500 simultaneously rotate to perform connection through the detachable connecting mechanism 903-3, in order to save the manufacturing cost, the connecting and fixing mechanism 903-3-1 and the electrical joint 903-3-2 or water joint 903-3-3 may be designed into an integral body under the condition of ensuring the connection strength. Of course, in order to further enhance the connection strength, the connecting and fixing mechanism 903-3-1 may be separately arranged.

During storage, the connecting and fixing mechanism 903-3-1, the electrical joint 903-3-2 and the water joint 903-3-3 are simultaneously disconnected, then the front end 903-1 of the visual oral irrigator 903 is separated from the main body 903-2 thereof, and then, the front end 903-1 and the main body 903-2 of the visual oral irrigator 903 can be stored separately. When it is necessary to use, the connecting and fixing mechanism 903-3-1, the electrical joint 903-3-2 and the water joint 903-3-3 may be reconnected.

The foldable connecting mechanism 903-4 is a rotating shaft connecting mechanism, the foldable connecting mechanism 903-4 includes a rotating shaft 903-4-1 and a rotating shaft hole 903-4-2, and the rotating shaft 903-4-1 can move in the rotating shaft hole 903-4-2; when the front end 200-1 of the oral viewer 200 rotates around the rotating shaft 903-4-1 of the foldable connecting mechanism 903-4, the front end 200-1 of the oral viewer 200 can be unfolded or folded relative to the main body 200-2 of the oral viewer 200; the circuit 25-1 at the front end 200-1 of the oral viewer 200 is connected with the circuit 25-2 of the main body 200-2 of the oral viewer 200 through a bendable flexible circuit; when the front end 500-1 of the oral irrigator 500 rotates around the rotating shaft 903-4-1 of the foldable connecting mechanism 903-4, the front end 500-1 of the oral irrigator 500 can be unfolded or folded relative to the main body 500-2 of the oral irrigator 500; and the waterway at the front end 500-1 of the oral irrigator 500 is connected with the waterway of the main body 500-2 of the oral irrigator 500 through the bendable flexible waterway.

The foldable connecting mechanism 903-4 is a concave-convex snap fit connecting mechanism; the circuit 25-1 at the front end 200-1 of the oral viewer 200 is connected with the circuit of the main body 200-2 of the oral viewer 200 through a bendable flexible circuit; the front end 200-1 of the oral viewer 200 can be unfolded or folded through the concave-convex snap fit mechanism relative to the main body 200-2 of the oral viewer 200; the waterway at the front end 500-1 of the oral irrigator 500 is connected with the waterway of the main body 500-2 of the oral irrigator 500 through the bendable flexible waterway; and the front end 500-1 of the oral irrigator 500 can be unfolded or folded through the concave-convex snap fit mechanism relative to the main body 500-2 of the oral irrigator 500.

When the oral viewer 200 and the oral irrigator 500 of the visual oral irrigator 903 are simultaneously connected by using the foldable connecting mechanism 903-4, the visual oral irrigator 903 can be folded and unfolded by just rotating the front end 903-1 of the visual oral irrigator 903 around the foldable connecting mechanism 903-4, the storage is convenient, and the folding and unfolding processes are very simple and convenient.

The visual oral irrigator 903 of the present disclosure includes an oral irrigator 500, an oral viewer 200 and a connecting mechanism 300; the oral irrigator 500 includes a spray head 51, a spray gun 52, a control switch 53, a pressure vessel 54, a connecting tube 55 and a union joint 56; the spray head 51 is arranged at the front end of the spray gun 52; the control switch 53 is arranged on the spray gun 52; and a fluid in the pressure vessel 54 is connected with the spray gun 52 through the connecting tube 55 and the union joint 56. The oral irrigator 500 is mounted on the oral viewer 200 through the connecting mechanism 300. The spray head 51 of the spray gun 52 is within the visual field of the viewing system 24 of the oral viewer 200. The pressure vessel 54 of the oral irrigator 500 includes a pressurizer 54-1, a housing 54-2 and a fluid containing space 54-3. The fluid pressure is increased by the pressurizer 54-1, the control switch 53 is turned on, water is sprayed out from the spray head 51 of the spray gun 52, and the user can clean the teeth and the oral cavity under direct vision, and perform picture and video recording of the cleaning process.

The visual oral irrigator 903 of the present disclosure is convenient to use, can be used for clearly viewing the tooth gaps, gingivae, dental crowns and oral mucosa, and can also be used for viewing the position of food residues in real time and cleaning the food residues under direct vision.

The visual toothbrush of the present disclosure, characterized in that

The visual toothbrush characterized in that the visual toothbrush 904 includes a toothbrush 600, an oral viewer 200 and a connecting mechanism 300;

A. the toothbrush 600 includes a brush head 61, a brush rod 62 and a mounting base 63; the brush head 61 of the toothbrush 600 at least includes one brush hair 61-1; the brush head 61 is arranged at the front end of the brush rod 62, and the mounting base 63 is arranged at the rear end of the brush rod 62;

B. the oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; the lighting system 23, the viewing system 24, the power supply system 22 and the switch 26 are connected together through the circuit system 25; and C. the toothbrush 600 is mounted on the oral viewer 200 through the connecting mechanism 300.

The brush head 61 may directly plant the brush hair 61-1 on the front end of the brush rod 62 by integral manufacturing to form an integral body with the brush rod 62, and may also be connected to the front end of the brush rod 62 in a detachable manner.

During use, the toothbrush 600 is mounted on the oral viewer 200 through the connection mechanism 300, and the brush head 61 of the toothbrush 600 is used to clean the oral cavity under direct vision by using the viewing function of the oral viewer 200, so the cleaning process is very convenient; and especially for deep in the oral cavity, by using the viewing function of the oral viewer 200, the user can clearly know whether the position to be cleaned is completely cleaned. In addition, the visual toothbrush is also especially suitable for cleaning food residues between teeth and gingivae, thereby implementing precise cleaning.

The brush head 61 is within the visual field of the viewing system 24 of the oral viewer 200, so the cleaned position and the cleaning effect of the brush head 61 can be clearly viewed through the viewing system 24.

The included angle β between the brush head 61 and the brush rod 62 is 90°-170°. In order to ensure that the brush head 61 can be within the visual field of the viewing system 24 of the oral viewer 200, the included angle β between the brush head 61 and the brush rod 62 is generally greater than 90°; and in order to ensure the viewing effect, the included angle β between the brush head 61 and the brush rod 62 is generally controlled at 600°-150°.

There is a curvature 61-4 that meets the requirements of the human oral cavity between the brush head 61 of the toothbrush 600 and the brush rod 62. When cleaning the deep position of the oral cavity, the curvature 61-4 that meets the requirements of the human oral cavity between the brush head 61 and the brush rod 62 can conveniently deliver the brush head 61 to the deep position of the oral cavity to be cleaned.

The mounting base 63 of the toothbrush 600 is provided with a locating block 32 used to be connected with the oral viewer 200.

The connecting mechanism 300 is a detachable mechanical connecting mechanism; the connecting mechanism 300 may be a separate component, and may be arranged on the toothbrush 600 or arranged on the oral viewer 200; alternatively, the connecting mechanism 300 may also be a combined mechanical connecting mechanism formed by arranging a part of the detachable mechanical connecting mechanism on the toothbrush 600 and the other part on the oral viewer 200. The detachable mechanical connecting mechanism is convenient for the user to replace the toothbrush 600, so the use process is more convenient and hygienic, and the use cost of the user is saved.

The mechanical connecting mechanism includes: a concave-convex snap fit connection, or a sliding slot connection, or a pin connection, or a key connection, or a threaded connection, or a screw connection, or a buckle connection, or a hook connection, or an interference fit connection. Those skilled in the art can perform various specific product designs according to the technical solutions disclosed in the present disclosure without departing from the protection scope of the present patent.

The housing 21 of the oral viewer 200 is provided with a locating slot 35 and a clamping block 36; the locating block 32 of the toothbrush 600 can be embedded in the locating slot 35, and the clamping block 36 can prevent the mounting base 63 of the toothbrush 600 from sliding backward; and the coordination of the locating block 32, the locating slot 35 and the clamping block 36 constitutes the connecting mechanism 300.

The viewing system 24 is a camera system 24-1, and the camera system 24-1 includes a camera 24-1-1, a data processing and output system 24-1-2, a circuit system 25 and a power supply system 22.

Video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device 24-1-33, or a television 24-1-34.

During use, the camera 24-1-1 can perform picture and video recording of the cleaning process, the video data output by the data processing and output system 24-1-2 can be displayed on the display device 24-1-3 in real time, and the user only needs to view the cleaning process in real time through the real-time pictures of the cleaning process displayed on the display device 24-1-3 to clearly see which positions have been cleaned and which positions have not yet been cleaned.

The lighting system 23 is arranged around the camera 24-1-1.

The lighting system 23 adopts an LED lighting system 23-1.

The camera 24-1-1 is in the heat affected zone of the lighting system 23, and heat generated by the lighting system 23 can heat the camera 24-1-1, thereby preventing the camera 24-1-1 from generating fog during use.

Heat generated by the lighting system 23 can increase the temperature of the camera 24-1-1 to 35° C.-45° C.

The housing 21 can generate a dynamic thermal balance between the heat dissipation capacity of the housing 21-5 near the camera 24-1-1 and the heat generated by the lighting system 23, so that the temperature of the camera 24-1-1 and the attached waterproof lens 24-1-4 is within the range of 35° C.-45° C., thereby achieving the purpose of anti-fog.

In order to enhance the lighting intensity of the LED lighting system 23-1, control the dynamic thermal balance around the camera 24-1-1 to reach the required level and ensure that the temperature of the camera 24-1-1 and the periphery thereof is maintained within the required temperature range, multiple LED lights, such as 4, 6 or 8 LED lights, may be arranged around the camera 24-1-1 according to needs. On the one hand, the multiple LED lights enhance the lighting intensity of the LED lighting system 23-1 and increase the definition of the shooting process of the camera 24-1-1; and on the other hand, the heat generated by the LED lights of the LED lighting system 23-1 can still maintain the temperature of the camera 24-1-1 and the attached waterproof lens 24-1-4 thereof at 35-45° C. after the heat dissipation by the housing 21-5 near the camera 24-1-1, thereby achieving the goal of anti-fog.

The front end of the camera 24-1-1 is provided with a waterproof lens 24-1-4, and the waterproof lens 24-1-4 is treated with an anti-fog coating. After the waterproof lens 24-1-4 is treated through the anti-fog coating, even if a small amount of water vapor is formed at the front end of the waterproof lens 24-1-4 to form condensation on the surface of the waterproof lens 24-1-4, it does not exist in the form of water drops, but turns into a transparent water film, and cannot form a fog phenomenon in front of the camera 24-1-1, thereby further enhancing the anti-fog effect.

The oral viewer 200 adopts a waterproof design. The oral viewer 200 adopts a waterproof design, so the user can clean the visual toothbrush of the present disclosure in time in the use process; and the waterproof design can also avoid the influence on the functions of the power supply system 22, lighting system 23, viewing system 24, circuit system 25 or switch 26 in the housing 21 in the use process since water or human conductive secretion enters the oral viewer 200, so the use process is more convenient and secure.

The visual toothbrush of the present disclosure includes a toothbrush 600, an oral viewer 200 and a connecting mechanism 300. The toothbrush 600 includes a brush head 61, a brush rod 62 and a mounting base 63, and the mounting base 63 is provided with a locating block 32. The housing 21 of the oral viewer 200 is provided with a locating slot 35 and a clamping block 36. The locating block 32 of the toothbrush 600 can be embedded in the locating slot 35, and the clamping block 36 can prevent the mounting base 63 of the toothbrush 600 from sliding backward. The coordination of the locating block 32, the locating slot 35 and the clamping block 36 constitutes the connecting mechanism 300. The toothbrush 600 and the oral viewer 200 are detachably connected together through the connecting mechanism 300. Since the oral viewer 200 includes the lighting system 23 and the viewing system 24 and transmits the viewed video to the display device 24-1-3 in a wired or wireless manner, by using the visual toothbrush of the present disclosure, the user can clean the oral cavity under direct vision, and can view the cleaning process and the effect after cleaning and perform picture or video recording.

The detachable visual interdental brush of the present disclosure, characterized in that the detachable visual interdental brush 905 includes a built-in interdental brush 701, an oral viewer 200 and a connecting mechanism 300;

A. the built-in interdental brush 701 includes a brush body 71 and a delivery device 72; the brush body 71 is movably built in an elbow tube 72-1-1 at the front end of the delivery device 72;

B. the oral viewer 200 includes a housing 21, a power supply system 22, a lighting system 23, a viewing system 24, a circuit system 25 and a switch 26; the lighting system 23, the viewing system 24 and the power supply system 22 are mounted in the housing 21, and the switch 26 is mounted on the housing 21; the lighting system 23, the viewing system 24, the power supply system 22 and the switch 26 are connected together through the circuit system 25; and C. the built-in interdental brush 701 is detachably mounted on the oral viewer 200 through the connecting mechanism 300.

The core of the present disclosure lies in the fact that the two independent units, the built-in interdental brush 701 and the oral viewer 200, are flexibly assembled together through the connecting mechanism 300. The two independent units may be assembled together to be operated by one hand operation to clean the tooth gaps; and the two independent units may also be separated, the oral viewer 200 is held by one hand to view, and the built-in interdental brush 701 is held by the other hand to clean the tooth gaps, so the two independent units are convenient to carry and assemble and flexible to use.

The connecting mechanism 300 is a detachable mechanical connecting mechanism, and may be a separate component, or arranged on the built-in interdental brush 701 or the oral viewer 200.

The connecting mechanism 300 may be a separate component, and is respectively connected with the built-in interdental brush 701 and the oral viewer 200 to connect the built-in interdental brush 701 and the oral viewer 200 into an integral body. The connecting mechanism 300 and the built-in interdental brush 701 may also be manufactured into an integral body or the oral viewer 200, and then connected with the oral view 200 or the built-in interdental brush 701 to form an integral body. Regardless of the type of connection, the ultimate goal is to implement a detachable connection between the built-in interdental brush 701 and the oral viewer 200. Therefore, the detachable connection between the built-in interdental brush 701 and the oral viewer 200 can be implemented as long as the connecting mechanism 300 implements a detachable mechanical connection with one of the built-in interdental brush 701 or the oral viewer 200.

The mechanical connecting mechanism may be a concave-convex snap fit connection, or a sliding slot connection, or a pin connection, or a key connection, or a threaded connection, or a screw connection, or a buckle connection, or a hook connection, or an interference fit connection, or the like. Of course, those skilled in the art can select other mechanical connection manners without departing from the protection scope of the present application.

The brush body 71 of the built-in interdental brush 701 includes a working portion 71-1 and a connecting body 72; the working portion 71-1 is arranged at the front end of the connecting body 72; the delivery device 72 includes a guide head 72-1 and a sliding mechanism 72-2; the guide head 72-1 is arranged at a front end 721 of the delivery device 72; the guide head 72-1 includes an elbow tube 72-1-1, and an outlet 72-1-2 of the elbow tube 72-1-1 is arranged at an end 72-1-3 of the guide head 72-1; the brush body 71 is mounted in the elbow tube 72-1-1, the working portion 71-1 of the brush body 71 can slide in the elbow tube 72-1-1, and the connecting body 72 of the brush body 71 is mounted on the sliding mechanism 72-2 of the delivery device 72; the movement of the sliding mechanism 72-2 can drive the working portion 71-1 of the brush body 71 to slide in the elbow tube 72-1-1; and driving the sliding mechanism 72-2 allows the working portion 71-1 of the brush body 71 to protrude from the outlet 72-1-2 of the elbow tube at the end of the guide head.

The sliding mechanism 72-2 of the built-in interdental brush 701 includes an interdental brush connecting mechanism 72-2-1 and a sliding block 72-2-2, and the interdental brush connecting mechanism 72-2-1 is arranged on the sliding block 72-2-2; and the connecting body 72 of the interdental brush and the interdental brush connecting mechanism 72-2-1 are connected together, and the sliding block 72-2-2 can be pushed and pulled to drive the brush body 71 to reciprocate within the elbow tube 72-1-1, so that the working portion 71-1 of the interdental brush protrudes or retracts from the elbow tube outlet 72-1-2 at the end of the guide head 72-1.

Since the built-in interdental brush 701 adopts the structure of the brush body 71 being built in the elbow tube 72-1-1 of the guide head 72-1 of the delivery device 72, after the guide head 72-1 is aligned with the tooth gap, the working portion 71-1 of the brush body 71 made of the elastic material pushes the sliding mechanism 72-2 on the delivery device 72 to drive the working portion 71-1 of the brush body 71 to automatically bend along the curvature of the elbow tube 72-1-1, and to be aligned with and enter the tooth gap, and the sliding block 72-2-2 on the sliding mechanism 72-2 of the delivery device 72 is pushed and pulled back and forth, so that the working portion 71-1 of the interdental brush reciprocates in the tooth gap to clean the tooth gap. Since the delivery device 72 has favorable rigidity, after the elbow tube outlet 72-1-2 of the guide head 72-1 of the delivery device 72 is aligned with the tooth gap, the working portion 71-1 of the brush body 71 that is pushed out directly enters the tooth gap; since the elbow tube outlet 72-1-2 of the guide head 72-1 of the delivery device 72 is almost attached to the tooth gap and is very near to the tooth gap and the working portion 71-1 of the interdental brush cannot easily bend, the conductivity of force of the brush body 71 is greatly enhanced, and the operability of the brush body 71 is enhanced, thereby avoiding the defect that the interdental brush in the prior art can easily bend and easily hurt the gingivae when cleaning the gap between molars.

The connecting mechanism 300 is arranged on the guide head 72-1 of the built-in interdental brush 701; and the connecting mechanism 300 includes a locating block 32.

The connecting mechanism 300 and the guide head 72-1 of the built-in interdental brush 701 may be integrally manufactured to implement the connection, or bonded together, or detachably connected.

The housing 21 of the oral viewer 200 is provided with a sliding slot 211-2 for allowing the sliding block 72-2-2 of the built-in interdental brush 701 to reciprocate, and a locating slot 35 capable of fixing the connecting mechanism 300.

The sliding block 72-2-2 of the sliding mechanism 72-2 of the built-in interdental brush 701 includes an arched housing 72-2-21, and the inner side of the arched housing 72-2-21 is provided with a guide block 72-2-22; and the guide block 72-2-22 can reciprocate within the sliding slot 211-2 of the oral viewer 200.

In order to conveniently push the sliding block 72-2-2 to move, the arched housing 72-2-21 may be provided with an antiskid line. When the arched housing 72-2-21 is slightly pressed down, the guide block 72-2-22 may be embedded in the sliding slot 211-2 of the oral viewer 200; and when the arched housing 72-2-21 is pushed back and forth, the sliding block 72-2-2 can conveniently slide back and forth along the sliding slot 211-2 of the oral viewer 200 under the guide action of the guide block 72-2-22.

The locating block 32 of the connecting mechanism 300 is an inverted T-shaped locating block 32-1; the inverted T-shaped locating block 32-1 is arranged below the connecting mechanism 300; the housing 21 of the oral viewer 200 is provided with a fixing mechanism 211, and the fixing mechanism 211 includes the locating slot 35, the sliding slot 211-2 and a clamping block 36; the T-shaped locating block 32-1 is detachably embedded in the locating slot 35, and the clamping block 36 bouncing upward can prevent the connecting mechanism 300 from moving back and prevent the built-in interdental brush 701 from being accidentally released from the oral view 200; and the connecting mechanism 300 can be released from the oral viewer 200 only by pressing down the clamping block 36 and pulling the connecting mechanism 300 backward at the same time.

When mounting, the connecting mechanism 300 is fixed to a proper position on the guide head 72-1 of the delivery device 72 of the built-in interdental brush 701; the brush body 71 of the built-in interdental brush 701 is connected to the sliding block 72-2-2 of the delivery device 72; the brush body 71 is mounted in the elbow tube 72-1-1 of the guide head 72-1 of the delivery device 72; and the sliding block 72-2-2 is pushed forward to bring the connecting mechanism 300 and the sliding block 72-2-2 of the built-in interdental brush together.

Then, the built-in interdental brush 701 and the connecting mechanism 300 downwardly fit the fixing mechanism 211 on the housing 21 of the oral viewer 200 along the locating end 212 of the housing 21 of the oral viewer 200; the built-in interdental brush 701 and the connecting mechanism 300 are pressed down, and the guide block 72-2-22 on the inner side of the arched housing 72-2-21 of the sliding block 72-2-2 of the built-in interdental brush 701 is embedded in the sliding slot 211-2 of the oral viewer 200; and meanwhile, the clamping block 36 is pressed down, the inverted T-shaped locating block 32-1 enters the locating slot 35 of the oral viewer 200.

While the sliding block 72-2-2 and the brush body 71 of the built-in interdental brush 701 are kept still, the connecting mechanism 300 is pushed forward, so that the inverted T-shaped locating block 32-1 of the connecting mechanism 300 is embedded in the locating slot 35 of the oral viewer 200 until the clamping block 36 bounces up to abut against the rear end the connecting mechanism 300, and thus, the connecting mechanism 300 is mounted in place, thereby establishing a firm connection between the built-in interdental brush 701 and the oral viewer 200.

When the built-in interdental brush 701 needs to be removed, the connecting mechanism 300 is moved backward with force, so the clamping block 36 is pressed down, the connecting mechanism 300 can move backward, and the inverted T-shaped locating block 32-1 is withdrawn from the locating slot 35 until the connection between the T-shaped locating block 32-1 and the locating slot 35 is released, thereby removing the built-in interdental brush 701 from the oral viewer 200.

Since the inverted T-shaped locating block 32-1 adopts an inverted T-shaped structure, when the T-shaped locating block 32-1 is embedded in the locating slot 35, the bottom of the inverted T-shaped structure and the locating slot 35 can form a concave-convex snap fit structure, thereby effectively limiting the movement of the connecting mechanism 300 in the vertical direction, and further preventing the built-in interdental brush 701 and the oral viewer 200 from departing along the vertical direction during use. Meanwhile, the clamping block 36 is arranged at the rear end of the connecting mechanism 300; when the clamping block 36 is lifted up, since the top of the clamping block 36 is higher than the tail of the connecting mechanism 300, the connecting mechanism 300 can be effectively prevented from moving backward; and only when the connecting mechanism 300 is moved backward consciously and forcefully, the connecting mechanism 300 can be released from the oral viewer 200 after withdrawing along the guide surface of the clamping block 36, thereby effectively preventing the built-in interdental brush 701 from being accidentally released from the oral viewer 200 due to the fact that the connecting mechanism 300 can easily move backward.

The locating block 32 of the connecting mechanism 300 is an arc-shaped locating block 32-2; the arc-shaped locating hook 32-2 includes a locating groove 32-2-1; the locating slot 35 in the oral viewer 200 includes a locating convex stair 211-1-1 matched with the locating groove 32-2-1; the arc-shaped locating hook 32-2 is embedded in the locating slot 35 to form a concave-convex snap fit, thereby limiting the movement of the connecting mechanism 300 in the vertical direction; and the locating convex stair 211-1-1 is embedded in the locating groove 32-2-1, thereby limiting the forward and backward movement of the connecting mechanism 300.

When mounting, after the built-in interdental brush 701 and the connecting mechanism 300 are mounted as described above, the sliding block 72-2-2 of the built-in interdental brush 701 is aligned with the sliding slot 211-2 in the housing 21 of the oral viewer 200, and the arc-shaped locating hook 32-2 of the connecting mechanism 300 is aligned with the locating slot 35 in the housing 21 of the oral viewer 200; the built-in interdental brush 701 and the connecting mechanism 300 are pressed down, so that the guide block 72-2-22 on the inner side of the arched housing 72-2-21 of the sliding block 72-2-2 of the built-in interdental brush 701 is embedded in the sliding slot 211-2 of the oral viewer 200; the arc-shaped locating hook 32-2 of the connecting mechanism 300 is embedded in the locating slot 35 to form a concave-convex snap fit, thereby limiting the movement of the connecting mechanism 300 in the vertical direction; and the connecting mechanism 300 is slid forward until the locating convex stair 211-1-1 of the oral viewer 200 is embedded in the locating groove 32-2-1 of the connecting mechanism 300, thereby limiting the forward and backward movement of the connecting mechanism 300. When it is necessary to remove the built-in interdental brush 701, the connecting mechanism 300 is moved backward with force, so that the locating groove 32-2-1 of the connecting mechanism 300 is released from the locating convex stair 211-1-1 of the oral viewer 200; and the connecting mechanism 300 is continuously slid backward along the locating slot 35 of the oral viewer 200, and then the connecting mechanism 300 can be released from the oral viewer 200.

The dual concave-convex snap fit connection manner formed between arc-shaped locating hook 32-2 and the locating slot 35 and between the locating convex stair 211-1-1 and the locating groove 32-2-1 can implement an effective connection and fixation between the connecting mechanism 300 and the oral viewer 200.

The connecting mechanism 300 is arranged on the oral viewer 200; and the connecting mechanism 300 is a connecting ring 32-3, and the built-in interdental brush 701 passes through a mounting hole 32-3-1 of the connecting ring 32-3, so that the built-in interdental brush 701 is fixed to the oral viewer 200. Compared with the concave-convex snap fit connection manner, the ring structure of the connecting ring 32-3 can prevent the built-in interdental brush 701 from being separated from the oral viewer 200 along the vertical direction more effectively, and thus, is more secure and reliable.

The connecting mechanism 300 is a surrounding arm 32-4, and the built-in interdental brush 701 and the oral viewer 200 are detachably connected together through the surrounding arm 32-4. The surrounding arm 32-4 may be arranged on the built-in interdental brush 700 and then surround the oral viewer 200 to implement the detachable connection of the two, and may also be arranged on the oral viewer 200 and then surround the built-in interdental brush 701 to implement the detachable connection of the two.

The viewing system 24 is a camera system 24-1, and the camera system 24-1 includes a camera 24-1-1, a data processing and output system 24-1-2, a circuit system 25 and a power supply system 22.

Video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device 24-1-33, or a television 24-1-34.

The lighting system 23 is arranged around the camera 24-1-1.

The detachable visual interdental brush 905 of the present disclosure includes a built-in interdental brush 701, an oral viewer 200 and a connecting mechanism 300. The built-in interdental brush 701 and the oral viewer 200 are detachably connected together through the connecting mechanism 300. The connecting mechanism 300 is a detachable mechanical connecting mechanism, and may be a separate component, or arranged on the built-in interdental brush 701 or the oral viewer 200. The detachable visual interdental brush of the present disclosure may be freely combined according to the use habit and preference of the user, and the built-in interdental brush 701 and the oral viewer 200 are flexibly assembled together through the connecting mechanism 300 to be operated by one hand and clean the tooth gap; and they may also be separated, the oral viewer 200 is held by one hand to perform viewing, and the built-in interdental brush 701 is held by the other hand to clean the tooth gaps, so the detachable visual interdental brush 905 is convenient to carry and assemble and flexible to use.

BRIEF DESCRIPTION OF THE DRAWINGS

The aforementioned features and advantages of the invention as well as additional features and advantages thereof will be more clearly understood hereinafter as a result of a detailed description of preferred embodiments when taken in conjunction with the drawings.

FIG. 1-1 is an exploded view of FIG. 1.

FIG. 1-2 is a three-dimensional structure diagram of the visual dental floss of FIG. 1 according to the present disclosure when cut along the midline and viewed from front to back.

FIG. 1-3 is a three-dimensional structure diagram of the visual dental floss of FIG. 1 according to the present disclosure when cut along the midline and viewed from back to front.

FIG. 1-4 is a broken-out section three-dimensional structure diagram of A-A Area of FIG. 1.

FIG. 1-5 is a front view of FIG. 1.

FIG. 1-6 is a B-B section view of FIG. 1-5.

FIG. 2 is a three-dimensional structure diagram of the visual dental floss according to the present disclosure when viewed from the front end to the back end.

FIG. 2-1 is an enlarged view of C Area of FIG. 2.

FIG. 3 is a three-dimensional structure diagram of a visual dental floss of the visual dental floss according to the present disclosure.

FIG. 3-1 is a three-dimensional structure diagram of the visual dental floss of the visual dental floss according to the present disclosure.

FIG. 3-2 is a three-dimensional structure diagram of the visual dental floss of the visual dental floss according to the present disclosure.

FIG. 4 is a three-dimensional structure diagram of a connecting mechanism of the visual dental floss according to the present disclosure.

FIG. 4-1 is a three-dimensional structure diagram of the connecting mechanism of the visual dental floss according to the present disclosure when viewed from the bottom.

FIG. 5 is a three-dimensional structure diagram of a nut-connection-type visual dental floss according to the present disclosure.

FIG. 5-1 is an enlarged view of D Area of FIG. 5.

FIG. 6 is a three-dimensional structure diagram of a screw-connection-type visual dental floss according to the present disclosure.

FIG. 6-1 is an enlarged view of E Area of FIG. 6.

FIG. 7-1 is an enlarged view of F Area of FIG. 7.

FIG. 8-1 is an enlarged view of G Area of FIG. 8.

FIG. 11-1 is a top view of FIG. 11.

FIG. 11-2 is a side view of FIG. 11.

FIG. 11-3 is a bottom view of FIG. 11.

FIG. 11-4 is a top structure diagram of the visual oral forceps of FIG. 11 when the jaws are opened.

FIG. 11-5 is a G-G section view of FIG. 11-4.

FIG. 11-6 is a top structure diagram of the visual oral forceps of FIG. 11 when the jaws are closed.

FIG. 11-7 is an H-H section view of FIG. 11-6.

FIG. 11-8 is an exploded view of FIG. 11.

FIG. 12-1 is an exploded view of FIG. 12.

FIG. 12-2 is a front three-dimensional structure diagram of FIG. 12.

FIG. 12-3 is a structure diagram of the jaws and the mounting base of the oral forceps of FIG. 12 when viewed from the top.

FIG. 12-4 is a structure diagram of the jaws and the mounting base of the oral forceps of FIG. 12 when viewed from the bottom.

FIG. 12-5 is a structure diagram of an opening/closing mechanism of the oral forceps of FIG. 12 when viewed from the top.

FIG. 12-6 is a structure diagram of the opening/closing mechanism of the oral forceps of FIG. 12 when viewed from the bottom.

FIG. 12-7 is a structure diagram of the visual oral forceps according to the present disclosure when the oral forceps are in the opened state.

FIG. 12-8 is a structure diagram of the visual oral forceps according to the present disclosure when the oral forceps are in the closed state.

FIG. 13-1 is a structure diagram of the hinged visual oral forceps according to the present disclosure in the closed state.

FIG. 14 is a structure diagram of visual oral forceps having bent jaws according to the present disclosure.

FIG. 15 is a structure diagram of hinged visual oral forceps having bent jaws according to the present disclosure.

FIG. 18-1 is an exploded view of FIG. 18.

FIG. 19-1 is an exploded view of FIG. 19.

FIG. 21-1 is a bottom view of FIG. 21.

FIG. 21-2 is a side view of FIG. 21.

FIG. 21-3 is an I-I section view of the spray gun of FIG. 21 in a closed state.

FIG. 21-4 is an I-I section view of the spray gun of FIG. 21 in an open state.

FIG. 22-1 is a J-J section view of the FIG. 22.

FIG. 22-2 is an enlarged view of K area of a pressure vessel of FIG. 22-1 when the piston moves outward.

FIG. 22-3 is an enlarged view of K area of the pressure vessel of FIG. 22-1 when the piston moves inward (pressurized).

FIG. 23-1 is a side view of FIG. 23.

FIG. 23-2 is a top view of FIG. 23.

FIG. 23-3 is an L-L section view of FIG. 23-2.

FIG. 23-4 is an enlarged view of M Area of FIG. 23-3 when the adjustable spray head is in a multi-nozzle state.

FIG. 23-5 is an enlarged view of M Area of FIG. 23-3 when the adjustable spray head is in a single-nozzle state.

FIG. 27-1 is an exploded view of FIG. 27.

FIG. 28-1 is a three-dimensional structure diagram of the back of FIG. 28.

FIG. 29-1 is an exploded view of FIG. 29.

FIG. 30-1 is an exploded view of FIG. 30.

FIG. 31-1 is an enlarged view of N Area of FIG. 31.

FIG. 31-2 is a structure diagram that the interdental brush is removed from the multifunctional visual oral irrigator according to the present disclosure.

FIG. 32-1 is an enlarged view of O Area of FIG. 32.

FIG. 32-2 is a structure diagram that the dental floss is removed from the multifunctional visual oral irrigator according to the present disclosure.

FIG. 33-1 is an enlarged view of P Area of FIG. 33.

FIG. 33-2 is a structure diagram that the toothbrush is removed from the multifunctional visual oral irrigator according to the present disclosure.

FIG. 34-1 is an enlarged view of Q Area of FIG. 34.

FIG. 34-2 is a structure diagram that the oral forceps are removed from the multifunctional visual oral irrigator according to the present disclosure.

FIG. 37-1 is a structure diagram of the visual oral irrigator according to the present disclosure in a folded state, FIG. 37-2 is a three-dimensional structure diagram of the visual oral irrigator according to the present disclosure in an unfolded state.

FIG. 38-1 is an enlarged view of R Area of FIG. 38.

FIG. 38-2 is a three-dimensional structure diagram of the visual oral irrigator according to the present disclosure in a detached state.

FIG. 38-3 is an exploded view of FIG. 21.

FIG. 39-1 is an enlarged view of S Area of FIG. 39.

FIG. 39-2 is a three-dimensional structure diagram of the visual toothbrush according to the present disclosure when the toothbrush and the oral viewer are separated.

FIG. 39-3 is an enlarged view of T Area of FIG. 39-2.

FIG. 40-1 is a front three-dimensional structure diagram of FIG. 40.

FIG. 40-2 is a structure diagram of the brush head and the mounting base of the toothbrush of FIG. 40 when viewed from the bottom.

FIG. 41-1 is an enlarged view of U Area of FIG. 41.

FIG. 41-2 is a three-dimensional structure diagram of a waterproof lens of FIG. 41 when removed.

FIG. 41-3 is an enlarged view of V Area of FIG. 41-2.

FIG. 42-1 is a structure diagram of the visual toothbrush according to the present disclosure when connected with the display device in a wireless manner.

FIG. 44-1 is a structure diagram of the detachable visual interdental brush of FIG. 44 when the forward movement of the sliding block causes the protrusion of the interdental brush.

FIG. 44-2 is a structure diagram of the detachable visual interdental brush of FIG. 44 when the backward movement of the connecting mechanism causes the release between the locating block and the locating slot.

FIG. 44-3 is a structure diagram of the detachable visual interdental brush of FIG. 44 when the built-in interdental brush is completely separated from the oral viewer.

FIG. 45-1 is a W-W section view of FIG. 45.

FIG. 45-2 is an X-X section view of FIG. 45-1.

FIG. 45-3 is a Y-Y section view of FIG. 45-1.

FIG. 46 is a top view of the detachable visual interdental brush according to the present disclosure when the backward movement of the connecting mechanism causes the release between the locating block and the locating slot.

FIG. 46-1 is a Z-Z section view of FIG. 46.

FIG. 47 is a structure diagram of a built-in interdental brush of the detachable visual interdental brush according to the present disclosure.

FIG. 47-1 is a three-dimensional structure diagram of the built-in interdental brush of the detachable visual interdental brush according to the present disclosure when viewed from the top.

FIG. 47-2 is a three-dimensional structure diagram of the built-in interdental brush of the detachable visual interdental brush according to the present disclosure when viewed from the bottom.

FIG. 47-3 is an exploded view of FIG. 47-1.

FIG. 47-4 is an exploded view of FIG. 47-3.

FIG. 48 is a schematic diagram of the detachable visual interdental brush according to the present disclosure when connected with the display device in a wired manner.

FIG. 49 is a schematic diagram of the detachable visual interdental brush according to the present disclosure when connected with the display device in a wireless manner.

Figure 50:
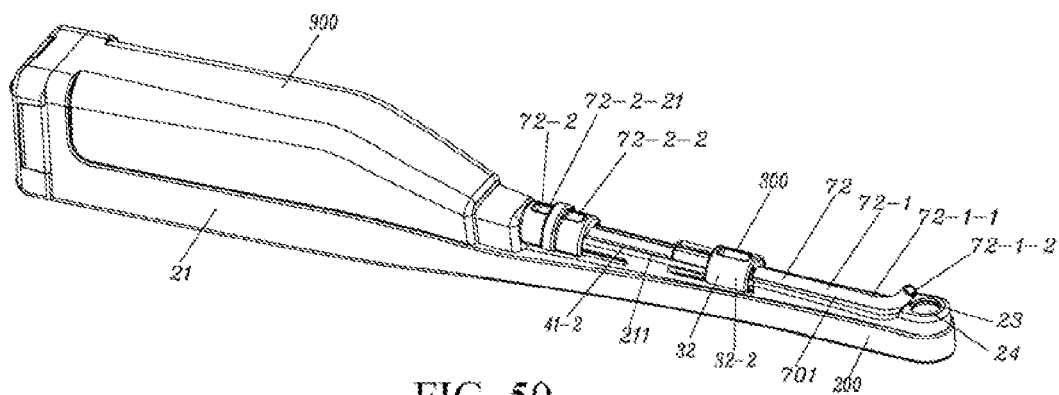
Figures 1, 50:
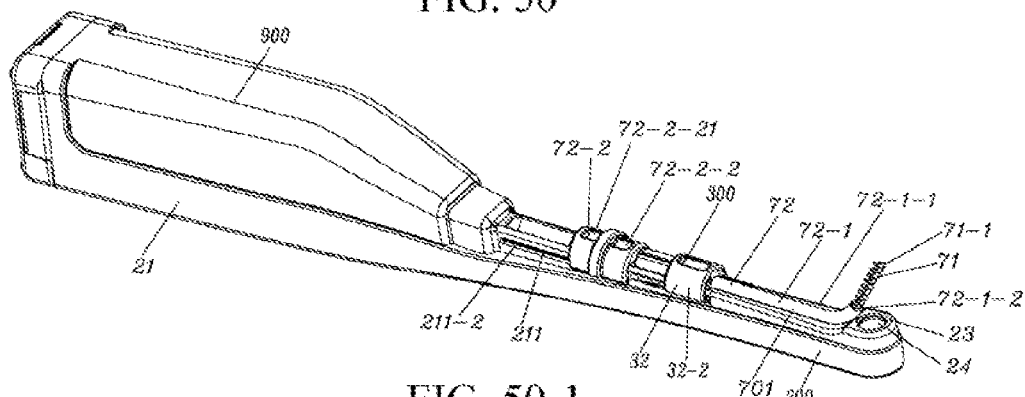
Figures 2, 50:
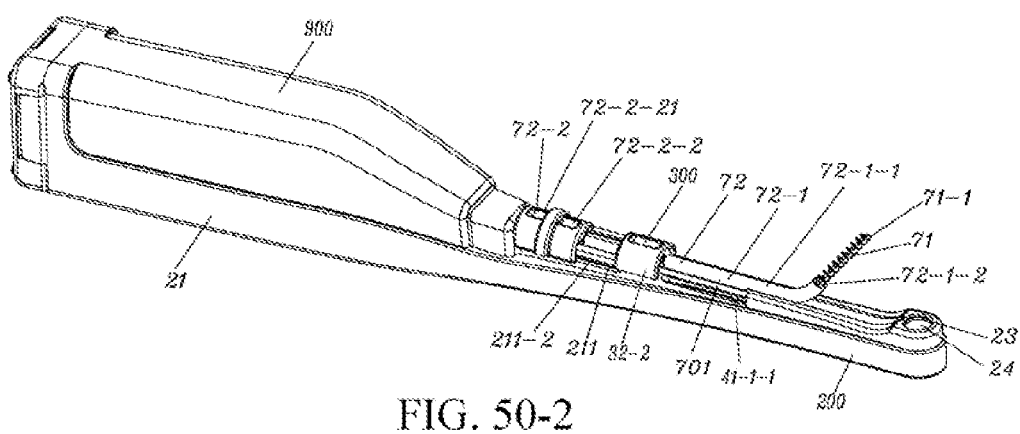
Figures 3, 50:
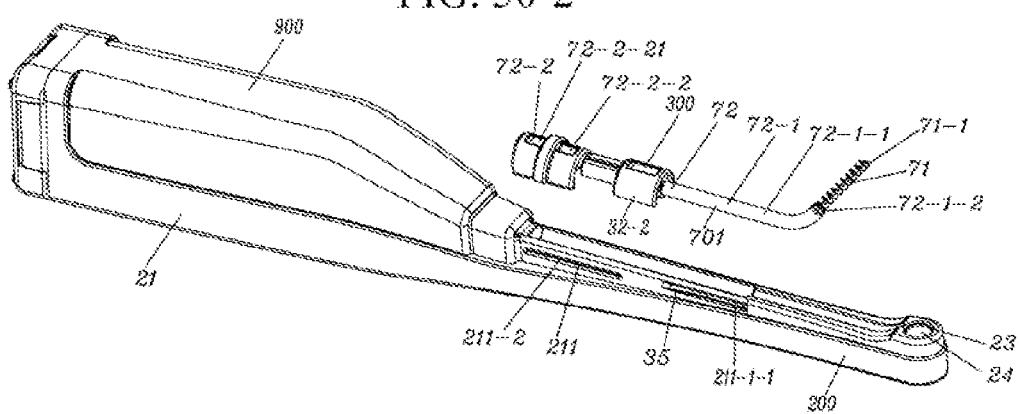

FIG. 50 is a structure diagram of a detachable visual interdental brush including an arc-shaped locating hook type locating block according to the present disclosure.

Figure 1:
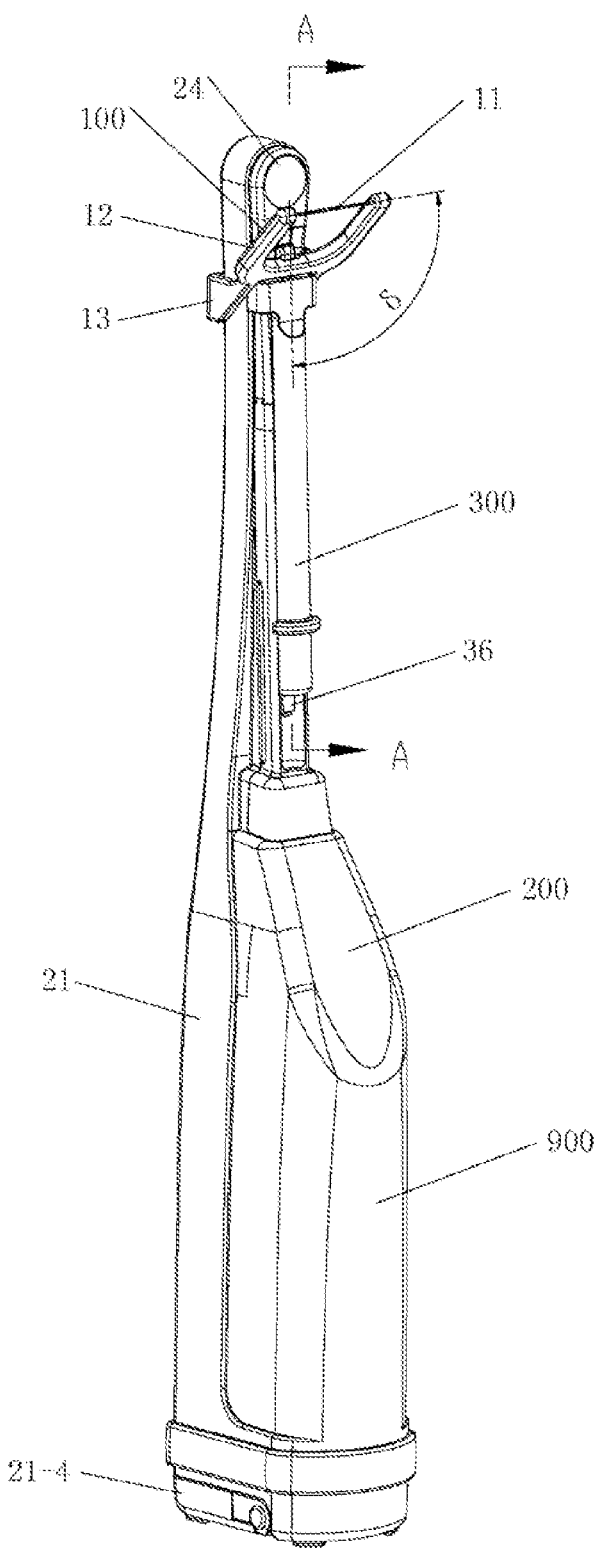
FIG. 1 is a three-dimensional structure diagram of a visual dental floss according to the present disclosure.
Figure 1:
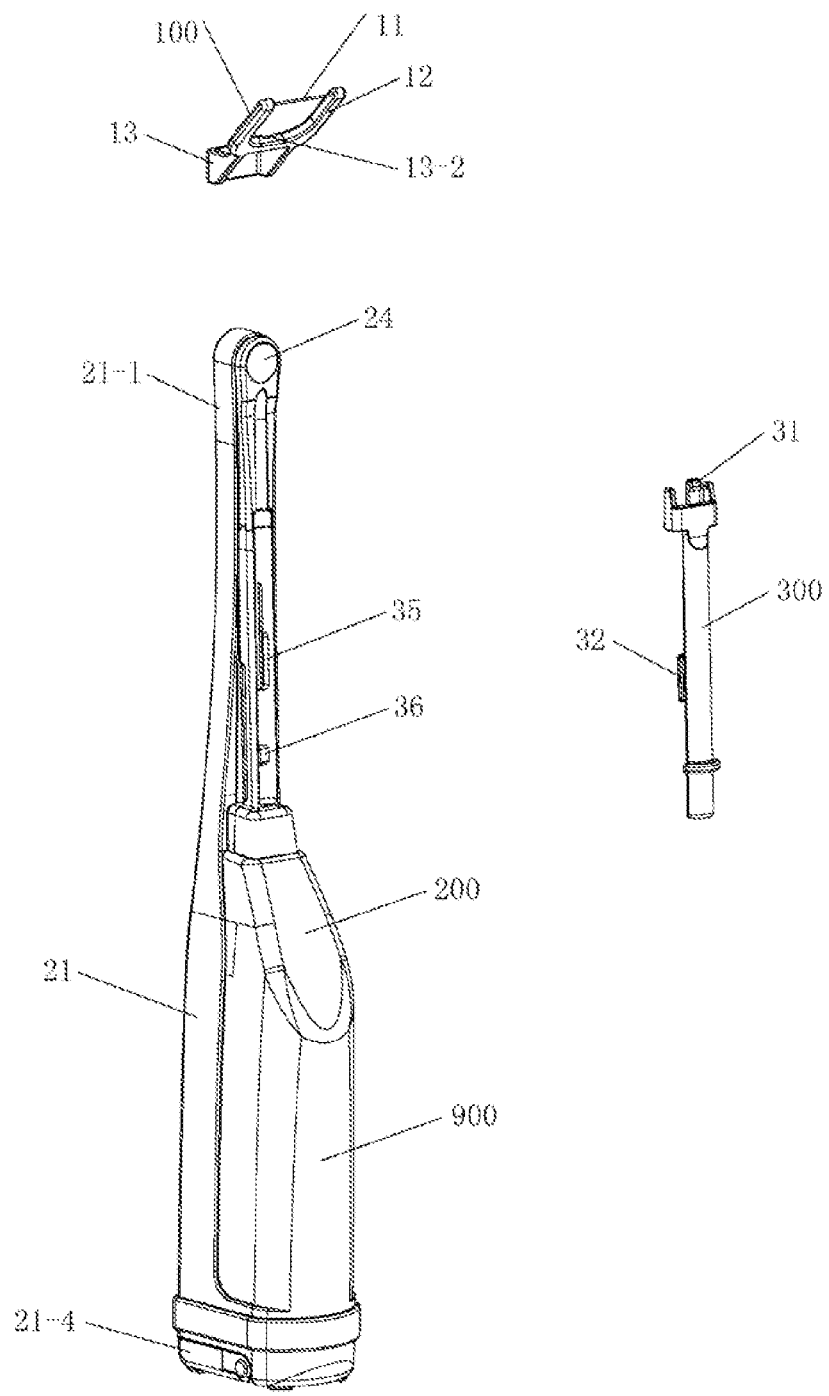

FIG. 50-1 is a structure diagram of the detachable visual interdental brush of FIG. 50 when the forward movement of the sliding block causes the protrusion of the interdental brush.

Figures 1, 2, 3:
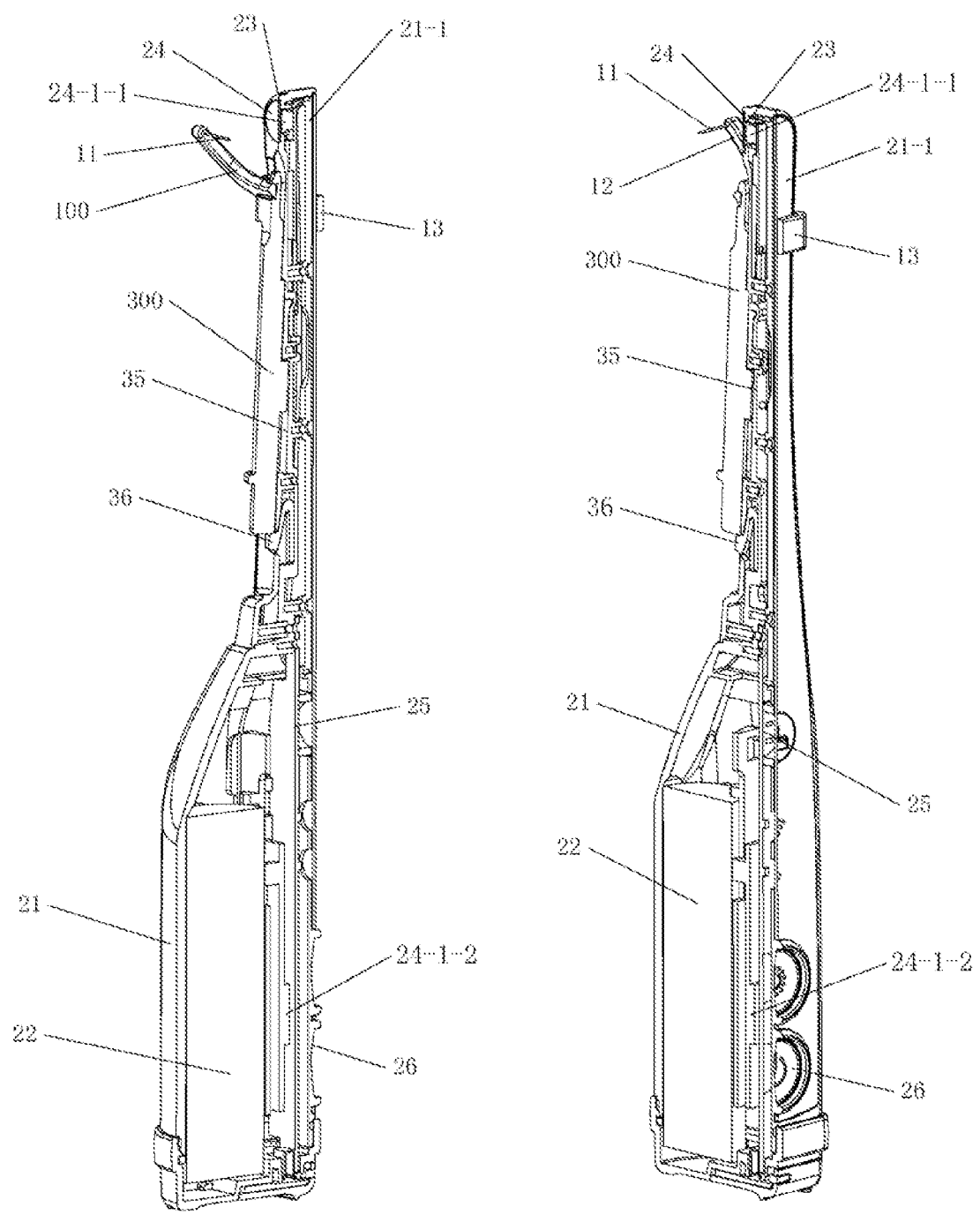

FIG. 50-2 is a structure diagram of the detachable visual interdental brush of FIG. 50 when the backward movement of the connecting mechanism causes the release between the locating block and the locating slot.

FIG. 50-3 is a structure diagram of the detachable visual interdental brush of FIG. 50 when the built-in interdental brush is completely separated from the oral viewer.

FIG. 51 is a front view of FIG. 50-2.

FIG. 51-1 is an a-a section view of FIG. 51.

FIG. 51-2 is a b-b section view of FIG. 51.

Figure 52:
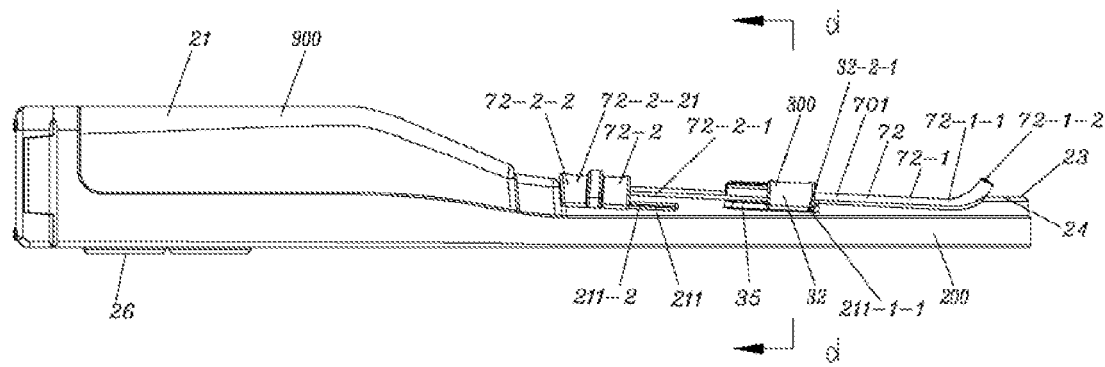
Figures 1, 52:
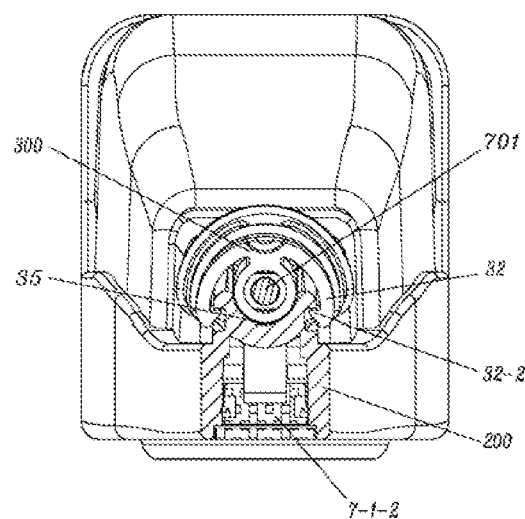

FIG. 52 is a front view of FIG. 50.

FIG. 52-1 is a c-c section view of FIG. 52.

FIG. 53 is a three-dimensional structure diagram of the built-in interdental brush of the detachable visual interdental brush of FIG. 50 when viewed from the top.

FIG. 53-1 is a three-dimensional structure diagram of the built-in interdental brush of FIG. 53 when viewed from the bottom.

FIG. 53-2 is an exploded view of FIG. 53.

FIG. 53-3 is an exploded view of FIG. 53-1.

Figures 1, 2, 3, 4:
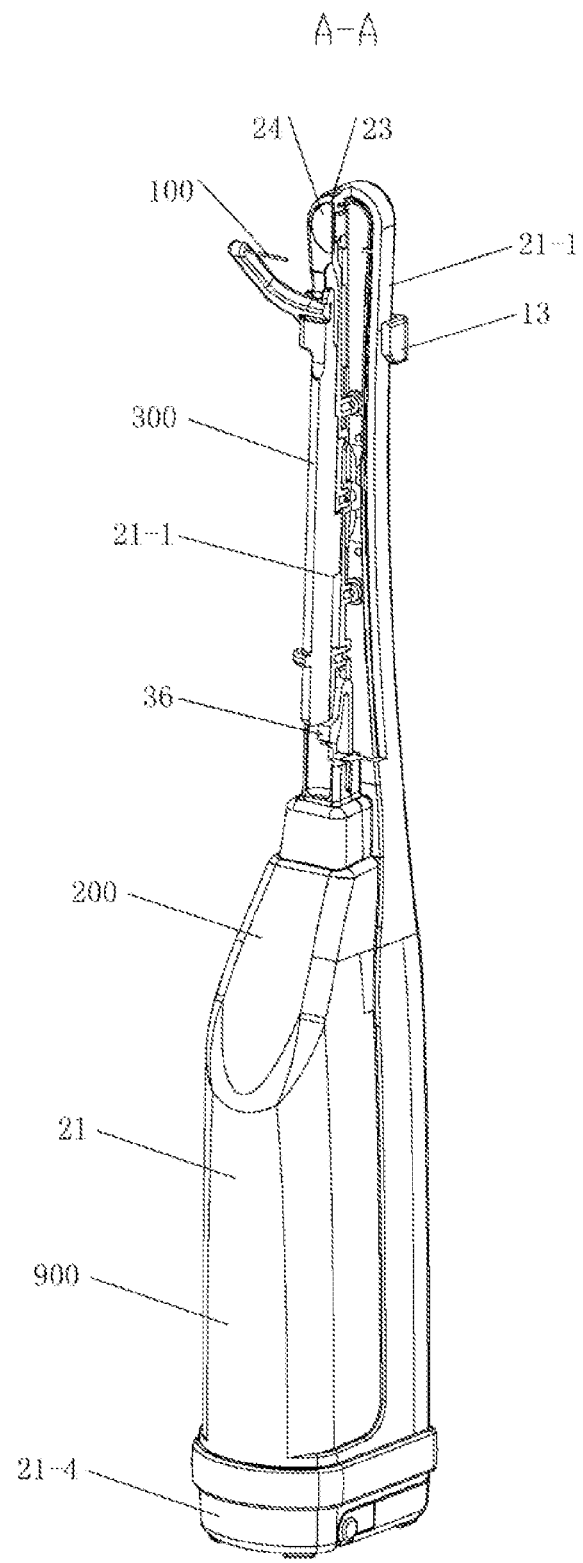

FIG. 53-4 is an exploded view of FIG. 53-2.

Figures 1, 2, 3, 4, 5:
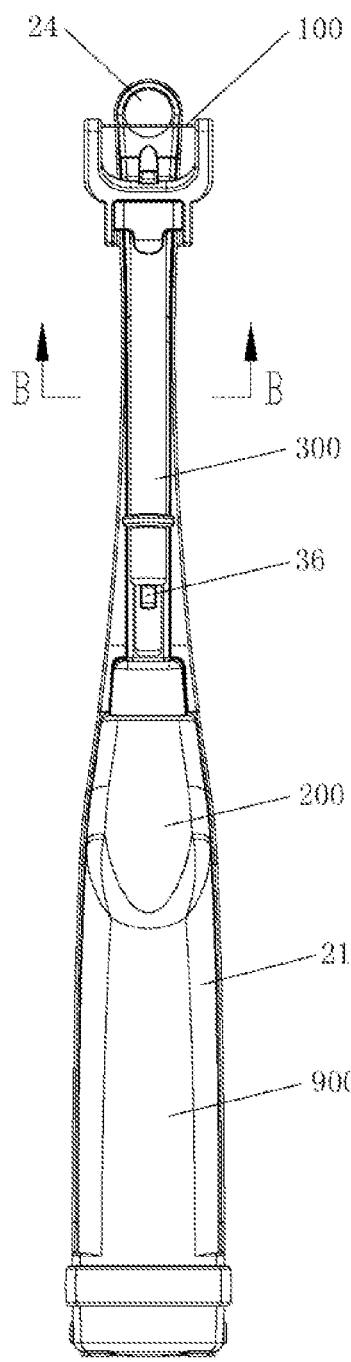

FIG. 53-5 is an exploded view of FIG. 53-3.

Figure 54:
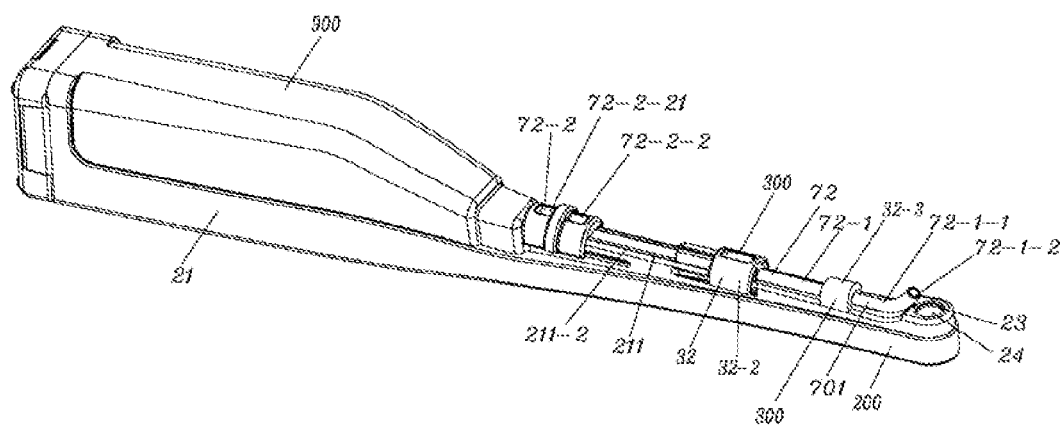
Figures 1, 54:
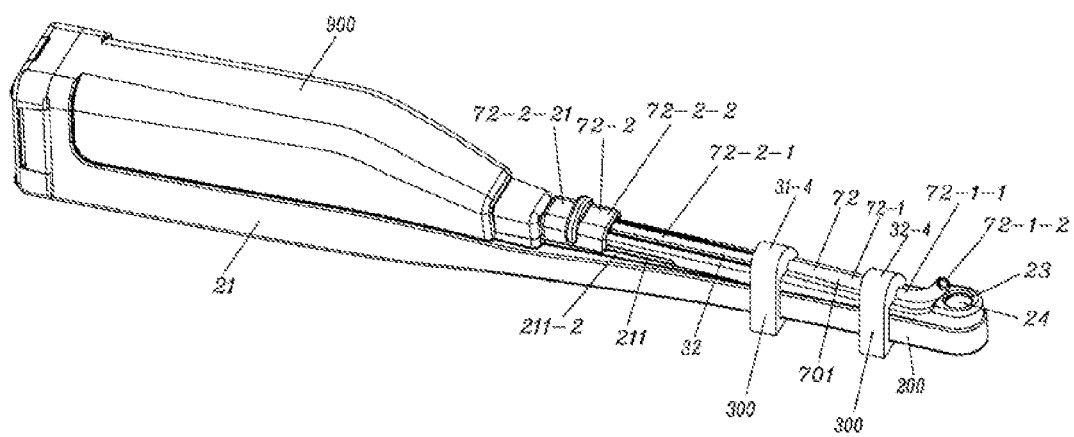

FIG. 54 is a structure diagram of a detachable visual interdental brush including a connecting ring type locating block according to the present disclosure.

FIG. 54-1 is a structure diagram of a detachable visual interdental brush including a surrounding arm type locating block according to the present disclosure.

In the Above Drawings:

100 is a dental floss, 200 is an oral viewer, 300 is a connecting mechanism, 400 is oral forceps, 500 is an oral irrigator, 600 is a toothbrush, 700 is an interdental brush, 901 is a visual dental floss of the present disclosure, 902 is visual oral forceps of the present disclosure, 903 is a visual oral irrigator of the present disclosure, 904 is a visual toothbrush of the present disclosure, and 905 is a detachable visual interdental brush of the present disclosure.

On the Dental Floss:

11 is a floss, 12 is a bracket, and 13 is a mounting base.

13-1 is a through hole in mounting base, 13-2 is a locating groove, and 13-3 is a thread.

On the Oral Viewer:

200-1 is a front end of the oral viewer, and 200-2 is a main body of the oral viewer.

211 is a fixing mechanism, 211-2 is a sliding slot, 211-1-1 is a locating convex stair, and 212 is a locating end.

21 is a housing, 22 is a power supply system, 23 is a lighting system, 24 is a viewing system, 25 is a circuit system, and 26 is a switch.

21-1 is a head of the housing, 21-2 is a supporting rib plate, 21-3 is a mounting slot of the oral forceps, and 21-4 is a sealing device.

22-1 is a boosting device, 22-2 is a power supply, and 22-3 is a connecting base.

24-1 is a camera system.

25-1 is a circuit at the front end of the oral viewer, 25-2 is a circuit of the main body of the oral viewer, and 25-3 is a sealed charging interface; 25-1-1 is an interface of the circuit at the front end, and 25-2-1 is an interface of the circuit of the main body.

26-1 is a status light.

21-2-1 is a sliding slot arranged on the outer side of the supporting rib plate; and 21-4-0 is a seal groove, 21-4-1 is a seal ring, 21-4-2 is a pressure plate, 21-4-3 is a sliding plate, and 21-4-4 is a sliding plate locating slot.

24-1-1 is a camera, 24-1-2 is a data processing and output system, and 24-1-3 is a display device.

24-1-31 is a smartphone, 24-1-32 is a computer, 24-1-33 is a liquid crystal display device/television, and 24-1-34 is a tablet computer.

On the Connecting Mechanism:

30 is a sliding bar, 31 is a locating hook, 31-1 is a left locating hook, 31-2 is a right locating hook, 32 is a locating block, 33 is a threaded connecting mechanism, 34 is an antiskid convex line, 35 is a locating slot, and 36 is a clamping block.

32-1 is an inverted T-shaped locating block, 32-2 is an arc-shaped locating hook, 32-3 is a connecting ring, 32-4 is a surrounding arm, and 32-2-1 is a locating groove.

δ is an included angle between the dental floss and the center line of the head of the housing of the oral viewer.

On the Oral Forceps:

41 is jaws, 42 is an opening/closing mechanism, and 43 is a mounting base.

41-1 is a left arm of the jaws, 41-2 is a right arm of the jaws, 41-3 is bite teeth on the jaws, 41-4 is a curvature of the jaws, and 41-5 is a pin.

41-1-1 is a left arm connecting rod, and 41-2-1 is a right arm connecting rod.

42-1 is a push rod.

42-1-1 is a sliding block on the push rod.

42-1-2 is a push block.

42-1-21 is a sliding slot on the push block, and 42-1-22 is a sliding block on the push block.

42-2 is a sleeve.

42-2-1 is a hole in the sleeve.

43-2 is a sliding slot.

On the Oral Irrigator:

500-1 is a front end of the oral irrigator, and 500-2 is a main body of the oral irrigator.

903-1 is a front end of the visual oral irrigator of the present disclosure, 903-2 is a main body of the visual oral irrigator of the present disclosure, 903-3 is a detachable connecting mechanism, and 903-4 is a foldable connecting mechanism.

903-3-1 is a connecting and fixing mechanism, 903-3-2 is an electrical joint, and 903-3-3 is a water joint.

903-3-11 is an internal screw, 903-3-12 is a rotation stop block, 903-3-13 is a connecting component, and 903-3-14 is an external nut; 903-3-111 is a mounting slot, and 903-3-112 is a locating groove; 903-3-121 is a locating convex stair, 903-3-122 is a rotation stop slot, and 903-3-123 is a rotation stop convex stair; 903-3-131 is a limit convex stair, 903-3-132 is an electrical connector, and 903-3-133 is a water tube; and 903-3-141 is a joint platform.

903-4-1 is a rotating shaft, and 903-4-2 is a rotating shaft hole.

51 is a spray head, 52 is a spray gun, 53 is a control switch, 54 is a pressure vessel, 55 is a connecting tube, 56 is a union joint, and 57 is a base.

51-1 is a spray head regulating valve, 51-2 is a curvature of the spray head, 51-1-1 is a water outlet, and 51-1-2 is a regulating cone.

52-1 is a fluid channel of the spray gun, 52-2 is a housing of the spray gun, and 52-3 is a mounting base of the spray gun.

53-1 is a return spring of the control switch, and 53-2 is a water inlet.

54-1 is a pressure device of the pressure vessel, 54-2 is a housing of the pressure vessel, 54-3 is a fluid containing space of the pressure vessel, 54-4 is a water filling port of the pressure vessel, 54-41 is an interface of the water filling port, 54-42 is a seal cap of the water filling port, 54-5 is a partition, and 54-6 is a mounting interlayer.

54-2-1 is an air inlet hole, 54-2-2 is a locating seat, and 54-2-3 is an upper cover.

54-5-1 is a vent hole, 54-5-2 is a drainage hole, and 54-5-3 is a water discharge hole.

55-1 is a water discharge tube at the front end of the oral irrigator, 55-2 is a water discharge tube of the main body of the oral irrigator, 55-1-1 is an interface of the water discharge tube at the front end, and 55-2-1 is an interface of the water discharge tube of the main body.

57-1 is a lower cover, and 57-2 is a mounting slot.

541 is a manual pressurizer.

541-1 is a front check valve, 541-2 is a rear check valve, 541-3 is a valve barrel, 541-4 is a piston, 541-5 is a push rod, and 541-6 is a core rod.

541-1-1 is a front return spring, 541-1-2 is a front check block, and 541-1-3 is a front seal ring.

541-2-1 is a rear return spring, 541-2-2 is a rear check block, and 541-2-3 is a rear seal ring.

541-2-21 is a through hole in the rear check block.

542 is an electric pressurizer.

542-1 is an electric air pressurizer, and 542-2 is an electric water pressurizer.

542-51 is an electric air compressor, 542-51-1 is an air inlet, 542-51-2 is an inflation tube, 542-51-21 is an inflation port, 542-51-22 is an elbow, 542-51-23 is a straight tube, and 542-51-3 is an air compressor.

542-21 is a submersible pump, 542-21-1 is a submersible pump water inlet system, 542-21-51 is a water inlet, 542-21-2 is a submersible pump pressurizing system, 542-21-3 is a submersible pump water discharge system, and 542-21-31 is a water outlet.

542-22 is a water pump, 542-22-1 is a pumping system, 542-22-51 is a pumping port, 542-22-2 is a vacuum suction system, 542-22-3 is a water pump water discharge system, and 542-22-31 is a water outlet.

On the Toothbrush:

61 is a brush head, 62 is a brush rod, and 63 is a mounting base.

61-1 is a brush hair, and 61-4 is a curvature of the brush head.

32 is a locating block on the mounting base, and 63-2 is a sliding slot.

β is an included angle between the brush head and the brush rod.

On the Interdental Brush:

701 is a built-in interdental brush;

71 is a brush body, 71-1 is a working portion of the interdental brush, 71-2 is a connecting body of the interdental brush, and 71-1-1 is a brush head.

72 is a delivery device, 72-1 is a guide head, 72-1-1 is an elbow tube, and 72-1-2 is an elbow tube outlet; and 72-2 is a sliding mechanism, 72-2-1 is a connecting mechanism connected with the interdental brush, 72-2-2 is a sliding block, 72-2-21 is an arched housing of the sliding block, and 72-2-22 is a guide block on the inner side of the arched housing.

Like reference numerals refer to corresponding parts throughout the several views of the drawings.

DESCRIPTION OF EMBODIMENTS

Reference will now be made in detail to embodiments, examples of which are illustrated in the accompanying drawings. In the following detailed description, numerous specific details are set forth in order to provide a thorough understanding of the subject matter presented herein. But it will be apparent to one skilled in the art that the subject matter may be practiced without these specific details. In other instances, well-known methods, procedures, components, and circuits have not been described in detail so as not to unnecessarily obscure aspects of the embodiments.

The present disclosure relates to a multifunctional visual oral cleaning instrument which includes a visual dental floss, and/or visual oral forceps, and/or a visual oral irrigator, and/or a visual toothbrush, and/or a detachable visual interdental brush. The dental floss, and/or oral forceps, and/or oral irrigator, and/or toothbrush, and/or interdental brush are/is connected with an oral viewer through a connecting mechanism. By using a smartphone or tablet computer, the dental floss, oral forceps, oral irrigator, toothbrush or interdental brush and the gap between teeth can be clearly seen, so that tooth gaps can be conveniently cleaned and treated under direct vision during use, and the cleaning effect of the tooth gaps can be viewed and recorded in real time.

Embodiment 1: A Concave-Convex Snap Fit Type Visual Dental Floss According to the Present Disclosure With reference to FIG. 1 to FIG. 4-1, the visual dental floss 901 of this embodiment includes a dental floss 100, an oral viewer 200 and a connecting mechanism 300.

The dental floss 100 includes a floss 11, a bracket 12 and a mounting base 13; and both ends of the floss 11 of the dental floss 100 are respectively fixed on a left arm 12-1 and a right arm 12-2 of the bracket 12, and the bracket 12 is arranged on the mounting base 13.

The oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; and the lighting system 23, the viewing system 24, the power supply system 22 and the switch 26 are connected together through the circuit system 25.

The dental floss 100 is mounted on the oral viewer 200 through the connecting mechanism 300. In this embodiment, the dental floss 100 is detachably connected to the oral viewer 200 through the connecting mechanism 300 in a concave-convex snap fit manner. The mounting base 13 of the dental floss 100 is provided with a through hole 13-1, and the head 21-1 of the housing of the oral viewer 200 may be embedded in the through hole 13-1, with reference to FIG. 2, FIG. 2-1 and FIG. 3 to FIG. 3-2.

The floss 11 of the dental floss 100 is within the visual field of the viewing system 24 of the oral viewer 200, with reference to FIG. 1. Thus, the dental floss and the gap between teeth can be clearly seen, so that the tooth gaps can be conveniently cleaned and treated under direct vision during use, and the cleaning effect of the tooth gaps can be viewed and recorded in real time.

In this embodiment, the connecting mechanism 300 is a separate component. With reference to FIG. 4 and FIG. 4-1, the connecting mechanism 300 includes a sliding bar 30, a locating hook 31, a left locating hook 31-1, a right locating hook 31-2, a locating block 32 and an antiskid convex line 34; the locating hook 31, the left locating hook 31-1 and the right locating hook 31-2 are arranged at the front end of sliding bar 30, the locating hook 31 is centered, and the left locating hook 31-1 and the right locating hook 31-2 are arranged on both sides; the locating block 32 is positioned in the middle of the sliding bar 30; the antiskid convex line 34 is arranged at the tail of the sliding bar 30; the locating block 32 is mounted in a locating slot 35 of the housing 21 of the oral viewer 200, and a clamping block 36 of the housing 21 of the oral viewer 200 abuts against the tail of the sliding bar 30, so that the connecting mechanism 300 is detachably mounted and fixed to the housing 21 of the oral viewer 200; and the head 21-1 of the housing 21 of the oral viewer 200 is embedded in the through hole 13-1 of the mounting base of the dental floss 100, the locating hook 31 of the connecting mechanism 300 is embedded in the locating groove 13-2 of the mounting base, and the left locating hook 31-1 and the right locating hook 31-2 surround the head 21-1 of the housing 21 of the oral viewer 200 from the left and right sides.

With reference to FIG. 1 and FIG. 2, during mounting, the locating block 32 of the connecting mechanism 300 is firstly embedded in the locating slot 35 of the housing 21 of the oral viewer 200, and the sliding bar 30 of the connecting mechanism 300 is slid forward until the clamping block 36 of the housing 21 of the oral viewer 200 is lifted up against the tail of the sliding bar 30; and at this time, the left locating hook 31-1 and the right locating hook 31-2 surround the head 21-1 of the housing 21 of the oral viewer 200 from the left and right sides so as to mount and connect the connecting mechanism 300 onto the oral viewer 200. The antiskid convex line 34 is arranged on the tail of the sliding bar 30, thereby increasing the friction force, and providing convenience for mounting or detaching the connecting mechanism 300. The combination of the surrounding action of the clamping block 36, the left locating hook 31-1 and the right locating hook 31-2 and the concave-convex snap fit of the locating block 32 and the locating slot 35 can effectively connect the connecting mechanism 300 firmly to the oral viewer 200.

Then, the head 21-1 of the housing 21 of the oral viewer 200 is embedded in the through hole 13-1 of the mounting base of the dental floss 100, and by pushing the dental floss 100 toward the connecting mechanism 300, the locating hook 31 of the connecting mechanism 300 may be embedded in the locating groove 13-2 of the mounting base 13, thereby forming the connection and fixation.

When detaching, the top of the locating hook 31 of the connecting mechanism 300 is pressed down to withdraw the dental floss 100, so that the concave-convex snap fit between the connecting mechanism 300 and the dental floss 100 can be released. When it is necessary to further remove the connecting mechanism 300 from the oral viewer 200, the sliding bar 30 is forced backwards, the clamping block 36 of the oral viewer 200 is pressed down, and the locating block 32 of the connecting mechanism 300 is withdrawn from the locating slot 35 of the oral viewer 200 until the connection of the connecting mechanism 300 and the oral viewer 200 is completely released.

Since the locating block 32 of the connecting mechanism 300 adopts an inverted T-shaped structure, when the T-shaped locating block 32 is embedded in the locating slot 35, the bottom of the inverted T-shaped structure and the locating slot 35 can form a concave-convex snap fit structure, thereby effectively limiting the movement of the connecting mechanism 300 in the vertical direction, and further preventing the connecting mechanism 300 and the oral viewer 200 from departing along the vertical direction during use. Meanwhile, the clamping block 36 of the oral viewer 200 is arranged at the rear end of the connecting mechanism 300; when the clamping block 36 of the oral viewer 200 is lifted up, since the top of the clamping block 36 is higher than the tail of the connecting mechanism 300, the connecting mechanism 300 can be effectively prevented from moving backward; and only when the connecting mechanism 300 is moved backward consciously and forcefully, the connecting mechanism 300 can be released from the oral viewer 200 after withdrawing along the guide surface of the clamping block 36, thereby effectively preventing the dental floss 100 from being accidentally released from the oral viewer 200 due to the fact that the connecting mechanism 300 can easily move backward.

Figure 9:
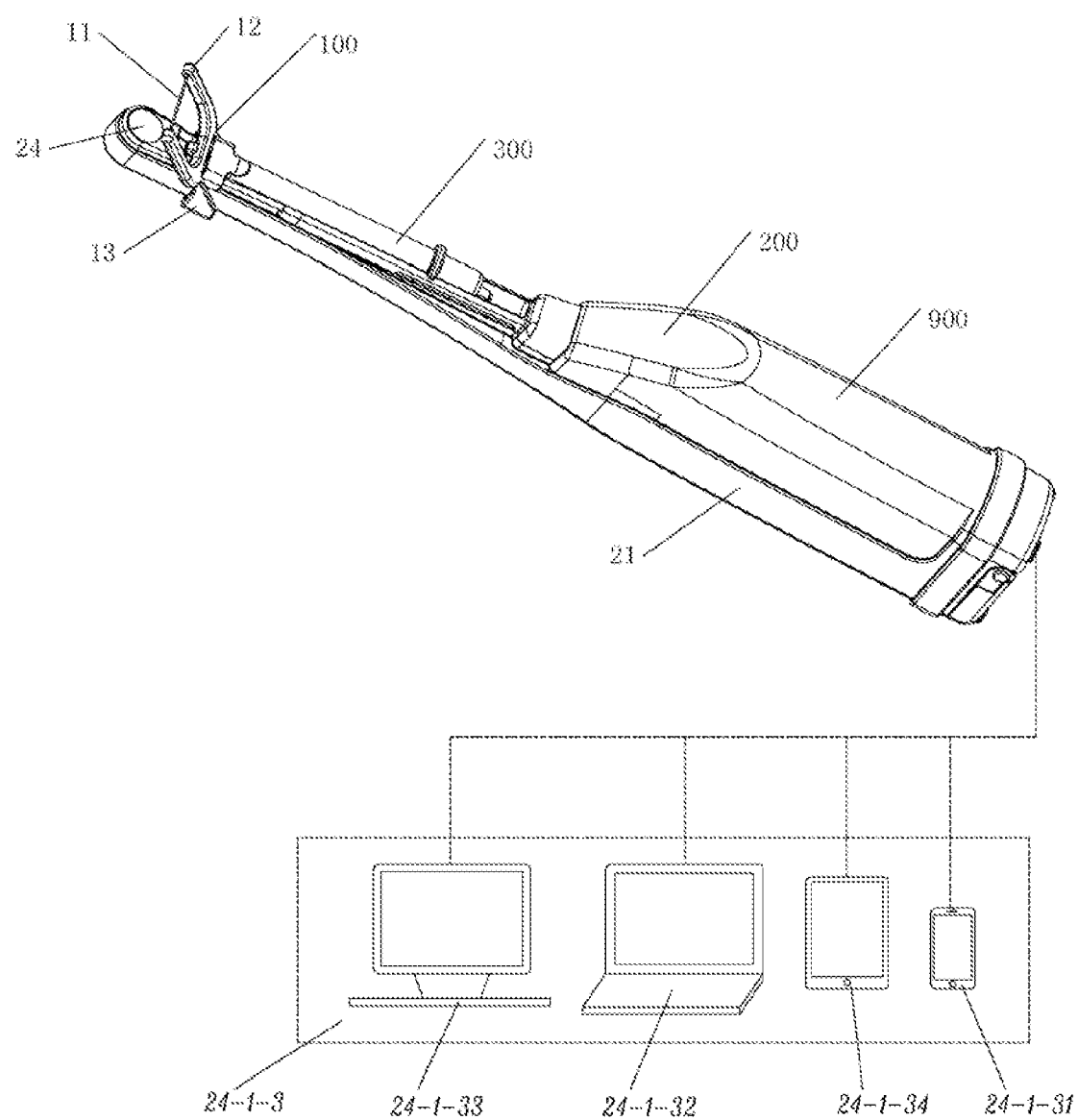
FIG. 9 is a diagram of a visual dental floss according to the present disclosure when connected to the display device in a wired connection manner.
Figure 10:
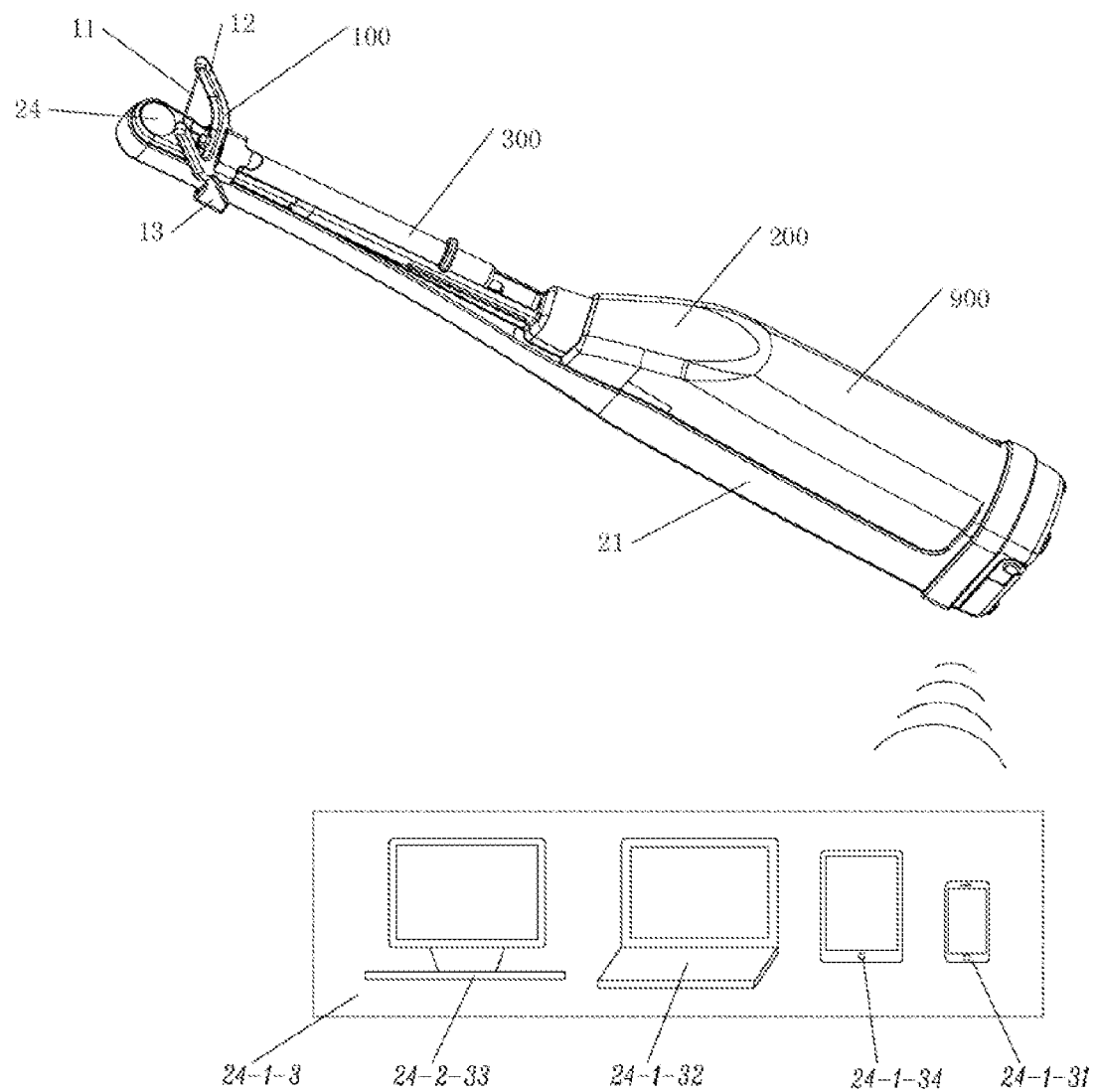
FIG. 10 is a diagram of the visual dental floss according to the present disclosure when connected to the display device in a wireless connection manner.

With reference to FIG. 9 and FIG. 10, the viewing system 24 is a camera system 24-1, and the camera system 24-1 includes a camera 24-1-1, a data processing and output system 24-1-2, a circuit system 25 and a power supply system 22.

Video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device/television 24-1-33, or a tablet computer 24-1-34 or the like.

The lighting system 6 is arranged around the camera 24-1-1, and generally adopts LED lights for lighting.

Figures 1, 7:
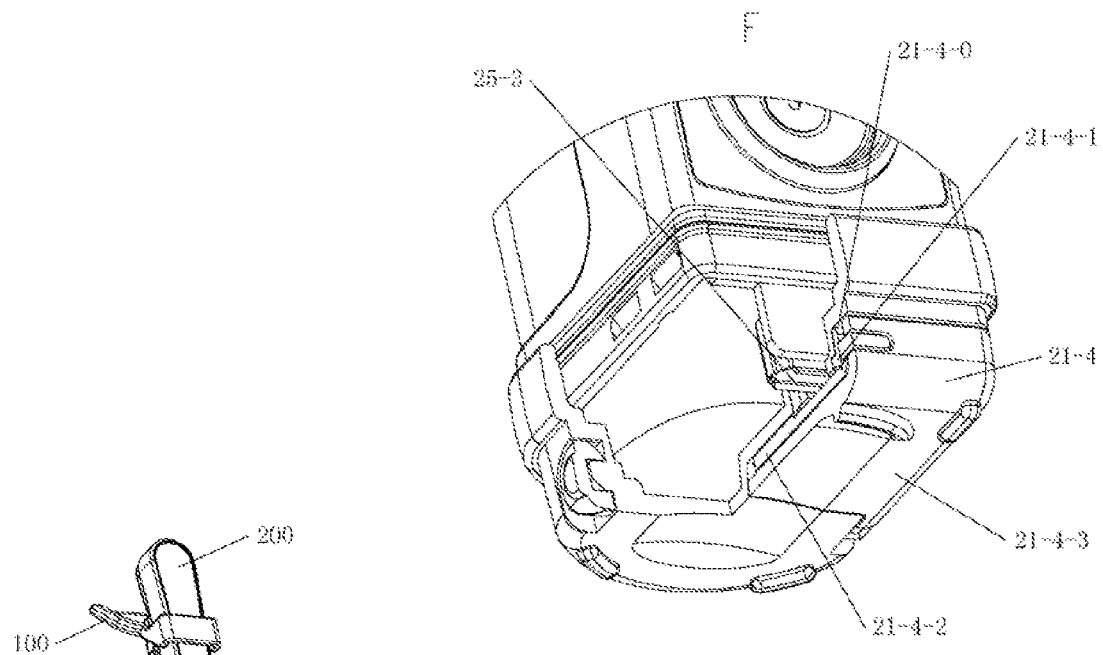
FIG. 7 is a three-dimensional structure diagram of a charging interface sealing device of the visual dental floss according to the present disclosure when sealed.
Figure 7:
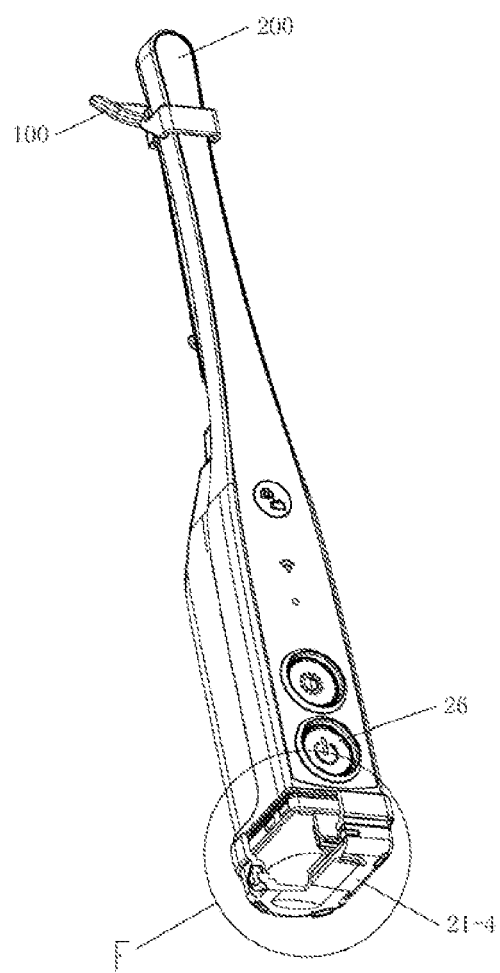
Figures 1, 8:
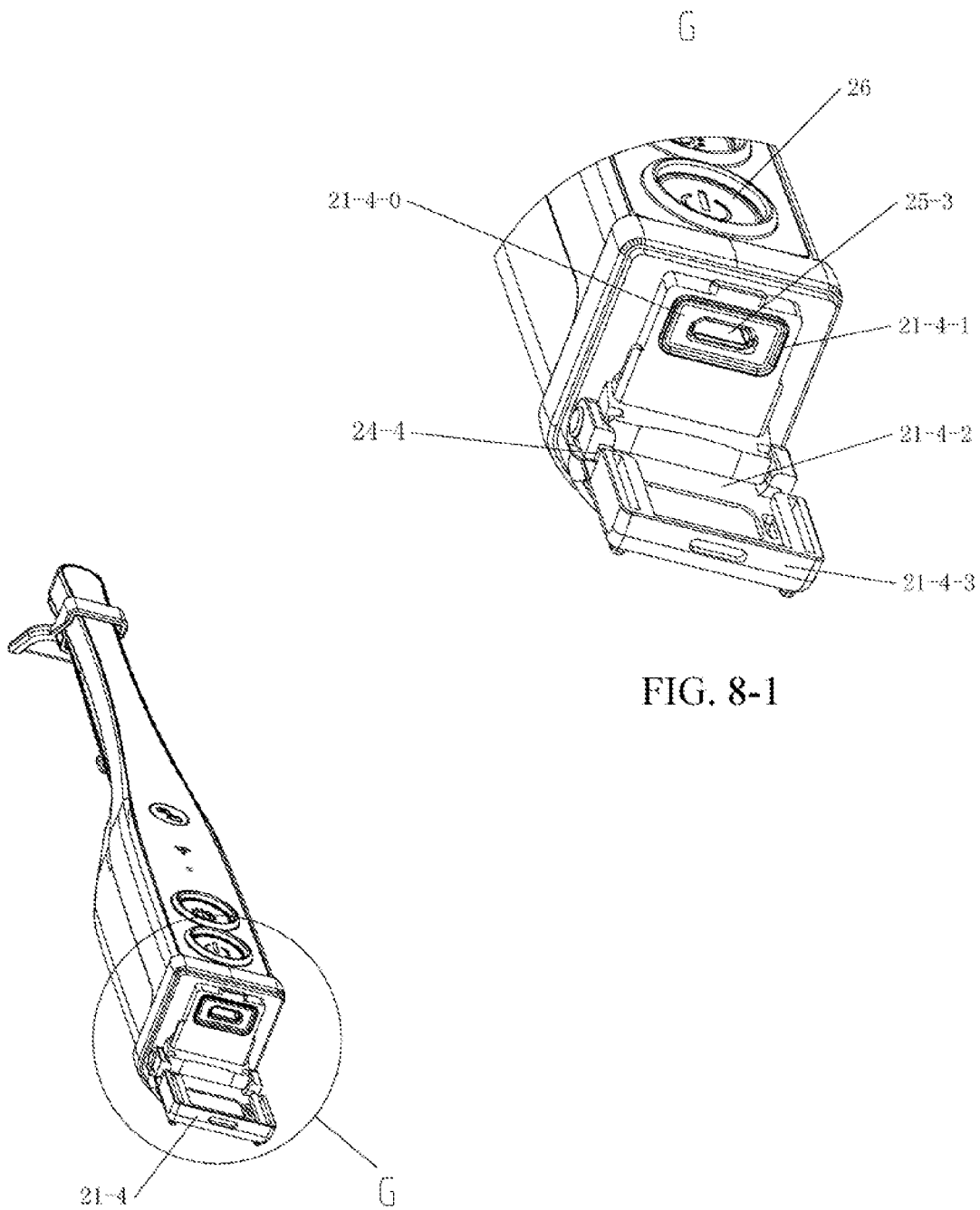
FIG. 8 is a three-dimensional structure diagram of the charging interface sealing device of the visual dental floss according to the present disclosure when opened.

With reference to FIG. 7 to FIG. 8-1, the oral viewer 200 adopts a waterproof design and includes a sealing device 21-4 for a sealed charging interface 25-3; the sealing device 21-4 includes a seal ring 21-4-1, a pressure plate 21-4-2 and a sliding plate 21-4-3; the pressure plate 21-4-2 and the sliding plate 21-4-3 can move relatively; the seal ring 21-4-1 is mounted in a seal groove 21-4-0 at the tail of the housing 21, the pressure plate 21-4-2 presses on the seal ring 21-4-1, and the sliding plate 21-4-3 detachably presses on the pressure plate 21-4-2; when the sliding plate 21-4-3 slides into a sliding plate locating slot 35-4-4 at the tail of the housing 21, the sliding plate 21-4-3 presses on the pressure plate 21-4-2, and the pressure plate 21-4-2 presses on the seal ring 21-4-1 to form a seal; and when the sliding plate 21-4-3 is pushed outward, the sliding plate 21-4-3 is released from the sliding plate locating slot 35-4-4 at the tail of the housing 21, the sliding plate 21-4-3 is lifted, the pressure plate 21-4-2 is driven to be lifted up, the pressure of the pressure plate 21-4-2 is released to expose the sealed charging interface 25-3, the seal is released, and the oral viewer 200 can be charged.

Since the oral viewer 200 adopts a waterproof design, when the oral viewer 200 does not need charging, the sliding plate 21-4-3 slides into the sliding plate locating slot 35-4-4, the seal ring 21-4-1 forms a seal, and at this time, the oral viewer 200 has favorable waterproofness and can be washed and cleaned conveniently.

The floss 11 of the dental floss 100 is within the visual field of the viewing system 24 of the oral viewer 200. Therefore, the dental floss and the gap between teeth can be clearly seen, so that the tooth gaps can be conveniently cleaned and treated under direct vision during use, and the cleaning effect of the tooth gaps can be viewed in real time. The visual dental floss 901 of the present disclosure is convenient to carry and assembly and flexible to use.

Figures 1, 2, 3, 4, 5, 6:
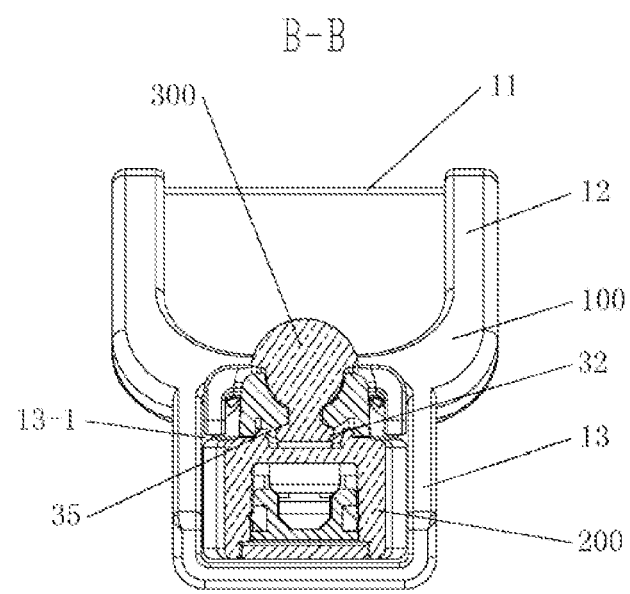
Figure 2:
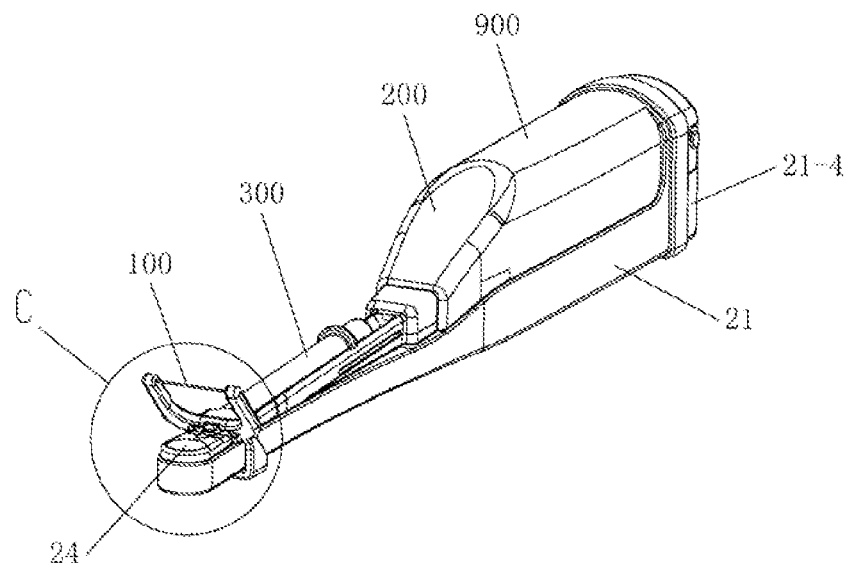
Figures 1, 2:
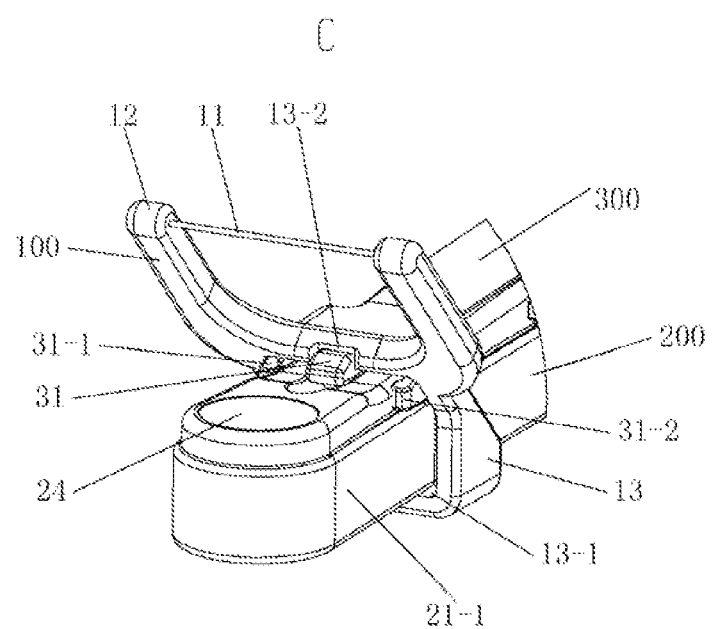
Figures 1, 5:
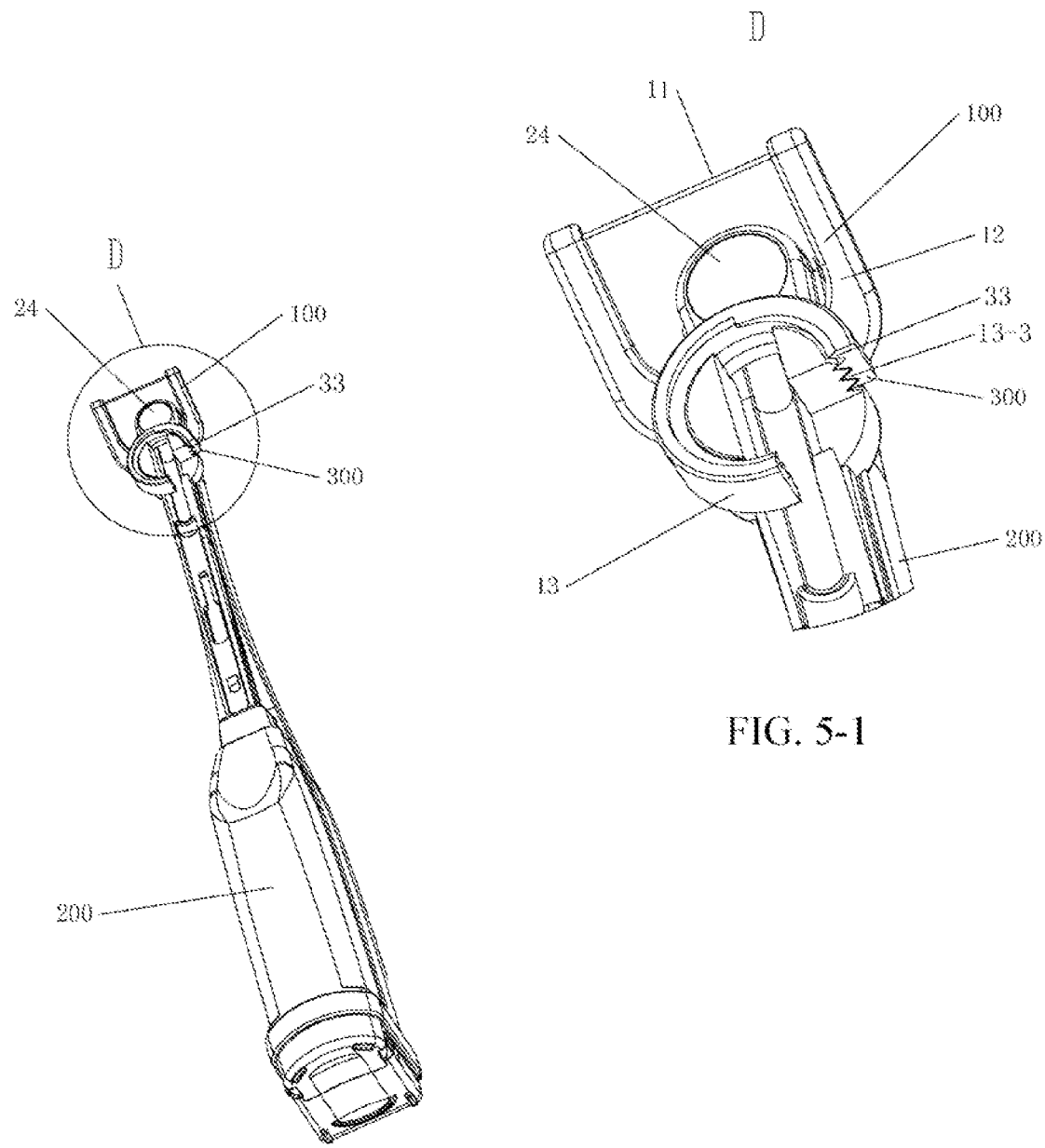
Figures 1, 6:
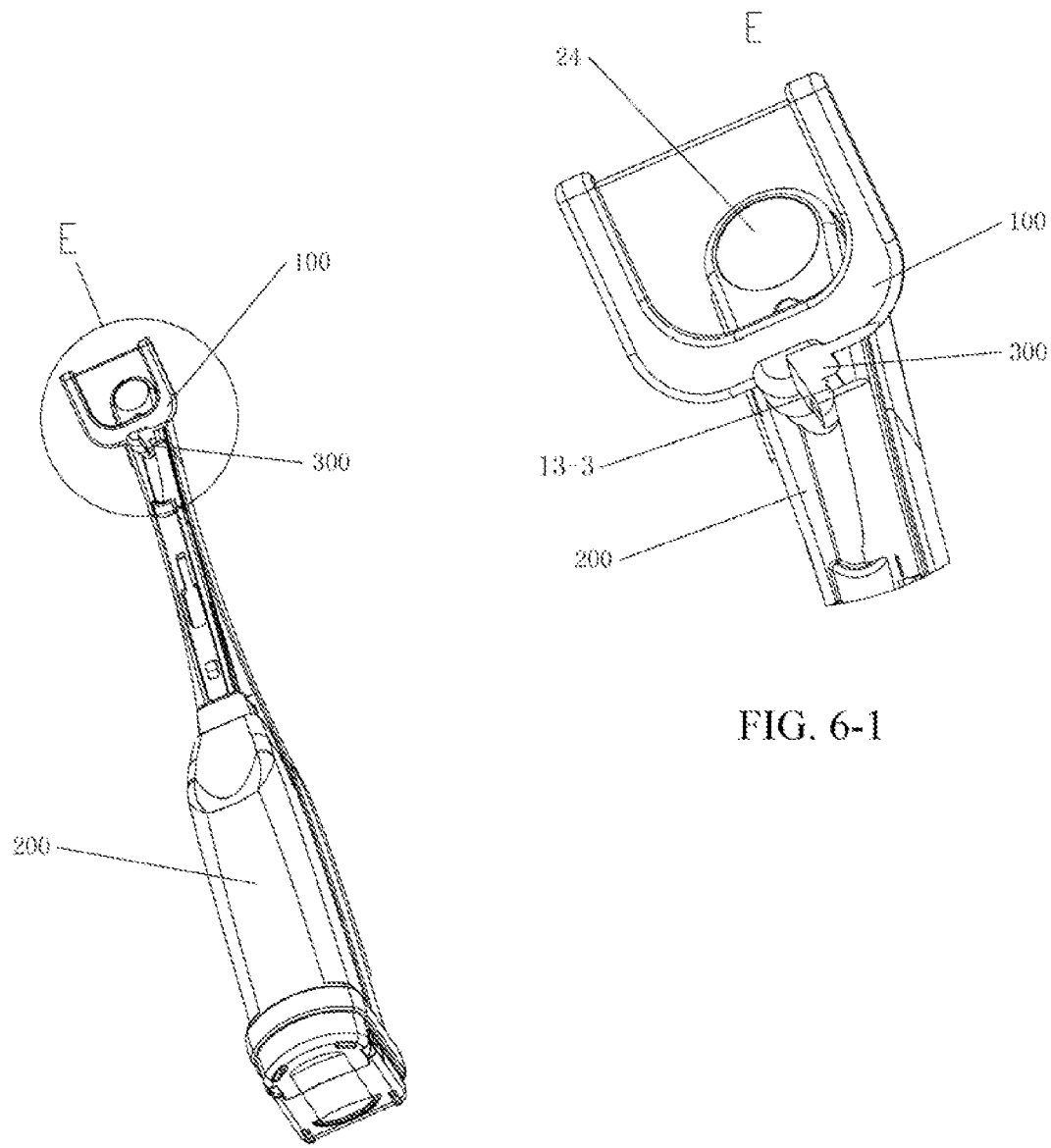

Embodiment 2: A Threaded Connection Type Visual Dental Floss According to the Present Disclosure With reference to FIG. 5 to FIG. 6-1, the difference between this embodiment and Embodiment 1 lies in that the connecting mechanism 300 in this embodiment is a threaded connecting mechanism 33.

In this embodiment, the mounting base 13 of the dental floss 100 is provided with a thread 13-3, and the threaded connecting mechanism 33 is matched with the thread 13-3 and arranged on the head 21-1 of the housing of the oral viewer 200; by rotating the dental floss 100, the thread 13-3 of the dental floss 100 can be mounted on the threaded connecting mechanism 33; and by rotating the dental floss 100 in the opposite direction, the thread 13-3 of the dental floss 100 can be removed from the threaded connecting mechanism 33. At this time, the thread 13-3 on the mounting base 13 may be set as a screw or bolt type, and the threaded connecting mechanism 33 of the connecting mechanism 300 is a corresponding nut; and contrarily, the thread 13-3 on the mounting base 13 may be set as a nut type, and the threaded connecting mechanism 33 of the connecting mechanism 300 is a corresponding screw or bolt.

By rotating the thread 13-3 of the dental floss 100, the included angle between the floss 11 of the dental floss 100 and the center line of the head 21-1 of the housing of the oral viewer 200 can be adjusted. Thus, the included angle β can be adjusted in time according to the angles of the teeth of different parts, so that the dental floss can conveniently enter the tooth gaps and clean the tooth gaps.

In order to implement the adjustability of the included angle δ, a thread structure is adopted in this embodiment. Of course, the adjustment of the included angle β can be implemented by adopting a passive mechanical structure, such as a concave-convex snap fit structure, or a moderate interference fit structure or the like, or by an active electric control manner, such as transmission of a motor or the like.

Compared with Embodiment 1, the included angle δ between the floss 11 of the dental floss 100 and the center line of the head 21-1 of the housing of the oral viewer 200 may be adjusted by rotating the thread 13-3 in this embodiment; and during use, the included angle δ may be adjusted in time according to the angle of the tooth gap in different positions so as to better adapt to different tooth gap angles, and thus, the use process is more convenient.

The present application discloses a technical solution that the dental floss 100 and the oral viewer 200 are detachably connected together. In this connection manner, the connecting mechanism 300 may be a separate component, and is respectively connected with the dental floss 100 and the oral viewer 200 to connect the dental floss 100 and the oral viewer 200 into an integral body. The connecting mechanism 300 may also be manufactured as a whole with the dental floss 100 or the oral viewer 200, and then connected with the oral view 200 or the dental floss 100 to form an integral body. Therefore, the detachable connection between the dental floss 100 and the oral viewer 200 can be implemented as long as the connecting mechanism 300 implements a detachable mechanical connection with one of the dental floss 100 or the oral viewer 200.

The embodiments of the present application only specifically disclose the connecting mechanism 300 of a concave-convex snap fit and a threaded connection manner. The mechanical connecting mechanism may also be a sliding slot connection, or a pin connection, or a key connection, or a screw connection, or a buckle connection, or a hook connection, or an interference fit connection, or the like. Of course, those skilled in the art can select other mechanical connection manners without departing from the protection scope of the present application.

In addition, the dental floss 100 and the oral viewer 200 may also be undetachably connected together through the connecting mechanism 300 into an integral body. Corresponding structures will not be specifically described in the embodiments of the present application, but they do not depart from the protection scope of the present application.

Embodiment 3: Sleeve Sliding Bar Type Visual Oral Forceps According to the Present Disclosure With reference to FIG. 11 to FIG. 12-8, the visual oral forceps 902 of the present embodiment include oral forceps 400, an oral viewer 200 and a connecting mechanism 300.

The oral forceps 400 include jaws 41, an opening/closing mechanism 42 and a mounting base 43. The jaws 41 of the oral forceps 400 include a left arm 41-1 and a right arm 41-2, a fit clamping structure is formed between the left arm 41-1 and the right arm 41-2, and such jaws can hold food residues, fish bones or other oral foreign objects. The opening/closing mechanism 42 capable of controlling a closing or opening movement of the jaws 41 is arranged on the mounting base 43.

In this embodiment, the jaws 41 of the oral forceps 400 are made of an elastic material, and the jaws 41 remains in an open state when no external force is applied; the rear end of the jaws 41 is fixed on the mounting base 43 and is detachably connected with the oral viewer 200 together through the connecting mechanism 300; the front end of the jaws 41 passes through a hole 42-2-1 of the sleeve 42-2 of the opening/closing mechanism 42; by pushing the push rod 42-1 of the opening/closing mechanism 42 forward, the sleeve 42-2 moves toward the front end of the jaws 41 to close the jaws 41 until the left arm 41-1 and the right arm 41-2 of the jaws 41 fit together; and by pushing the push rod 42-1 of the opening/closing mechanism 42 backward, the sleeve 42-2 moves toward the rear end of the jaws 41, and the left arm 41-1 and the right arm 41-2 of the jaws 41 are opened under the action of the elastic force of the jaws 41.

The elastic material adopts a medical elastic material, including but not limited to: an elastic polymer material, an elastic metal material, a metal-plastic composite elastic material and the like, such as a polyurethane material (PU), a polypropylene material (PP), an elastic stainless steel, shape memory metal and the like.

The jaws 41 of the oral forceps 400 of this embodiment is made of elastic medical stainless steel or a titanium-nickel shape memory alloy.

With reference to FIG. 12-3, FIG. 12-4, FIG. 12-7 and FIG. 13, the jaws 41 of the oral forceps 400 are provided with bite teeth 41-3 which fit each other, thereby increasing the bite force.

Figure 11:
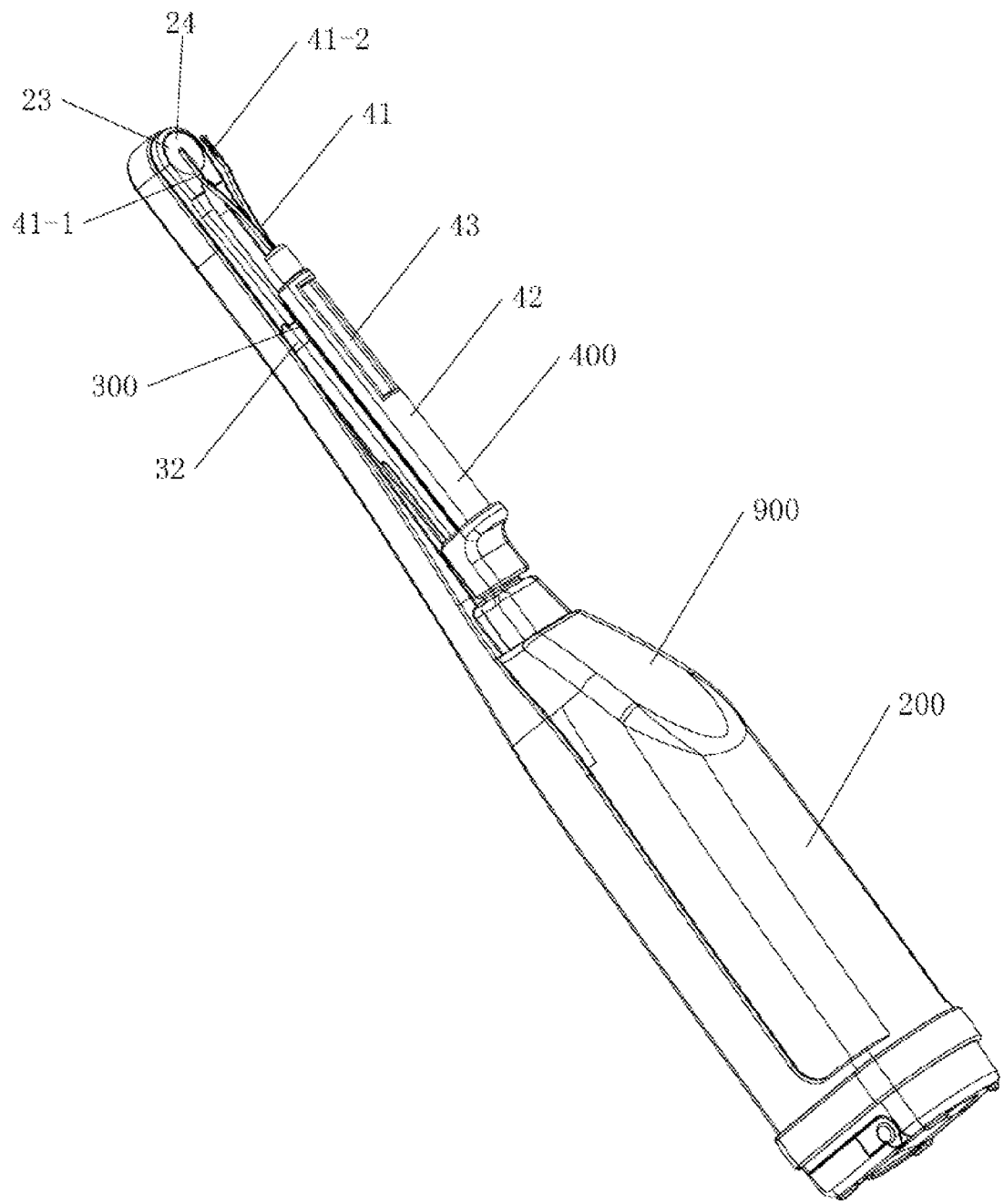
FIG. 11 is a three-dimensional structure diagram of visual oral forceps according to the present disclosure.
Figures 8, 11:
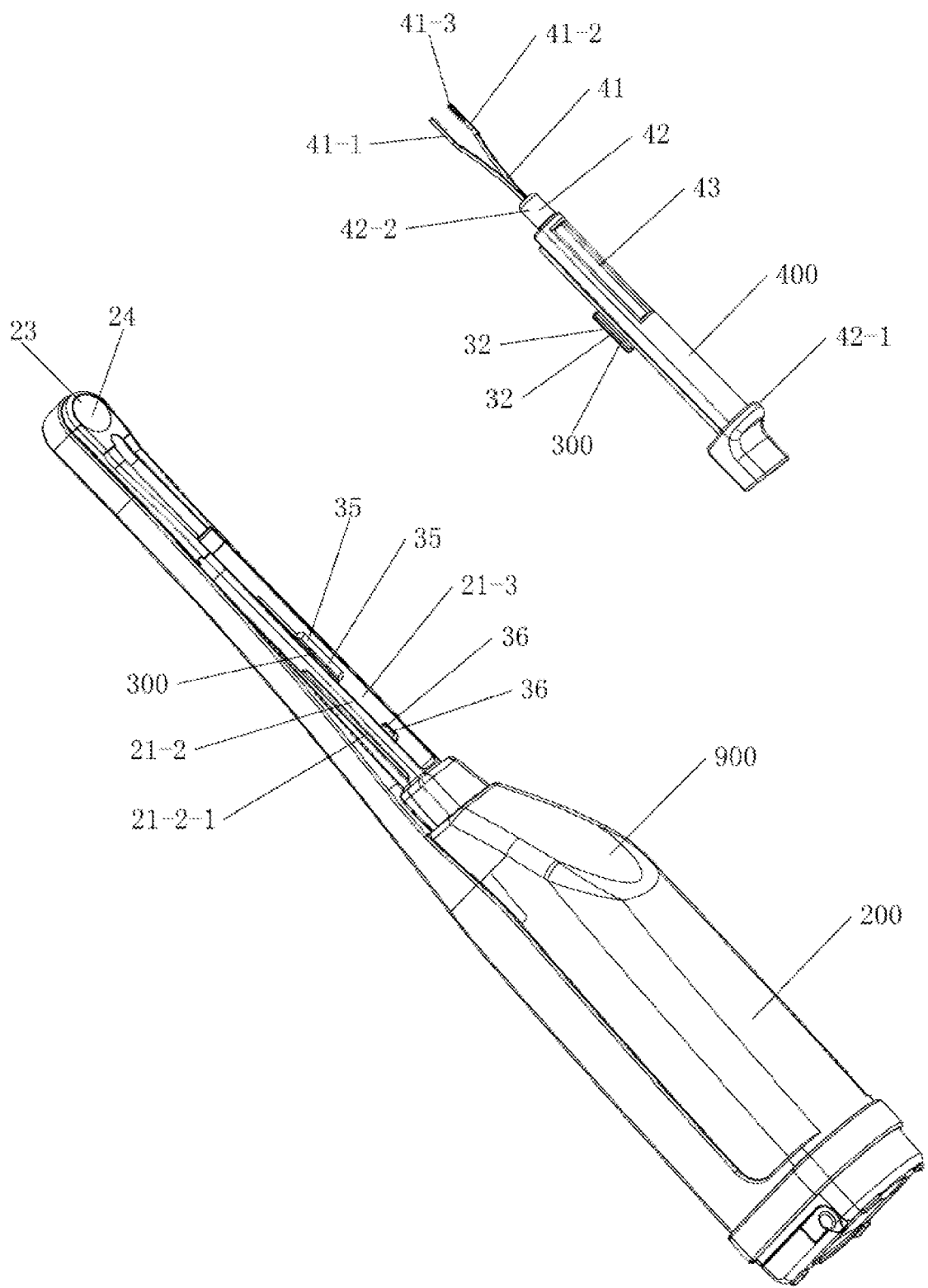
Figure 12:
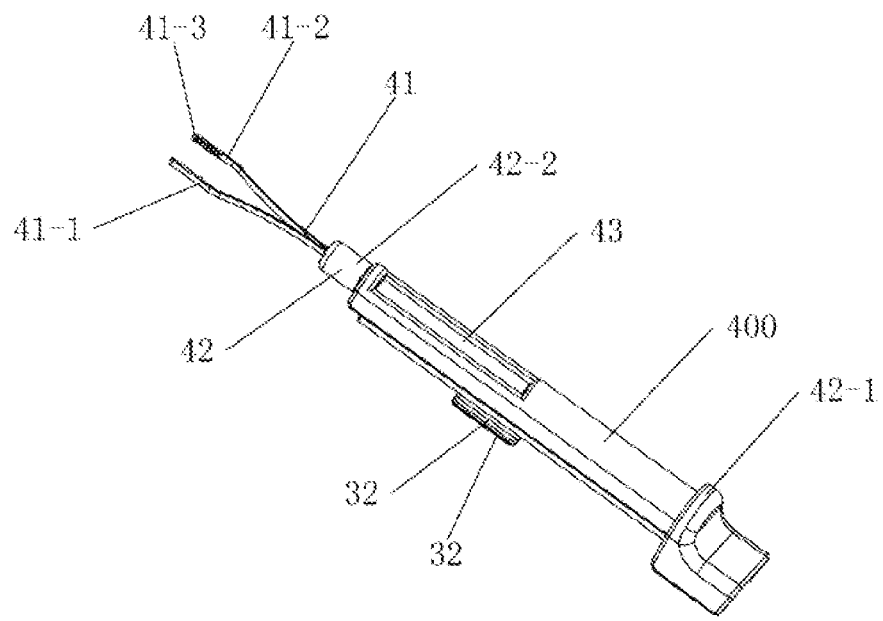
FIG. 12 is a three-dimensional structure diagram of the visual oral forceps according to the present disclosure when the oral forceps are in the opened state.
Figures 1, 12:
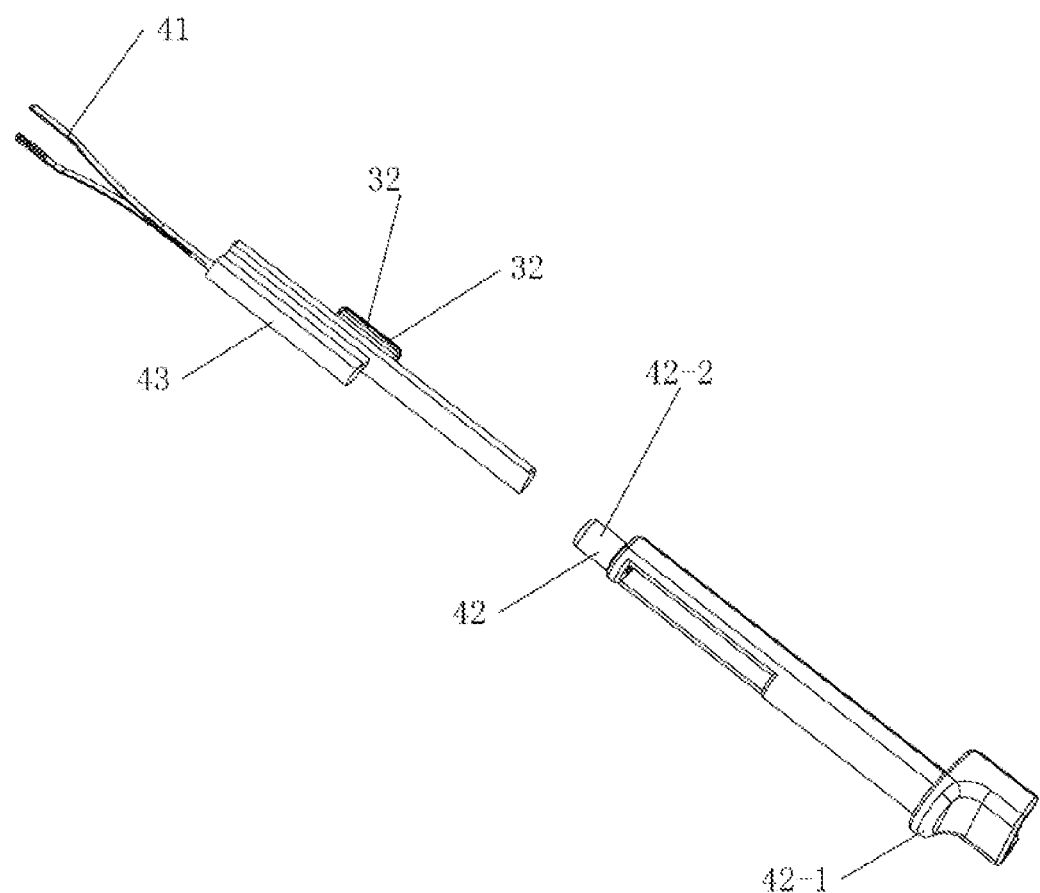
Figures 2, 12:
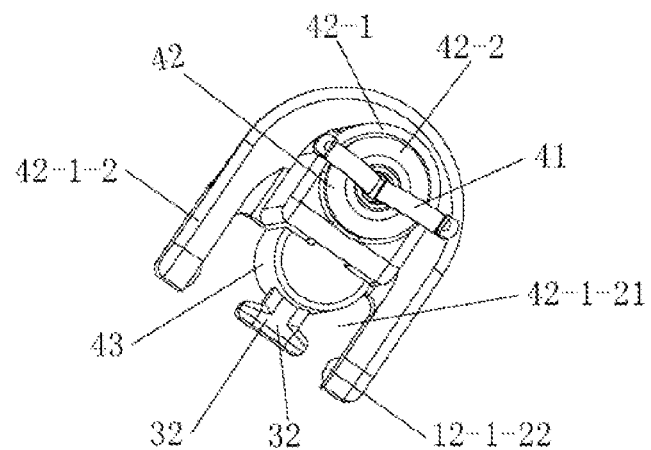
Figures 3, 12:
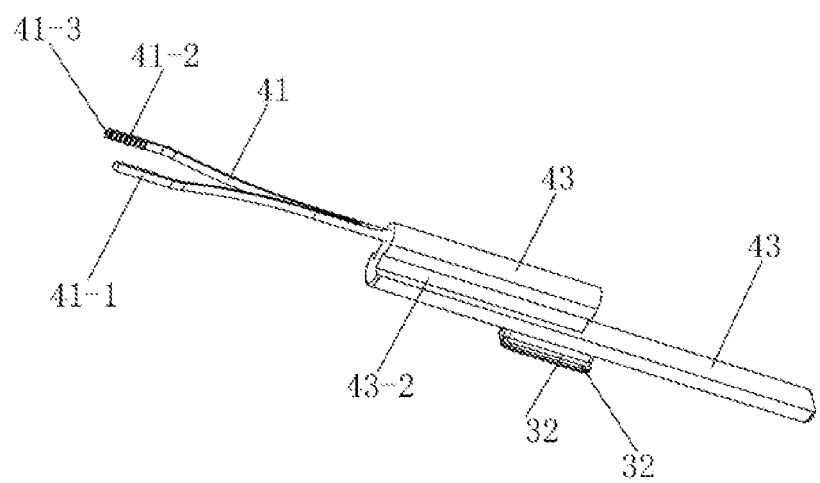
Figures 4, 12:
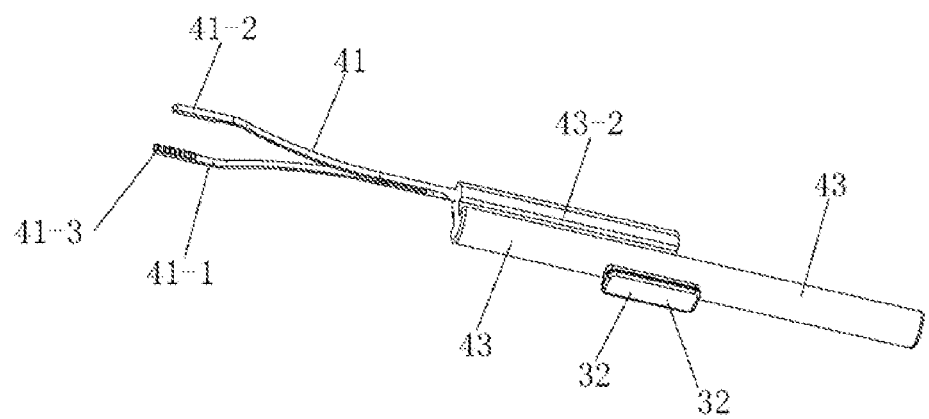
Figures 5, 12:
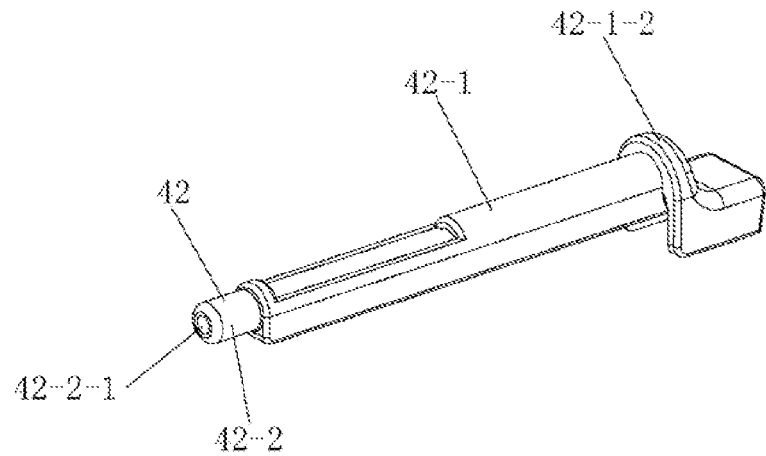
Figures 6, 12:
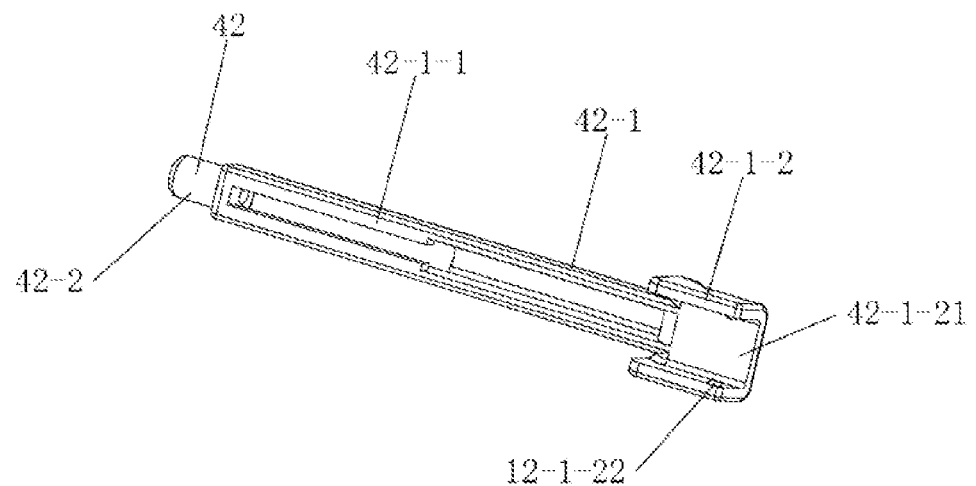
Figures 7, 12:
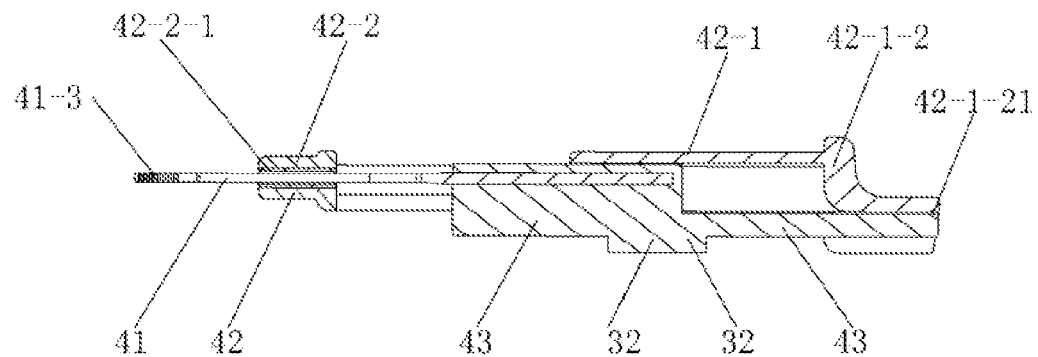
Figures 8, 12:
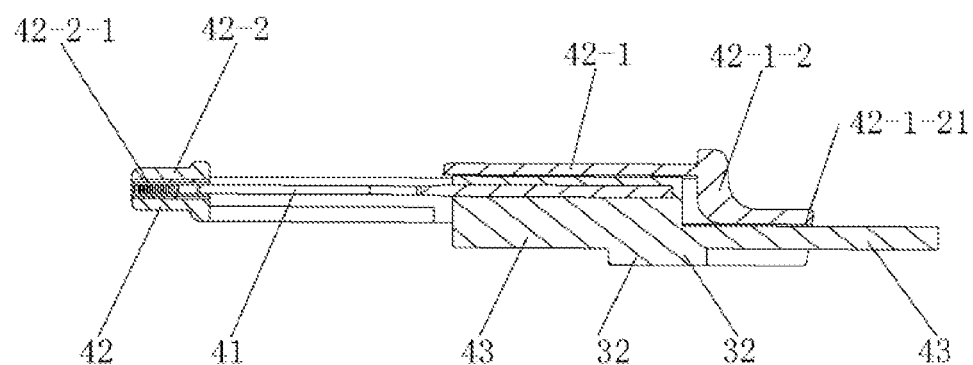

With reference to FIG. 12-3 and FIG. 12-4, and with reference to FIG. 11-5 and FIG. 11-7, the mounting base 43 of the oral forceps 400 is provided with a locating block 32 used to be connected with the oral viewer 200.

With reference to FIG. 12-3, FIG. 12-4, FIG. 12-7 and FIG. 12-8, in this embodiment, the jaws 41 of the present disclosure are firstly made of the titanium-nickel shape memory alloy by a universal processing technique. Then, according to the universal technique of the metal-plastic encapsulation universal technique, the tail of the jaws 41 is fixed into the mounting base 43, so that the left arm 41-1 and the right arm 41-2 of the jaws 41 are exposed to the front end of the mounting base 43, and are maintained in an opened state when no external force is applied.

The mounting base 43 is provided with a sliding slot 43-2, the sliding slot 43-2 and a sliding block 42-1-1 on the push rod 42-1 of the opening/closing mechanism 42 form a slide fit, and the sliding block 43-1-1 can slide along the sliding slot 43-2.

The mounting base 43 is provided with the locating block 32, and the locating block 32 may be embedded in the locating slot 35 of the housing 21 of the oral viewer 200; and the mounting base 43 may be embedded in the oral forceps mounting slot 21-3 of the housing 21, and the tail of the mounting base 43 abuts against and is fixed by the clamping block 36 of the housing 21 of the oral viewer 200.

With reference to FIG. 12-5, FIG. 12-6, FIG. 12-7 and FIG. 12-8, the opening/closing mechanism 42 is made of plastics, and may be injection-molded according to a plastic universal technique. The opening/closing mechanism 42 includes the push rod 42-1 and the sleeve 42-2. The sleeve 42-2 is provided with a hole 42-2-1, and the jaws 41 can pass through the hole 42-2-1. The rear end of the push rod 42-1 is provided with a push block 42-1-2, and the push block 42-1-2 is convenient for a finger to move the opening/closing mechanism 42 back and forth. The push block 42-1-2 is provided with the sliding slot 42-1-21, and the sliding slot 42-1-21 can fit a supporting rib plate 21-2 on the housing 21 of the oral viewer 200. The inner side of the sliding slot 42-1-21 is provided with the sliding block 42-1-22, and the sliding block 42-1-22 may be embedded in a locating sliding slot 21-2-1 on the outer side of the supporting rib plate 21-2 of the housing 21 of the oral viewer 200, and slide back and forth along the locating sliding slot 21-2-1.

When assembling, the left arm 41-1 and the right arm 41-2 at the front end of the jaws 41 are closed, the front end of the jaws 41 passes through the through hole 42-2-1 of the sleeve 42-2, the sliding block 42-1-1 is slid in along the sliding slot 43-2, and the opening/closing mechanism 42 is mounted on the mounting base 43, thereby completing the assembly of the oral forceps 400.

With reference to FIG. 11-5, FIG. 11-7 and FIG. 1-3, the oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; and the lighting system 23, the viewing system 24, the power supply system 22 and the switch 26 are connected together through the circuit system 25.

The viewing system 24 is a camera system 24-1, and the camera system 24-1 includes a camera 24-1-1, a data processing and output system 24-1-2, a circuit system 25 and a power supply system 22.

Figure 16:
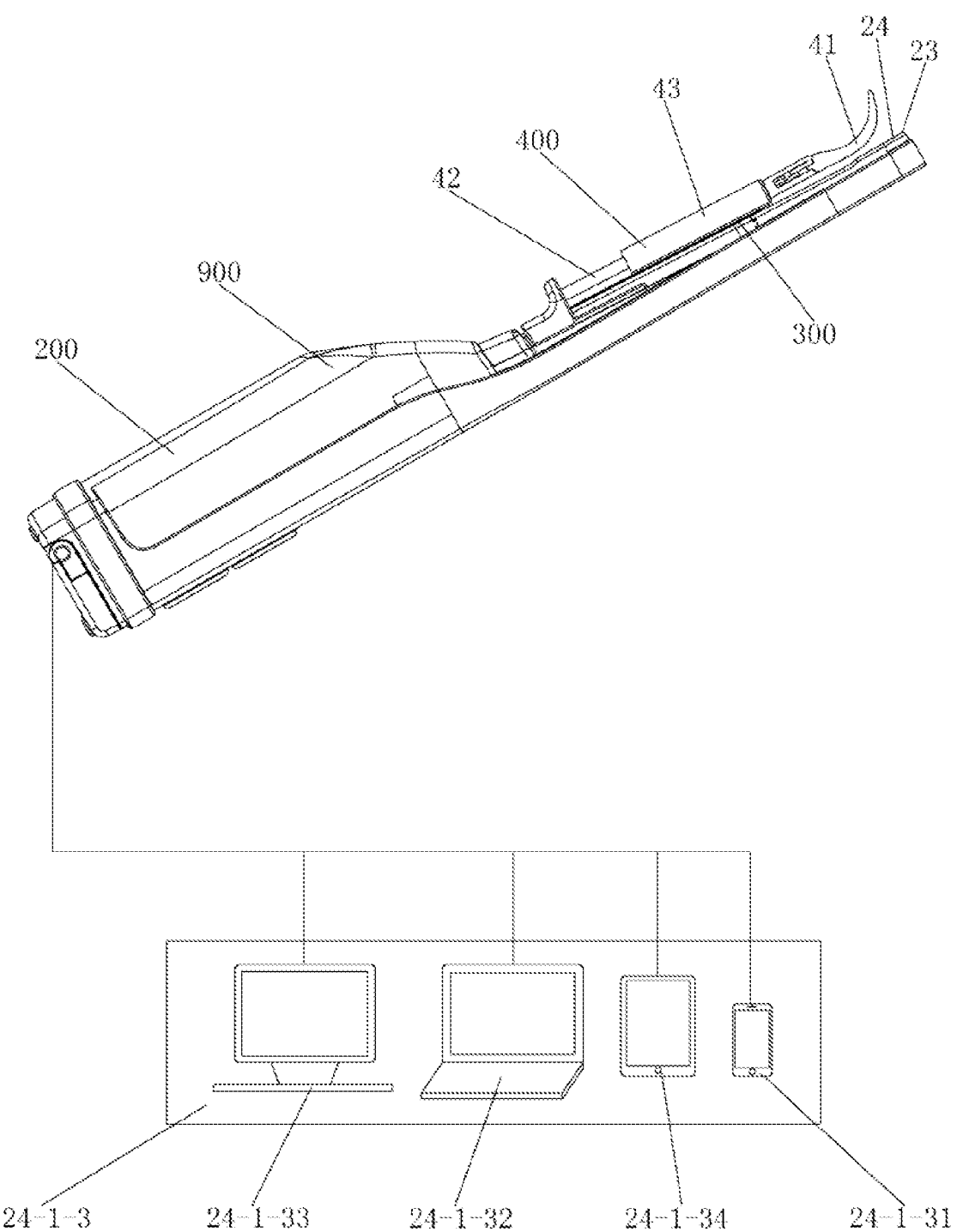
FIG. 16 is a structure diagram of visual oral forceps according to the present disclosure when connected with the display device in a wired manner.
Figure 17:
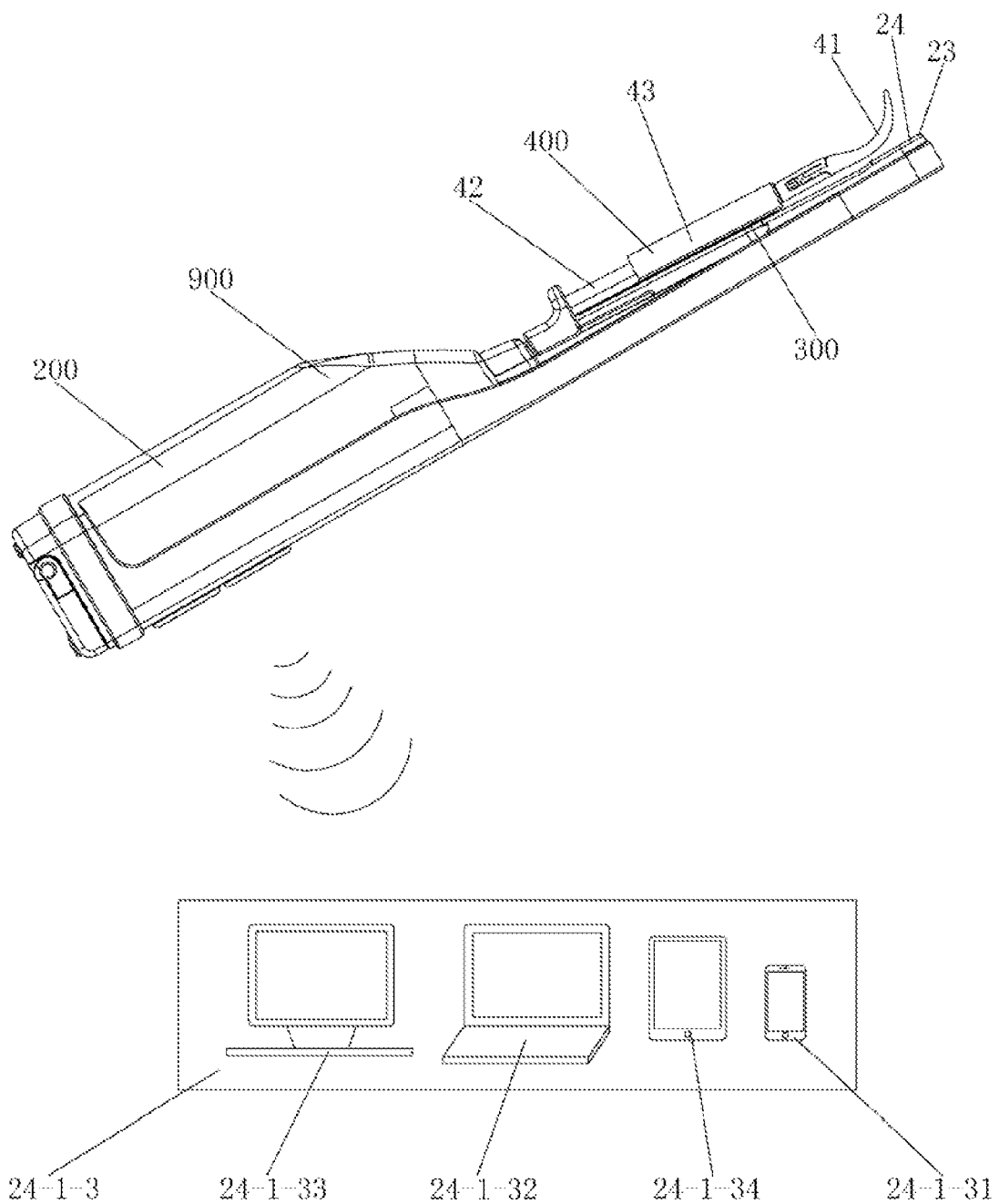
FIG. 17 is a structure diagram of the oral forceps according to the present disclosure when connected with the display device in a wireless manner.
Figure 18:
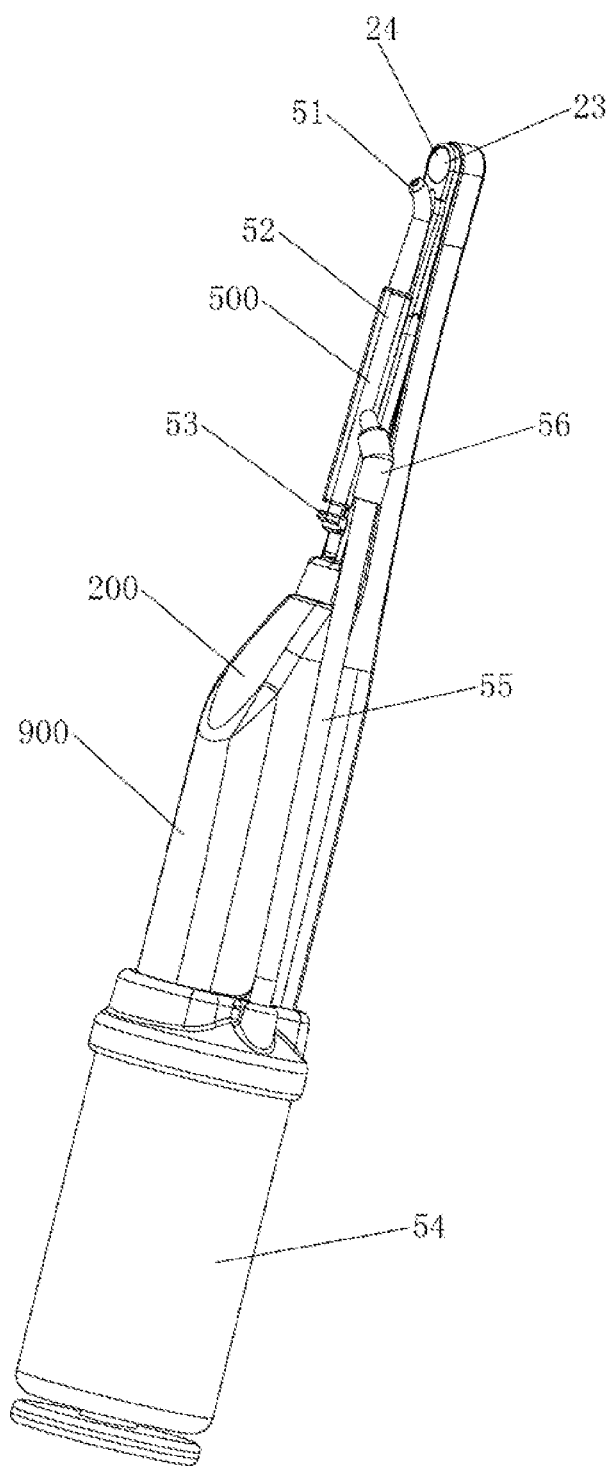
FIG. 18 is a three-dimensional structure diagram of visual oral irrigator according to the present disclosure.
Figures 1, 18:
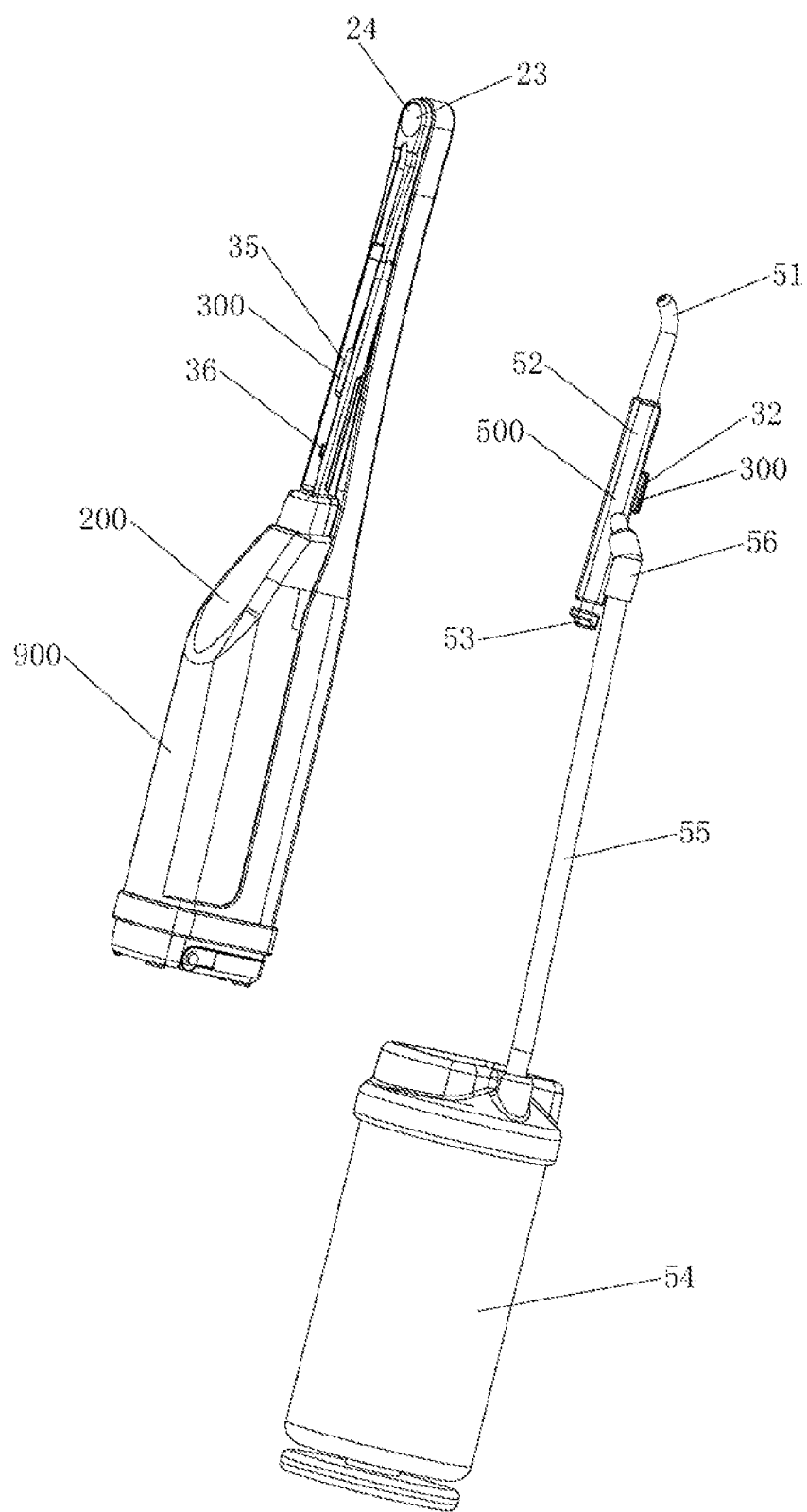
Figure 19:
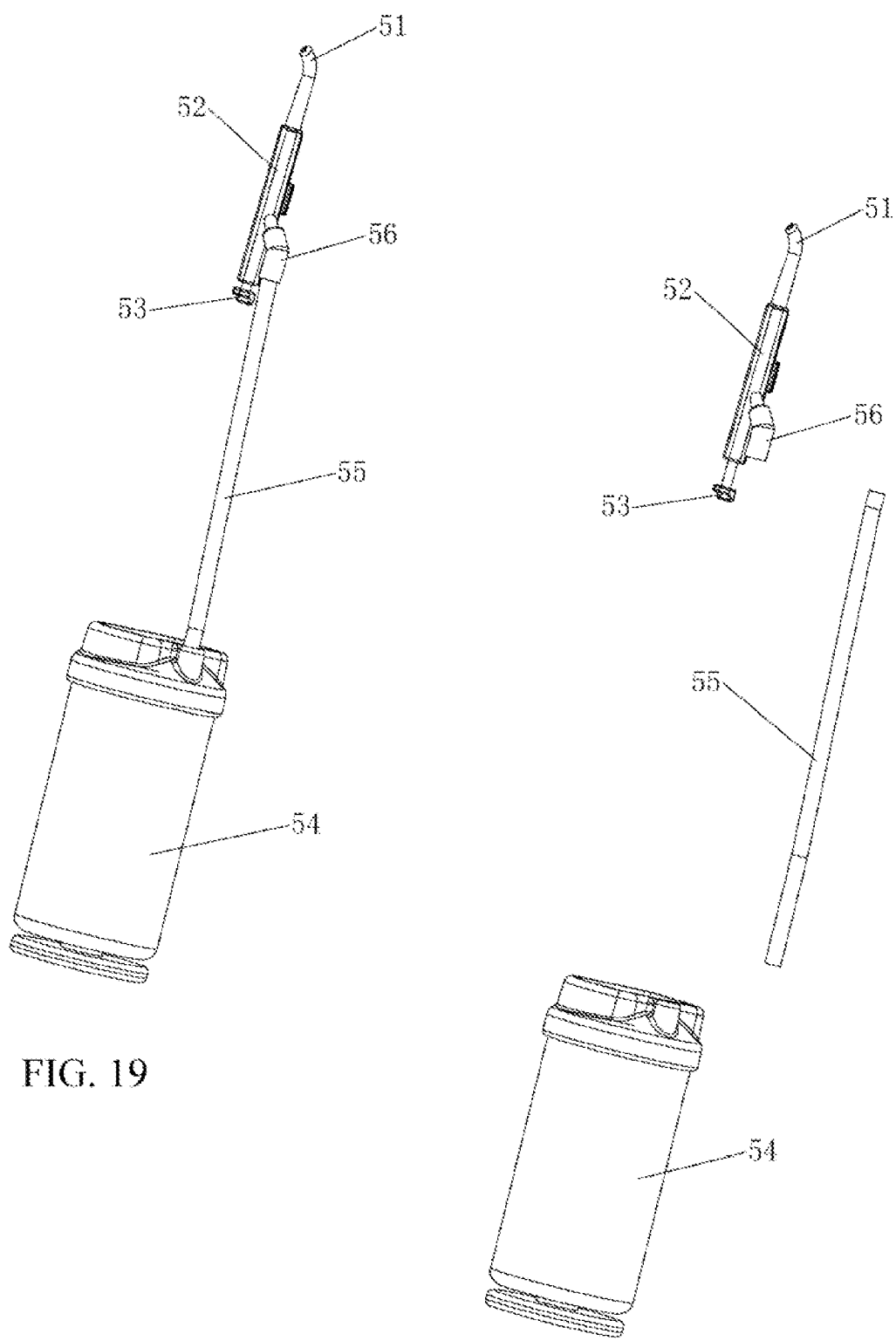
FIG. 19 is a three-dimensional structure diagram of an oral irrigator of the visual oral irrigator according to the present disclosure.
Figures 1, 19:
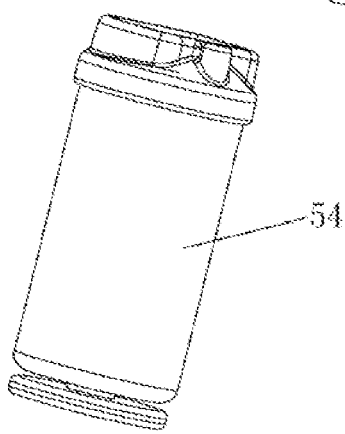
Figure 20:
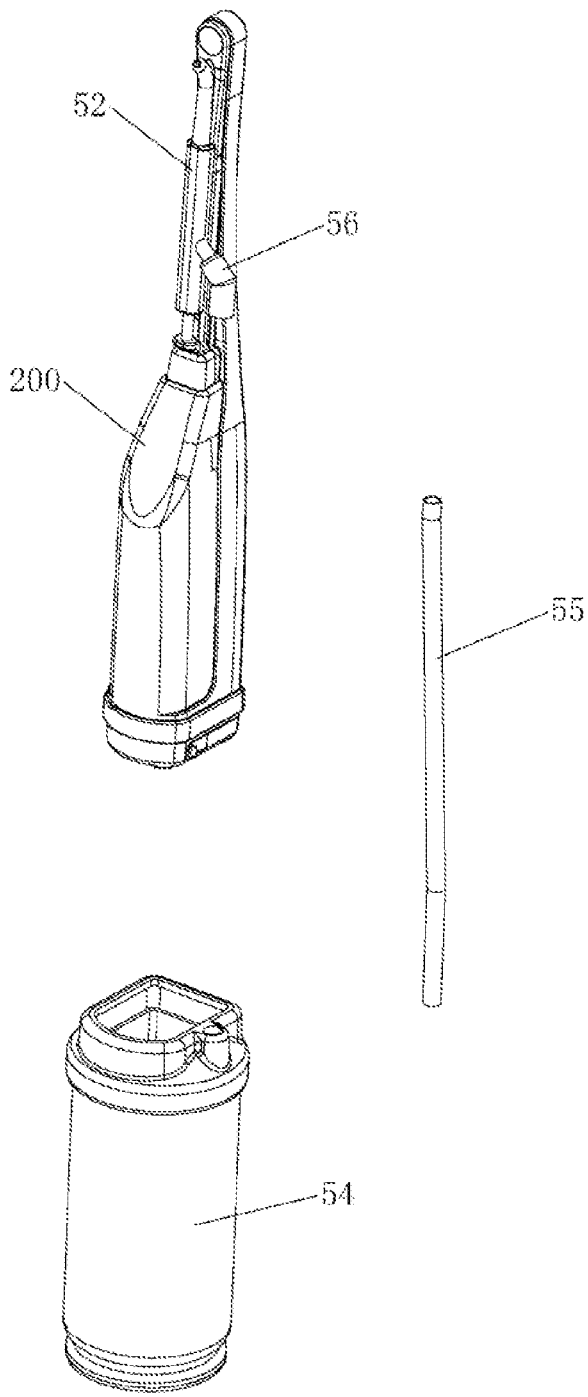
FIG. 20 is a mounting relationship diagram of the visual oral irrigator according to the present disclosure.
Figure 21:
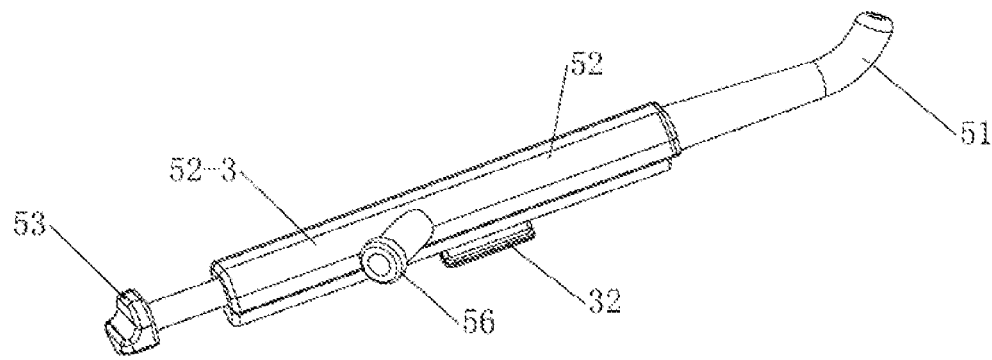
FIG. 21 is a three-dimensional structure diagram of a spray gun of the visual oral irrigator according to the present disclosure.
Figures 1, 21:
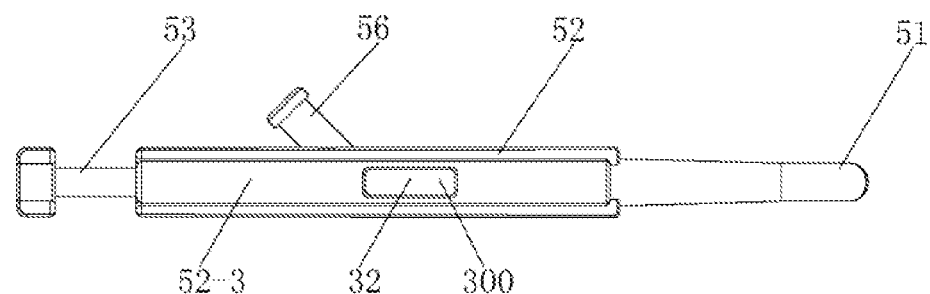
Figures 2, 21:
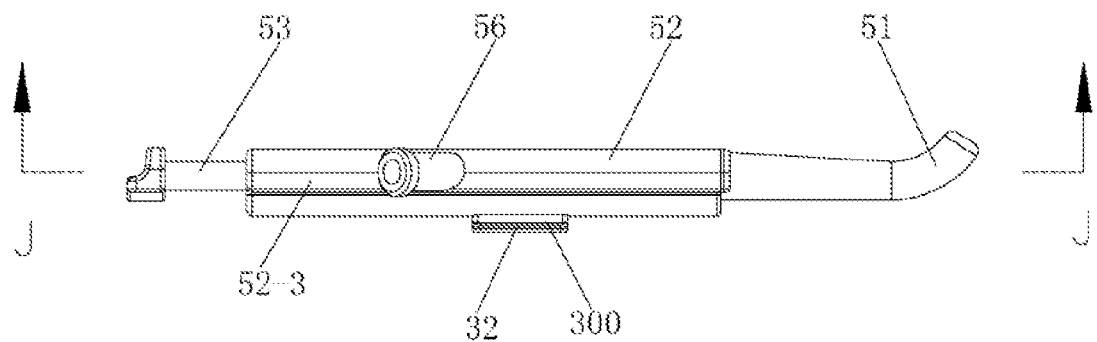

With reference to FIG. 16 and FIG. 17, video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device 24-1-33, or a television 24-1-34, or any other display device.

The lighting system 23 is arranged around the camera 24-1-1. In order to increase lighting, more LED lights may also be arranged on the housing 21 of the oral viewer 200 for adjusting the lighting brightness.

The oral viewer 200 adopts a waterproof design, thereby facilitating cleaning and operation.

The oral forceps 400 are mounted on the oral viewer 200 through the connecting mechanism 300, so that the jaws 41 is within the visual field of the viewing system 24 of the oral viewer 200, thereby facilitating viewing.

The housing 21 of the oral viewer 200 is provided with a locating slot 35 and a clamping block 36; the locating block 32 of the oral forceps 400 may be embedded in the locating slot 35, and the clamping block 36 can prevent the mounting base 43 of the oral forceps 400 from sliding backward; the coordination of the locating block 32, the locating slot 35 and the clamping block 36 constitutes the connecting mechanism 300; and the locating block 32 is matched with the locating slot 35, thereby limiting the up-and-down and left-and-right movements of the oral forceps 400 on the housing 21 of the oral viewer 200. The clamping block 36 abuts against the tail of the mounting base 43, so that the mounting base 43 is embedded in the mounting slot 21-3 of the mounting base 43, and thus, the forward and backward movement of the oral forceps 400 is limited, thereby mounting and fixing the oral forceps 400 to the housing 21 of the oral viewer 200. The clamping block 36 is pressed down to release the limit effect of the clamping block 36 on the tail of the mounting base 43, so that the mounting base 43 can be withdrawn backward, and the oral forceps 400 can be removed from the oral viewer 200.

In addition, those skilled in the art can perform various specific product designs according to the technical solutions disclosed in the present disclosure, and especially, can perform many specific designs on the shape and structure of the oral forceps 400 without departing from the protection scope of the present patent.

For example, the jaws 41 of the oral forceps 400 have a curvature 41-4 that meets the requirements of the human oral cavity, thereby facilitating the capture of foreign objects, with reference to FIG. 14 and FIG. 15.

Embodiment 4: A Hinged Visual Oral Forceps According to the Present Disclosure

Figure 13:
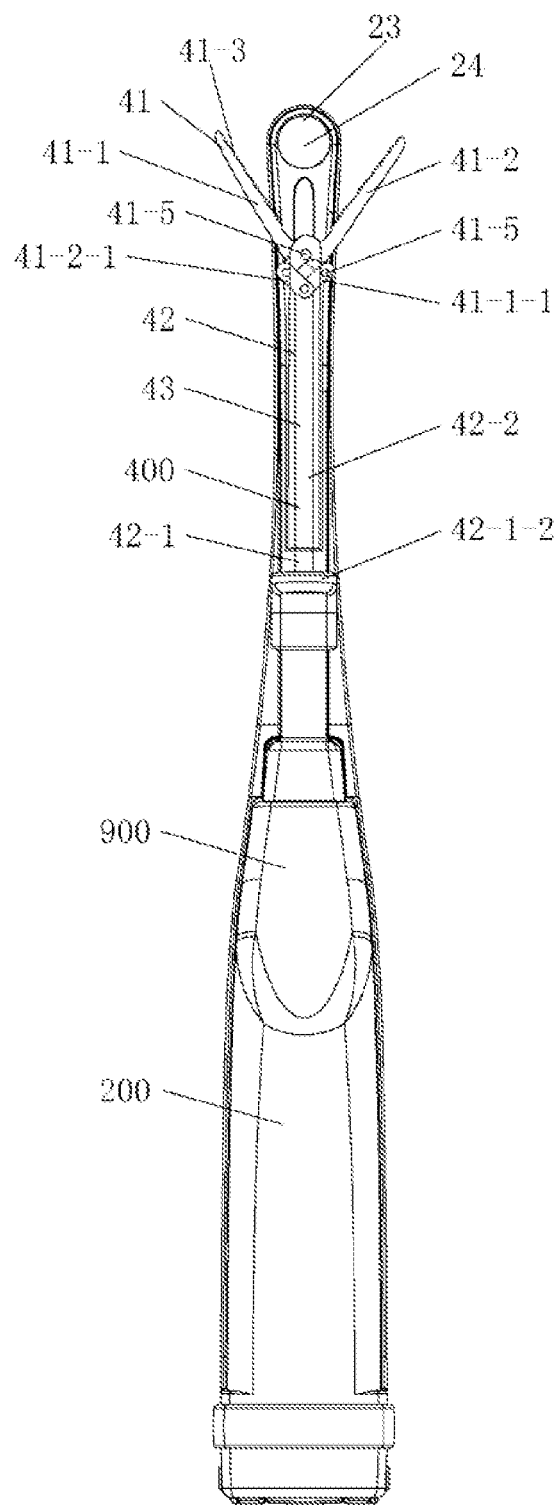
FIG. 13 is a structure diagram of a hinged visual oral forceps according to the present disclosure in the opened state.
Figure 1:
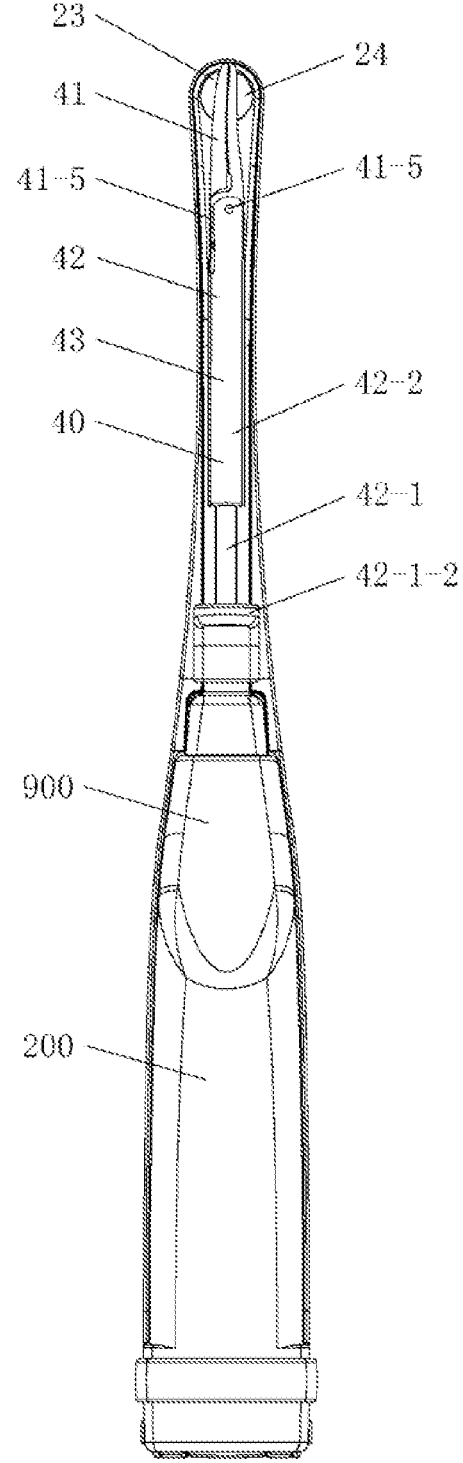

With reference to FIG. 13, FIG. 13-1 and FIG. 15, in this embodiment, the jaws 41 of the oral forceps 400 adopts a hinged structure, and are provided with 4 pins 41-5 which are arranged in a prismatic manner. The left arm 41-1 and the right arm 41-2 of the jaws 41 are movably mounted on the sleeve 42-2 through the pins 41-5 at the front end; and the sleeve 42-2 is arranged on the mounting base 43 and is detachably connected with the oral viewer 200 together through the connecting mechanism 300. The rear end of the left arm 41-1 and the rear end of the right arm 41-2 of the jaws 41 are respectively movably connected with a left arm connecting rod 41-1-1 and a right arm connecting rod 41-2-1 through the pins 41-5 on the left and right sides. The rear ends of the left arm connecting rod 41-1-1 and the right arm connecting rod 41-2-1 are connected with the front end of the push rod 42-1 of the opening/closing mechanism 42 together through the pins 41-5 which are distributed at the rear end in a prismatic manner. And when the push rod 42-1 is pushed backward, the left arm 41-1 and the right arm 41-2 of the jaws 41 rotate around the pin 41-5, and the left arm 41-1 and the right arm 41-2 of the jaws 41 are closed until they fit together; and when the push rod 42-1 is pushed forward, the left arm 41-1 and the right arm 41-2 of the jaws 41 rotate around the pin 41-5, and the left arm 41-1 and the right arm 41-2 of the jaws 41 are opened.

The steps of detachably mounting the hinged visual oral forceps 400 of this embodiment to the housing 21 of the oral viewer oral viewer through the connecting mechanism 300 are basically the same as those of Embodiment 1, which will not be repeated herein.

In addition, the embodiments only enumerate 2 specific structures of the visual oral forceps of the present disclosure in which the oral forceps 400 of the present disclosure are controlled to be opened or closed in a push-and-pull manner. The adoption of a button type opening/closing mechanism to control the opening or closing of the oral forceps 400 is also a good practical option; when the button is pressed down, the jaws of the oral forceps 400 may be closed to capture the foreign object in the oral cavity; and when the button is released, the jaws of the oral forceps 400 may naturally open, thereby facilitating the capture of the objects.

The opening/closing mechanism 42 of the oral forceps 400 includes, but is not limited to, a sleeve sliding bar opening/closing mechanism, or a hinge opening/closing mechanism, or a lever regulation opening/closing mechanism, or a button regulation opening/closing mechanism, or a spring regulation opening/closing mechanism, or a push-and-pull regulation opening/closing mechanism, or a rotation regulation opening/closing mechanism. Those skilled in the art can perform various specific product designs according to the technical solutions disclosed in the present disclosure without departing from the protection scope of the present patent.

The connecting mechanism 300 is a detachable mechanical connecting mechanism; the connecting mechanism 300 may be a separate component, and may be arranged on the oral forceps 400 or arranged on the oral viewer 200; alternatively, the connecting mechanism 300 may also be a combined mechanical connecting mechanism formed by arranging a part of the detachable mechanical connecting mechanism on the oral forceps 400 and the other part on the oral viewer 200.

The mechanical connecting mechanism includes: a concave-convex snap fit connection, or a sliding slot connection, or a pin connection, or a key connection, or a threaded connection, or a screw connection, or a buckle connection, or a hook connection, or an interference fit connection, or any other connecting mechanism. Those skilled in the art can perform various specific product designs according to the technical solutions disclosed in the present disclosure without departing from the protection scope of the present patent.

The visual oral forceps 902 of the present disclosure include oral forceps 400, an oral viewer 200 and a connecting mechanism 300. The oral forceps 400 include jaws 41, an opening/closing mechanism 42 and a mounting base 43; the jaws 41 of the oral forceps 400 include a left arm 41-1 and a right arm 41-2, and a fit clamping structure is formed between the left arm 41-1 and the right arm 41-2; the opening/closing mechanism 42 capable of controlling a closing or opening movement of the jaws 41 is arranged on the mounting base 43. The oral forceps 400 and the oral viewer 200 are detachably connected together through the connecting mechanism 300. Since the oral viewer 200 includes the lighting system 23 and the viewing system 24 and transmits the viewed video to a smartphone or any other display device in a wired or wireless manner, by using the visual oral forceps 902 of the present disclosure, the food residues, or fish bones or other foreign objects can be taken out of the oral cavity safely and conveniently under direct vision, and the user can view the taking out process and the effect after taking out, and perform picture or video recording.

Embodiment 5: A Visual Oral Irrigator According to the Present Disclosure

With reference to FIG. 18 to FIG. 22-3, the visual oral irrigator 903 of this embodiment includes an oral irrigator 500, an oral viewer 200 and a connecting mechanism 300.

The oral irrigator 500 includes a spray head 51, a spray gun 52, a control switch 53, a pressure vessel 54, a connecting tube 55 and a union joint 56. The spray head 51 is arranged at the front end of the spray gun 52; the control switch 53 capable of controlling a fluid in the spray gun 52 is arranged on the spray gun 52; and a fluid in the pressure vessel 54 is connected with the spray gun 52 through the connecting tube 55 and the union joint 56.

The oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; and the lighting system 23, the viewing system 24, the power supply system 22 and the switch 26 are connected together through the circuit system 25.

The oral irrigator 500 is mounted on the oral viewer 200 through the connecting mechanism 300.

The spray head 51 is within the visual field of the viewing system 24 of the oral viewer 200. Therefore, during use, the cleaning effect of the position to be cleaned can be viewed in real time, and the use process is more convenient.

The spray head 51 of the oral irrigator 500 has a curvature 51-2 that meets the requirements of the human oral cavity. Especially when it is necessary to clean the molars on the rear side along the outer side of the teeth, the curvature 51-2 can allow the spray head 51 to smoothly reach the molar position, so the use process is more comfortable.

In this embodiment, the control switch 53 adopts a sleeve sliding bar opening/closing mechanism, and the control switch 53 includes a return spring 53-1 and a water inlet 53-2. When the control switch 53 is pushed into the far end, the return spring 53-1 is compressed, the water inlet 53-2 is in an open state, and water stored in the pressure vessel 54 enters the spray gun 52 through the water inlet 53-2 under the action of pressure and is sprayed out from the spray head 51 to clean the teeth and oral cavity. When the control switch 53 is released, the control switch 53 moves to the near end under the action of the elastic force of the return spring 53-1, the water inlet 53-2 is in a closed state, and the spray head 51 of the spray gun 52 does not spray water.

The control switch 53 of the oral irrigator 500 may also be a button regulation opening/closing mechanism, or a rotation regulation opening/closing mechanism, or a solenoid-operated switch or the like. Of course, those skilled in the art may also perform other designs according to the technical solutions disclosed in the present disclosure without departing from the protection scope of the present patent.

The spray gun 52 of the oral irrigator 500 includes a flow channel 52-1 for allowing a fluid to pass therethrough, a housing 52-2 and a mounting base 52-3; the flow channel 52-1 is arranged in the housing 52-2; and the mounting base 52-3 is arranged on the housing 52-2, and the mounting base 52-3 includes a locating block 32 capable of being connected with the oral viewer 200.

The connecting mechanism 300 is a detachable mechanical connecting mechanism; the connecting mechanism 300 may be a separate component, and may be arranged on the oral irrigator 500 or arranged on the oral viewer 200; alternatively, the connecting mechanism 300 may also be a combined mechanical connecting mechanism formed by arranging a part of the detachable mechanical connecting mechanism on the oral irrigator 500 and the other part on the oral viewer 200.

In this embodiment, the mechanical connecting mechanism is a concave-convex snap fit connection. The mechanical connecting mechanism may also be a sliding slot connection, or a pin connection, or a key connection, or a threaded connection, or a screw connection, or a buckle connection, or a hook connection, or an interference fit connection, or the like. Those skilled in the art can perform various specific product designs according to the technical solutions disclosed in the present disclosure without departing from the protection scope of the present patent.

In this embodiment, the housing 21 of the oral viewer 200 is provided with a locating slot 35 and a clamping block 36 which can be connected with the spray gun 52; the locating block 32 on the spray gun 52 may be embedded in the locating slot 35, and the clamping block 36 can prevent the mounting base 52-3 of the spray gun 52 from sliding backward; and the coordination of the locating block 32, the locating slot 35 and the clamping block 36 constitutes the connecting mechanism 300.

Figure 22:
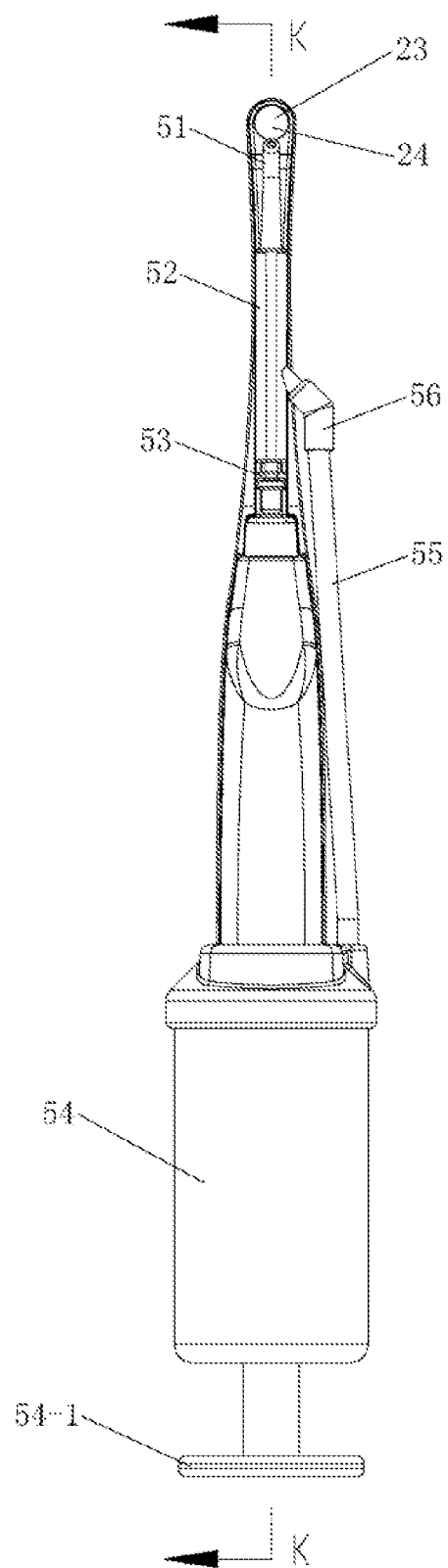
FIG. 22 is a top view of the visual oral irrigator according to the present disclosure.
Figure 1:
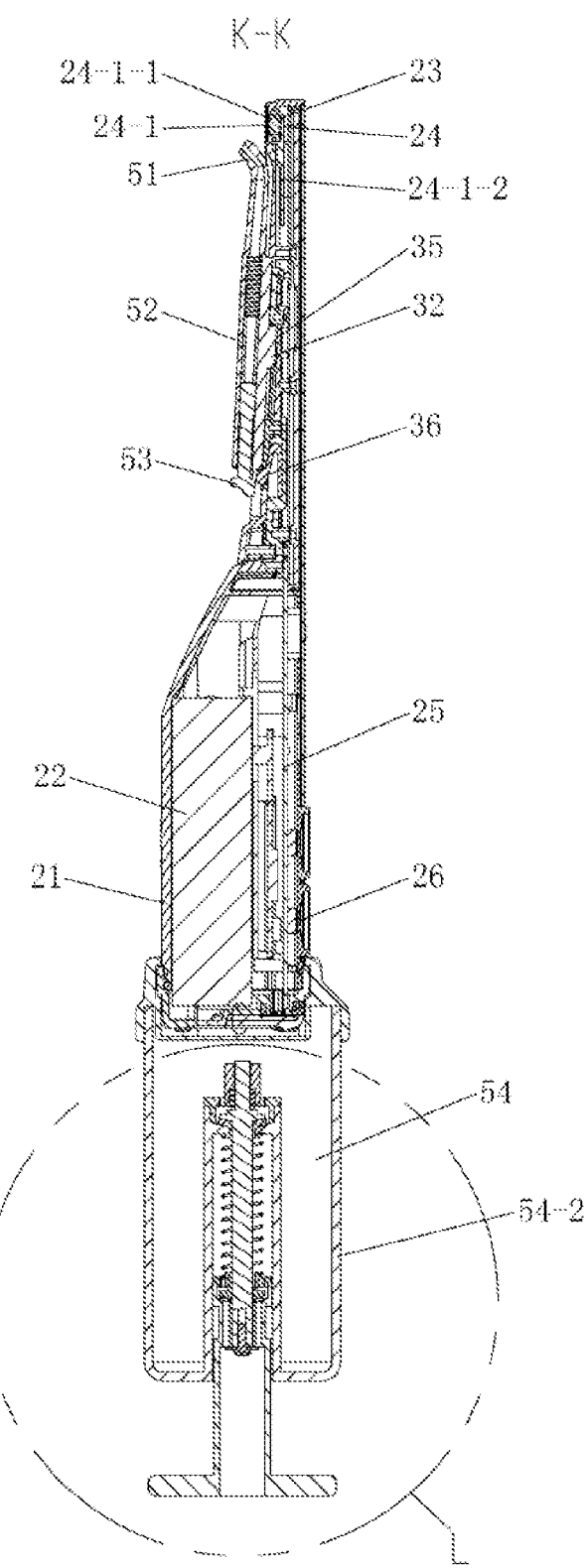
Figures 2, 22:
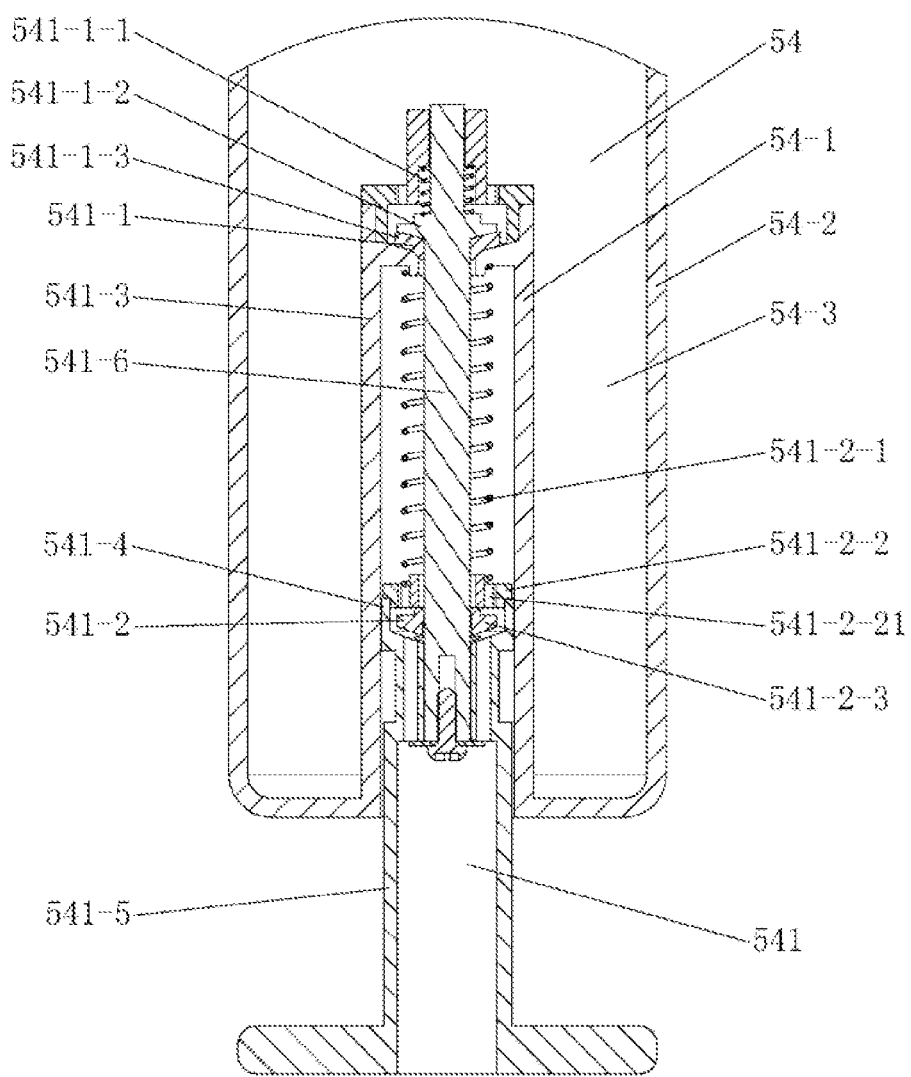
Figures 3, 22:
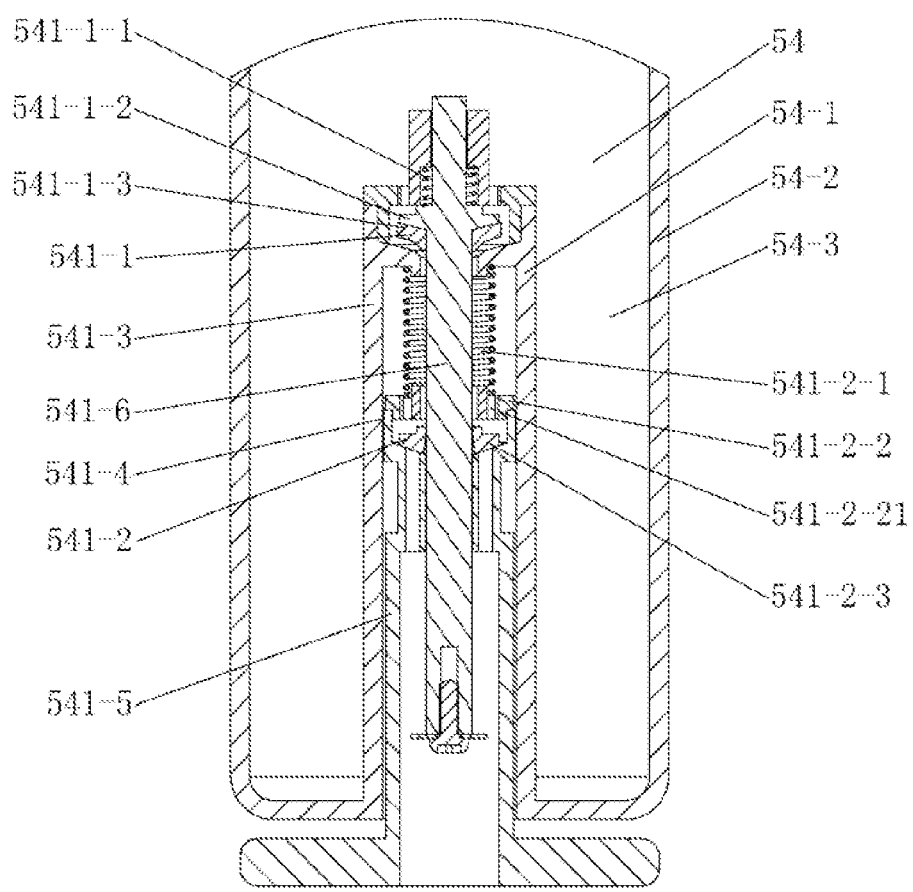

With reference to FIG. 22-1, the viewing system 24 is a camera system 24-1, and the camera system 24-1 includes a camera 24-1-1, a data processing and output system 24-1-2, a circuit system 25 and a power supply system 22.

Figure 25:
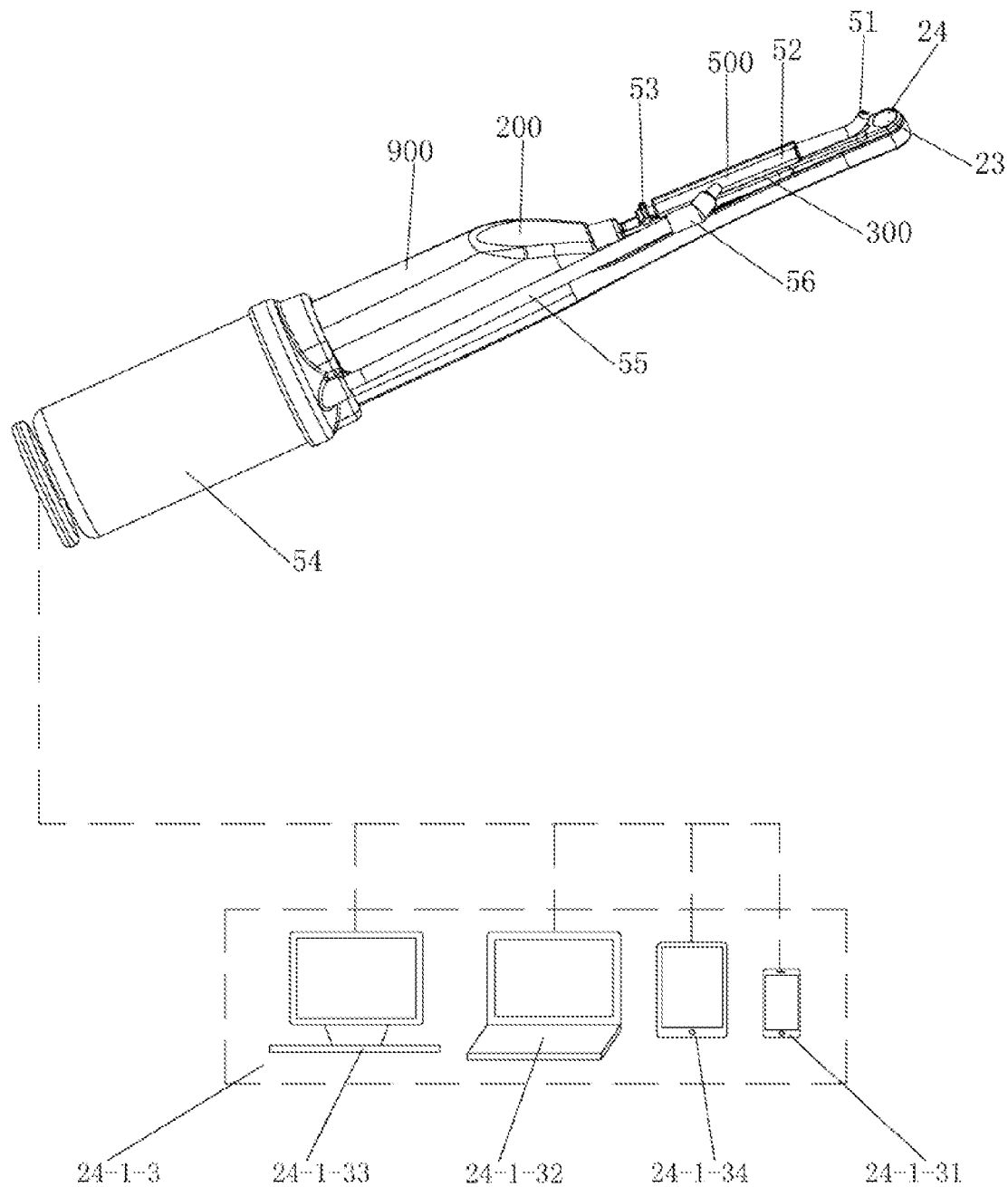
FIG. 25 is a structure diagram of the visual oral irrigator according to the present disclosure when connected with the display device in a wired manner.
Figure 26:
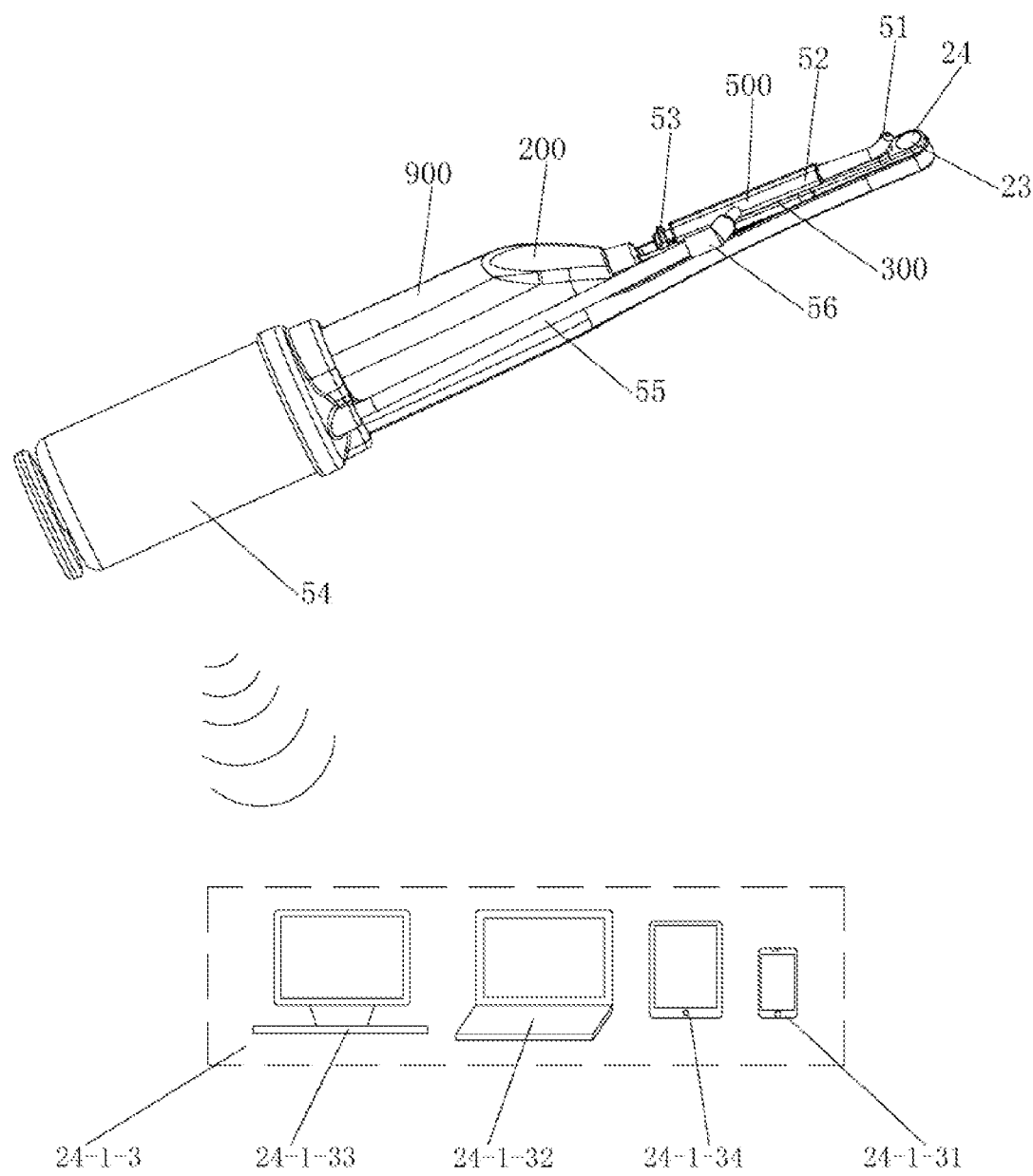
FIG. 26 is a structure diagram of the visual oral irrigator according to the present disclosure when connected with the display device in a wireless manner.

With reference to FIG. 25 and FIG. 26, video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device 24-1-33, or a television 24-1-34.

The lighting system 23 is arranged around the camera 24-1-1. In order to increase lighting, more LED lights may also be arranged on the housing 21 of the oral viewer 200 for adjusting the lighting brightness.

The oral viewer 200 adopts a waterproof design, thereby facilitating cleaning and operation.

The pressure vessel 54 of the oral irrigator 500 includes a pressurizer 54-1, a housing 54-2 and a fluid containing space 54-3; and the pressurizer 54-1 capable of increasing pressure of the fluid containing space 54-3 is mounted on the housing 54-2.

The pressure vessel 54 of the oral irrigator 500 can be mounted at the near end of the oral viewer 200. The pressure vessel 54 is detachably mounted at the near end of the oral viewer 200, thereby facilitating mounting. After use, the pressure vessel 54 can be removed from the near end of the oral viewer 200, thereby facilitating storage and carrying. Those skilled in the art may also perform other designs according to the technical solutions disclosed in the present disclosure, installing the pressure vessel 54 on other parts of the oral viewer 200, such as the middle of the oral viewer 200, or the side of the oral viewer 200 or integrating with the spray gun 52, without departing from the protection scope of present patent.

The pressurizer 54-1 is a mechanical pressurizer, or an electric pressurizer. The mechanical pressurizer generally needs manual pressure increase; but the electric pressurizer can implement automatic pressure increase and keep the pressure stable after the switch is pressed down and turned on. Those skilled in the art may also perform other designs according to the technical solutions disclosed in the present disclosure without departing from the protection scope of the present patent.

In this embodiment, the pressurizer 54-1 is a manual pressurizer 541; the manual pressurizer 541 includes a front check valve 541-1, a rear check valve 541-2, a valve barrel 541-3, a piston 541-4, a push rod 541-5 and a core rod 541-6; the front check valve 541-1, the rear check valve 541-2, the piston 541-4 and the core rod 541-6 are mounted in the valve barrel 514-3; the front end of the push rod 541-5 is provided with the piston 541-4, the front check valve 541-1 is arranged at the far end of the core rod 541-6, and the rear check valve 541-2 is arranged at the near end of the core rod 541-6; the push rod 541-5 can push the piston 541-4 to reciprocate in the valve barrel 541-3; when the push rod 541-5 is pulled outward, the front check valve 541-1 is in a closed state, the fluid in the fluid containing space 54-3 of the pressure container 54 cannot enter the valve barrel 541-3, the rear check valve 541-2 is in an open state, and an external fluid can enter the valve barrel 541-3; when the push rod 541-5 is pushed inward, the rear check valve 541-2 is in a closed state, the fluid in the valve barrel 541-3 is compressed, the pressure in the valve barrel 541-3 increases, under the action of pressure, the front check valve 541-1 is in an open state, and the fluid compressed in the valve barrel 541-3 enters the fluid containing space 54-3 through the front check valve 541-1; and by repeating in this way, the pressure in the fluid containing space 54-3 of the pressure vessel 54 can be continuously increased.

The front check valve 541-1 includes a front return spring 541-1-1, a front check block 541-1-2 and a front seal ring 541-1-3, the front return spring 541-1-1 abuts against the far end of the front check block 541-1-2, and the front seal ring 541-1-3 is arranged at the near end of the front check block 541-1-2; the rear check valve 541-2 includes a rear return spring 541-2-1, a rear check block 541-2-2 and a rear seal ring 541-2-3, the rear return spring 541-2-1 abuts against the far end of the rear check block 541-2-2, and the rear seal ring 541-2-3 is arranged at the near end of the rear check block 541-2-2; and the rear check block 541-2-2 is provided with a through hole 541-2-21 capable of allowing a fluid to pass therethrough.

The spray gun 52 is firstly mounted to the front of the oral viewer 200; then, water is added into the pressure vessel 54, and the pressure vessel 54 is mounted at the near end of the oral viewer 200; and the pressure vessel 54 and the spray gun 52 are connected together by the connecting tube 55 through the union joint 56, thereby completing the work of mounting the oral irrigator 500 on the oral viewer 200.

Before use, the water pressure in the pressure vessel 54 is increased by the pressurizer 54-1. With the viewing system 24 of the oral viewer 200, the teeth or tooth gaps can be clearly seen on a display device such as a mobile phone, and the food residues can be targeted. The control switch 53 is turned on, and water is sprayed out from the spray head 51 of the spray gun 52 to clean the teeth and oral cavity under direct vision.

The visual oral irrigator 903 of the present disclosure includes an oral irrigator 500, an oral viewer 200 and a connecting mechanism 300; the oral irrigator 500 includes a spray head 51, a spray gun 52, a control switch 53, a pressure vessel 54, a connecting tube 55 and a union joint 56; the spray head 51 is arranged at the front end of the spray gun 52; the control switch 53 is arranged on the spray gun 52; and a fluid in the pressure vessel 54 is connected with the spray gun 52 through the connecting tube 55 and the union joint 56. The oral irrigator 500 is mounted on the oral viewer 200 through the connecting mechanism 300. The spray head 51 of the spray gun 52 is within the visual field of the viewing system 24 of the oral viewer 200. The pressure vessel 54 of the oral irrigator 500 includes a pressurizer 54-1, a housing 54-2 and a fluid containing space 54-3. The water pressure in the pressure vessel 54 is increased by the pressurizer 54-1, the control switch 53 is turned on, water is sprayed out from the spray head 51 of the spray gun 52, and the user can clean the teeth and the oral cavity under direct vision, and perform picture and video recording of the cleaning process.

The visual oral irrigator 903 of the present disclosure is convenient to use, can be used for clearly viewing the tooth gaps, gingivae, dental crowns and oral mucosa, and can also be used for viewing the position of food residues in real time and cleaning the food residues under direct vision, so the use process is secure and convenient.

Figure 23:
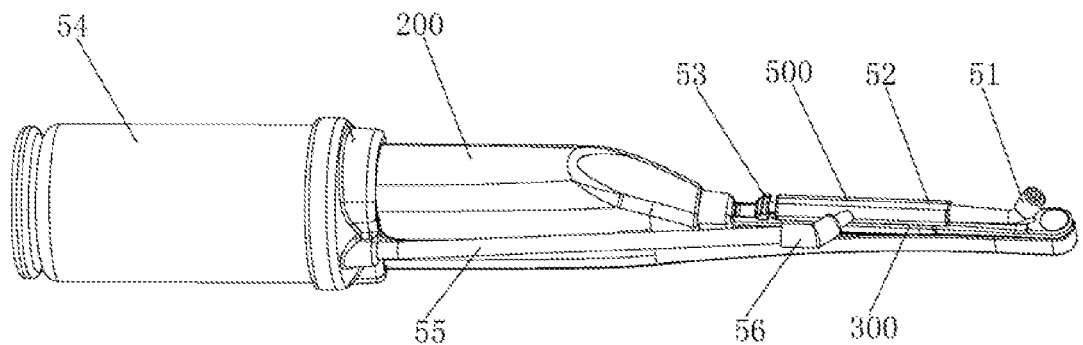
FIG. 23 is a three-dimensional structure diagram of a visual oral irrigator with an adjustable spray head according to the present disclosure.
Figures 1, 23:
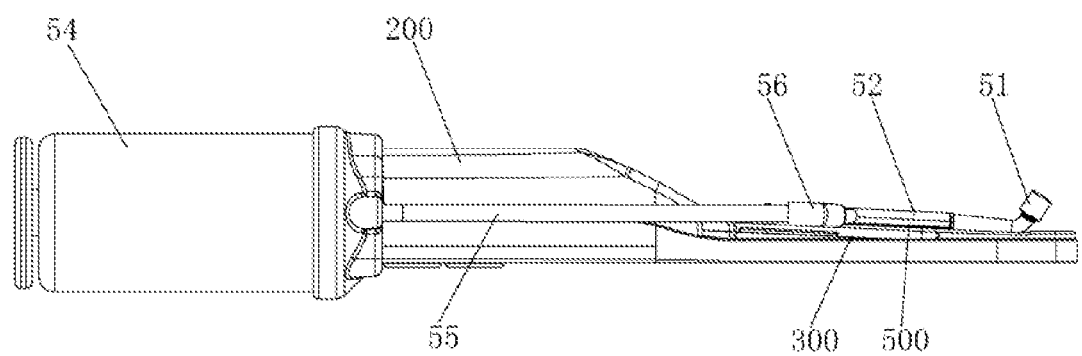
Figures 2, 23:
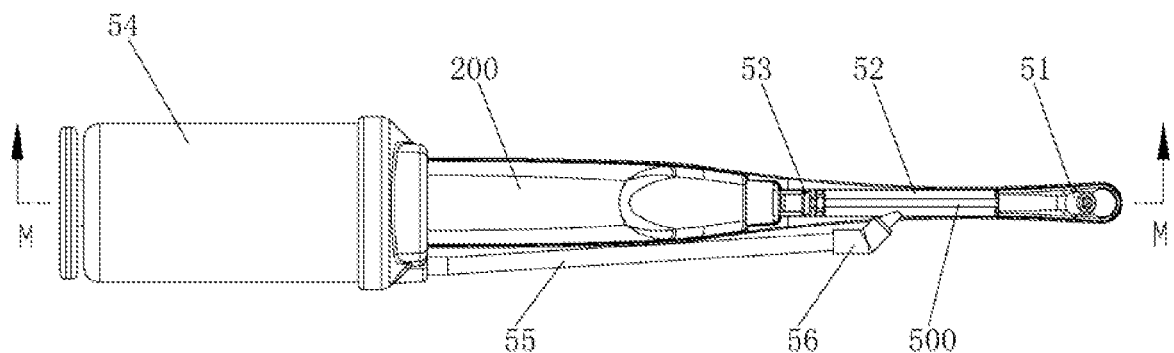
Figures 3, 23:
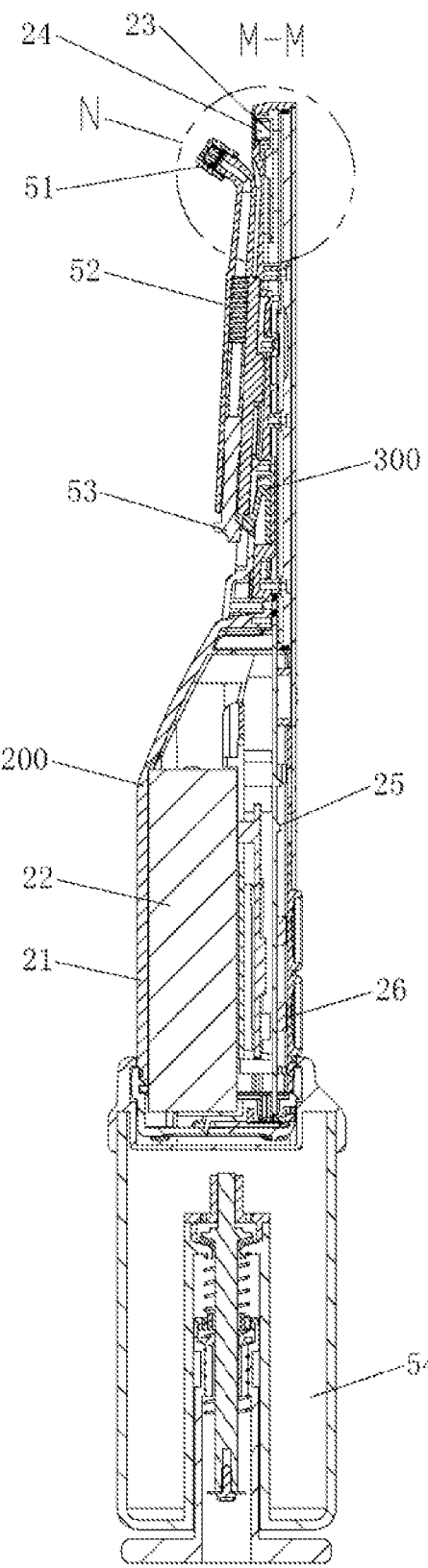
Figures 4, 23:
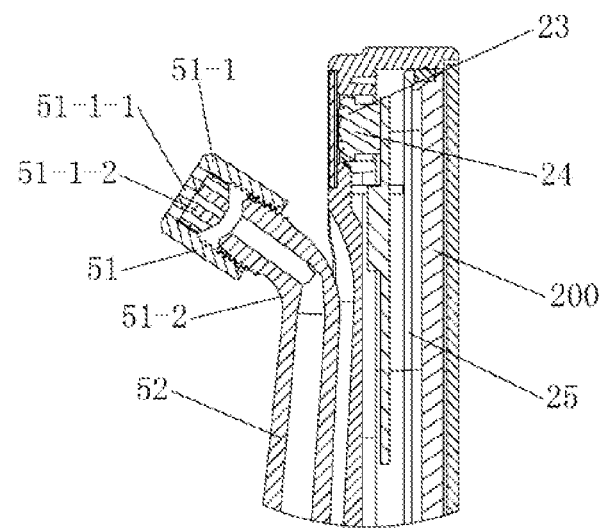
Figures 5, 23:
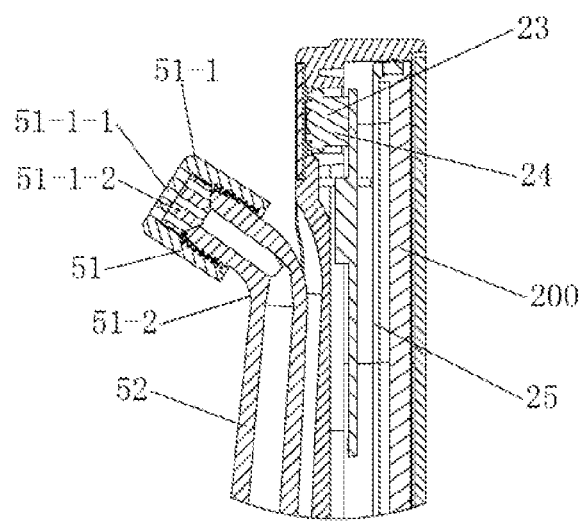

Embodiment 6: A Visual Oral Irrigator with a Regulating Valve According to the Present Disclosure With reference to FIG. 23 to FIG. 23-5, the difference between this embodiment and Embodiment 1 lies in that: in this embodiment, the spray head 51 of the spray gun 52 of the oral irrigator 500 is provided with a regulating valve 51-1 capable of regulating the shape and speed of the sprayed fluid. The regulating valve 51-1 includes a fine water outlet 51-1-1 and a regulating cone 51-1-2; and by rotating the regulating valve 51-1, the gap and corresponding relationship between the regulating cone 51-1-2 and the water outlet 51-1-1 can be regulated, thereby regulating the shape and speed of the sprayed water jet. Of course, those skilled in the art may also perform other designs according to the technical solutions disclosed in the present disclosure without departing from the protection scope of the present patent.

Figure 24:
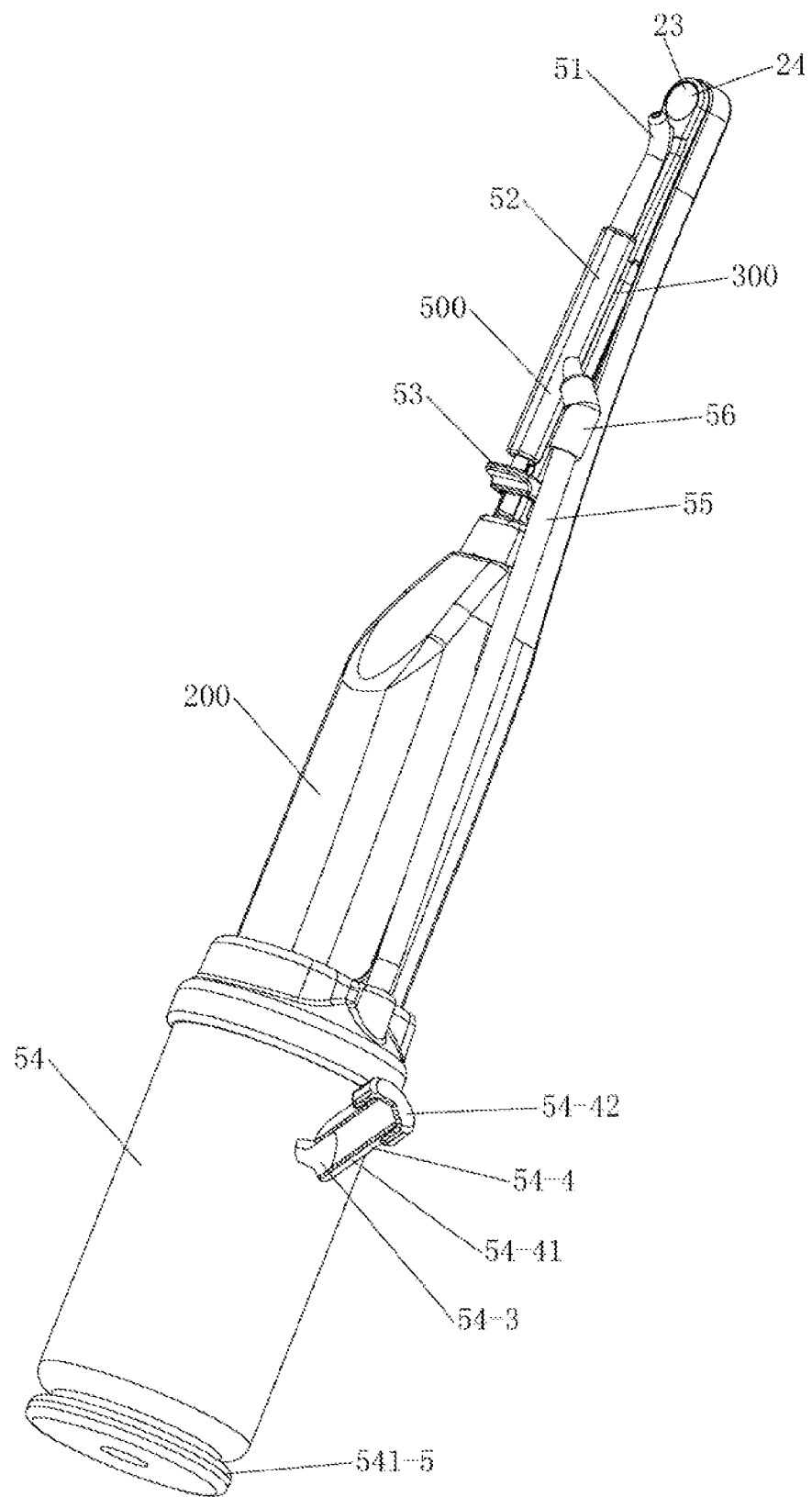
FIG. 24 is a three-dimensional structure diagram of a visual oral irrigator with a water filling port according to the present disclosure.

In addition, the pressure vessel 54 of the oral irrigator 500 is provided with a water filling port 54-4; and the water filling port 54-4 is arranged on the housing 54-2 of the pressure vessel 54, and includes an interface 54-41 and a seal cap 54-42, the far end of the interface 54-41 communicates with the fluid containing space 54-3 of the pressure vessel 54, and the seal cap 54-42 is detachably mounted on the interface 54-41. By adding the water filling port 54-4, after water in the pressure vessel 54 is used up, water can be conveniently refilled into the pressure vessel 54 to perform tooth rinsing, with reference to FIG. 24.

Those skilled in the art can perform various specific product designs according to the technical solutions disclosed in the present disclosure, and especially, can perform many specific designs on the shape and structure of the oral irrigator 500 without departing from the protection scope of the present patent.

Embodiment 7: A Visual Oral Irrigator Including an Electric Air Compressor According to the Present Disclosure With reference to FIG. 27 and FIG. 27-1, the difference between this embodiment and Embodiment 1 lies in that in this embodiment, the pressurizer 54-1 is an electric pressurizer 542.

In this embodiment, the electric pressurizer 542 is an air electric pressurizer 542-1, and the air electric pressurizer 542-1 is an electric air compressor 542-51.

Figure 27:
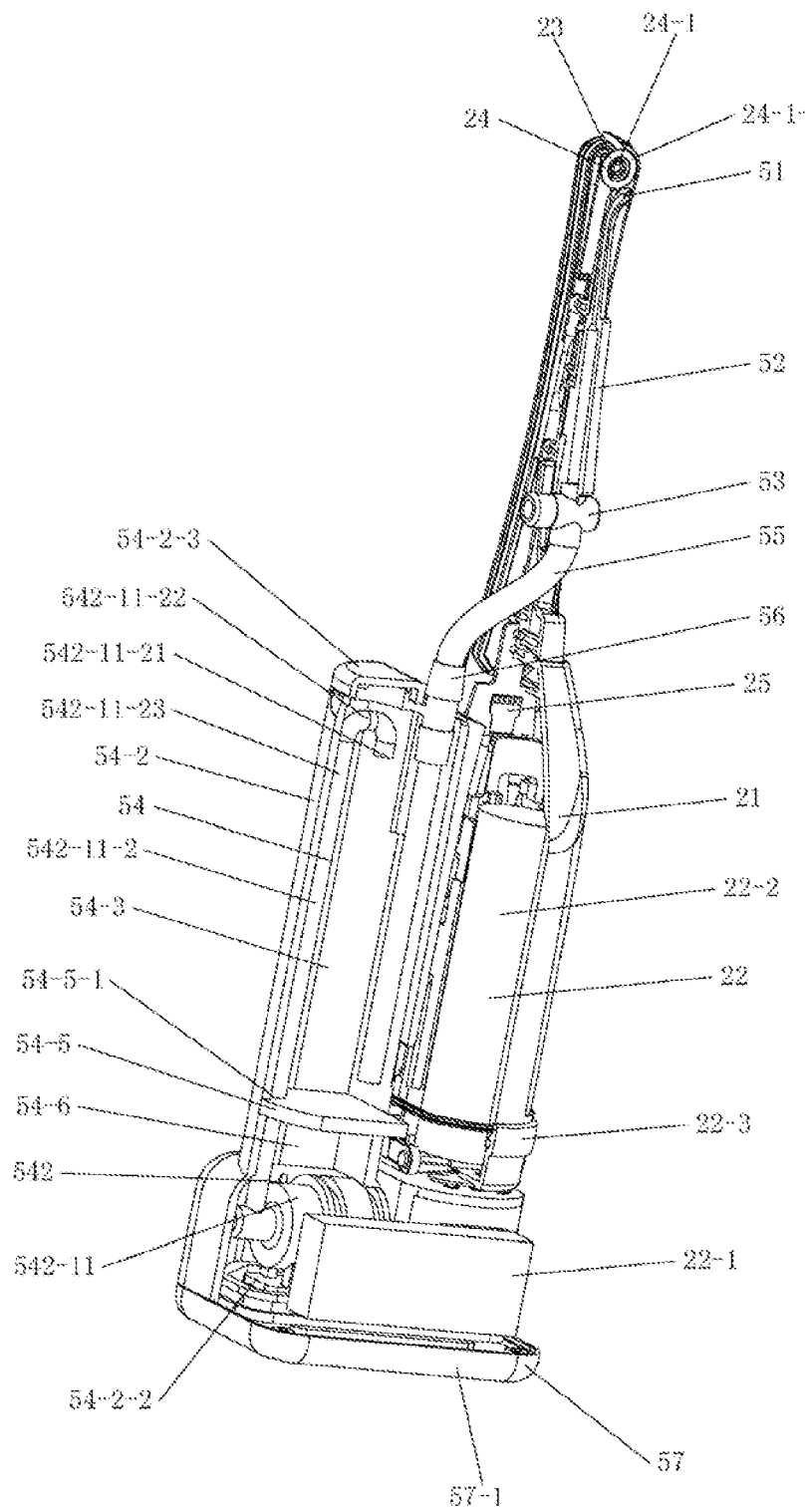
FIG. 27 is a structure diagram of a visual oral irrigator including an electric air compressor according to the present disclosure.
Figures 1, 27:
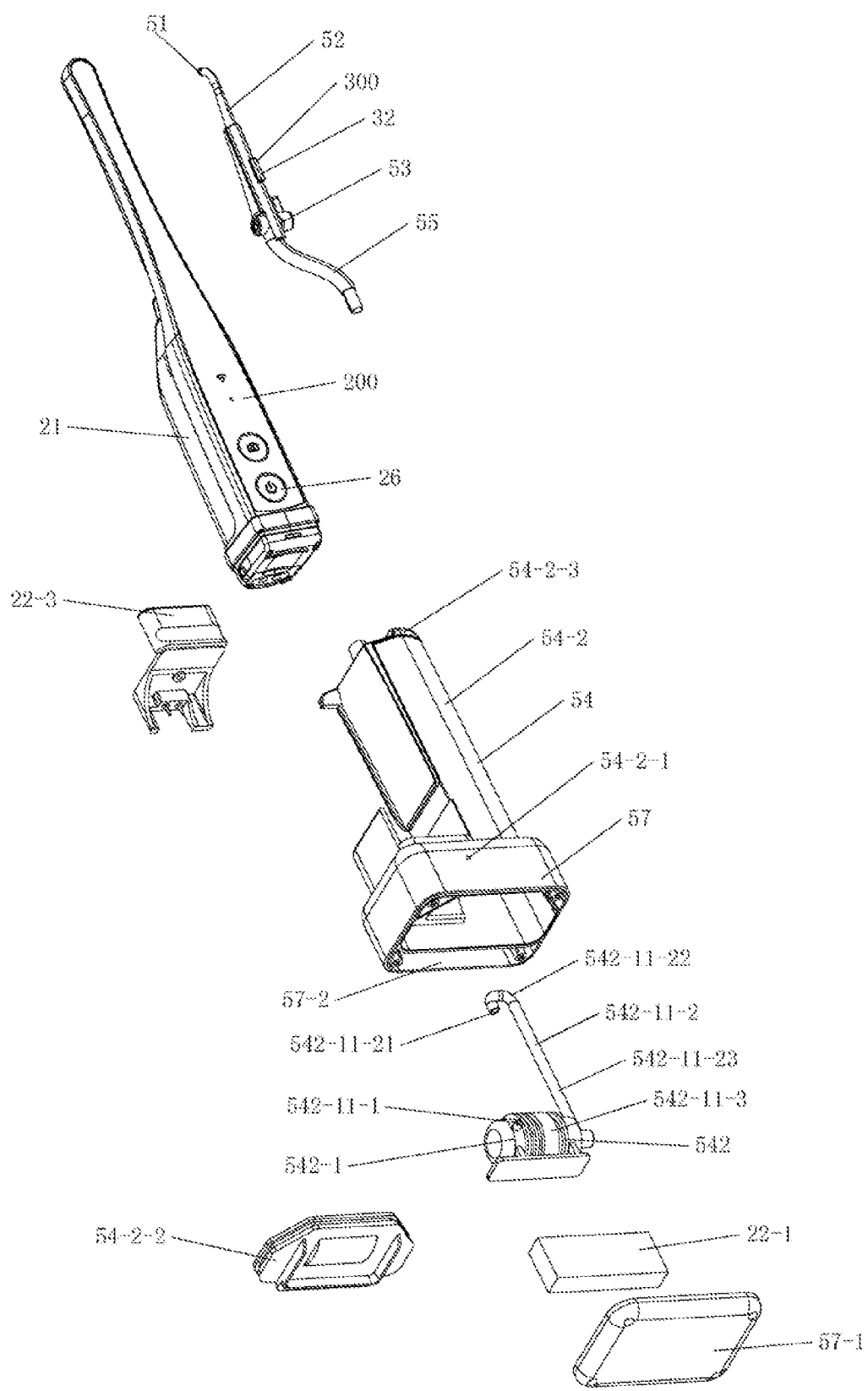

In this embodiment, the electric air compressor 542-51 includes an air inlet 542-51-1, an inflation tube 542-51-2 and a compressor 542-51-3, with reference to FIG. 27-1.

In this embodiment, a waterproof partition 54-5 is also arranged in the pressure vessel 54. The waterproof partition 54-5 separates the pressure vessel 54 into a fluid containing space 54-3 and a mounting interlayer 54-6 which are two independent spaces. The partition 54-5 is provided with a vent hole 54-5-1, one end of the inflation tube 542-51-2 of the electric air compressor 542-51 is connected with the compressor 542-51-3, and after the other end passes through the vent hole 54-5-1, an inflation port 542-51-21 is arranged above the water surface. The housing 54-2 at the mounting interlayer 54-6 is provided with an air inlet hole 54-2-1, so that air can be supplied into the mounting interlayer 54-6 in time when the electric air compressor 542-51 operates.

In this embodiment, in order to better drive the electric air compressor 542-51 to operate, the power supply system 22 is provided with a boosting device 22-1, a connecting base 22-3 is arranged between a power source 22-2 of the power supply system 22 and the pressurizer 22-1, and the boosting device 22-1 can increase the voltage of the power supply system 22.

In this embodiment, the oral irrigator 500 includes a pedestal 57. The boosting device 22-1 is mounted in the pedestal 57, and the connecting base 22-3 is mounted on the pedestal 57 and connected with the power source 22-2.

When mounting, a lower cover 57-1 of the pedestal 57 is firstly removed, and then a locating seat 54-2-2 on the bottom of the housing 54-2 is removed. An elbow 542-51 of the inflation tube 542-51-2 is taken down, a straight pipe 542-51-23 of the inflation tube 542-51-2 passes through the vent hole 54-5-1, the other end is connected to the compressor 542-51-3, the compressor 542-51-3 is mounted and fixed to the locating seat 54-2-2, and the locating seat 54-2-2 is remounted onto the housing 54-2. The boosting device 22-1 is mounted in the mounting slot 54-2 of the pedestal 57, and the lower cover 57-1 is put thereon. The upper cover 54-2-3 of the housing 54-2 is then opened, the elbow 542-51-22 of the inflation tube 542-51-2 is connected to the straight tube 542-51-23, and the upper cover 54-2-3 is put thereon, thereby completing the mounting of the electric air compressor 542-51.

With reference to FIG. 27, during operation, when the switch 26 is turned on, the power supply system 22 and the electric air compressor 542-51 are connected through the connecting base 22-3; and after the voltage is increased by the boosting device 22-1, the electric air compressor 542-51 operates, and the air is sucked into the electric air compressor 542-51 from the air inlet 542-51-1, pressurized by the air compressor 542-51-3, and charged into the fluid containing space 54-3 of the pressure vessel 54 via the inflation port 542-51-21 of the inflation tube 542-51-2, thereby increasing the water pressure. When the control switch 53 is turned on, the pressurized water enters the spray gun 52 via the connecting tube 55 arranged on the bottom of the fluid containing space 54-3 and is sprayed out from the spray head 51 to clean the teeth.

In this embodiment, the electric air compressor 542-51 is mounted in the mounting interlayer 54-6 of the pressure vessel 54, so that the electric air compressor 542-51 can be conveniently connected with the power supply system 22. Of course, those skilled in the art can also mount the electric air compressor 542-51 at any position in the pressure vessel 54 and even mount it outside the pressure vessel 54, and as long as the inflation port 542-51-21 is arranged above the water surface in the fluid containing space 54-3 and it is possible to pressurize the water in the fluid containing space 54-3, it does not depart from the protection scope of the present patent application.

In this embodiment, since the electric air compressor 542-51 is adopted to pressurize the water, compared with Embodiment 1, the pressurizing process is more stable and is convenient to operate.

Embodiment 8: A Visual Oral Irrigator Including a Submersible Pump According to the Present Disclosure With reference to FIG. 28 to FIG. 29-1, the difference between this embodiment and Embodiment 3 lies in that in this embodiment, the electric pressurizer 542 is a water electric pressurizer 542-2.

In this embodiment, the water electric pressurizer 542-2 is a submersible pump 542-21.

The submersible pump 542-21 includes a water inlet system 542-21-1, a pressurizing system 542-21-2 and a water discharge system 542-21-3.

The submersible pump 542-21 is mounted on the lower part of the fluid containing space 54-3, the water discharge system 542-21-3 is connected with the connecting tube 55, and the power system 542-3 is connected with the power supply system 22; and after the power supply system 22 supplies power to the submersible pump 542-21, the pressurizing system 542-21-2 operates to pressurize a fluid entering the submersible pump 542-21 via the water inlet system 542-21-1, and the pressurized fluid is discharged by the drainage system 542-21-3 through the connecting tube 55 to rinse the teeth.

When mounting, the lower cover 57-1 of the pedestal 57 is opened, the locating seat 54-2-2 on the bottom of the housing 54-2 of the pressure vessel 54 is removed, the submersible pump 542-21 is mounted onto the locating seat 54-2-2, the water outlet 542-21-31 of the water discharge system 542-21-3 is connected with the connecting tube 55, and the locating seat 54-2-2 is remounted onto the housing 54-2. Then, the boosting device 22-1 is mounted in the mounting slot 57-2 of the pedestal 57, and the lower cover 57-1 is put thereon, thereby completing the mounting of the submersible pump.

Figure 28:
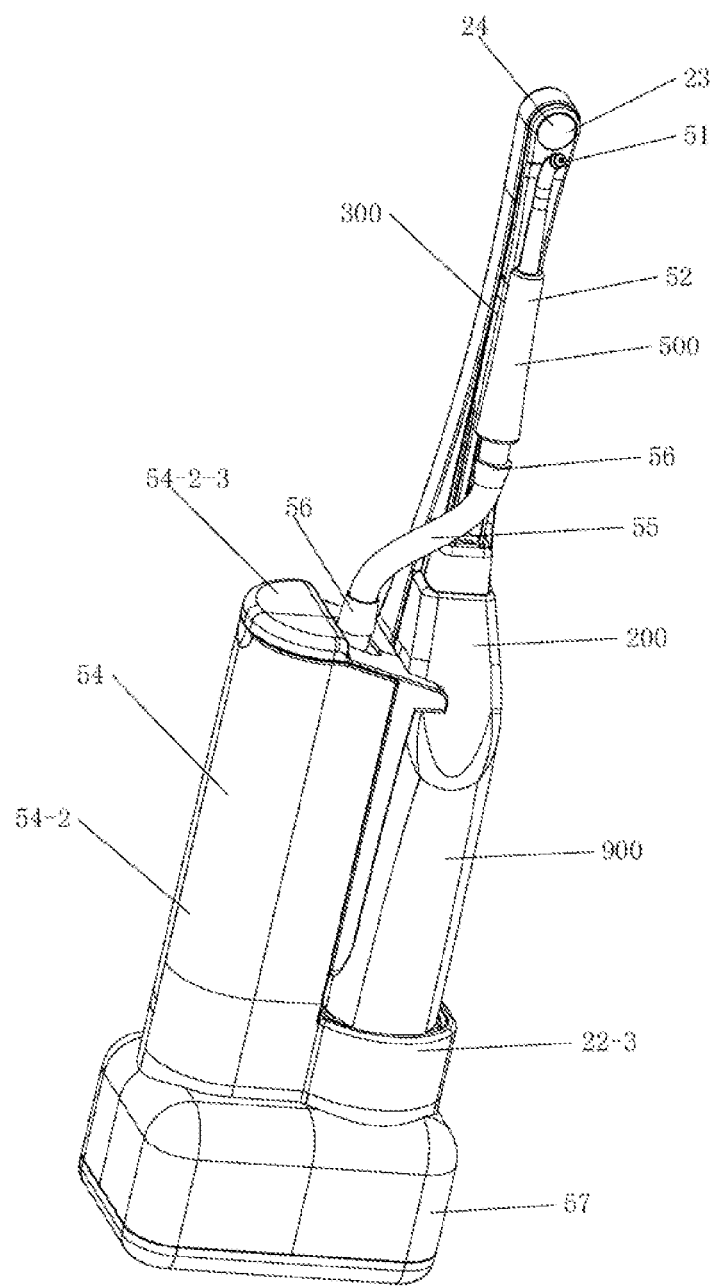
FIG. 28 is a three-dimensional structure diagram of a visual oral irrigator including a submersible pump according to the present disclosure.
Figures 1, 28:
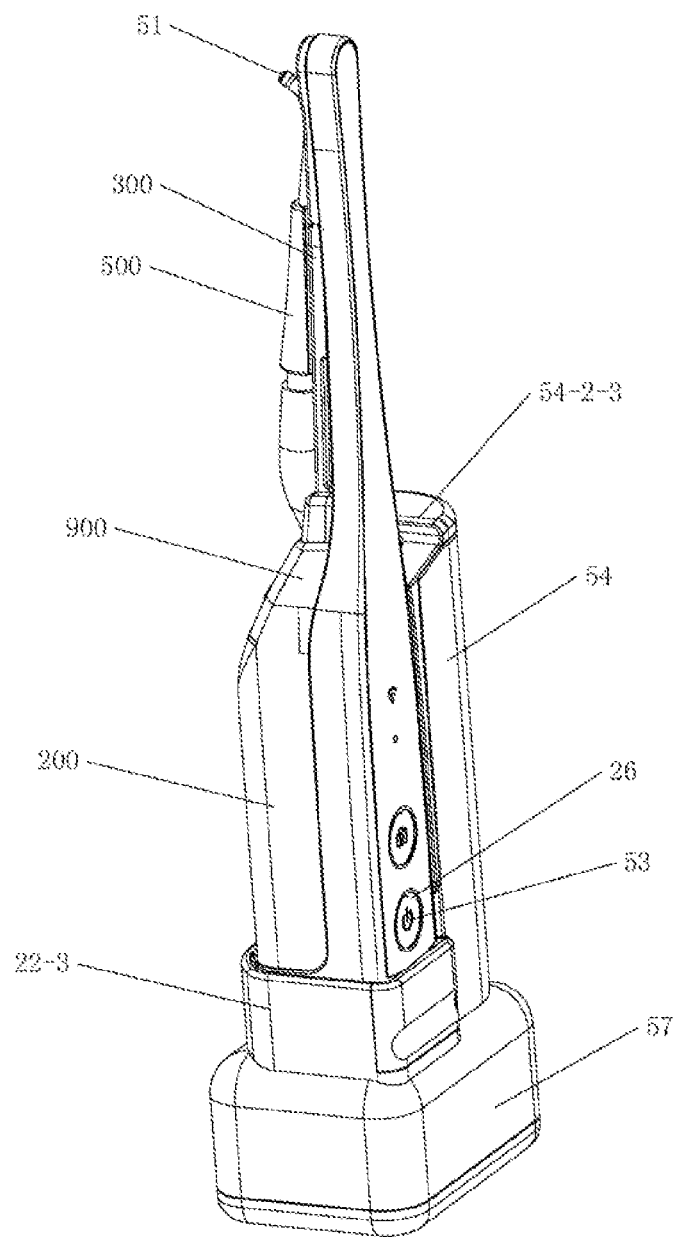
Figure 29:
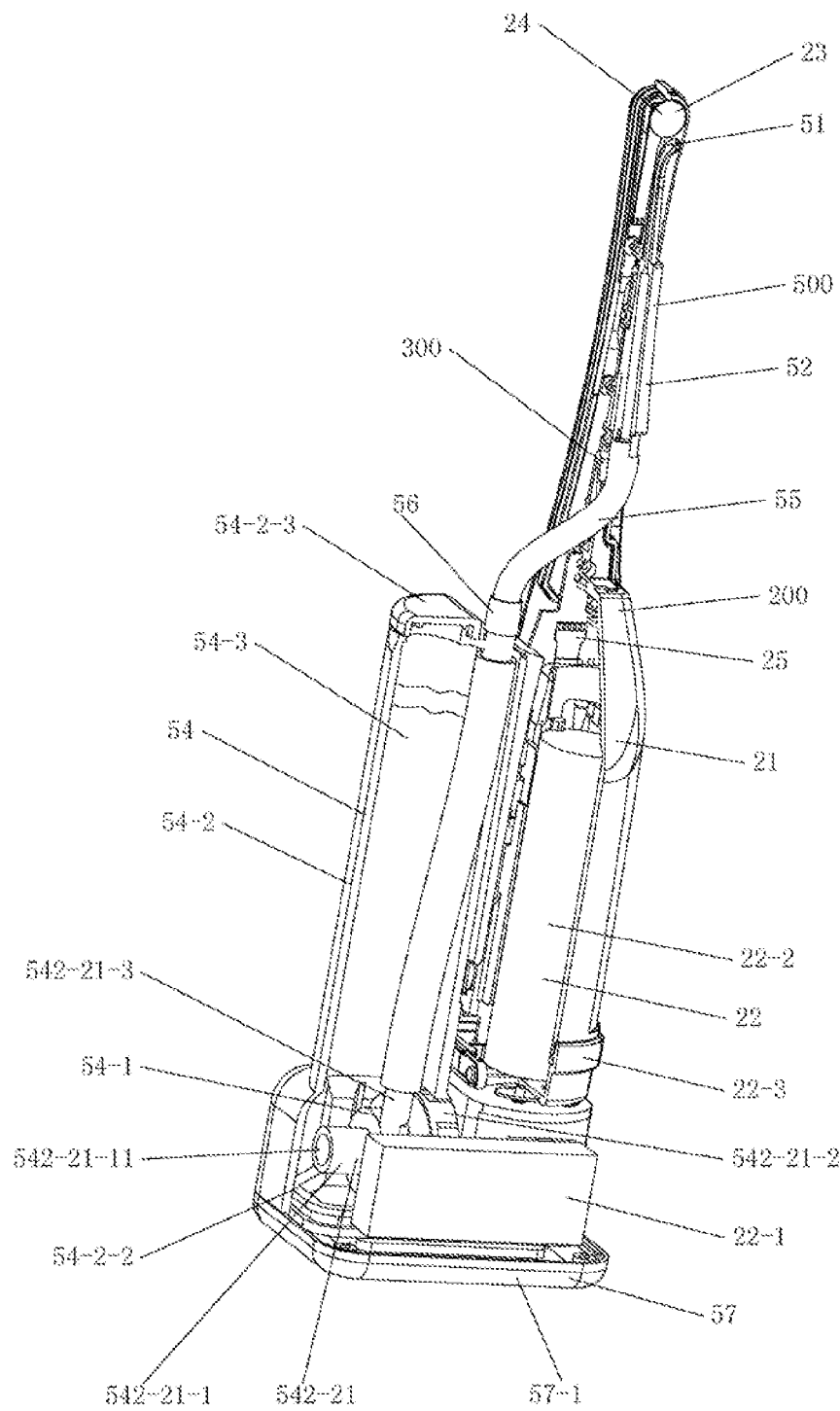
FIG. 29 is a structure diagram of the visual oral irrigator including the submersible pump according to the present disclosure.
Figures 1, 29:
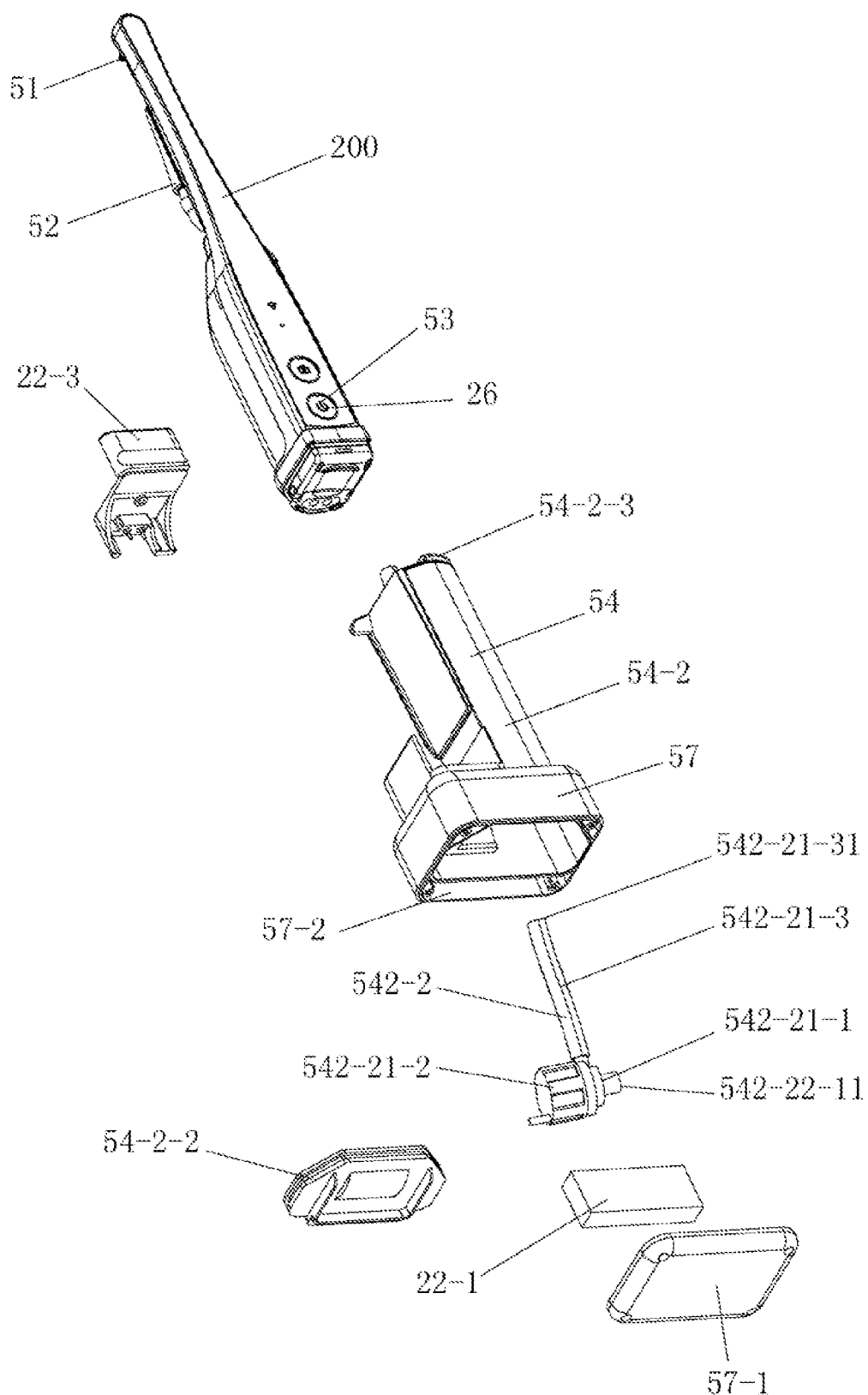

With reference to FIG. 28 and FIG. 28-1, in this embodiment, the switch 26 is the control switch 53. During use, the water surface needs to exceed the water inlet 542-21-51 of the water inlet system 542-21-1; when the control switch 53 is turned on, the power supply system 22 boosted by the boosting device 22-1 drives the pressurizing system 542-21-2 to operate, and water enters the pressurizing system 542-21-2 from the water inlet 542-21-51 of the water inlet system 542-21-1; and after the pressurizing system 542-21-2 pressurizes the water, the water enters the connecting tube 55 after being discharged from the water outlet 542-21-31 of the water discharge system 542-21-3, and the pressurized water in the connecting tube 55 enters the spray gun 52 and is sprayed out from the spray head 51 to rinse the teeth, with reference to FIG. 29 and FIG. 29-1.

In this embodiment, the submersible pump 542-21 can be directly mounted in water without additionally arranging the partition to a separate mounting space, so the pressure vessel 54 is simpler to manufacture; and besides, water directly enters the pressurizing system 542-21-2 to be pressurized, so the pressurizing process is more direct, the pressurizing degree is free from the influence of the volume of the fluid containing space 54-3, and thus, the pressurizing process is more stable.

Meanwhile, in order to better perform waterproofing and sealing, the power supply system 22 may drive the submersible pump 542-21 to operate in a non-contact connection manner, such as electromagnetic drive or the like.

Embodiment 9: A Visual Oral Irrigator Including a Water Pump According to the Present Disclosure With reference to FIG. 30 to FIG. 30-1, the difference between this embodiment and Embodiment 4 lies in that in this embodiment, the electric water pressurizer 542-2 is a water pump 542-22.

In this embodiment, the water pump 542-22 includes a pumping system 542-22-1, a vacuum suction system 542-22-2, a water discharge system 542-22-3 and a power system 542-3. The pumping system 542-22-1 includes a pumping tube 543-22-52. The power system 542-3 includes a switch 26, a boosting device 22-1 and a connecting base 542-33.

Figure 30:
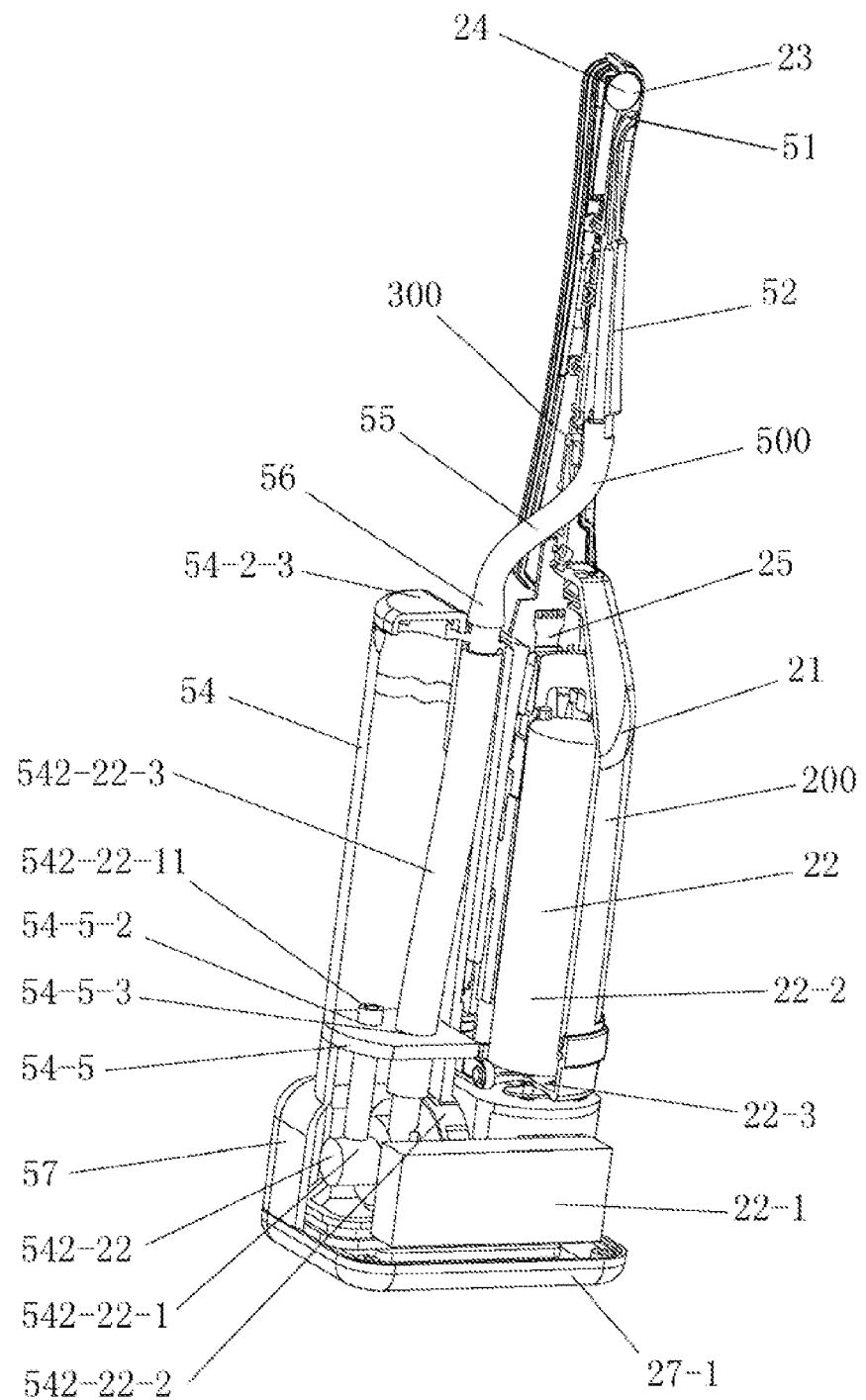
FIG. 30 is a structure diagram of a visual oral irrigator including a water pump according to the present disclosure.
Figures 1, 30:
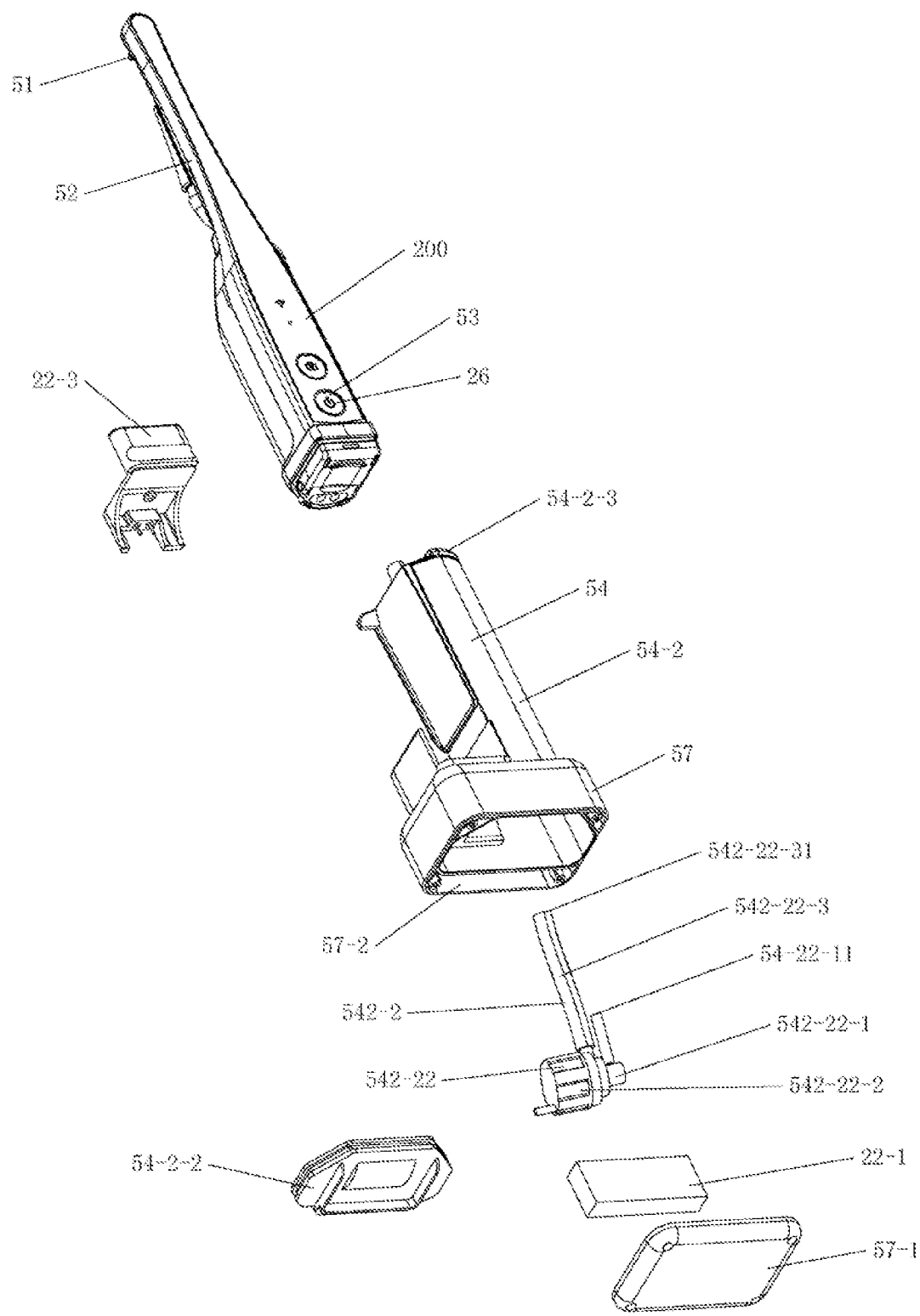

The water discharge system 542-22-3 is connected with the connecting tube 55, the power supply system 22 boosted by the boosting device 22-1 supplies power to the water pump 542-22, the vacuum suction system 542-22-2 operates to suck the fluid in the fluid containing space 54-3 into the water pump 542-22 via the pumping system 542-22-1, and the pressurized liquid is discharged by the water discharge system 542-22-3 via the connecting tube 55 to clean the teeth, with reference to FIG. 30.

In this embodiment, as in Embodiment 3, the pressure vessel 54 is also provided with a waterproof partition 54-5. The waterproof partition 54-5 separates the pressure vessel 54 into the a fluid containing space 54-3 and a mounting interlayer 54-6 which are two independent spaces, and the water pump 542-22 is mounted in the mounting interlayer 54-6.

In this embodiment, the waterproof partition 54-5 is provided with a drainage hole 54-5-2 and a water discharge hole 54-5-3.

The pumping port 542-22-51 of the pumping tube 543-22-52 is arranged on the bottom of the fluid containing space 54-3 via the drainage hole 54-5-2. The connecting tube 55 passes through the water discharge hole 54-5-3 and is connected to a water outlet 542-22-31 of the water pump 542-22.

When mounting, a lower cover 57-1 of the pedestal 57 is firstly removed, and then a locating seat 54-2-2 on the bottom of the housing 54-2 is removed. The pumping tube 543-22-52 passes through the drainage hole 54-5-2, the other end is connected to the water pump 542-22, and meanwhile, the connecting tube 55 passes through the water discharge hole 54-5-3 and is connected to the water outlet 542-22-31 of the water pump 542-22. Then, the water pump 542-22 is mounted and fixed to the locating seat 54-2-2, and the locating seat 54-2-2 is remounted on the housing 54-2. The boosting device 22-1 is mounted in the mounting slot 57-2 of the pedestal 57, and the lower cover 57-1 is put thereon, thereby completing the mounting of the water pump 542-22.

In this embodiment, the switch 26 is the control switch 53. During operation, when the control switch 53 is turned on, the power supply system 22 drives the water pump 542-22 to operate, water is sucked into the water pump 542-22-2 by the vacuum suction system 5432-22-2 of the water pump 542-22 via the pumping port 542-22-51 of the pumping system 542-22-1, and is discharged into the connecting tube 55 from the water outlet 542-22-31 of the water discharge system 542-22-3; and the pressurized water enters the spray gun 52 through the connecting tube 55 and is sprayed out from the spray head 51 to clean the teeth.

In this embodiment, the water pump 542-52 is mounted in the mounting interlayer 54-6 of the pressure vessel 54, so that the water pump 542-22 can be conveniently connected with the power supply system 22. Of course, those skilled in the art can also mount the water pump 542-22 at any position in the pressure vessel 54 and even mount it outside the pressure vessel 54, and as long as the pumping port 542-22-51 of the pumping system 542-22-1 is arranged on the bottom of the water in the fluid containing space 54-3 and the water in the fluid containing space 54-3 can be sucked into the water pump 542-22 and be pressurized and discharged, it does not depart from the protection scope of the present patent application.

Compared with Embodiment 4, in this embodiment, since the water pump 542-22 is isolated from water, it is possible to effectively prevent harmful substances possibly generated after long-term immersion of equipment in water from seeping, so it is more secure for long-term use.

Embodiment 10: A Multifunctional Visual Oral Irrigator According to the Present Disclosure With reference to FIG. 31 to FIG. 34-2, the difference between this embodiment and Embodiment 4 lies in that in this embodiment, the spray head 51 and the spray gun 52 are built into a position near the oral viewer 200 of the viewing system 24, and the water jet sprayed by the spray head 51 of the spray gun 52 is within the visual field of the viewing system 24.

With reference to FIG. 31 to FIG. 34-2, in this embodiment, the front end of the oral viewer 200 is also detachably equipped with an interdental brush 700, or dental floss 100, or toothbrush 600, or oral forceps 400 or any other special tooth cleaning tool through the connecting mechanism 300. The multifunctional visual oral irrigator can be used for rinsing teeth with water under vision, and can also be used for cleaning teeth or tooth gaps under vision, or taking out food residues in the tooth gaps and other positions difficult for cleaning and foreign objects attached to the gingivae by using the interdental brush 700, or the dental floss 100, or the toothbrush 600, or the oral forceps 400.

Figure 31:
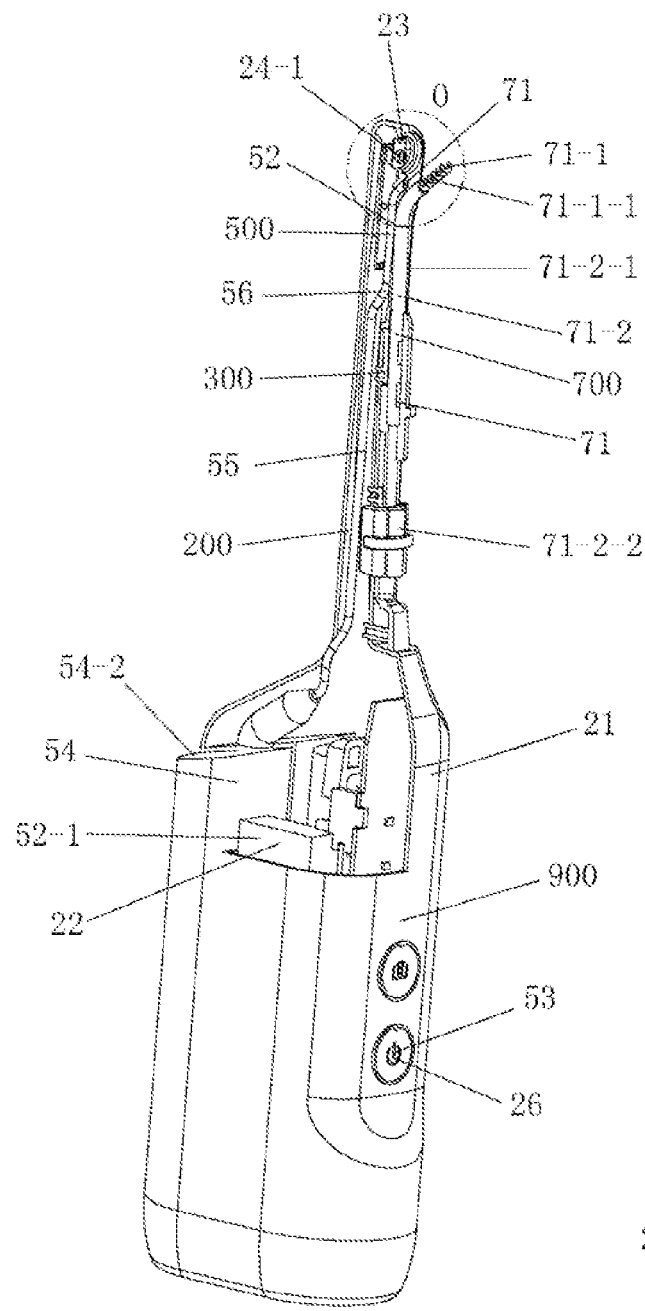
FIG. 31 is a multifunctional visual oral irrigator including an interdental brush according to the present disclosure.
Figure 1:
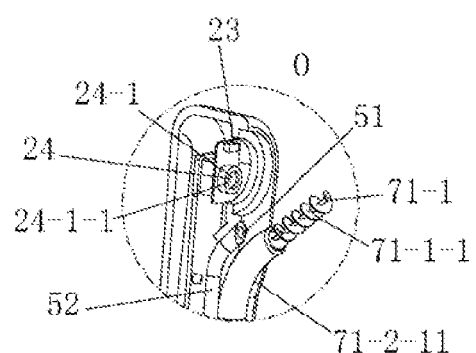
Figures 2, 31:
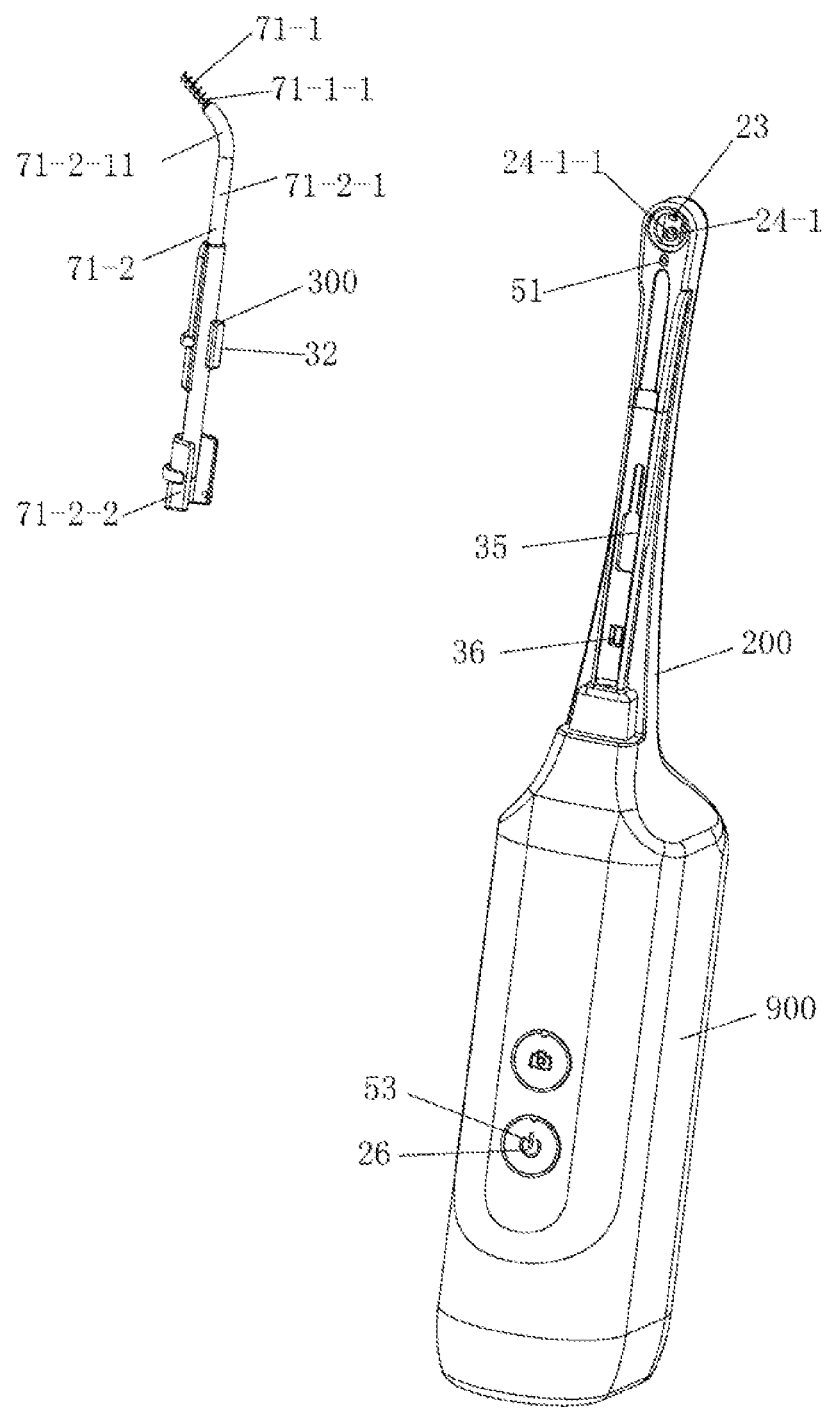

With reference to FIG. 31 to FIG. 31-2, the front end of the oral viewer 200 is detachably equipped with the interdental brush 700 through the connecting mechanism 300. In this embodiment, the interdental brush 700 is the built-in interdental brush 701. The built-in interdental brush 701 includes a brush body 71 and a delivery device 72. The delivery device 72 includes a guide head 72-1 and a sliding mechanism 72-2, and the guide head 72-1 includes an elbow tube 72-1-1-1. By pushing the sliding mechanism 72-2, the brush body 71 may reciprocate in the elbow tube 72-1-1-1 at the front end of the delivery device 72.

It is particularly important that the direction of the water flow at the spraying of the spray head 51 is substantially the same as the direction along which the brush head 71-1-1 of the interdental brush 700 enters the tooth gap; and thus, while the brush head 71-1-1 of the interdental brush 700 reciprocates in the tooth gap and performs cleaning, the water flow at the spraying point of the spray head 51 can assist in rinsing the food residues in the tooth gap. Therefore, when the oral irrigator 500 is used for rinsing the teeth, the interdental brush 700 can be used for the tooth gap or any narrow gap where the food residues cannot be easily rinsed out with water; the sliding mechanism 72-2 is pushed to drive the brush head 71-1-1 of the brush body 71 to reciprocate under direct vision to push the food residues out of the gap or loosen the food residues; and at this time, through the assisting effect of the water jet sprayed out by the spray head 51 of the oral irrigator 500, direct fixed-point cleaning on the tooth gap difficult to rinse can be effectively performed.

Figure 32:
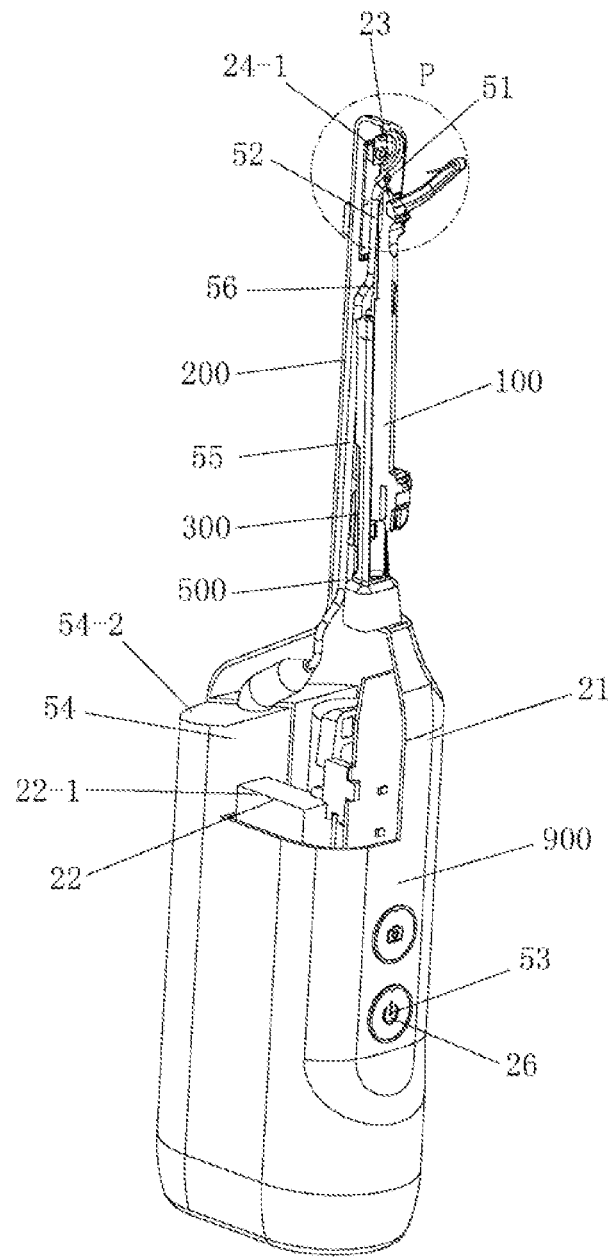
FIG. 32 is a multifunctional visual oral irrigator including a dental floss according to the present disclosure.
Figures 1, 32:
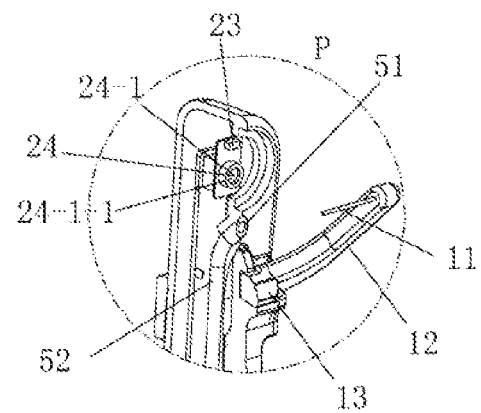
Figures 2, 32:
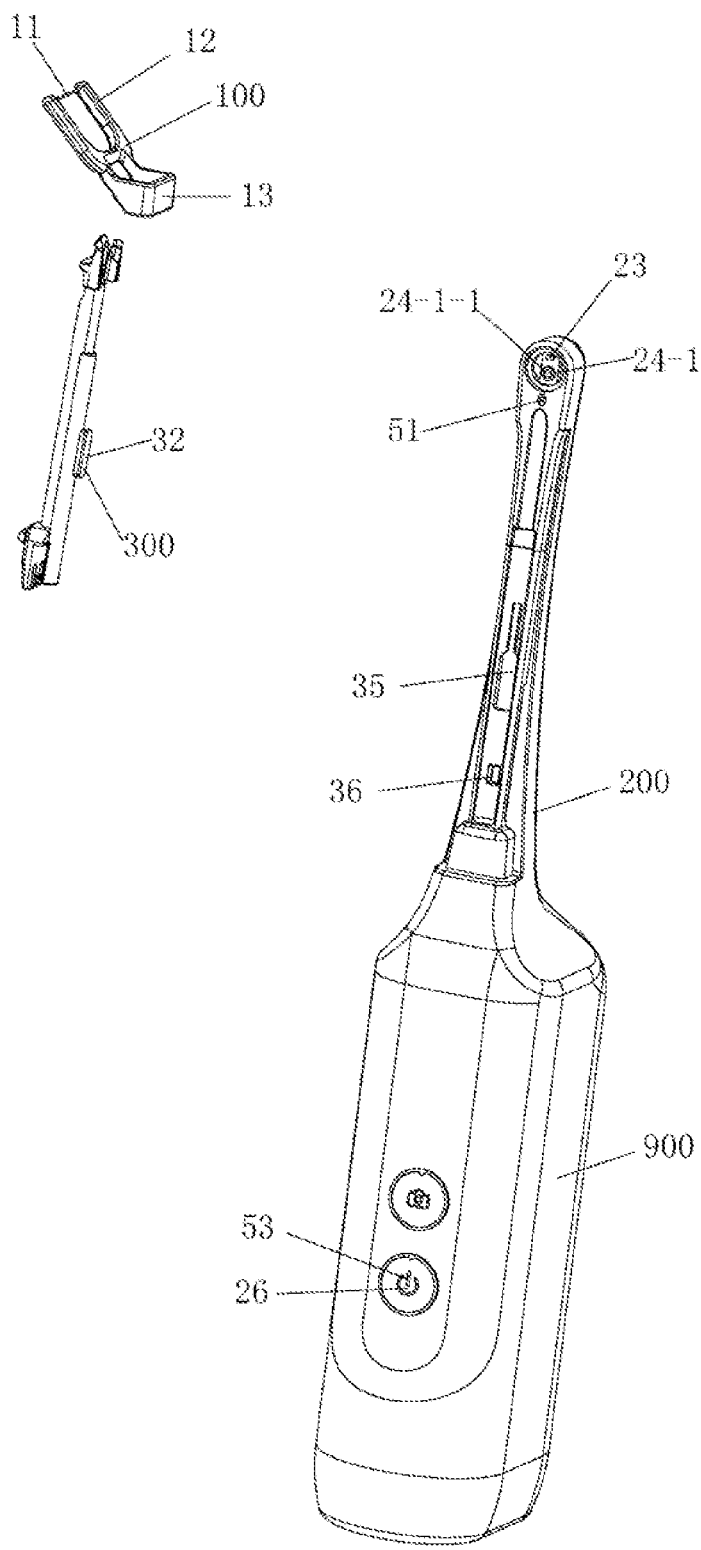

With reference to FIG. 32 to FIG. 32-2, the front end of the oral viewer 200 is detachably equipped with the dental floss 100 through the connecting mechanism 300. The dental floss 100 includes a floss 11, a bracket 12 and a mounting base 13. The floss 11 of the dental floss 100 is within the visual field of the viewing system. For some especially narrow tooth gaps where the interdental brush 700 cannot enter, the dental floss 100 can be used for further cleaning. During cleaning, when the viewing system 24 is used for viewing, by moving the dental floss 100 back and forth, the small-size floss 11 is utilized to clean the especially narrow tooth gap.

In addition, the direction of the water flow at the spraying point of the spray head 51 is substantially the same as the direction along which the dental floss 100 enters the tooth gap; and thus, while the floss 11 of the dental floss 100 reciprocates in the tooth gap and performs cleaning, the water flow at the spraying point of the spray head 51 can assist in rinsing the food residues in the tooth gap. Therefore, when the oral irrigator 500 is used for rinsing the teeth, the floss 11 of the dental floss 100 can be used for the tooth gap or any narrow gap where the food residues cannot be easily rinsed out with water; the floss 11 of the dental floss 100 is shaken to take the food residues out of the gap or move the food residues under direct vision; and at this time, through the assisting effect of the water jet sprayed out by the spray head 51 of the oral irrigator 500, direct fixed-point cleaning on the tooth gap difficult to rinse can be effectively performed.

Figure 33:
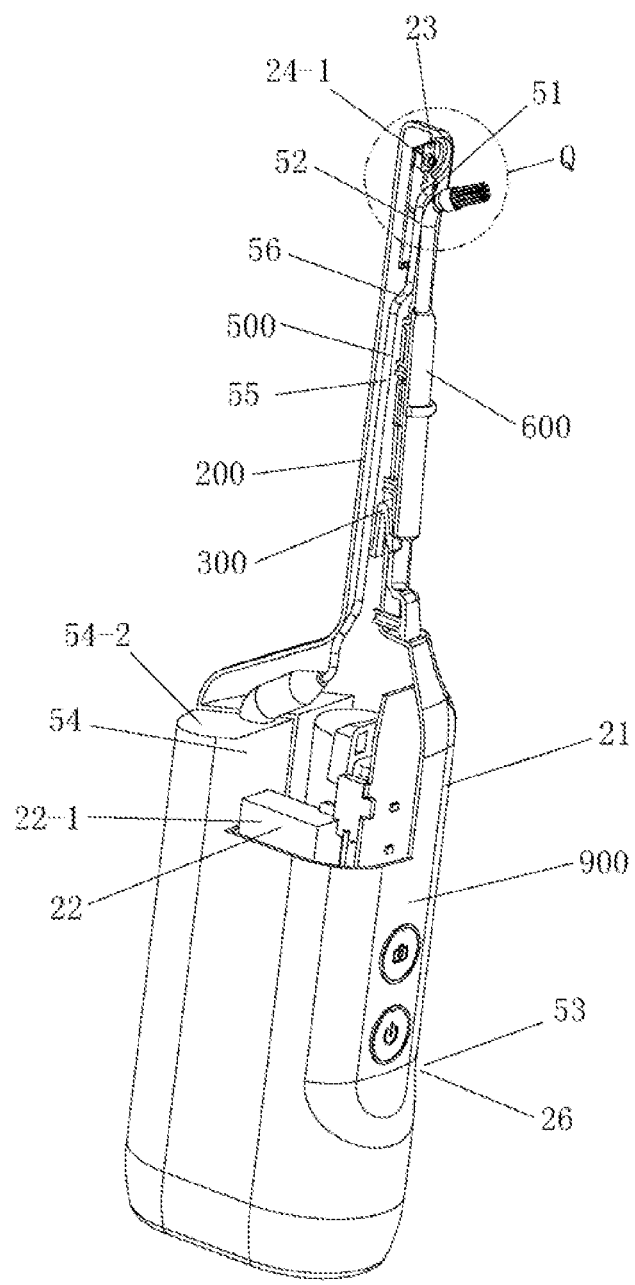
FIG. 33 is a multifunctional visual oral irrigator including a toothbrush according to the present disclosure.
Figures 1, 33:
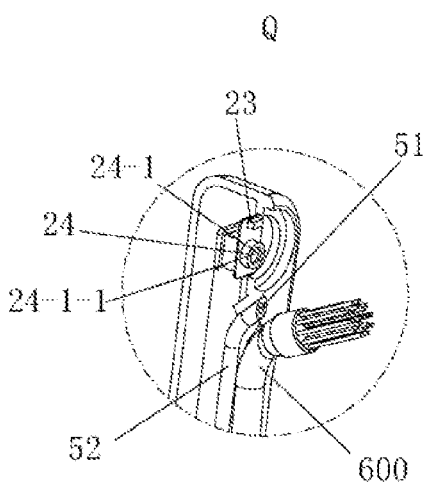
Figures 2, 33:
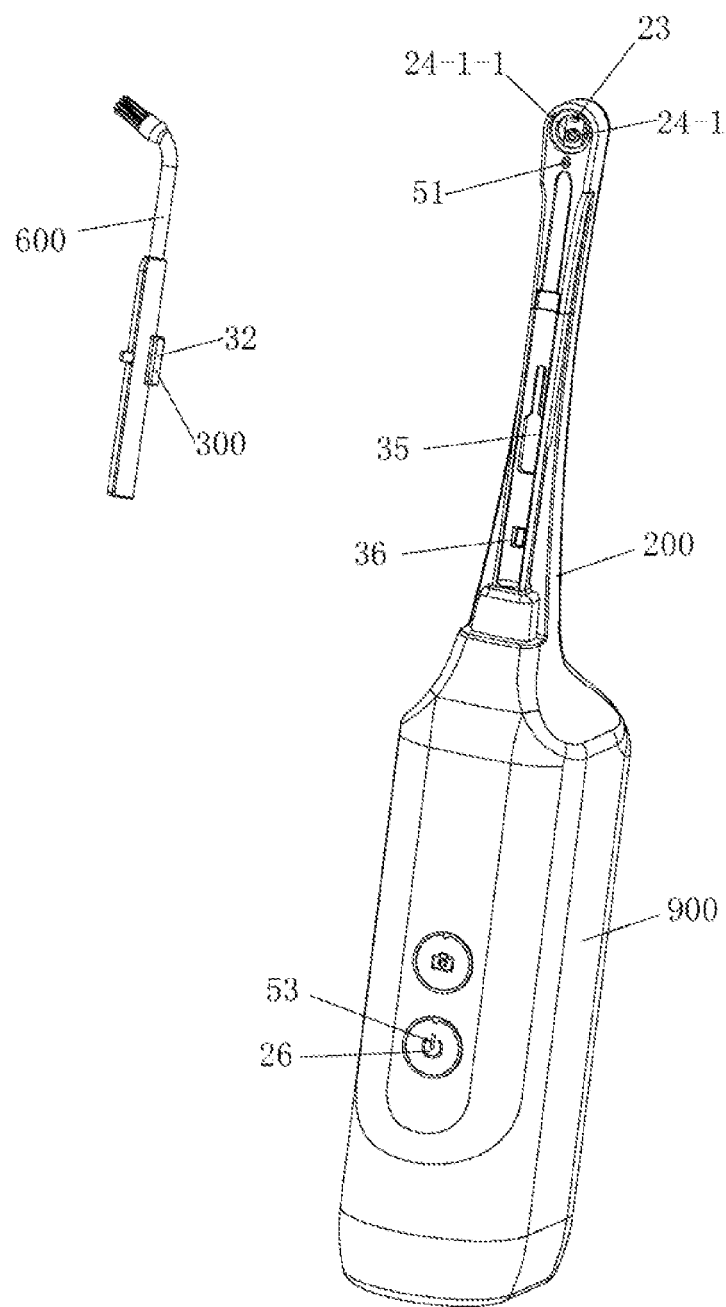

With reference to FIG. 33 to FIG. 33-2, the front end of the oral viewer 200 is detachably equipped with the toothbrush 600 through the connecting mechanism 300, and the toothbrush 600 is positioned within the visual field of the viewing system 24. In the tooth brushing process, while the toothbrush 600 is used for brushing teeth, the oral irrigator 500 may be used for rinsing, so that the tooth brushing process is more direct-viewing, and the oral cavity can be cleaned more thoroughly.

Figure 34:
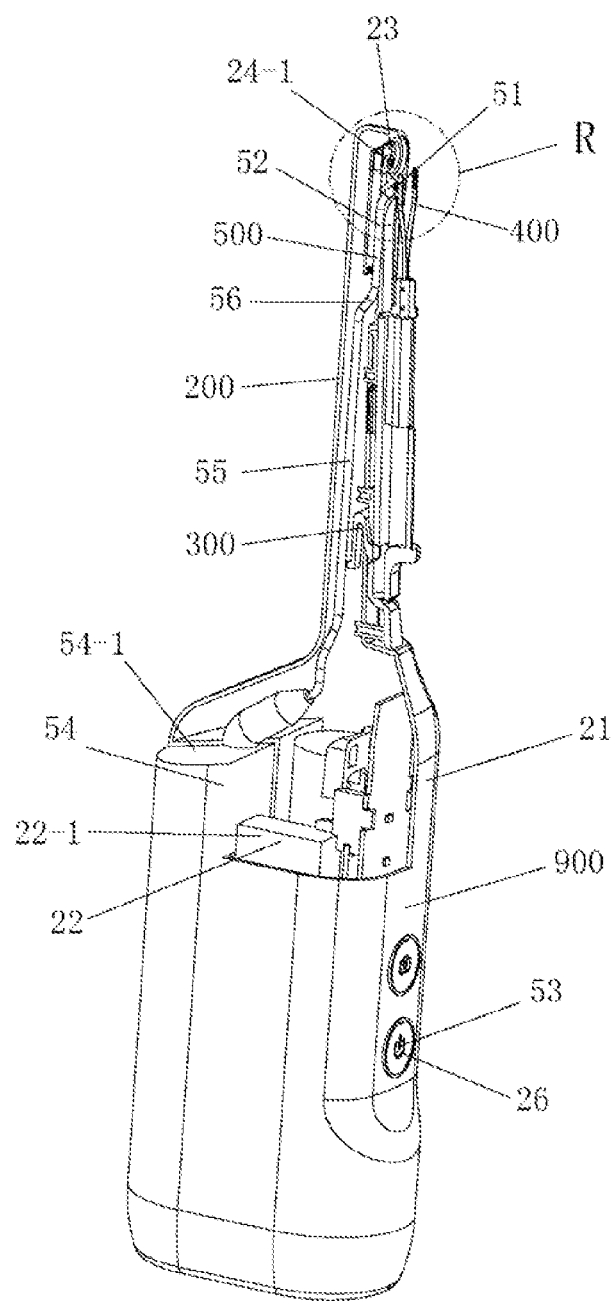
FIG. 34 is a multifunctional visual oral irrigator including oral forceps according to the present disclosure.
Figures 1, 34:
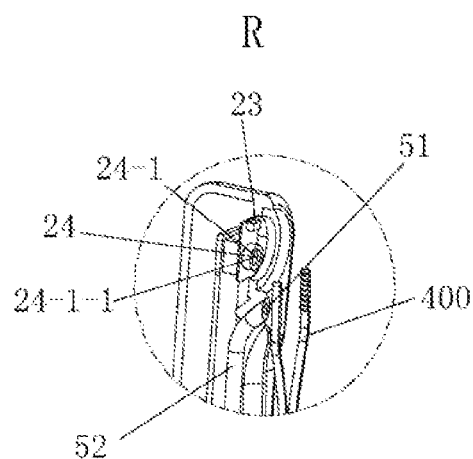
Figures 2, 34:
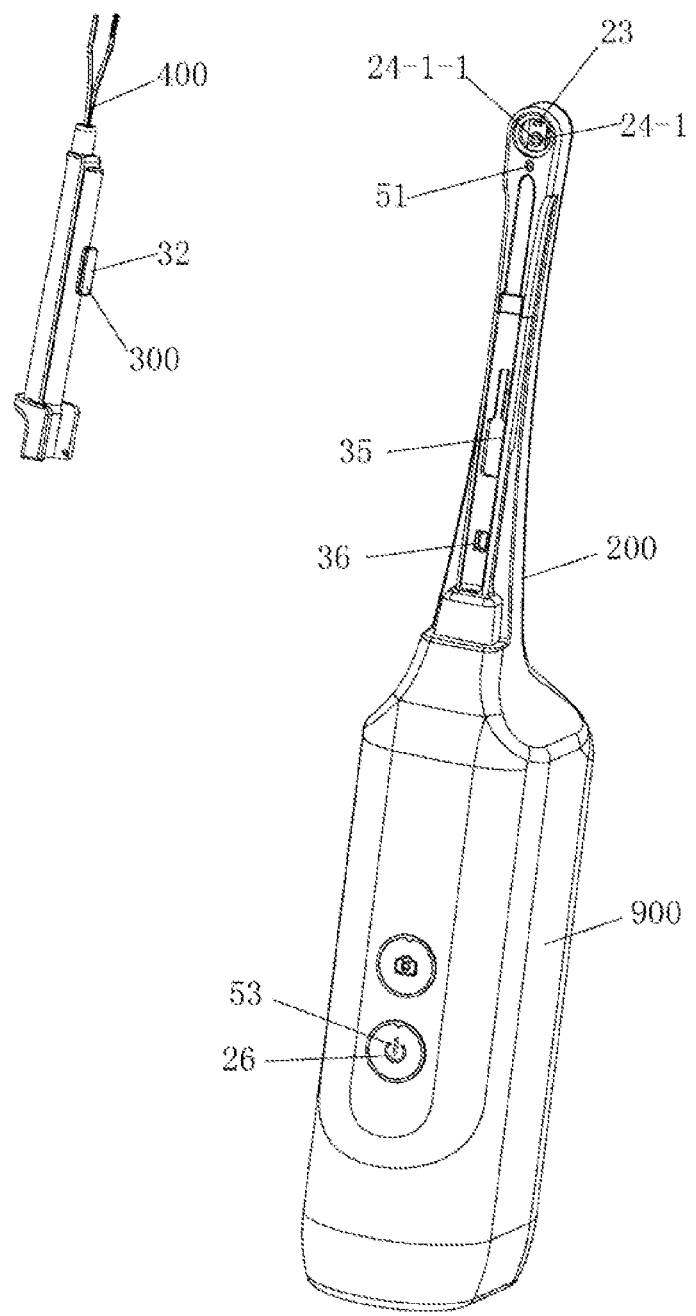

With reference to FIG. 34 to FIG. 34-2, the front end of the oral viewer 200 is detachably equipped with the oral forceps 400 through the connecting mechanism 300. When the food residues are stuck to the tooth gap or a foreign object pierces into the gingivae or other soft tissues, the oral forceps 400 can be controlled to open and close by pushing and pulling the grips of the oral forceps 400, and under direct vision, the stuck food residue or the piercing foreign object can be taken out safely and conveniently.

Figure 35:
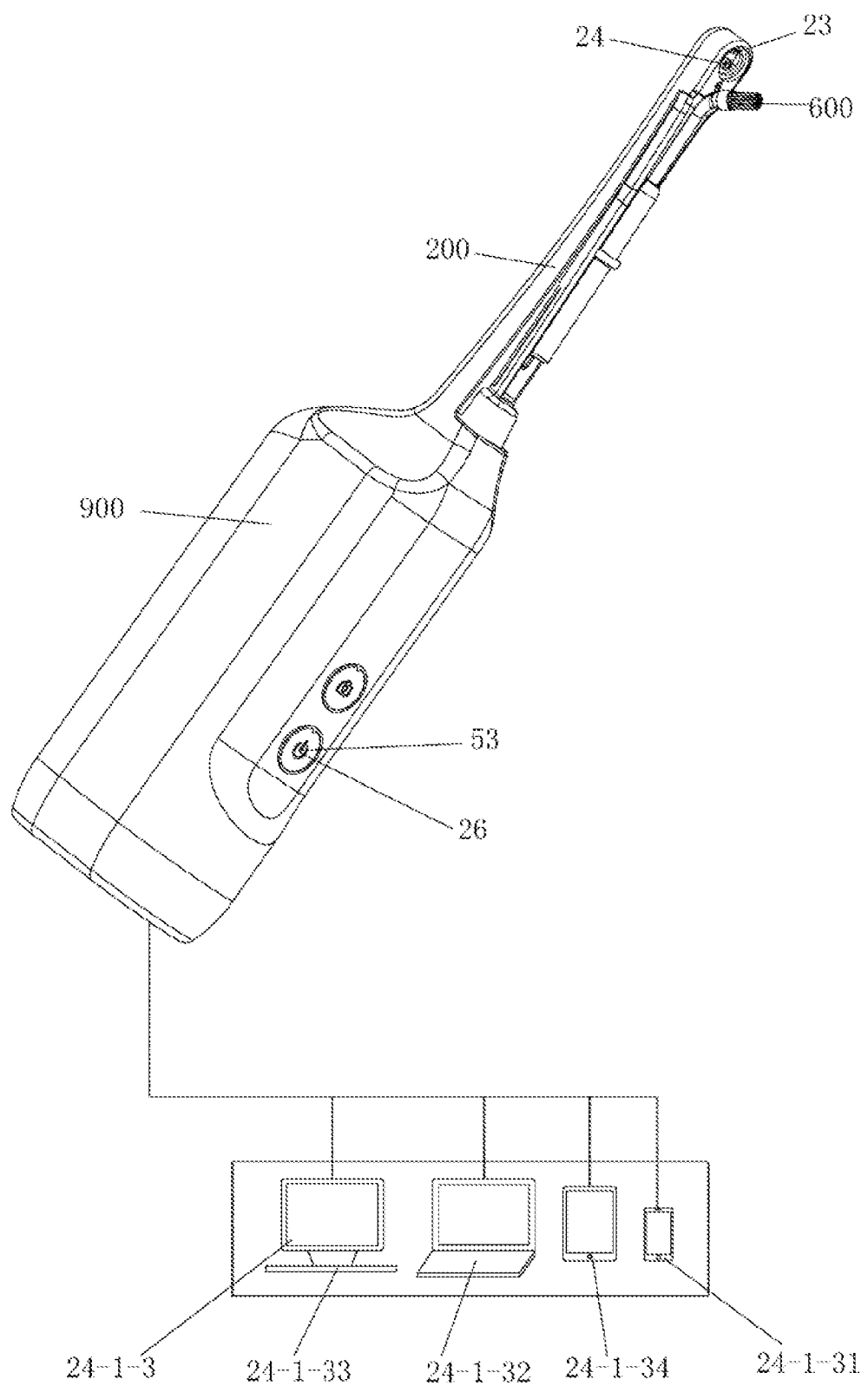
FIG. 35 is a structure diagram of the multifunctional visual oral irrigator according to the present disclosure when connected with the display device in a wired manner.
Figure 36:
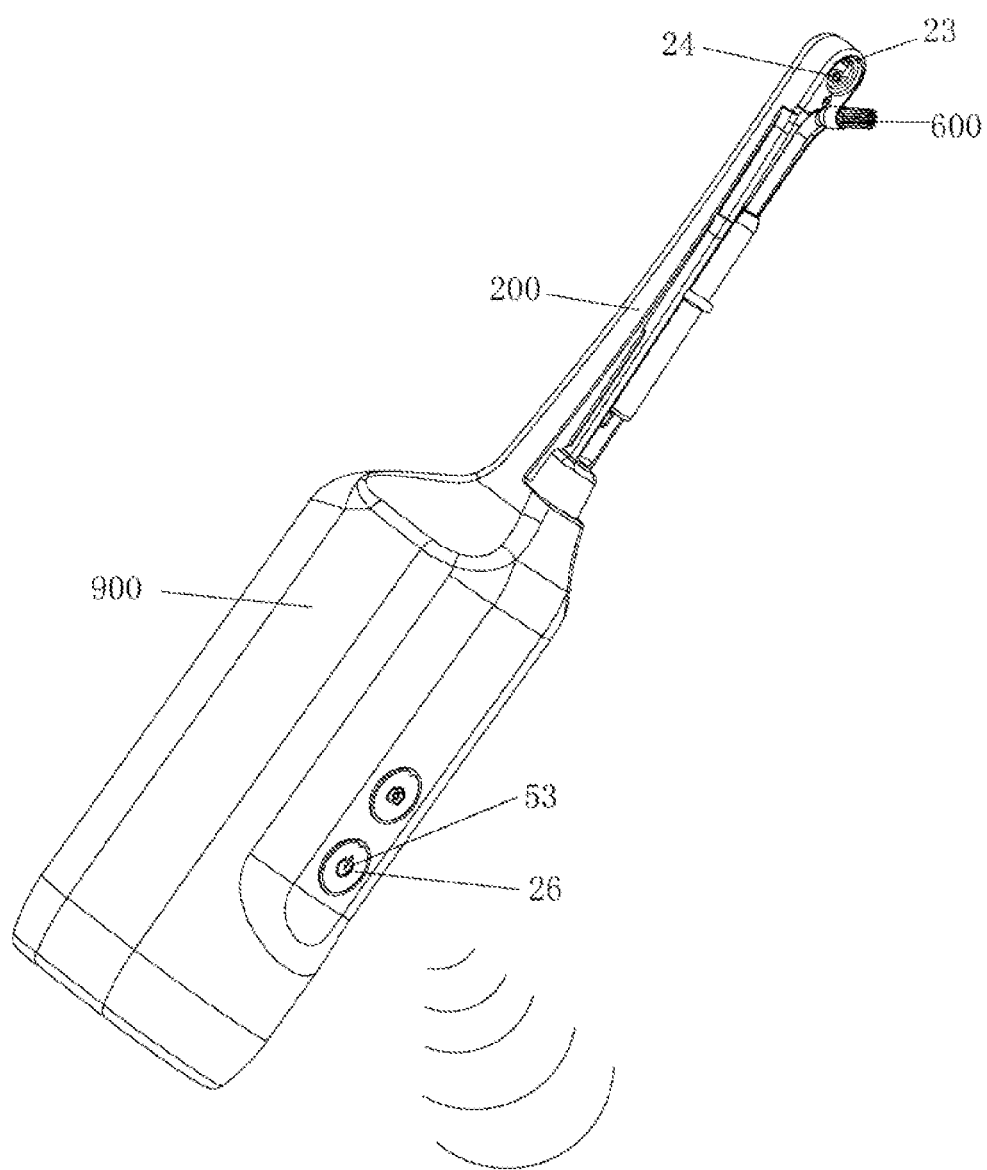
FIG. 36 is a structure diagram of the multifunctional visual oral irrigator according to the present disclosure when connected with the display device in a wireless manner.
Figure 36:
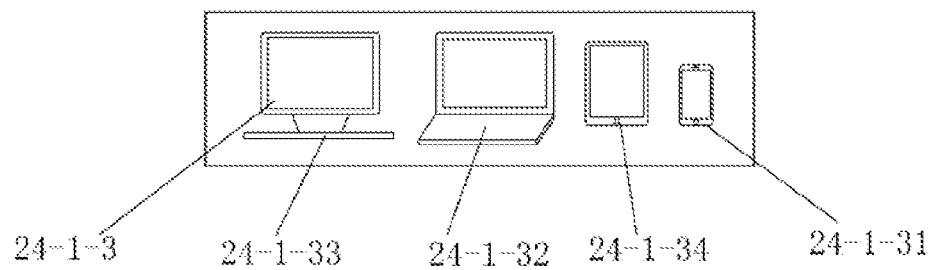

Compared with the above-mentioned embodiments, in the visual oral irrigator of the present disclosure of this embodiment, since the front end of the oral viewer 200 may be equipped with the interdental brush 700, or the dental floss 100, or the toothbrush 600, or the oral forceps 400, in the process of cleaning the oral cavity, the interdental brush 700, or the dental floss 100, or the toothbrush 600, or the oral forceps 400 may be used for cleaning according to needs while water is used for rinsing; especially, the operating process may be transmitted to various display devices in real time, and under direct vision, precise fixed-point cleaning may be performed on the food residues or various foreign objects in the oral cavity may be taken out; and thus, the cleaning effect is greatly enhanced, and the use process is more secure and convenient, with reference to FIG. 35 and FIG. 36.

Here, the applicant only exemplifies several cleaning tools which can be mounted at the same time as the dental irrigator 500 at the front end of the oral viewer 200. Those skilled in the art can design any other cleaning tools as required without departing from the protection scope of the present patent application.

Figure 37:
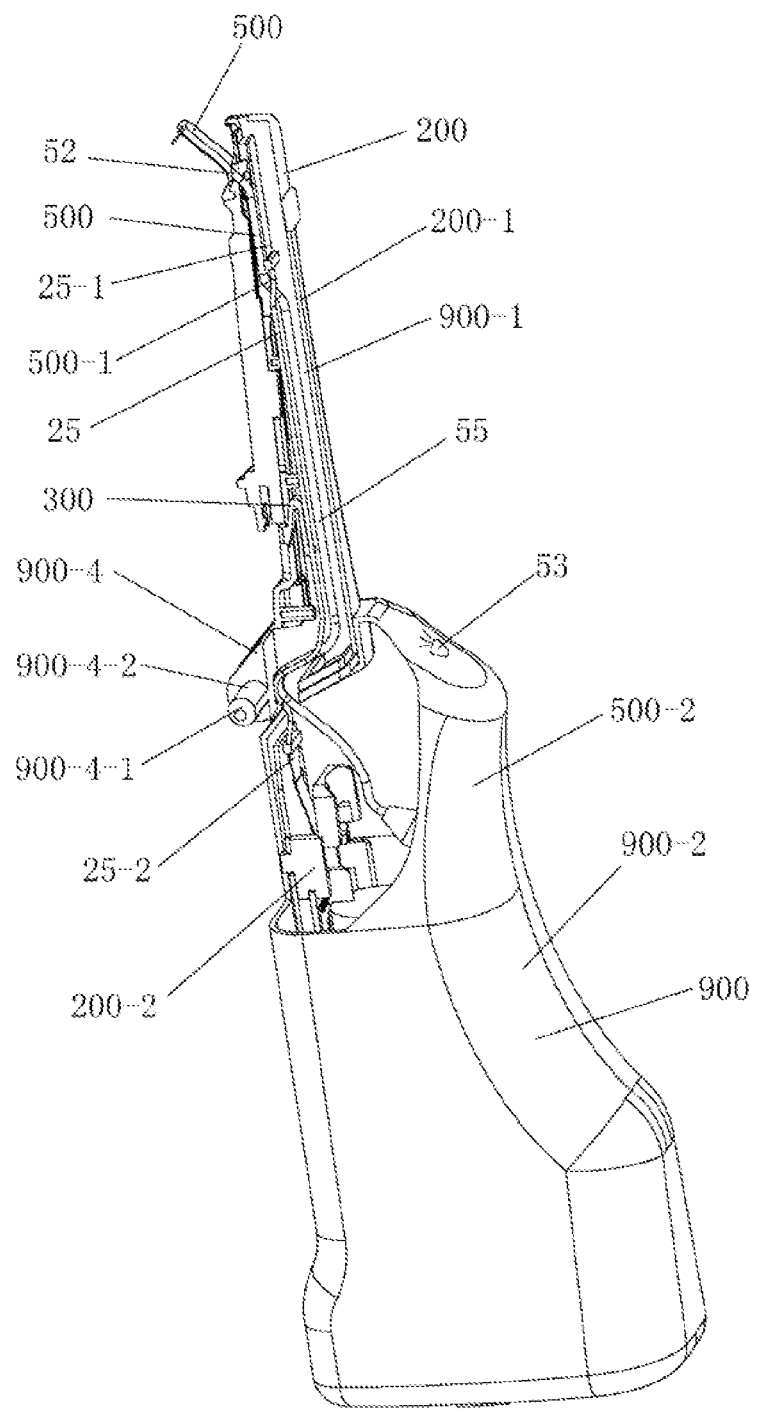
FIG. 37 is a structure diagram of a foldable visual oral irrigator according to the present disclosure.
Figures 1, 37:
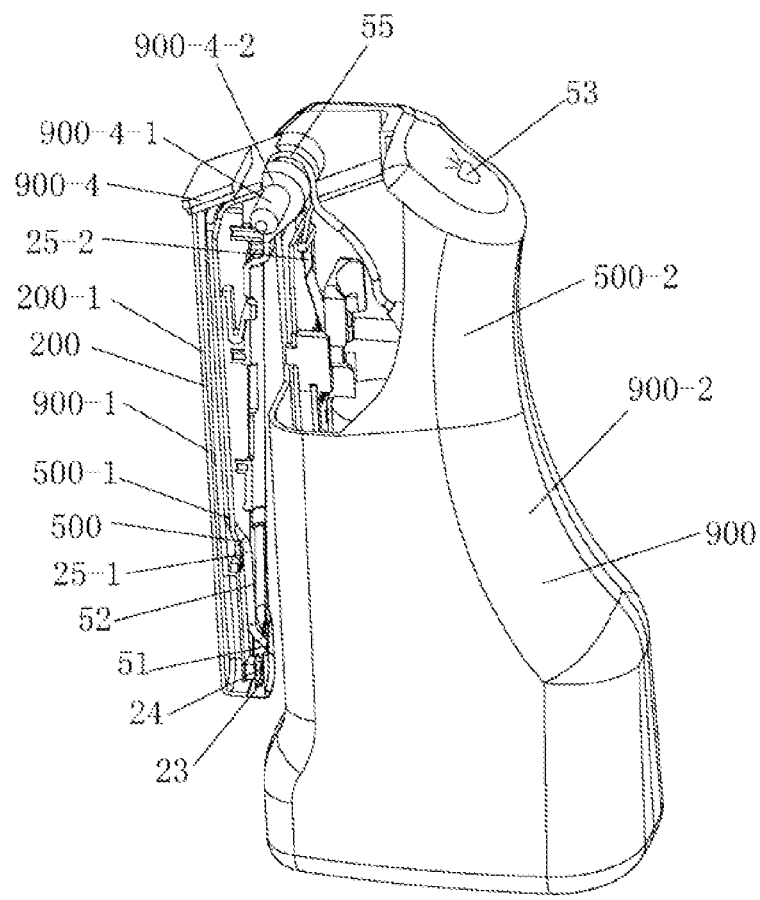
Figures 2, 37:
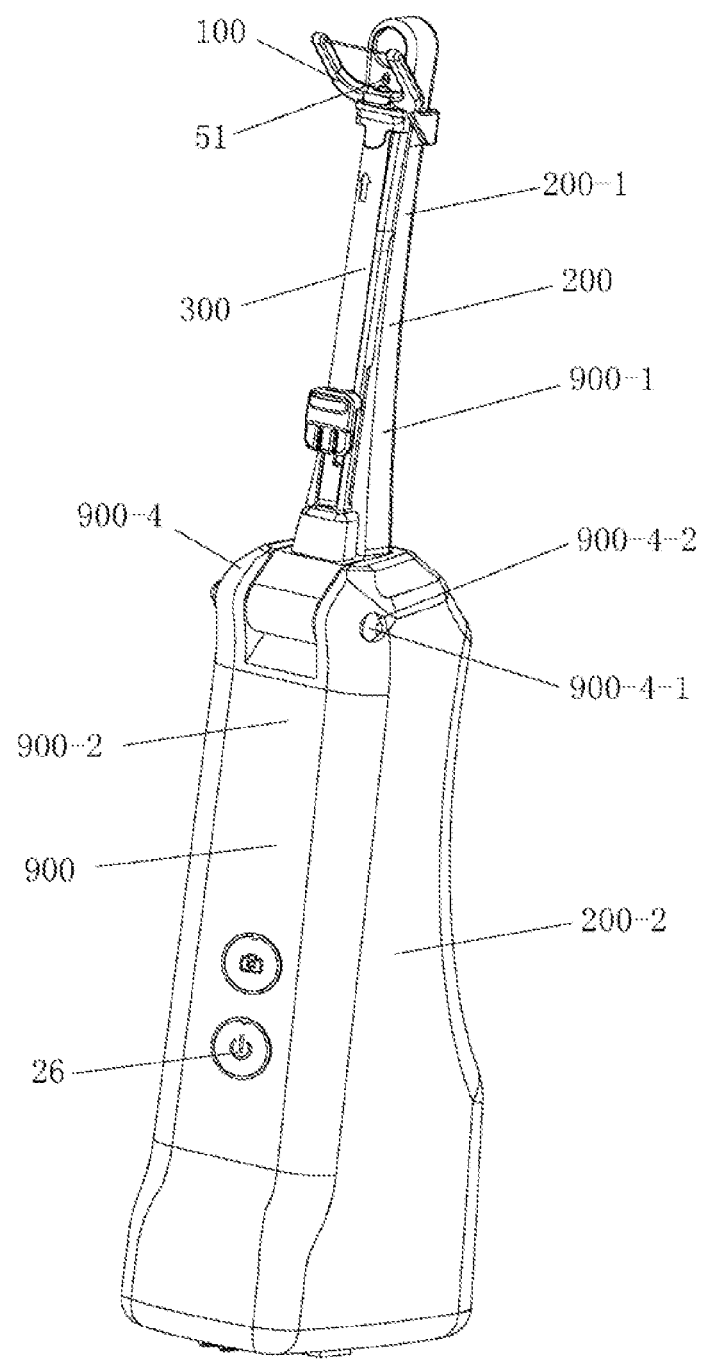

Embodiment 11: A Foldable Visual Oral Irrigator According to the Present Disclosure With reference to FIG. 37 to FIG. 37-2, the difference between this embodiment and Embodiment 6 lies in that in this embodiment, the visual oral irrigator 903 adopts a foldable connection manner.

The front end 903-1 of the visual oral irrigator 903 of the visual oral irrigator 903 and the main body 903-2 of the visual oral irrigator 903 in this embodiment are connected together through the foldable connecting mechanism 903-4.

In this embodiment, the front end 500-1 of the oral irrigator 500 and the main body 500-2 of the oral irrigator 500, and the front end 200-1 of the oral viewer 200 and the main body 200-2 of the oral viewer 200 are simultaneously connected through the foldable connecting mechanism 903-4.

In this embodiment, the foldable connecting mechanism 903-4 is a rotating shaft connecting mechanism. The foldable connecting mechanism 903-4 includes a rotating shaft 903-4-1 and a rotating shaft hole 903-4-2. The rotating shaft 903-4-1 can move in the rotating shaft hole 903-4-2.

The circuit 25-1 at the front end 200-1 of the oral viewer 200 is connected with the circuit 25-2 of the main body 200-2 of the oral viewer 200 through a bendable flexible circuit; when the front end 200-1 of the oral viewer 200 rotates around the rotating shaft 903-4-1 of the foldable connecting mechanism 903-4, the front end 200-1 of the oral viewer 200 can be unfolded or folded relative to the main body 200-2 of the oral viewer 200.

The waterway at the front end 500-1 of the oral irrigator 500 is connected with the waterway of the main body 500-2 of the oral irrigator 500 through the bendable flexible waterway. When the front end 500-1 of the oral irrigator 500 rotates around the rotating shaft 903-4-1 of the foldable connecting mechanism 903-4, the front end 500-1 of the oral irrigator 500 can be unfolded or folded relative to the main body 500-2 of the oral irrigator 500.

In addition, the foldable connecting mechanism 903-4 may also be a concave-convex snap fit connecting mechanism or another type of foldable connecting mechanism. When the foldable connecting mechanism 903-4 is the concave-convex snap fit connecting mechanism, a circuit 25-1 at the front end 200-1 of the oral viewer 200 is connected with a circuit of the main body 200-2 of the oral viewer 200 through a bendable flexible circuit; the front end 200-1 of the oral viewer 200 can be unfolded or folded through the concave-convex snap fit mechanism relative to the main body 200-2 of the oral viewer 200; the waterway at the front end 500-1 of the oral irrigator 500 is connected with the waterway of the main body 500-2 of the oral irrigator 500 through the bendable flexible waterway; and the front end 500-1 of the oral irrigator 500 can be unfolded or folded through the concave-convex snap fit mechanism relative to the main body 500-2 of the oral irrigator 500.

Since the oral viewer 200 and the oral irrigator 500 of the visual oral irrigator 903 are simultaneously connected by using the foldable connecting mechanism 903-4, the visual oral irrigator 903 can be folded and unfolded by just rotating the front end 903-1 of the visual oral irrigator 903 around the foldable connecting mechanism 903-4, so that the visual oral irrigator 903 is convenient to store, and the folding and unfolding processes are very simple and convenient.

Embodiment 12: A Foldable Visual Oral Irrigator According to the Present Disclosure With reference to FIG. 38 to FIG. 38-3, the difference between this embodiment and Embodiment 7 lies in that in this embodiment, the front end 903-1 and the main body 903-2 of the visual oral irrigator 903 are connected in a detachable manner.

Figure 38:
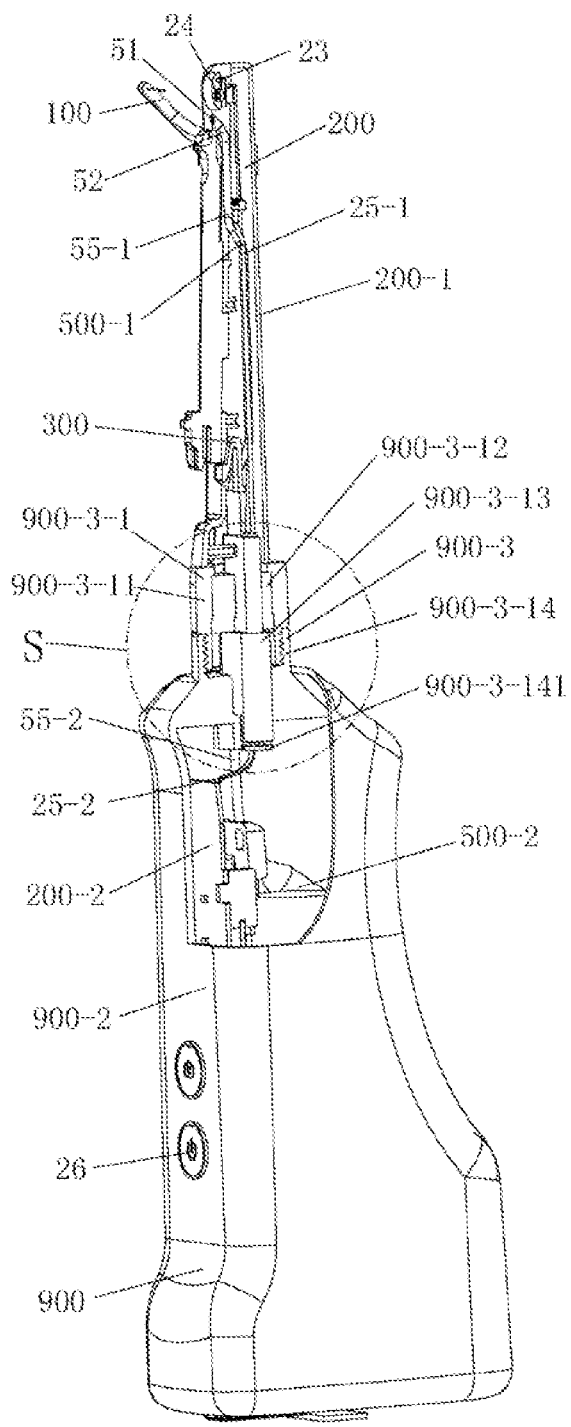
FIG. 38 is a structure diagram of a detachable visual oral irrigator according to the present disclosure.
Figures 1, 38:
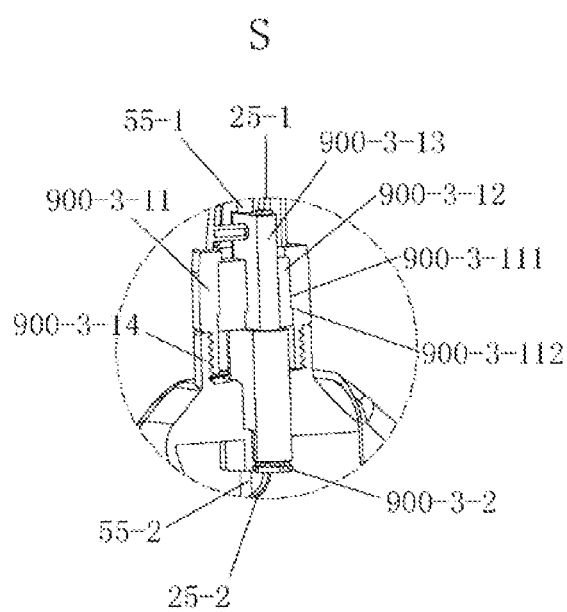
Figures 2, 38:
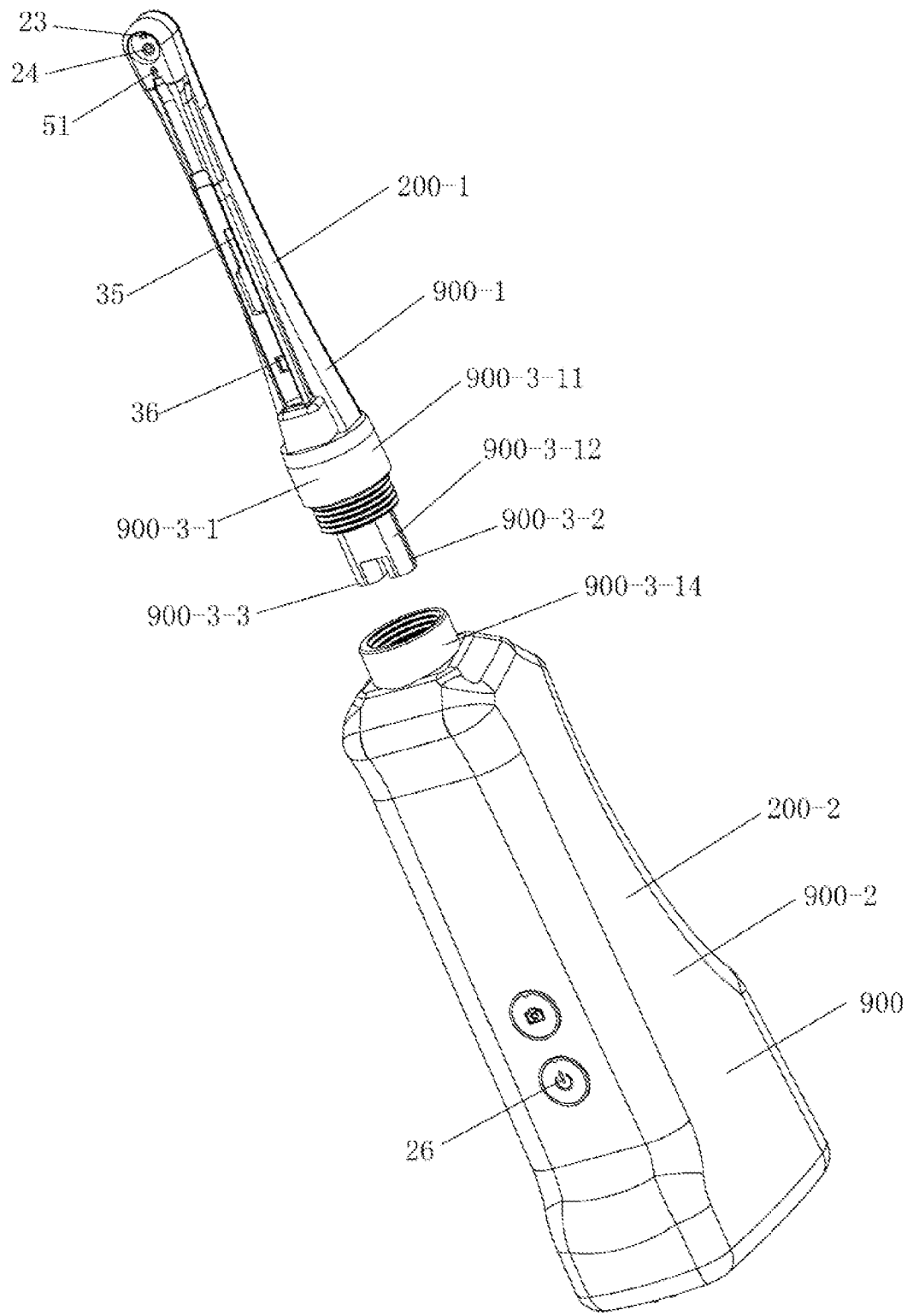
Figures 3, 38:
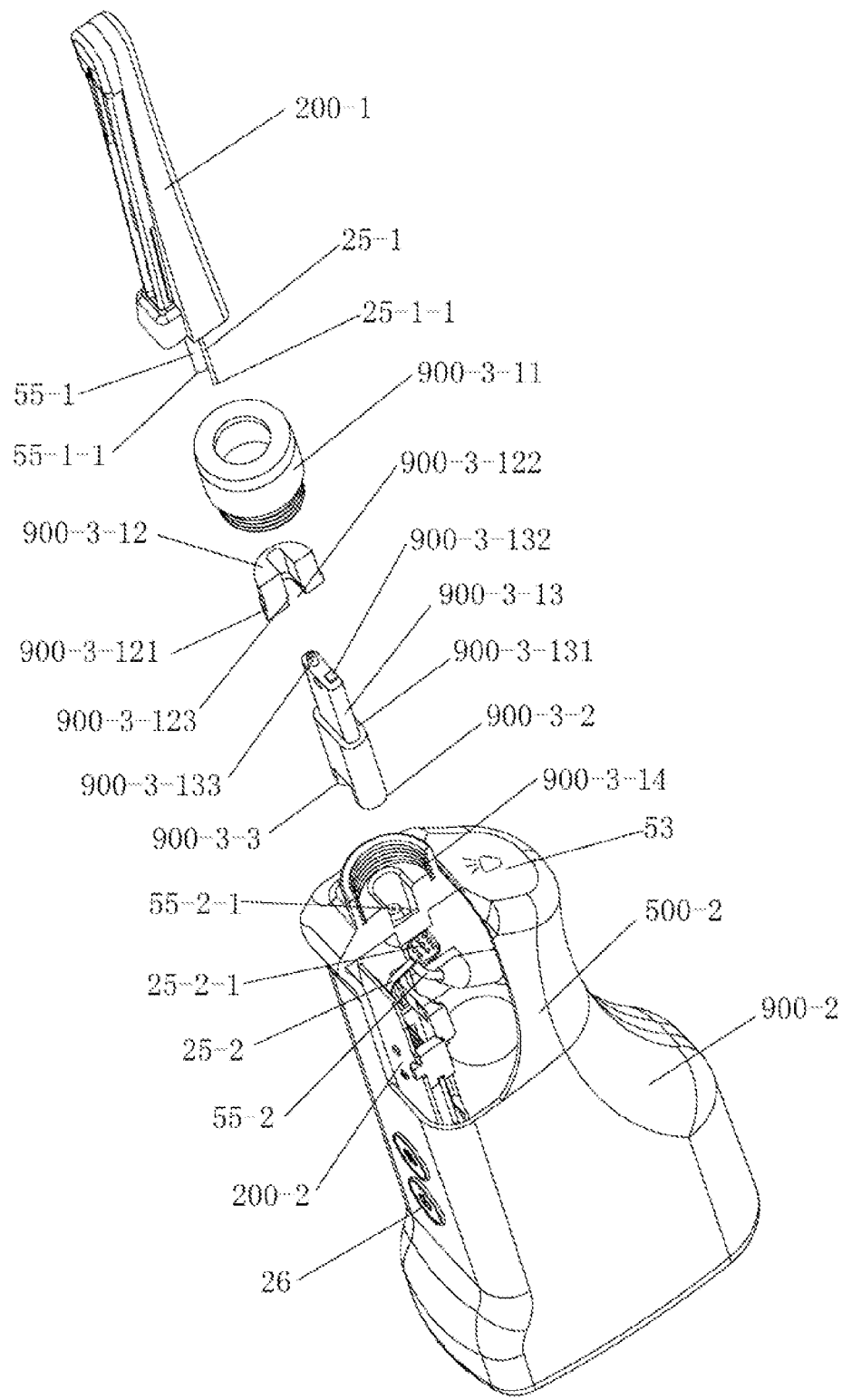

In this embodiment, the front end 903-1 of the visual oral irrigator 903 and the main body 903-2 of the visual oral irrigator 903 are connected together through the detachable connecting mechanism 903-3, with reference to FIG. 38 to FIG. 38-2.

The front end 500-1 of the oral irrigator 500 and the main body 500-2 of the oral irrigator 500, and the front end 200-1 of the oral viewer 200 and the main body 200-2 of the oral viewer 200 are simultaneously connected through the detachable connecting mechanism 903-3.

In this embodiment, the detachable connecting mechanism 903-3 includes a connecting and fixing mechanism 903-3-1, an electrical joint 903-3-2 and a water joint 903-3-3.

The connecting and fixing mechanism 903-3-1 can simultaneously and respectively connect and fix the front end 500-1 of the oral irrigator 500 and the front end 200-1 of the oral viewer 200 to the main body 500-2 of the oral irrigator 500 and the main body 200-2 of the oral viewer 200.

The electrical joint 903-3-2 can connect a circuit 25-1 at the front end 200-1 of the oral viewer 200 with a circuit 25-2 of the main body 200-2. The water joint 903-3-3 can connect the waterway at the front end 500-1 of the oral irrigator 500 with the waterway of the main body 500-2.

With reference to FIG. 38-3, in this embodiment, the connecting and fixing mechanism 903-3-1 is a rotary connecting and fixing mechanism, the connecting and fixing mechanism 903-3-1 includes an internal screw 903-3-11, a rotation stop block 903-3-12, a connecting component 903-3-13 and an external nut 903-3-14.

The internal screw 903-3-11 is connected to the front end 903-1 of the visual oral irrigator 903.

The rotation stop block 903-3-12 is provided with a locating convex stair 903-3-121, and has a rotation stop slot 903-3-122 and a rotation stop convex stair 903-3-123 of which the shapes are matched with the shape of the connecting component 903-3-13.

The connecting component 903-3-13 is provided with a limit convex stair 903-3-131, an electrical connector 903-3-132 and a water tube 903-3-133.

The external nut 903-3-14 is connected to the main body 903-2 of the visual oral irrigator 903. The lower end of the external nut 903-3-14 is provided with a joint platform 903-3-141.

An interface 25-1-1 of the circuit 25-1 at the front end 200-1 of the oral viewer 200 and an interface 55-1-1 of the water discharge tube 55-1 at the front end 500-1 of the oral irrigator 500 are arranged at the upper end of the connecting component 903-3-13.

An interface 25-2-1 of the circuit 25-2 of the main body 200-2 of the oral viewer 200 and an interface 55-2-1 of the water discharge tube 55-2 of the main body 500-2 of the oral irrigator 500 are arranged on the joint platform 903-3-141 on the lower end of the external nut 903-3-14.

The interface 25-1-1 of the circuit 25-1 at the front end 200-1 of the oral viewer 200 and the interface 25-2-1 of the circuit 25-2 of the main body 200-2 of the oral viewer 200 are connected through the electrical connector 903-3-132 of the connecting component 903-3-13 to constitute the electrical joint 903-3-2. The interface 55-1-1 of the water discharge tube 55-1 at the front end 500-1 of the oral irrigator 500 is connected with the upper end of the water tube 903-3-133 of the connecting component 903-3-13, and the interface 55-2-1 of the water discharge tube 55-2 of the main body 500-2 of the oral irrigator 500 is connected with the lower end of the water tube 903-3-133 of the connecting component 903-3-13 to constitute the water joint 903-3-3.

When mounting, the connecting component 903-3-13 is embedded in the rotation stop slot 903-3-122 of the rotation stop block 903-3-12, the rotation stop convex stair 903-3-123 of the rotation stop block 903-3-12 abuts against the limit convex stair 903-3-131 of the connecting component 903-3-13, the connecting component 903-3-13 and the rotation stop block 903-3-12 are mounted together into the mounting slot 903-3-111 of the internal screw 903-3-11, the locating convex stair 903-3-121 of the rotation stop block 903-3-12 abuts against the locating groove 903-3-112 of the internal screw 903-3-11, and the front end 903-1 of the visual oral irrigator 903 is connected to the connecting component 903-3-13, thereby completing the connection between the fixing and connecting mechanism 903-3-1 and the front end 903-1 of the visual oral irrigator 903, with reference to FIG. 38 and FIG. 38-1.

When storage, by rotating the internal screw 903-3-11 of the connecting and fixing mechanism 903-3-1, the external nut 903-3-14 and the internal screw 903-3-11 are separated, so that the front end 903-1 of the visual oral irrigator 903 can be removed from the main body 903-2, and the front end 903-1 and the main body 903-2 of the visual oral irrigator 903 can be stored respectively and are convenient to store and carry, with reference to FIG. 38-2.

When the visual oral irrigator needs to be taken out and used, by rotating the internal screw 903-3-11 in the reverse direction, the external nut 903-3-14 and the internal screw 903-3-11 are connected firmly, and at this time, the interface 25-1-1 of the circuit 25-1 at the front end 200-1 of the oral viewer 200 is connected with the interface 25-2-1 of the circuit 25-2 of the main body 200-2 of the oral viewer 200 so as to connect the electrical joint 903-3-2; and the interface 55-1-1 of the water discharge tube 55-1 at the front end 200-1 of the oral irrigator 500 is connected with the interface 55-2-1 of the water discharge tube 55-2 of the main body 500-2 of the oral irrigator 500 so as to connect the water joint 903-3-3. The visual oral irrigator of the present disclosure can be used normally to clean the teeth, with reference to FIGS. 38 and 38-1.

In this embodiment, the applicant only enumerates the connecting and fixing mechanism 903-3-1 in a rotary connection manner, and the connecting and fixing mechanism 903-3-1 may also be a concave-convex snap fit connecting and fixing mechanism, or a magnetic connecting and fixing mechanism, or other types of detachable connection mechanisms, which are not described here in detail by the applicant, but they do not depart from the protection scope of the present patent application.

In this embodiment, the connecting and fixing mechanism 903-3-1 is separately arranged; and if the connection strength of the electrical joint 903-3-2 and/or the water joint 903-3-3 is sufficient, and can ensure that the visual oral irrigator 903 may be used normally after the connection, the connecting and fixing mechanism 903-3-1 and the electrical joint 903-3-2 or water joint 903-3-3 may also be designed as an integral body, which will not be described here in detail by the applicant.

In this embodiment, the front end 903-1 and the main body 903-2 of the visual oral irrigator 903 may be completely detached, and thus, are more convenient to store and carry; and since the front end 903-1 and the main body 903-2 are completely detached, the accidental rupture of the flexibly connected circuit system and waterway system caused by repeated rotation and bends can be effectively avoided, and thus, the long-term use process is more secure and reliable.

Embodiment 13: A Visual Toothbrush According to the Present Disclosure

Figures 1, 39:
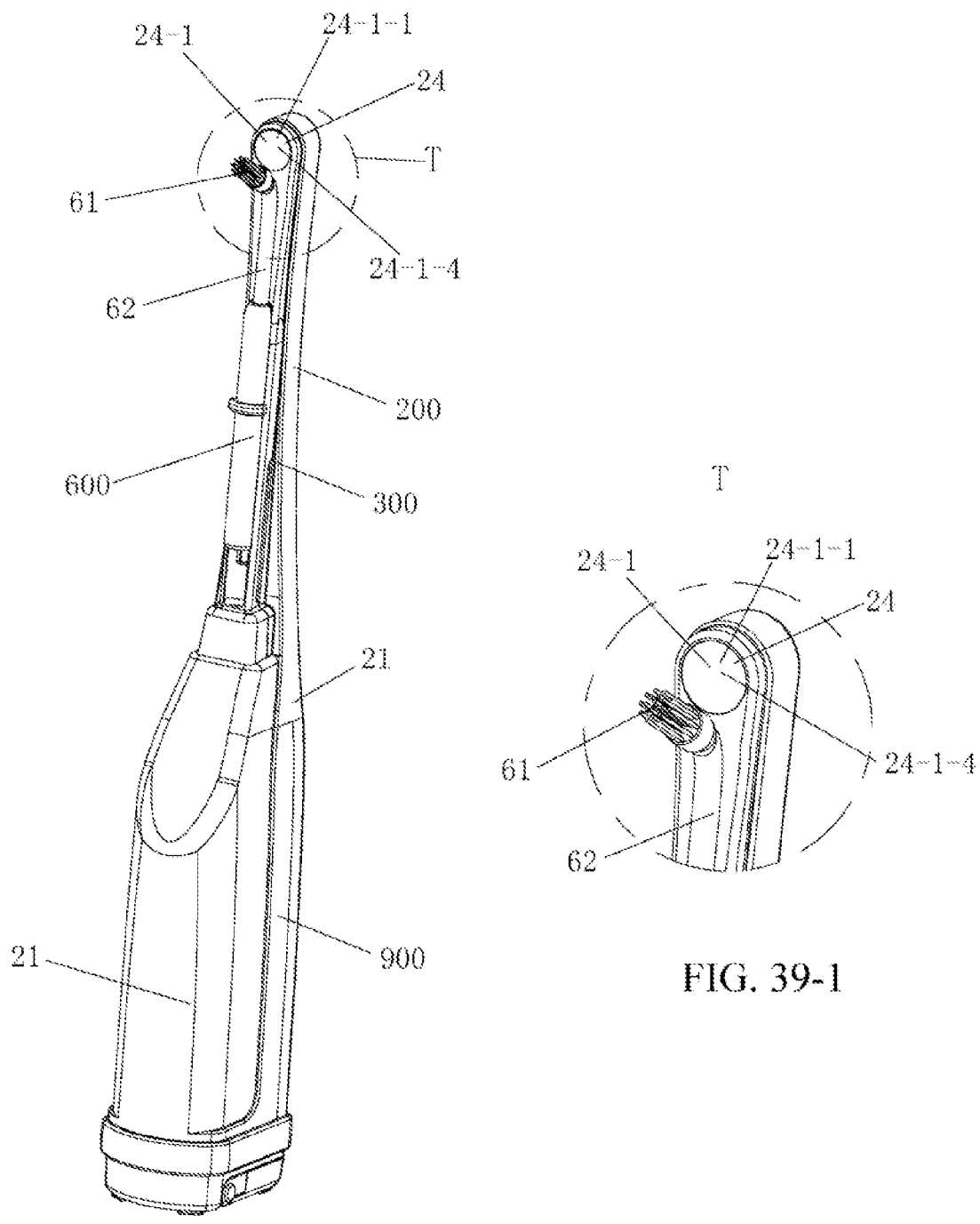
FIG. 39 is a three-dimensional structure diagram of a visual toothbrush according to the present disclosure.
Figures 2, 3, 39:
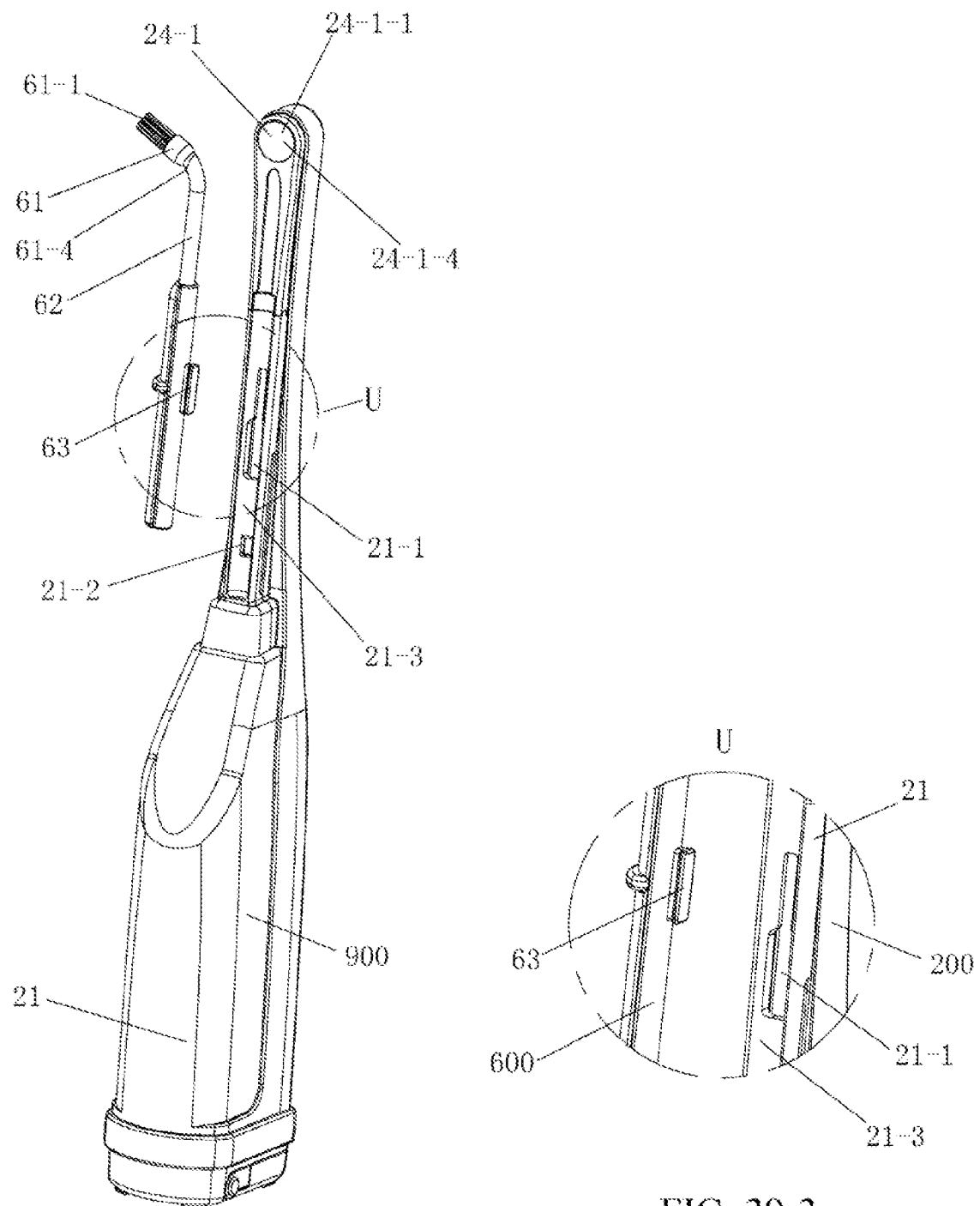
Figure 40:
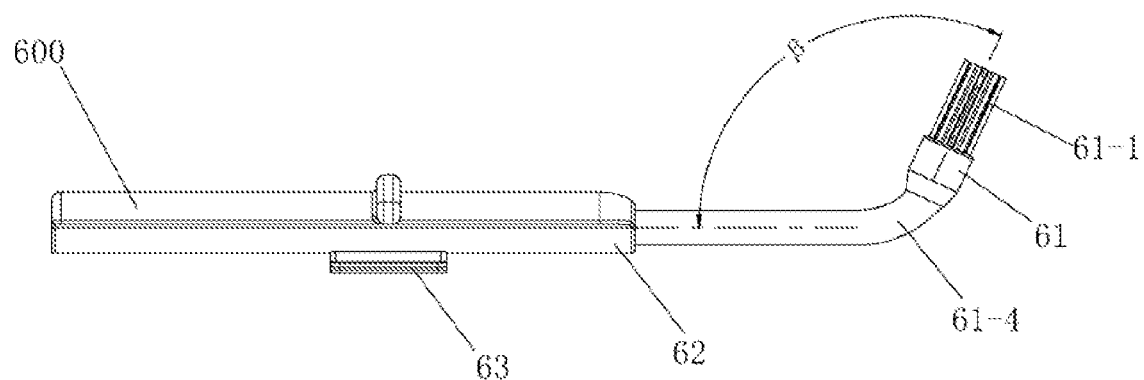
FIG. 40 is a structure diagram of a toothbrush.
Figures 1, 40:
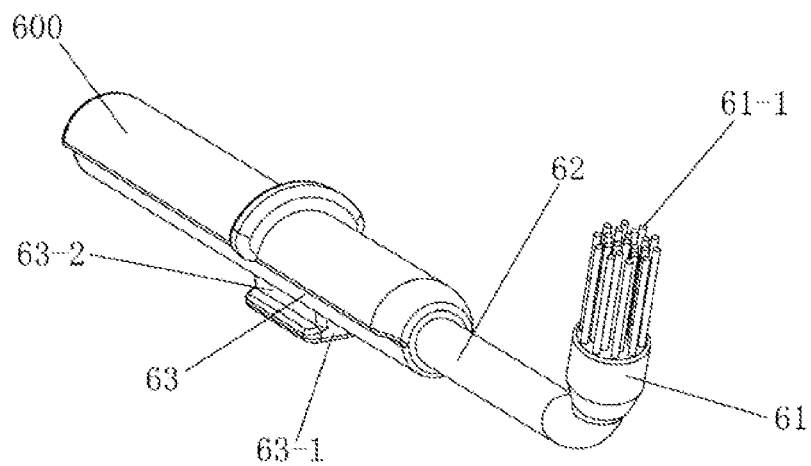
Figures 2, 40:
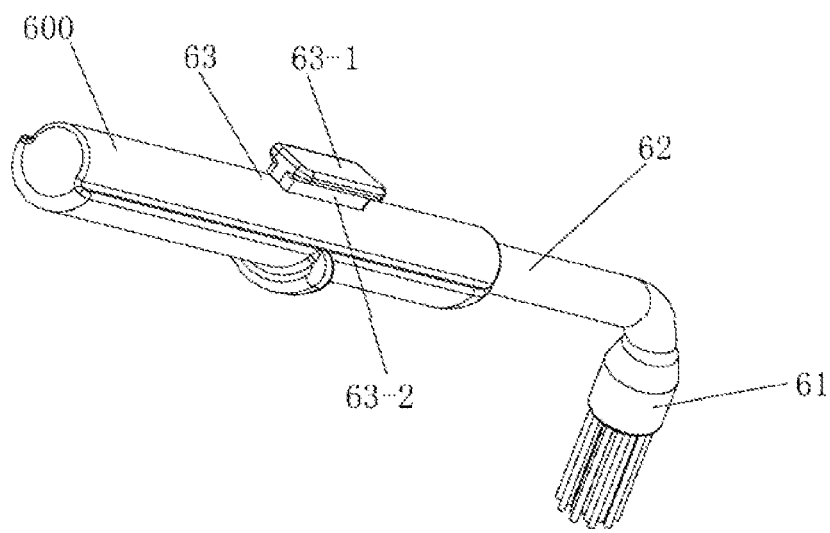

With reference to FIG. 39 to FIG. 40-3, the visual toothbrush 904 of this embodiment includes a toothbrush 600, an oral viewer 200 and a connecting mechanism 300.

The toothbrush 600 includes a brush head 61, a brush rod 62 and a mounting base 63.

In this embodiment, the brush head 61 of the toothbrush 600 includes multiple brush hairs 61-1, and the brush head 61 can achieve the cleaning effect of a common toothbrush.

The brush head 61 is arranged at the front end of the brush rod 62, and the mounting base 63 is arranged at the rear end of the brush rod 62.

In this embodiment, the brush hairs 61-1 of the brush head 61 are directly planted to the front end of the brush rod 62 by integral manufacturing so as to form an integral body with the brush rod 62. Of course, the brush head 61 may also be connected to the front end of the brush rod 62 in various detachable manners.

With reference to FIG. 39 FIG. 39-1, the brush head 61 is within the visual field of the viewing system 24 of the oral viewer 200, so the cleaned position and the cleaning effect of the brush head 61 can be clearly viewed through the viewing system 24.

With reference to FIG. 40, the included angle β between the brush head 61 and the brush rod 62 is 90°-170°. In order to ensure that the brush head 61 can be within the visual field of the viewing system 24 of the oral viewer 200, the included angle β between the brush head 61 and the brush rod 62 is generally greater than 90°; and in order to ensure the viewing effect, the included angle β between the brush head 61 and the brush rod 62 is generally controlled at 60°-150°.

With reference to FIG. 40 to FIG. 40-3, there is a curvature 61-4 that meets the requirements of the human oral cavity between the brush head 61 of the toothbrush 600 and the brush rod 62. When cleaning the deep position of the oral cavity, the curvature 61-4 that meets the requirements of the human oral cavity between the brush head 61 and the brush rod 62 can conveniently deliver the brush head 61 to the deep position of the oral cavity to be cleaned.

With reference to FIG. 39-2 and FIG. 39-3, the mounting base 63 of the toothbrush 600 is provided with a locating block 32 used to be connected with the oral viewer 200. In this embodiment, the mounting base 63 and the brush rod 62 are manufacture into an integral body. The mounting base 63 may also be connected with the brush rod 62 together through a detachable connection manner, which does not depart from the protection scope of the present patent.

The locating block 32 is of an inverted T-shaped structure, and a sliding slot 63-2 is formed in the inverted T-shape position of the locating block 32, with reference to FIG. 40 to FIG. 40-3.

The housing 21 of the oral viewer 200 is provided with a locating slot 35, a clamping block 36 and a mounting slot 21-3. The locating block 32 may be embedded in the locating slot 35 of the housing 21 of the oral viewer 200; and the mounting base 63 may be embedded in the toothbrush mounting slot 21-3 of the housing 21, and the tail of the mounting base 63 abuts against and is fixed by the clamping block 36 of the housing 21 of the oral viewer 200. The coordination of the locating block 32, the locating slot 35 and the clamping block 36 constitutes the connecting mechanism 300.

That is to say, in this embodiment, the inverted T-shaped locating block and the sliding slot 63-2 thereof cooperate with the locating slot 35 to limit the up-and-down and left-and-right movements of the toothbrush 600 on the housing 21 of the oral viewer 200. The clamping block 36 abuts against the tail of the mounting base 63, so that the mounting base 63 is embedded in the mounting slot 21-3 of the mounting base 63, and thus, the forward and backward movement of the toothbrush 600 is limited, thereby mounting and fixing the toothbrush 600 to the housing 21 of the oral viewer 200. The clamping block 36 is pressed down to release the limit effect of the clamping block 36 on the tail of the mounting base 63, so that the mounting base 63 can be withdrawn backward, and the toothbrush 600 can be removed from the oral viewer 200.

In this embodiment, the connecting mechanism 300 is the detachable mechanical connecting mechanism; the connecting mechanism 300 may also be a combined mechanical connecting mechanism formed by arranging a part of the detachable mechanical connecting mechanism on the toothbrush 600 and the other part on the oral viewer 200. Of course, the connecting mechanism 300 may also be a separate component, and is separately arranged on the toothbrush 600 or arranged on the oral viewer 200. Both do not depart from the protection scope of the present patent application. The detachable mechanical connecting mechanism is convenient for the user to replace the toothbrush 600, so the use process is more convenient and hygienic, and the use cost of the user is saved.

In this embodiment, the mechanical connecting mechanism adopts a concave-convex snap fit connection manner. The mechanical connecting manner may also be a sliding slot connection, or a pin connection, or a key connection, or a threaded connection, or a screw connection, or a buckle connection, or a hook connection, or an interference fit connection, or various other connection manners. Those skilled in the art can perform various specific product designs according to the technical solutions disclosed in the present disclosure without departing from the protection scope of the present patent.

The oral viewer 200 includes a housing 21, a power supply system 22, a lighting system 23, a viewing system 24, a circuit system 25 and a switch 26; the lighting system 23, the viewing system 24, the circuit system 25 and the power supply system 22 are mounted in the housing 21, and the switch 26 is mounted on the housing 21; and the lighting system 23, the viewing system 24, the power supply system 22 and the switch 26 are connected together through the circuit system 25.

In addition, the housing 21 may also be provided with a status light 26-1 for displaying the status of the visual toothbrush of the present disclosure, such as whether the visual toothbrush is turned on, whether Wi-Fi connection is on, whether the energy of the battery is sufficient, or the like, with reference to FIG. 4-1.

Figures 1, 41:
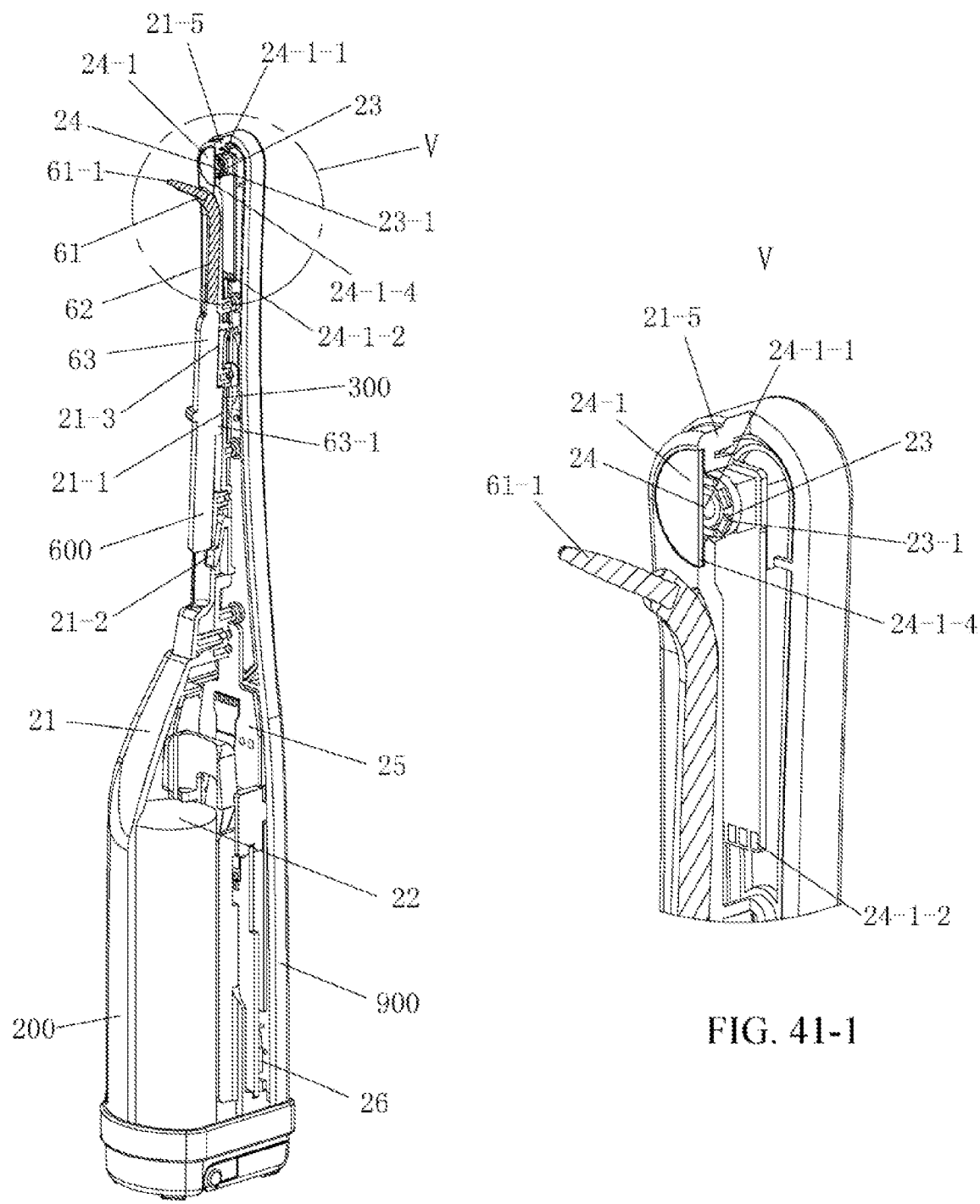
FIG. 41 is a three-dimensional structure diagram of a visual toothbrush including 1 brush hair according to the present disclosure.
Figures 2, 3, 41:
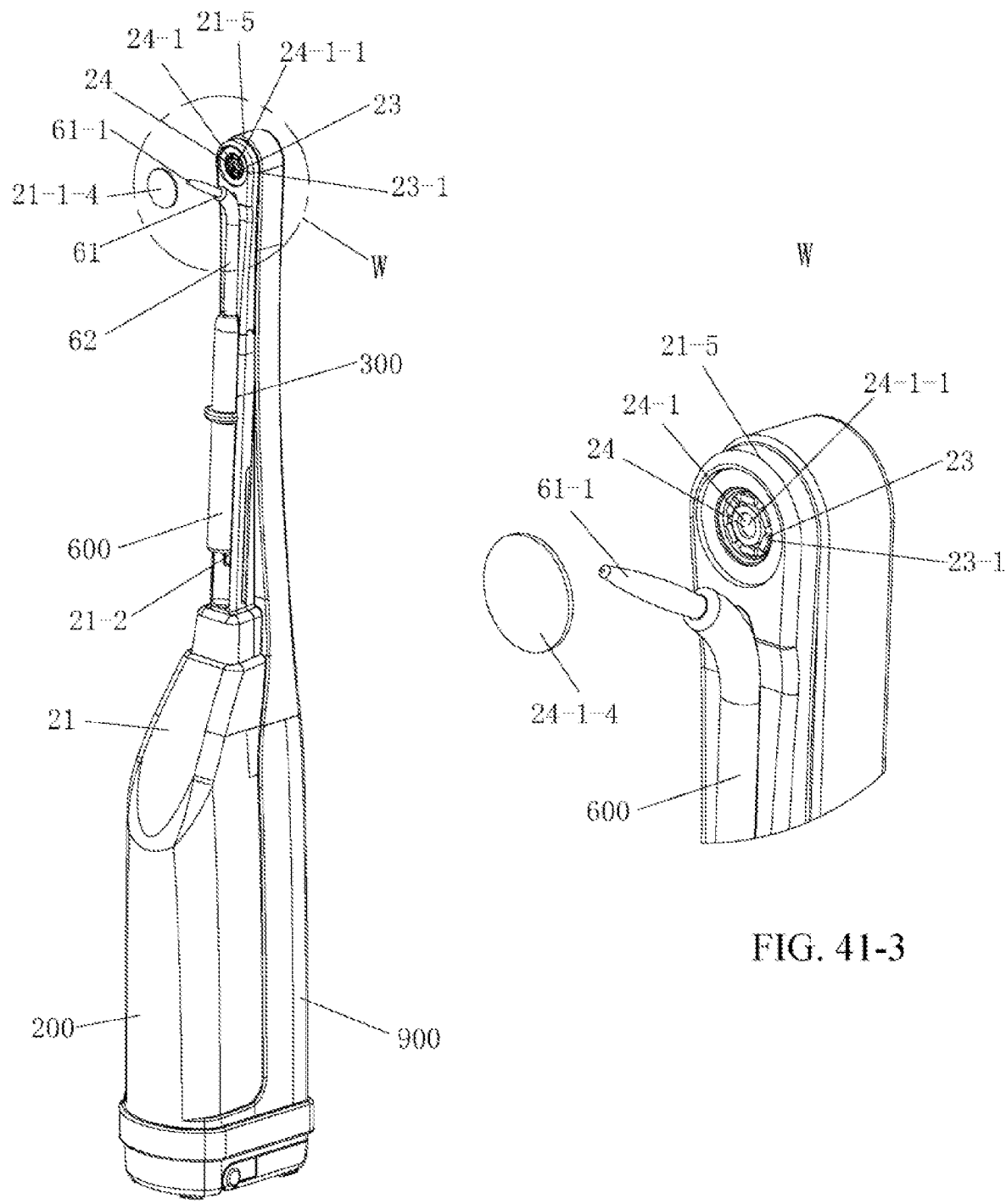
Figure 42:
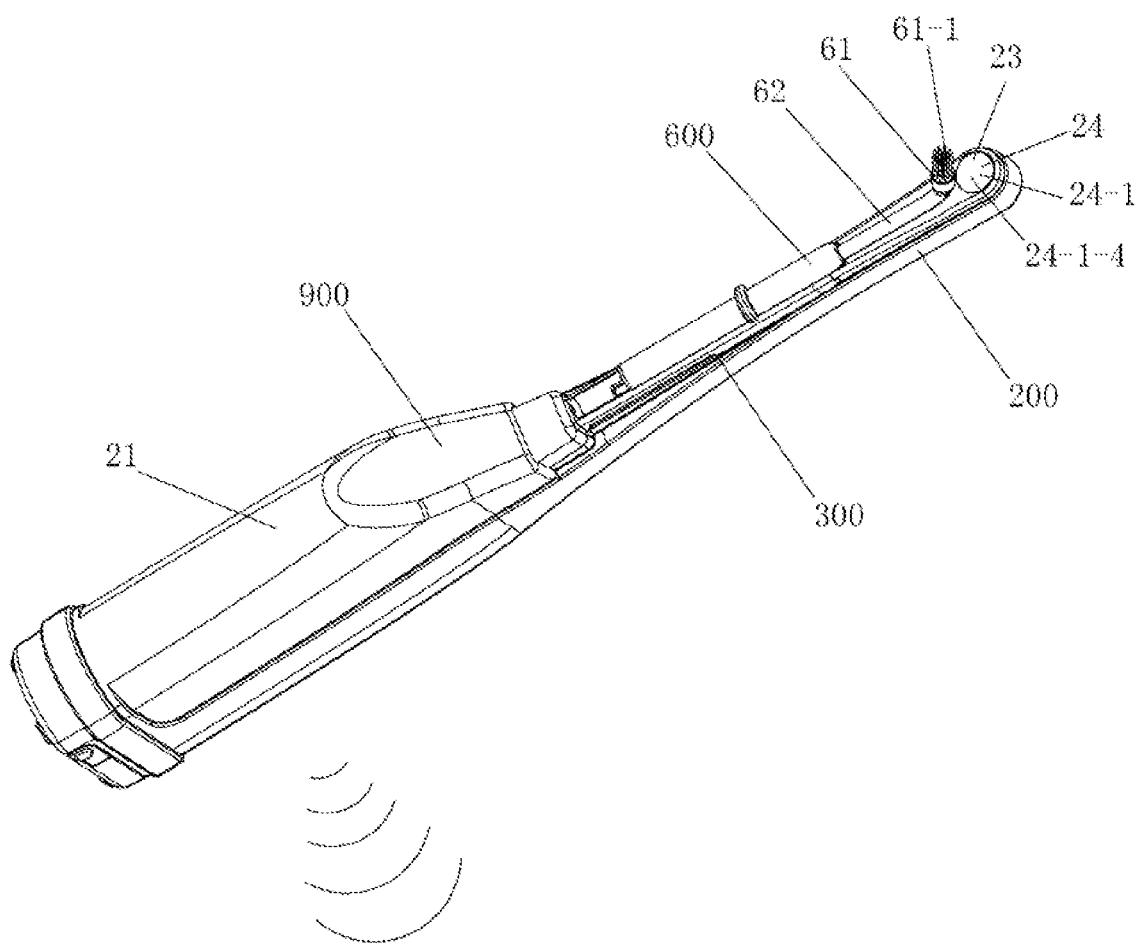
FIG. 42 is a structure diagram of the visual toothbrush according to the present disclosure when connected with the display device in a wireless manner.
Figure 42:
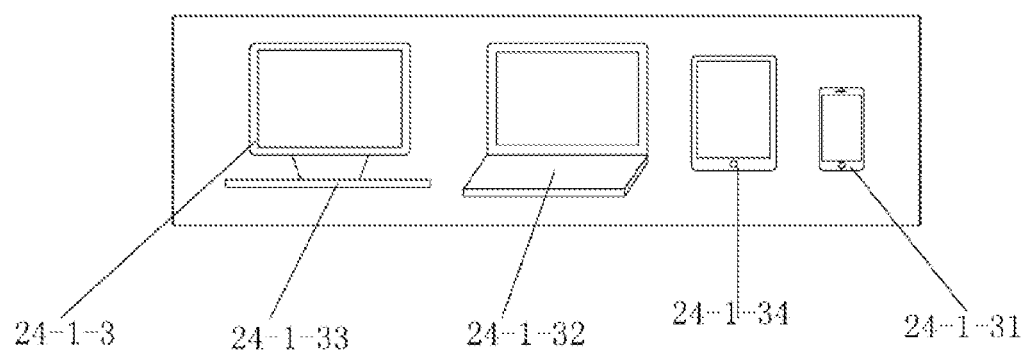
Figure 42:
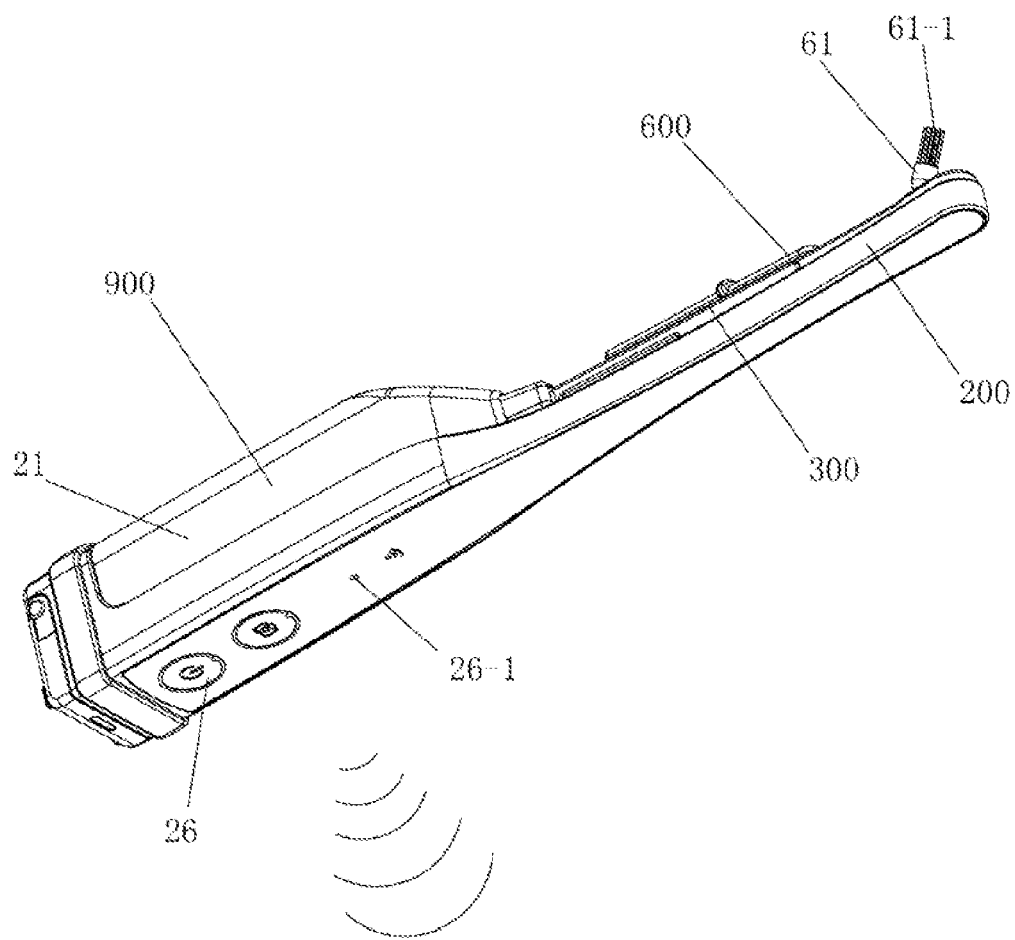
Figure 1:
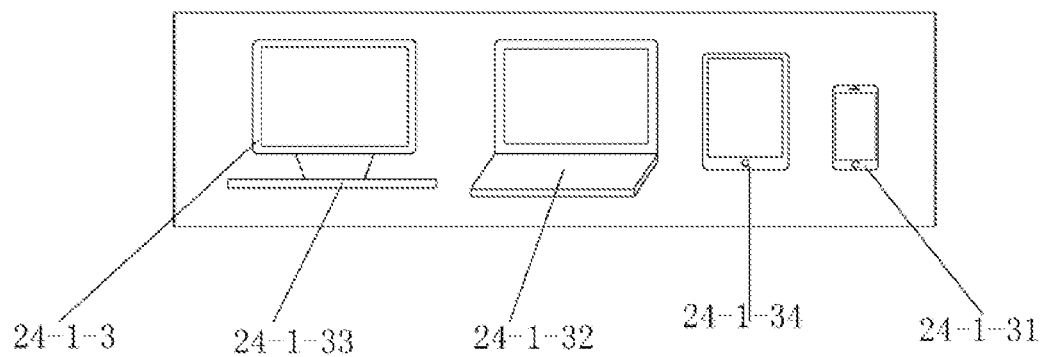
Figure 43:
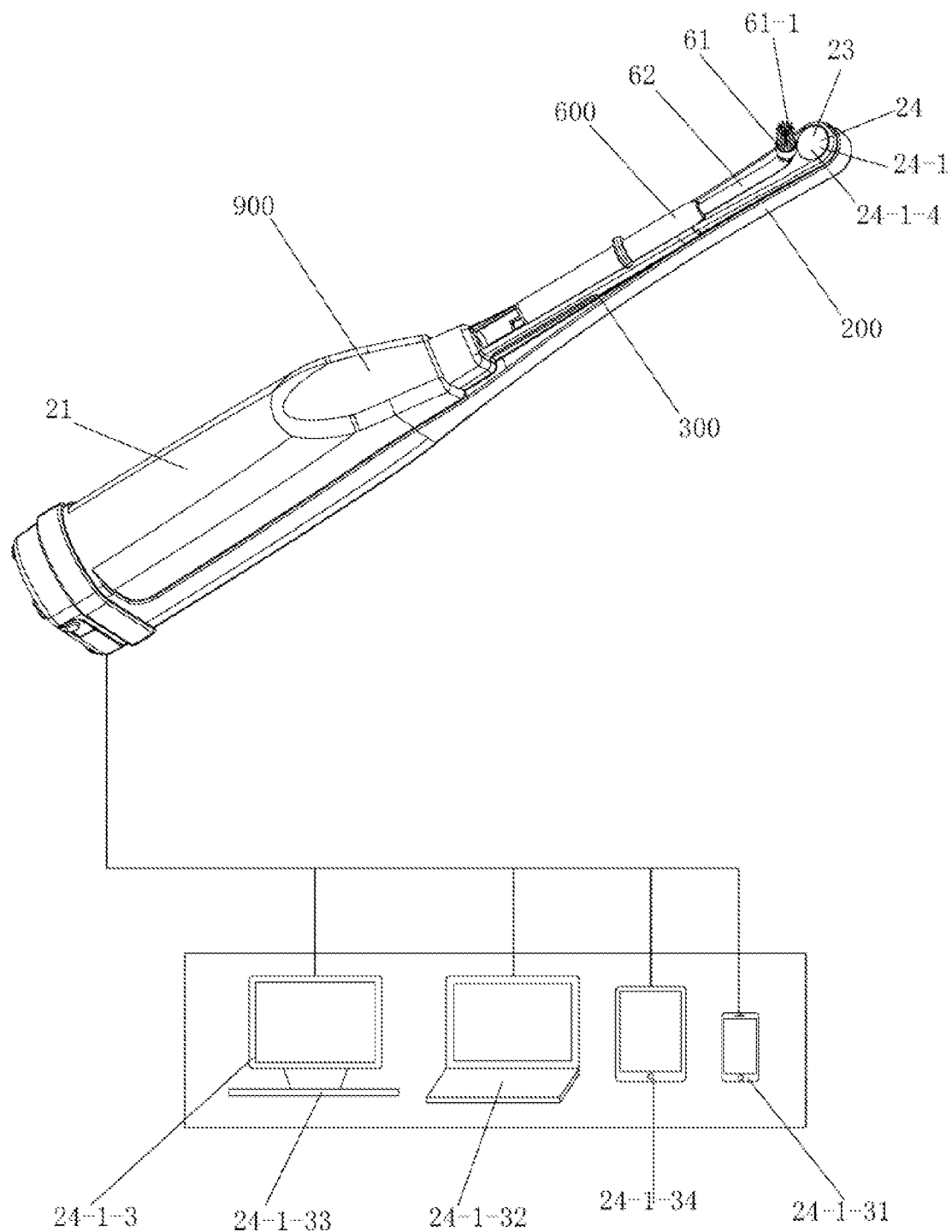
FIG. 43 is a structure diagram of the visual toothbrush according to the present disclosure when connected with the display device in a wired manner.
Figure 44:
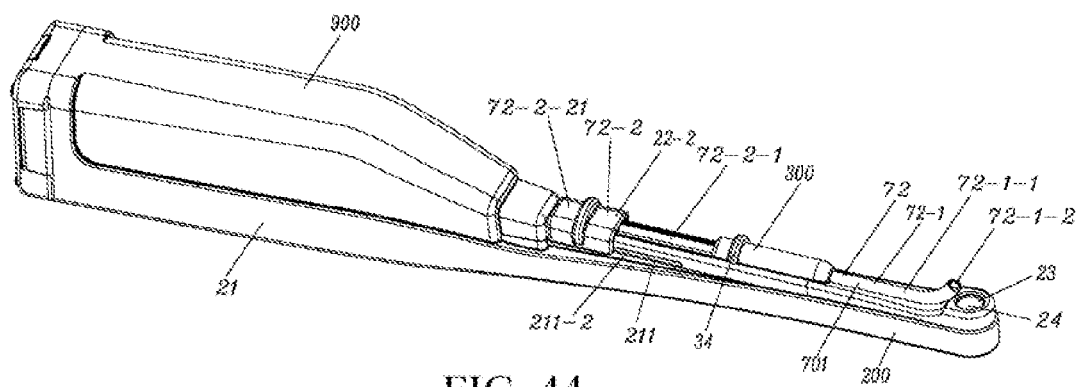
FIG. 44 is a structure diagram of a detachable visual interdental brush according to the present disclosure.
Figures 1, 44:
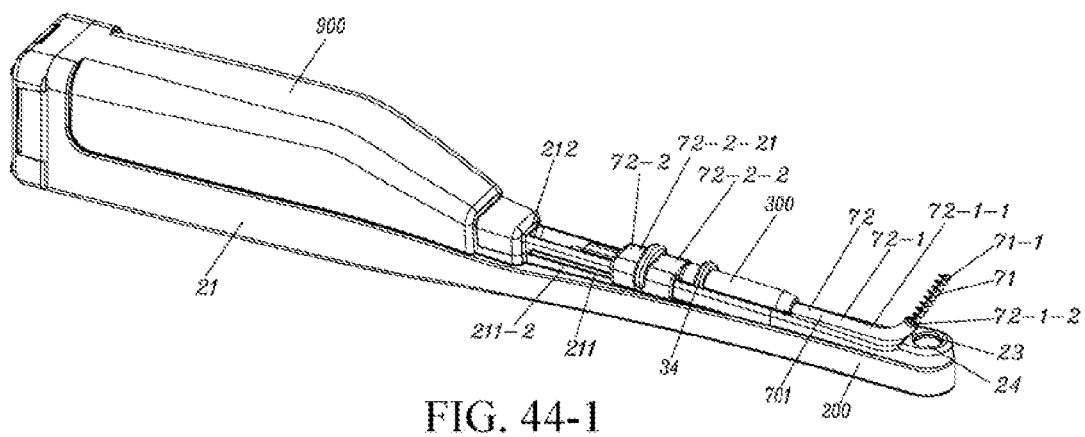
Figures 2, 44:
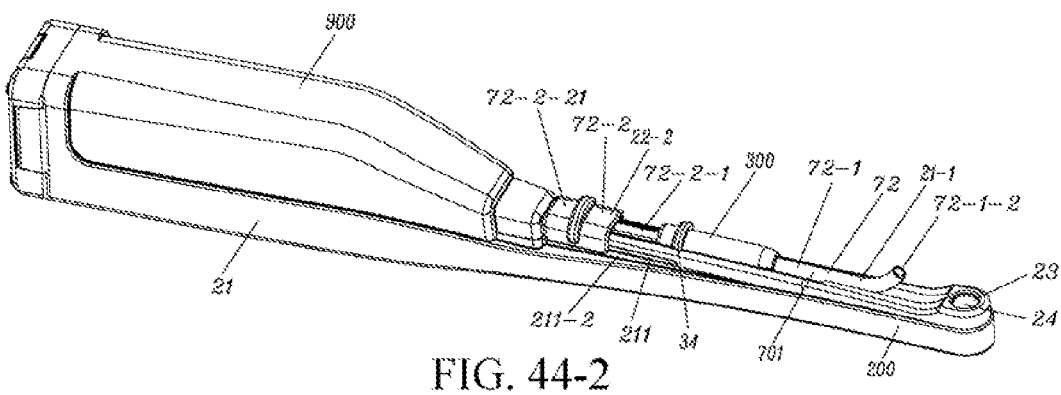
Figures 3, 44:
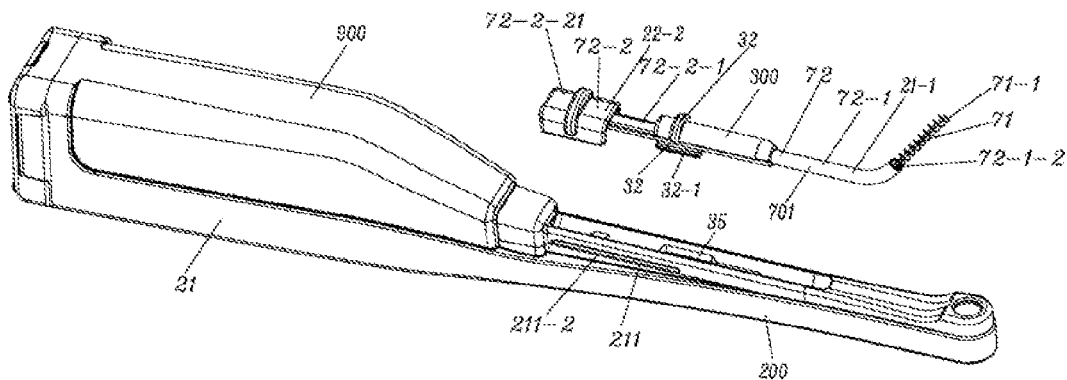

With reference to FIG. 41 to FIG. 43, the viewing system 24 is a camera system 24-1, and the camera system 24-1 includes a camera 24-1-1, a data processing and output system 24-1-2, a circuit system 25 and a power supply system 22.

Video data output by the data processing and output system 24-1-2 of the camera system 24-1 can be displayed on a display device 24-1-3 in a wired connection or wireless connection manner, and the display device 24-1-3 includes: a smartphone 24-1-31, or a computer 24-1-32, or a liquid crystal display device 24-1-33, or a television 24-1-34, with reference to FIG. 4 and FIG. 5.

During use, the camera 24-1-1 can perform picture and video recording on the cleaning process, the video data output by the data processing and output system 24-1-2 can be displayed on the display device 24-1-3 in real time, and the user only needs to view the cleaning process in real time through the real-time pictures of the cleaning process displayed on the display device 24-1-3 to clearly see which positions have been cleaned and which positions have not yet been cleaned.

With reference to FIG. 41 to FIG. 41-3, the lighting system 23 is arranged around the camera 24-1-1.

The lighting system 23 adopts an LED lighting system 23-1.

The camera 24-1-1 is in the heat affected zone of the lighting system 23, and heat generated by the lighting system 23 can heat the camera 24-1-1, thereby preventing the camera 24-1-1 from generating fog during use.

Heat generated by the lighting system 23 can increase the temperature of the camera 24-1-1 to 35° C.-45° C.

The housing 21 can generate a dynamic thermal balance between the heat dissipation capacity of the housing 21-5 near the camera 24-1-1 and the heat generated by the lighting system 23, so that the temperature of the camera 24-1-1 and the attached waterproof lens 24-1-4 is within the range of 35° C.-45° C., thereby achieving the purpose of anti-fog.

In order to enhance the lighting intensity of the LED lighting system 23-1, control the dynamic thermal balance around the camera 24-1-1 to reach the required level and ensure the temperature of the camera 24-1-1 and the periphery thereof to be maintained within the required temperature range, in this embodiment, 6 LED lights are arranged around the camera 24-1-1. On the one hand, the multiple LED lights enhance the lighting intensity of the LED lighting system 23-1 and increase the definition of the shooting process of the camera 24-1-1; and on the other hand, the heat generated by the LED lights of the LED lighting system 23-1 maintains the temperature of the camera 24-1-1 and the attached waterproof lens 24-1-4 thereof at 35-45° C. after the heat dissipation by the housing 21-5 near the camera 24-1-1, thereby achieving the goal of anti-fog.

The front end of the camera 24-1-1 is provided with a waterproof lens 24-1-4, and the waterproof lens 24-1-4 is treated with an anti-fog coating. After the waterproof lens 24-1-4 is treated through the anti-fog coating, even if a small amount of water vapor is formed at the front end of the waterproof lens 24-1-4 to form condensation on the surface of the waterproof lens 24-1-4, it does not exist in the form of water drops, but turns into a transparent water film, and cannot form a fog phenomenon in front of the camera 24-1-1, thereby further enhancing the anti-fog effect.

The oral viewer 200 adopts a waterproof design. The oral viewer 200 adopts a waterproof design, so the user can clean the visual toothbrush of the present disclosure in time in the use process; and the waterproof design can also avoid the influence on the functions of the power supply system 22, the lighting system 23, the viewing system 24, the circuit system 25 or the switch 26 in the housing 21 in the use process caused by water or human conductive secretion entering the oral viewer 200, so the use process is more convenient and secure.

During use, the toothbrush 600 is mounted on the oral viewer 200 through the connection mechanism 300, and the brush head 61 of the toothbrush 600 is utilized to clean the oral cavity under direct vision by using the viewing function of the oral viewer 200, so the cleaning process is very convenient; and especially for deep in the oral cavity, the oral viewer 200 is used for performing picture and video recording on the cleaning process, the video data output by the data processing and output system 24-1-2 can be displayed on the display device 24-1-3 in real time, and the user only needs to view the cleaning process in real time through the real-time pictures of the cleaning process displayed on the display device 24-1-3 to clearly see which positions have been cleaned and which positions have not yet been cleaned.

By using the visual toothbrush 904 of the present disclosure, the user can clean the oral cavity under direct vision, and can view the cleaning process and the effect after cleaning and perform picture or video recording, so that the cleaning process of the oral cavity is clearer and more convenient and secure.

Embodiment 14: A Visual Toothbrush Including 1 Brush Hair According to the Present Disclosure With reference to FIG. 41 to FIG. 41-3, the difference between this embodiment and Embodiment 1 lies in that in this embodiment, the brush head 61 of the toothbrush 600 only includes 1 brush hair 61-1.

The brush hair 61-1 is made of a medical elastic material, such as elastic silica gel, a polyurethane material (PU), a polypropylene material (PP) or the like.

In this embodiment, the diameter of the brush hair 61-1 may be increased to enhance the strength of the brush hair 61-1, and therefore, the single brush hair 61-1 in this embodiment may be used for effectively removing and cleaning food residues in some gaps which are adjacent to the gingivae and cannot be easily cleaned by a common toothbrush, especially the combination between the teeth and gingivae. In addition, the brush hair 61-1 in this embodiment has favorable elasticity and certain strength, and therefore, the brush hair 61-1 may be used for massaging gingivae.

Compared with Embodiment 1, the toothbrush 600 in this embodiment has the cleaning function and the massaging effect, and is especially suitable for cleaning the gaps which are adjacent to the gingivae and cannot be easily cleaned by a common toothbrush.

In addition, the front end of the oral viewer 200 may further be designed to have a certain curvature to adapt to the demands of people with special oral cavity shapes.

In addition, the power supply system 25 may further charge the battery in a wireless charging manner. This wireless charging manner can simplify the structure and enhance the waterproofing grade.

Embodiment 15: A Detachable Visual Interdental Brush Including an Inverted T-Shaped Locating Block According to the Present Disclosure With reference to FIG. 44 to FIG. 49, the detachable visual interdental brush 905 of this embodiment includes an built-in interdental brush 701, an oral viewer 200 and a connecting mechanism 300.

The built-in interdental brush 701 includes a brush body 71 and a delivery device 72. The brush body 71 is movably built in an elbow tube 72-1-1 at the front end of the delivery device 72, with reference to FIG. 47 to FIG. 47-4.

The oral viewer 200 includes a housing 21, a power supply system 22, a lighting system 23, a viewing system 24, a circuit system 25 and a switch 26. The lighting system 23, the viewing system 24 and the power supply system 22 are mounted in the housing 21, and the switch 26 is mounted on the housing 21. The lighting system 23, the viewing system 24, the power supply system 22 and the switch 26 are connected together through the circuit system 25, with reference to FIG. 45 to FIG. 45-1.

The built-in interdental brush 701 is detachably mounted on the oral viewer 200 through the connecting mechanism 300, with reference to FIG. 44 to FIG. 46-1.

The connecting mechanism 300 is a detachable mechanical connecting mechanism, and may be a separate component, or arranged on the built-in interdental brush 701 or the oral viewer 200. In this embodiment, the connecting mechanism 300 is arranged on the built-in interdental brush 701 and fixed to the middle rear position on the guide head 72-1 of the built-in interdental brush 701, with reference to FIG. 47 to FIG. 47-4; and then, the built-in interdental brush 701 and the oral viewer 200 are detachably assembled into an integral body through the connecting mechanism 300 in a concave-convex snap fit manner, with reference to FIG. 44 to FIG. 49.

In this embodiment, the connecting mechanism 300 is a mechanical connecting mechanism which is of a concave-convex snap fit connection. Of course, the connecting mechanism may also be another mechanical connecting mechanism, such as a sliding slot connection, or a pin connection, or a key connection, or a threaded connection, or a screw connection, or a buckle connection, or a hook connection, or an interference fit connection, or the like, which will not be listed here.

Figure 47:
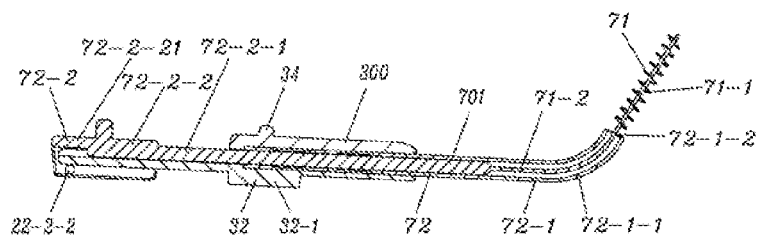
Figures 1, 47:
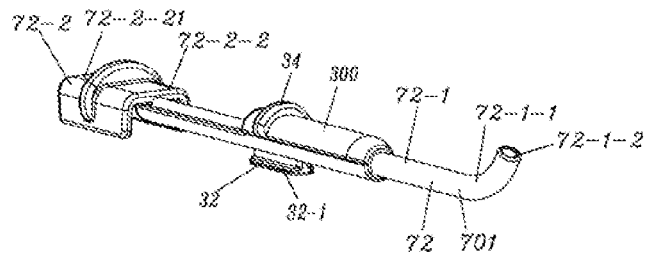
Figures 2, 47:
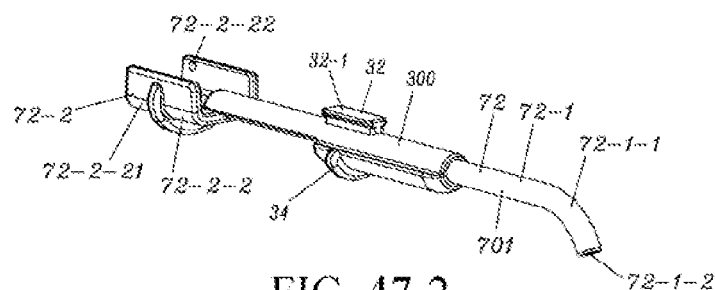
Figures 3, 47:
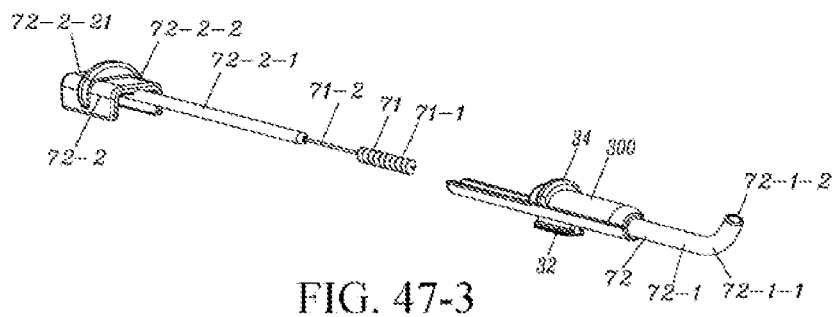
Figures 4, 47:
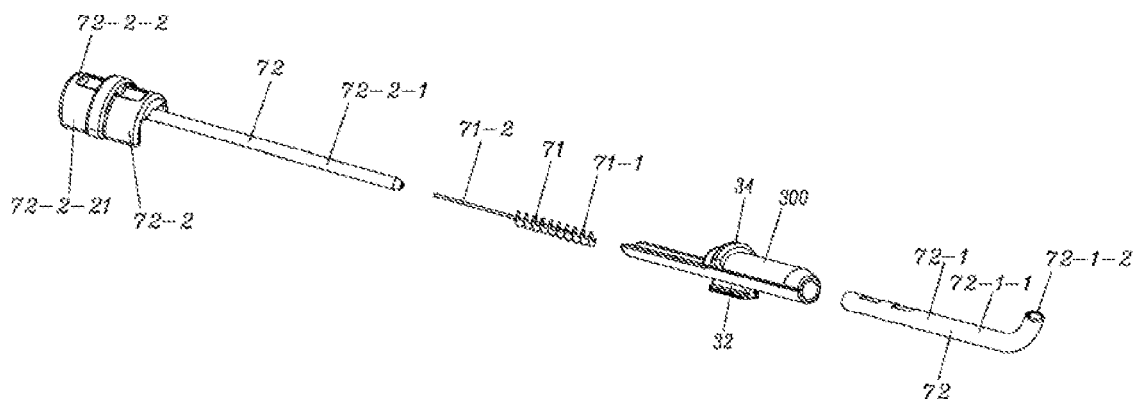
Figure 48:
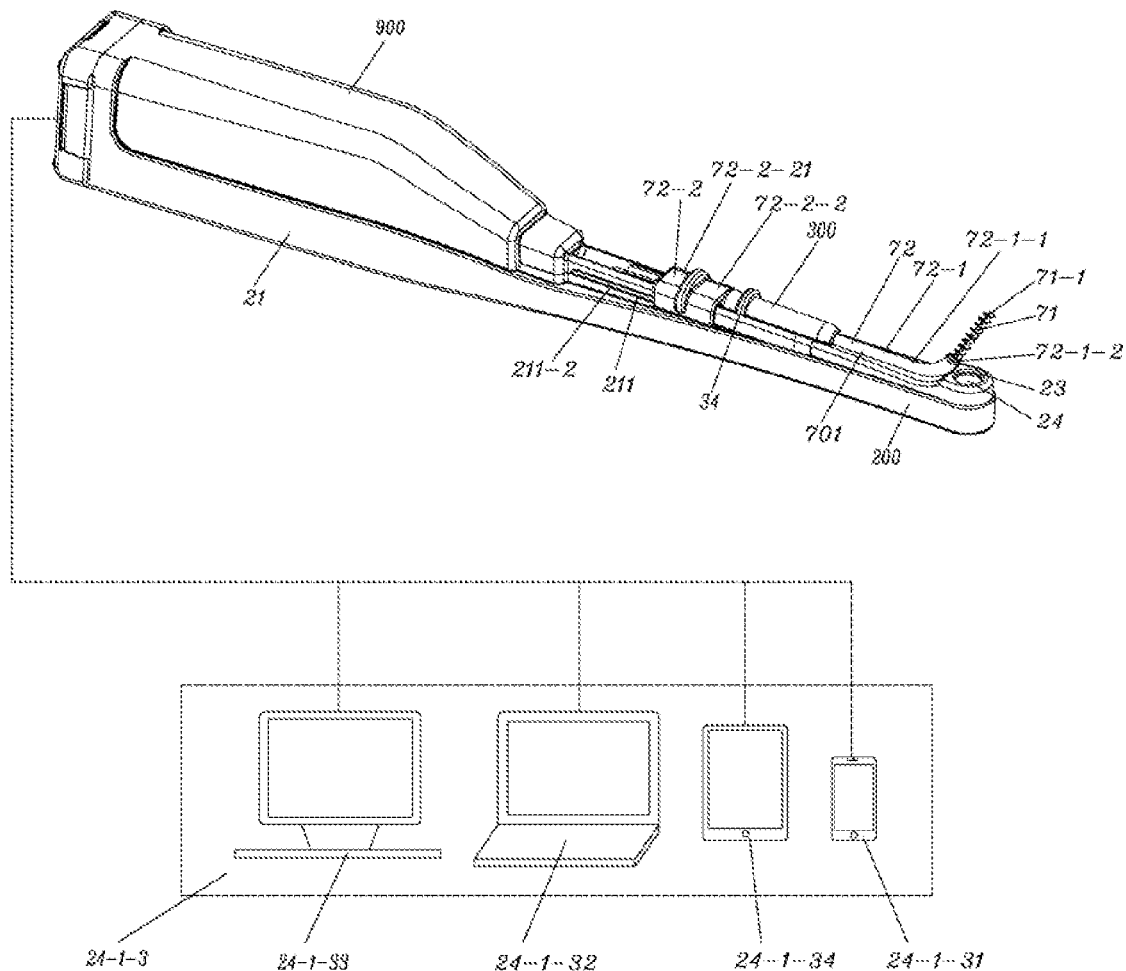
Figure 49:
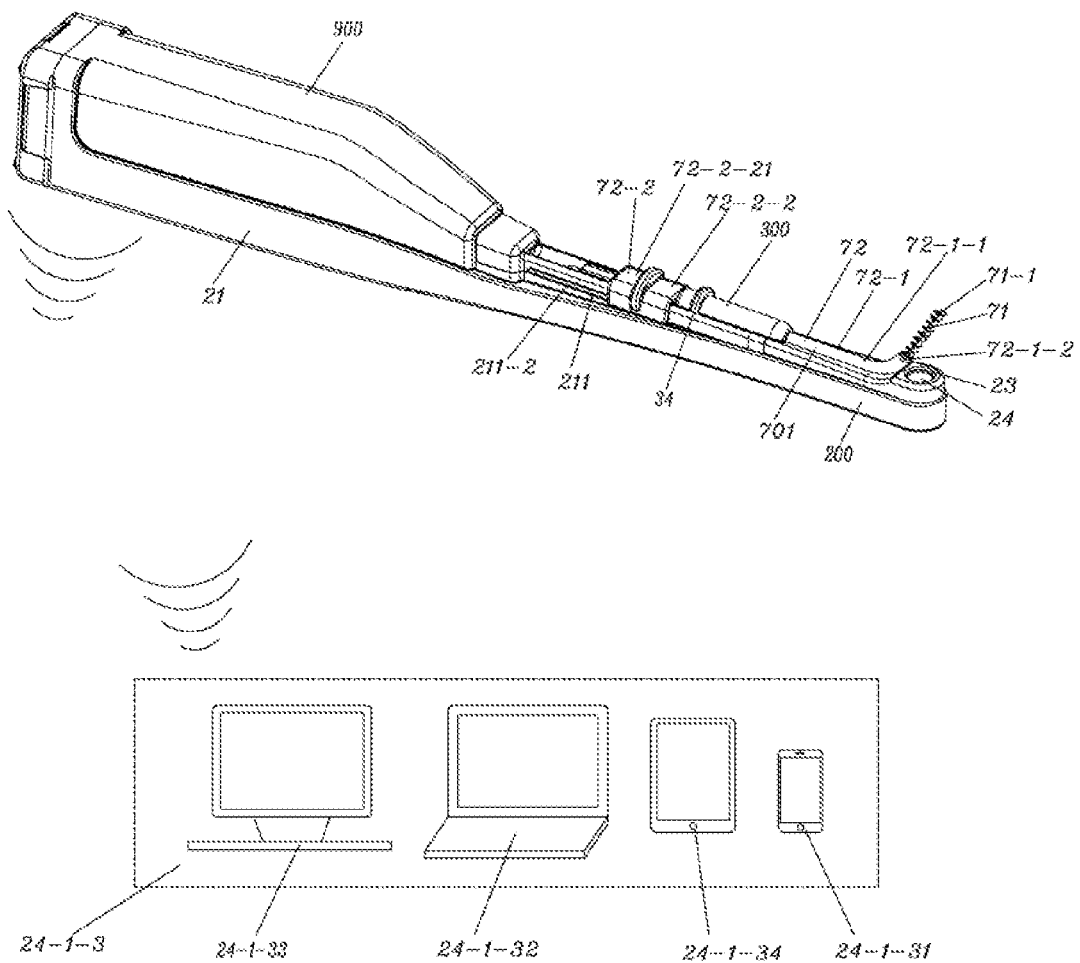

The brush body 71 of the built-in interdental brush 701 includes a working portion 71-1 and a connecting body 71-2; the working portion 71-1 is arranged at the front end of the connecting body 71-2; the delivery device 72 includes a guide head 72-1 and a sliding mechanism 72-2; the guide head 72-1 is arranged at a front end 721 of the delivery device 72; the guide head 72-1 includes an elbow tube 72-1-1, and an outlet 72-1-2 of the elbow tube 72-1-1 is arranged at an end 72-1-3 of the guide head 72-1; the brush body 71 is mounted in the elbow tube 72-1-1, the working portion 71-1 of the brush body 71 can slide in the elbow 72-1-1, and the connecting body 71-2 of the brush body 71 is mounted on the sliding mechanism 72-2 of the delivery device 72; the movement of the sliding mechanism 72-2 can drive the working portion 71-1 of the brush body 71 to slide in the elbow tube 72-1-1; and driving the sliding mechanism 72-2 allows the working portion 71-1 of the brush body 71 to protrude from the outlet 72-1-2 of the elbow tube at the end of the guide head, with reference to FIG. 47 to FIG. 47-4.

The sliding mechanism 72-2 of the built-in interdental brush 701 includes an interdental brush connecting mechanism 72-2-1 and a sliding block 72-2-2, and the interdental brush connecting mechanism 72-2-1 is arranged on the sliding block 72-2-2; and the connecting body 71-2 of the interdental brush and the interdental brush connecting mechanism 72-2-1 are connected together, and the sliding block 72-2-2 can be pushed and pulled to drive the brush body 71 to reciprocate within the elbow tube 72-1-1, so that the working portion 71-1 of the interdental brush protrudes or retracts from the outlet 72-1-2 of the elbow tube at the end of the guide head 72-1, with reference to FIG. 47 to FIG. 47-4.

Since the built-in interdental brush 701 adopts the structure that the brush body 71 is built in the elbow tube 72-1-1 of the guide head 72-1 of the delivery device 72, after the guide head 72-1 is aligned with the tooth gap, the working portion 71-1 of the brush body 71 made of the elastic material pushes the sliding mechanism 72-2 on the delivery device 72 to drive the working portion 71-1 of the brush body 71 to automatically bend along the curvature of the elbow tube 72-1-1, and to be aligned with and enter the tooth gap, and the sliding block 72-2-2 on the sliding mechanism 72-2 of the delivery device 72 is pushed and pulled back and forth, so that the working portion 71-1 of the interdental brush reciprocates in the tooth gap to clean the tooth gap. Since the delivery device 72 has favorable rigidity, after the outlet 72-1-2 of the elbow tube of the guide head 72-1 of the delivery device 72 is aligned with the tooth gap, the working portion 71-1 of the brush body 71 that is pushed out directly enters the tooth gap; since the outlet 72-1-2 of the elbow tube of the guide head 72-1 of the delivery device 72 is almost attached to the tooth gap and is very near to the tooth gap and the working portion 71-1 of the interdental brush cannot easily bend, the conductivity of force of the brush body 71 is greatly enhanced, and the operability of the brush body 71 is enhanced, thereby avoiding the defect that the interdental brush in the prior art can easily bend and easily hurt the gingivae when cleaning the gap between molars.

The connecting mechanism 300 is arranged on the guide head 72-1 of the built-in interdental brush 701; and the connecting mechanism 300 includes a locating block 32.

In this embodiment, the connecting mechanism 300 and the guide head 72-1 of the built-in interdental brush 701 are connected by integral manufacturing. Of course, they may also be bonded together, or connected detachably.

With reference to FIG. 44 to FIG. 47-4, the housing 21 of the oral viewer 200 is provided with a sliding slot 211-2 on which the sliding block 72-2-2 of the built-in interdental brush 701 can reciprocate, and a locating slot 35 capable of fixing the connecting mechanism 300.

Figure 45:
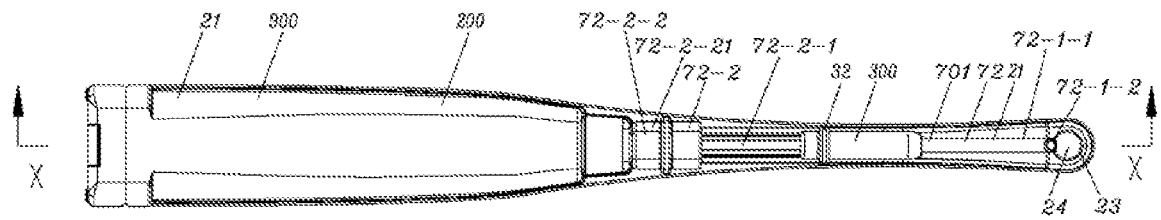
FIG. 45 is a top view of the detachable visual interdental brush according to the present disclosure.
Figures 1, 45:
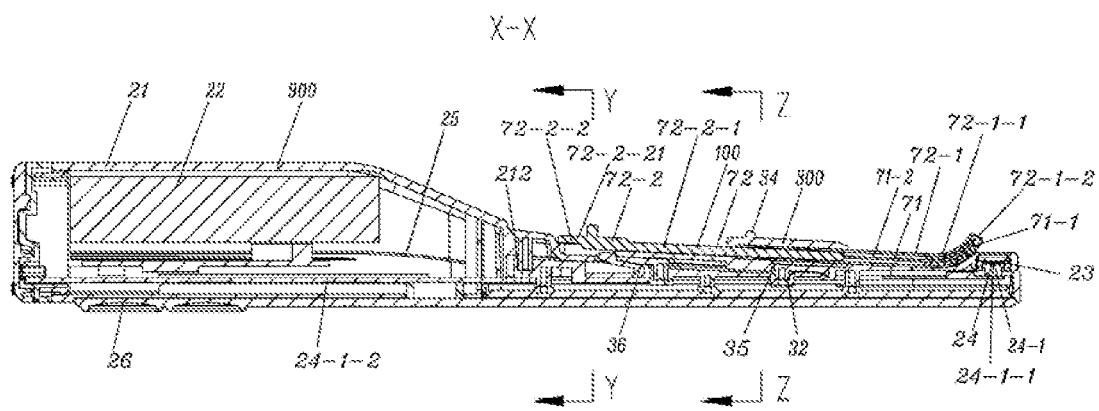
Figures 2, 3, 45:
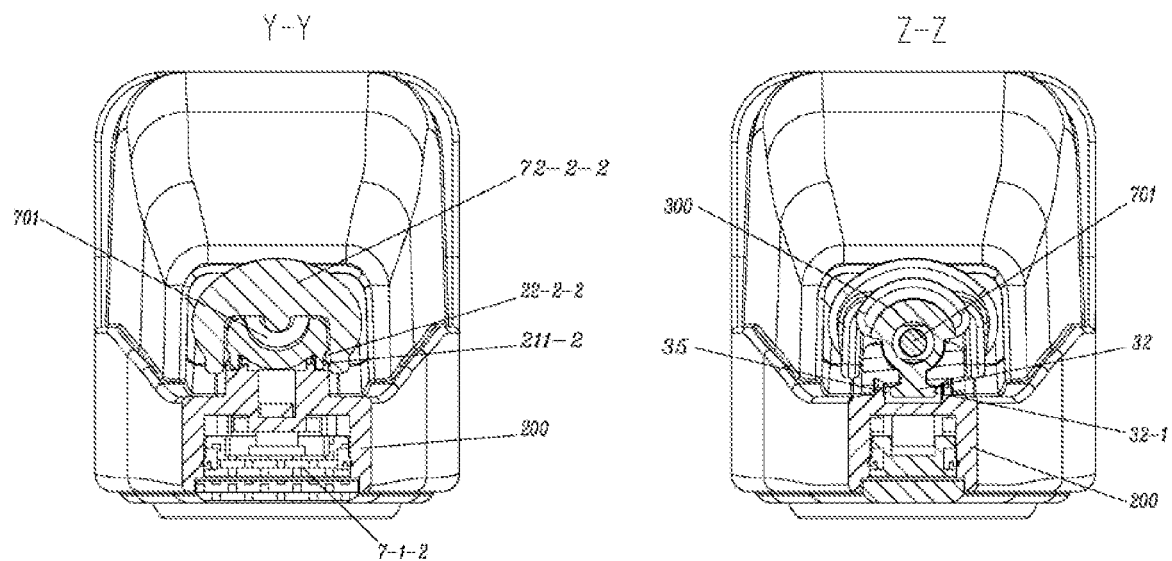
Figures 1, 46:
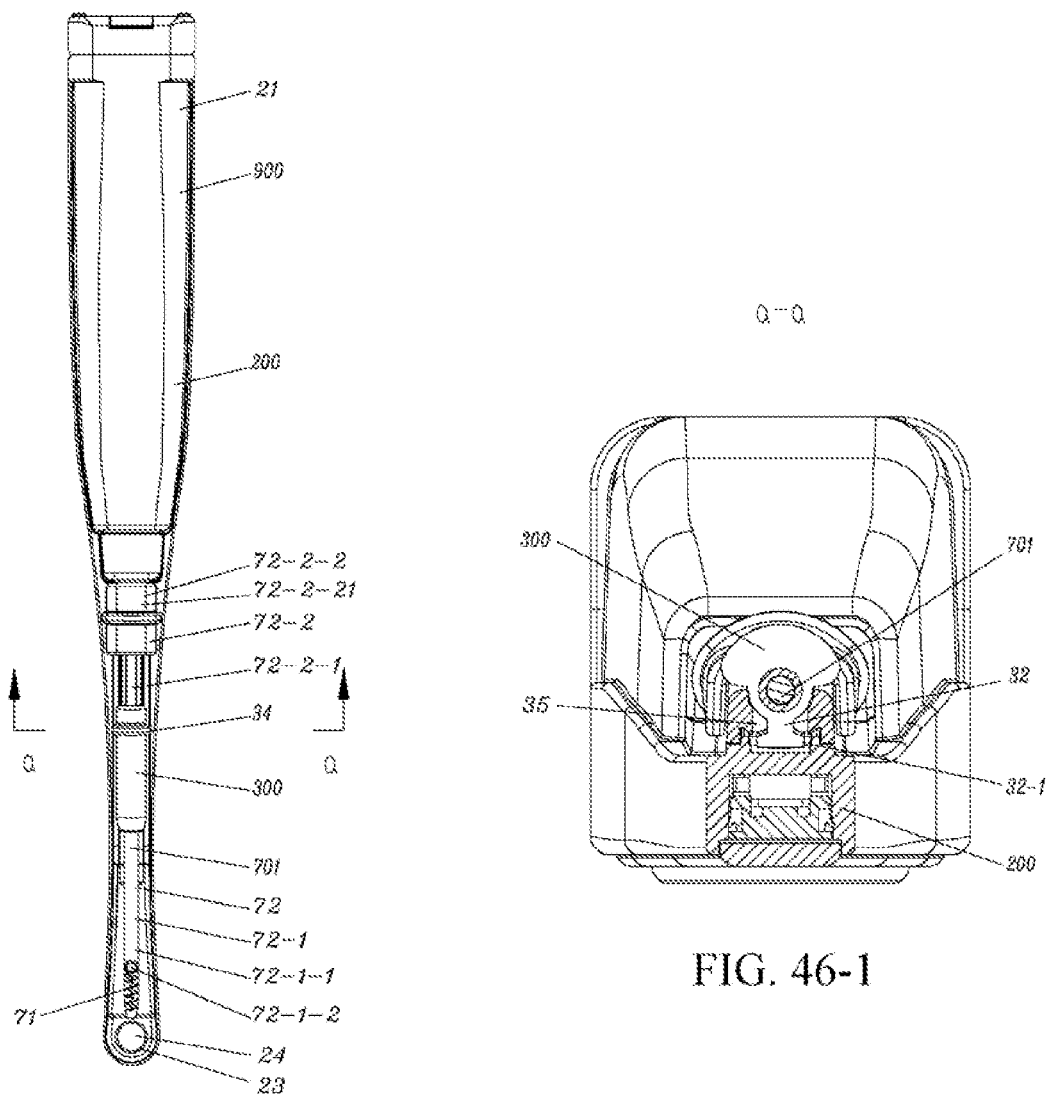

With reference to FIG. 47 to FIG. 47-4, the sliding block 72-2-2 of the sliding mechanism 72-2 of the built-in interdental brush 701 includes an arched housing 72-2-21, and the inner side of the arched housing 72-2-21 is provided with a guide block 72-2-22; and the guide block 72-2-22 can reciprocate within the sliding slot 211-2 of the oral viewer 200, with reference to FIG. 45-4.

In order to conveniently push the sliding block 72-2-2 to move, the arched housing 72-2-21 may be provided with an antiskid line. When the arched housing 72-2-21 is slightly pressed down, the guide block 72-2-22 can be embedded in the sliding slot 211-2 of the oral viewer 200; and when the arched housing 72-2-21 is pushed back and forth, the sliding block 72-2-2 can conveniently slide back and forth along the sliding slot 211-2 of the oral viewer 200 under the guide action of the guide block 72-2-22.

With reference to FIG. 44 to FIG. 47-4, in this embodiment, the locating block 32 of the connecting mechanism 300 is the inverted T-shaped locating block 32-1; the inverted T-shaped locating block 32-1 is arranged below the connecting mechanism 300; the housing 21 of the oral viewer 200 is provided with a fixing mechanism 211, and the fixing mechanism 211 includes the locating slot 35, the sliding slot 211-2 and a clamping block 36; the T-shaped locating block 32-1 is detachably embedded in the locating slot 35, and the clamping block 36 bouncing upward can prevent the connecting mechanism 300 from moving back and prevent the built-in interdental brush 701 from being accidentally released from the oral view 200; and the connecting mechanism 300 can be released from the oral viewer 200 only by pressing down the clamping block 36 and pulling the connecting mechanism 300 backward at the same time, with reference to FIG. 45-1.

When mounting, the connecting mechanism 300 is fixed to a proper position on the guide head 72-1 of the delivery device 72 of the built-in interdental brush 701; the brush body 71 of the built-in interdental brush 701 is connected to the sliding block 72-2-2 of the delivery device 72; the brush body 71 is mounted in the elbow tube 72-1-1 of the guide head 72-1 of the delivery device 72; and the sliding block 72-2-2 is pushed forward to bring the connecting mechanism 300 and the sliding block 72-2-2 of the built-in interdental brush 701 together.

Then, the built-in interdental brush 701 and the connecting mechanism 300 downwardly fit the fixing mechanism 211 on the housing 21 of the oral viewer 200 along the locating end 212 of the housing 21 of the oral viewer 200; the built-in interdental brush 701 and the connecting mechanism 300 are pressed down, and the guide block 72-2-22 on the inner side of the arched housing 72-2-21 of the sliding block 72-2-2 of the built-in interdental brush 701 is embedded in the sliding slot 211-2 of the oral viewer 200; and meanwhile, the clamping block 36 is pressed down, the inverted T-shaped locating block 32-1 enters the locating slot 35 of the oral viewer 200.

While the sliding block 72-2-2 and the brush body 71 of the built-in interdental brush 701 are kept still, the connecting mechanism 300 is pushed forward, so that the inverted T-shaped locating block 32-1 of the connecting mechanism 300 is embedded in the locating slot 35 of the oral viewer 200 until the clamping block 36 bounces up to abut against the rear end the connecting mechanism 300, and thus, the connecting mechanism 300 is mounted in place, thereby establishing a firm connection between the built-in interdental brush 701 and the oral viewer 200.

When the built-in interdental brush 701 needs to be removed, the connecting mechanism 300 is moved backward with force, so the clamping block 36 is pressed down, the connecting mechanism 300 can move backward, and the inverted T-shaped locating block 32-1 is withdrawn from the locating slot 35 until the connection between the T-shaped locating block 32-1 and the locating slot 35 is released, thereby removing the built-in interdental brush 701 from the oral viewer 200.

Since the inverted T-shaped locating block 32-1 adopts an inverted T-shaped structure, when the T-shaped locating block 32-1 is embedded in the locating slot 35, the bottom of the inverted T-shaped structure and the locating slot 35 can form a concave-convex snap fit structure, thereby effectively limiting the movement of the connecting mechanism 300 in the vertical direction, and further preventing the built-in interdental brush 701 and the oral viewer 200 from departing along the vertical direction during use. Meanwhile, the clamping block 36 is arranged at the rear end of the connecting mechanism 300; when the clamping block 36 is lifted up, since the top of the clamping block 36 is higher than the tail of the connecting mechanism 300, the connecting mechanism 300 can be effectively prevented from moving backward; and only when the connecting mechanism 300 is moved backward consciously and forcefully, the connecting mechanism 300 can be released from the oral viewer 200 after withdrawing along the guide surface of the clamping block 36, thereby effectively preventing the built-in interdental brush 701 from being accidentally released from the oral viewer 200 due to the fact that the connecting mechanism 300 can easily move backward.

In this embodiment, the viewing system 24 is a camera system 24-1, and the camera system 24-1 includes a camera 24-1-1, a data processing and output system 24-1-2, a circuit system 25 and a power supply system 22, with reference to FIG. 45-1, FIG. 45-2 and FIG. 48 to FIG. 49.

Video data output by the data processing and output system 24-1-2 of the camera system 24-1 can be displayed on a display device 24-1-3 in a wired connection or wireless connection manner, and the display device 24-1-3 includes:

a smartphone 24-1-31, or a computer 24-1-34, or a liquid crystal display device 24-1-33, or a television 24-1-34.

The lighting system 23 is arranged around the camera 24-1-1.

The detachable visual interdental brush 905 may be freely combined according to the use habit and preference of the user, and the built-in interdental brush 701 and the oral viewer 200 are flexibly assembled together through the connecting mechanism 300 to be operated by one hand and clean the tooth gap; and they may also be separated, the oral viewer 200 is held by one hand to perform viewing, and the built-in interdental brush 701 is held by the other hand to clean the tooth gaps, so the detachable visual interdental brush 905 is convenient to carry and assemble and flexible to use.

Embodiment 16: A Detachable Visual Interdental Brush Including an Arc-Shaped Locating Hook Type Locating Block According to the Present Disclosure With reference to FIG. 50 to FIG. 53-5, the difference between this embodiment and Embodiment 1 lies in that in this embodiment, the locating block 32 of the connecting mechanism 300 adopts an arc-shaped locating hook 32-2.

The arc-shaped locating hook 32-2 includes a locating groove 32-2-1. The locating slot 35 in the oral viewer 200 includes a locating convex stair 211-1-1 matched with the locating groove 32-2-1. The arc-shaped locating hook 32-2 is embedded in the locating slot 35 to form a concave-convex snap fit, thereby limiting the movement of the connecting mechanism 300 in the vertical direction, with reference to FIG. 9 and FIG. 9-1; and the locating convex stair 211-1-1 is embedded in the locating groove 32-2-1, thereby limiting the forward and backward movement of the connecting mechanism 300, with reference to FIG. 50-2, FIG. 50-3, FIG. 51, FIG. 52, FIG. 52-1 and FIG. 53-1.

When mounting, after the built-in interdental brush 701 and the connecting mechanism 300 are mounted as described above, the sliding block 72-2-2 of the built-in interdental brush 701 is aligned with the sliding slot 211-2 in the housing 21 of the oral viewer 200, and the arc-shaped locating hook 32-2 of the connecting mechanism 300 is aligned with the locating slot 35 in the housing 21 of the oral viewer 200; the built-in interdental brush 701 and the connecting mechanism 300 are pressed down, so that the guide block 72-2-22 on the inner side of the arched housing 72-2-21 of the sliding block 72-2-2 of the built-in interdental brush 701 is embedded in the sliding slot 211-2 of the oral viewer 200; the arc-shaped locating hook 32-2 of the connecting mechanism 300 is embedded in the locating slot 35 to form a concave-convex snap fit, thereby limiting the movement of the connecting mechanism 300 in the vertical direction; and the connecting mechanism 300 is slid forward until the locating convex stair 211-1-1 of the oral viewer 200 is embedded in the locating groove 32-2-1 of the connecting mechanism 300, thereby limiting the forward and backward movement of the connecting mechanism 300. When it is necessary to remove the built-in interdental brush 701, the connecting mechanism 300 is moved backward with force, so that the locating groove 32-2-1 of the connecting mechanism 300 is released from the locating convex stair 211-1-1 of the oral viewer 200; and when the connecting mechanism 300 is continuously slid backward along the locating slot 35 of the oral viewer 200, the connecting mechanism 300 can be released from the oral viewer 200.

Compared with Embodiment 1, in this embodiment, the dual concave-convex snap fit connection manner formed between arc-shaped locating hook 32-2 and the locating slot 35 and between the locating convex stair 211-1-1 and the locating groove 32-2-1 can implement an effective connection and fixation between the connecting mechanism 300 and the oral viewer 200.

Embodiment 17: A Detachable Visual Interdental Brush Including a Connecting Ring Type Locating Block According to the Present Disclosure With reference to FIG. 54, the difference between this embodiment and Embodiment 2 lies in that in this embodiment, the oral viewer 200 is further provided with a connecting ring type connecting mechanism 300. The connecting mechanism 300 of this embodiment includes a connecting ring 32-3, and the built-in interdental brush 701 passes through a mounting hole 32-3-1 of the connecting ring 32-3, so that the built-in interdental brush 701 is fixed to the oral viewer 200. Compared with the concave-convex snap fit connection manner, the connecting ring 32-3 ring structure can bear a higher tensile force and enhance the safety when the interdental brush 700 is withdrawn from between the teeth, and thus, is more reliable.

The connecting mechanism 300 may also be a surrounding arm 32-4, with reference to FIG. 54-1. The built-in interdental brush 701 and the oral viewer 200 are detachably connected together through the surrounding arm 32-4. The surrounding arm 32-4 may be arranged on the built-in interdental brush 700 and then surround the oral viewer 200 to implement the detachable connection of the two, and may also be arranged on the oral viewer 200 and then surround the built-in interdental brush 701 to implement the detachable connection of the two.

It should be particularly noted that in the present application, the connecting mechanism 300 may also be a separate component, and is respectively connected with the built-in interdental brush 701 and the oral viewer 200 to connect the built-in interdental brush 701 and the oral viewer 200 into an integral body. The connecting mechanism 300 may also be manufactured as a whole with the built-in interdental brush 701 or the oral viewer 200, and then connected with the oral view 200 or the built-in interdental brush 701 to form an integral body. Regardless of the type of connection, the ultimate goal is to implement a detachable connection between the built-in interdental brush 701 and the oral viewer 200. Therefore, the detachable connection between the built-in interdental brush 701 and the oral viewer 200 can be implemented as long as the connecting mechanism 300 implements a detachable mechanical connection with one of the built-in interdental brush 701 or the oral viewer 200.

It should be noted that the structures disclosed and described herein may be replaced with other structures having the same effect, and the embodiments described herein are not the only structures that implement the present disclosure. Although the preferred embodiments of the present disclosure have been described and illustrated herein, it will be apparent to those skilled in the art that these embodiments are merely illustrative and exemplary. Those skilled in the art can make numerous changes, improvements and substitutions without departing from the invention. Therefore, the protection scope of the present disclosure should be defined in accordance with the spirit and scope of the appended claims of the present disclosure.

While particular embodiments are described above, it will be understood it is not intended to limit the invention to these particular embodiments. On the contrary, the invention includes alternatives, modifications and equivalents that are within the spirit and scope of the appended claims. Numerous specific details are set forth in order to provide a thorough understanding of the subject matter presented herein. But it will be apparent to one of ordinary skill in the art that the subject matter may be practiced without these specific details. In other instances, well-known methods, procedures, components, and circuits have not been described in detail so as not to unnecessarily obscure aspects of the embodiments.

The terminology used in the description of the invention herein is for the purpose of describing particular embodiments only and is not intended to be limiting of the invention. As used in the description of the invention and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, operations, elements, and/or components, but do not preclude the presence or addition of one or more other features, operations, elements, components, and/or groups thereof.

As used herein, the term "if" may be construed to mean "when" or "upon" or "in response to determining" or "in accordance with a determination" or "in response to detecting," that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

Although some of the various drawings illustrate a number of logical stages in a particular order, stages that are not order dependent may be reordered and other stages may be combined or broken out. While some reordering or other groupings are specifically mentioned, others will be obvious to those of ordinary skill in the art and so do not present an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

The invention claimed is:

1. A visual dental floss, including a dental floss, an oral viewer and a connecting mechanism, wherein:
   A. the dental floss includes a floss, a bracket and a mounting base; both ends of the floss of the dental floss are respectively fixed on a left arm and a right arm of the bracket, and the bracket is arranged on the mounting base; the mounting base of the dental floss is provided with a locating groove;
   B. the oral viewer includes a housing, a power supply system, a lighting system, a viewing system, a circuit system and a switch; the lighting system, the viewing system, the circuit system and the power supply system are mounted in the housing, and the switch is mounted on the housing; the lighting system, the viewing system, the power supply system and the switch are connected together through the circuit system; and
   C. the dental floss is mounted on the oral viewer through the connecting mechanism; the connecting mechanism is provided with a locating hook and a locating block; the connecting mechanism is mounted on the oral viewer through the locating block; and the locating hook on the connecting mechanism is embedded in the locating groove of the dental floss to form a concave-convex snap fit connection, and a detachable connection is formed between the dental floss and the oral viewer.

2. The visual dental floss according to claim 1, wherein the floss of the dental floss is within a visual field of the viewing system of the oral viewer.

3. The visual dental floss according to claim 1, wherein an included angle $\delta$ between the floss of the dental floss and a center line of a head of the housing of the oral viewer is adjustable.

4. The visual dental floss according to claim 1, wherein the connecting mechanism is a detachable mechanical connecting mechanism and the connecting mechanism is a separate component arranged on the dental floss or arranged on the oral viewer.

5. The visual dental floss according to claim 4, wherein the mechanical connecting mechanism is one selected from the group consisting of a concave-convex snap fit connection, a sliding slot connection, a pin connection, a key connection, a threaded connection, a screw connection, a buckle connection, a hook connection, and an interference fit connection.

6. The visual dental floss according to claim 1, wherein the connecting mechanism is a detachable mechanical connecting mechanism and the connecting mechanism is a combined mechanical connecting mechanism formed by arranging a first part of the detachable mechanical connecting mechanism on the dental floss and a second part of the detachable mechanical connecting mechanism on the oral viewer.

7. The visual dental floss according to claim 1, wherein the mounting base of the dental floss is provided with a through hole, a head of the housing of the oral viewer is embedded in the through hole, and a detachable connection is formed between the dental floss and the oral viewer.

8. The visual dental floss according to claim 1, wherein the connecting mechanism includes a sliding bar, a locating hook, a left locating hook, a right locating hook, a locating block and an antiskid convex line; the locating hook, the left locating hook and the right locating hook are arranged at a front end of sliding bar, the locating hook is centered, and the left locating hook and the right locating hook are arranged on each side of the connecting mechanism; the locating block is positioned in the middle of the sliding bar; the antiskid convex line is arranged at a tail of the sliding bar; the locating block is mounted in a locating slot of the housing of the oral viewer, and a clamping block of the housing of the oral viewer abuts against the tail of the sliding bar, so that the connecting mechanism is detachably mounted and fixed to the housing of the oral viewer; and a head of the housing of the oral viewer is embedded in a through hole of the mounting base of the dental floss, the locating hook of the connecting mechanism is embedded in the locating groove of the mounting base, and the left locating hook and the right locating hook surround the head of the housing of the oral viewer from the left and right sides.

9. The visual dental floss according to claim 1, wherein the viewing system is a camera system including a camera, a data processing and output system, a circuit system and a power supply system.

10. The visual dental floss according to claim 9, wherein video data output by the data processing and output system of the camera system can be displayed on a display device in a wired connection or wireless connection manner, and the display device is one selected from the group consisting of a smartphone, a computer, a liquid crystal display device, and a television.

11. The visual dental floss according to claim 9, wherein the lighting system is arranged around the camera.

12. The visual dental floss according to claim 1, wherein the oral viewer includes a sealing device for a sealed charging interface; the sealing device includes a seal ring, a pressure plate and a sliding plate; the seal ring is mounted in a seal groove at a tail of the housing, the pressure plate presses on the seal ring, and the sliding plate detachably presses on the pressure plate; when the sliding plate slides into a sliding plate locating slot at the tail of the housing, the sliding plate presses on the pressure plate, and the pressure plate presses on the seal ring to form a seal; and when the sliding plate is pushed outward, the sliding plate is released from the sliding plate locating slot at the tail of the housing.

* * * * *